United States Patent [19]
Oku et al.

[11] Patent Number: 5,922,711
[45] Date of Patent: Jul. 13, 1999

[54] 8-SUBSTITUTED QUINAZOLINES, QUINOXALINES AND BENZOPYRIDAZINES

[75] Inventors: Teruo Oku; Hiroshi Kayakiri; Shigeki Satoh, all of Tsukuba; Yoshito Abe, Ibaraki; Yuki Sawada; Takayuki Inoue, both of Tsukuba; Hirokazu Tanaka, Takarazuka, all of Japan

[73] Assignee: Fujisawa Pharmaceutical Co., Ltd., Osaka, Japan

[21] Appl. No.: 08/933,354

[22] Filed: Sep. 19, 1997

Related U.S. Application Data

[62] Division of application No. 08/660,393, Jun. 7, 1996, Pat. No. 5,708,173, which is a division of application No. 08/233,771, Apr. 26, 1994, Pat. No. 5,563,162.

[30] Foreign Application Priority Data

Apr. 28, 1993 [GB] United Kingdom .................. 9308804
Sep. 13, 1993 [GB] United Kingdom .................. 9318929

[51] Int. Cl.⁶ .................. C07D 239/72; C07D 241/40; A61K 31/495; A61K 31/505
[52] U.S. Cl. .................. 514/248; 514/249; 514/259; 544/235; 544/285; 544/286; 544/287; 544/288; 544/289; 544/290; 544/291; 544/292; 544/293; 544/353; 544/354; 544/356
[58] Field of Search .................. 514/248, 259, 514/249; 544/235, 285–293, 353–356

[56] References Cited

U.S. PATENT DOCUMENTS

| | | | |
|---|---|---|---|
| 3,682,927 | 8/1972 | Carissimi et al. | 514/311 |
| 4,749,406 | 6/1988 | Martin | 514/311 |
| 5,006,534 | 4/1991 | Mohrs et al. | 514/311 |
| 5,212,182 | 5/1993 | Musser et al. | 514/311 |
| 5,294,622 | 3/1994 | Dreikorn et al. | 514/311 |
| 5,574,042 | 11/1996 | Oku et al. | 514/300 |
| 5,750,699 | 5/1998 | Oku et al. | 514/300 |

*Primary Examiner*—Matthew V. Grumbling
*Attorney, Agent, or Firm*—Oblon, Spivak, McClelland, Maier & Neustadt, P.C.

[57] ABSTRACT

A compound of the formula:

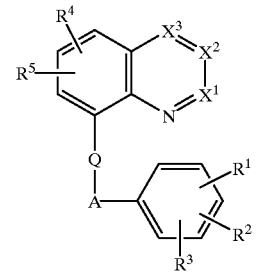

wherein $-X^3=X^2-X^1=N-$ is a group of the formula:

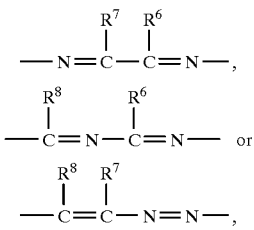

$R^1$ is hydrogen or halogen,
$R^2$ is halogen,
$R^3$ is hydrogen, nitro, amino optionally having at least one substituent or a heterocyclic group optionally having at least one substituent,
$R^4$ and $R^5$ are each hydrogen, or halogen,
$R^6$ and $R^8$ are each hydrogen, halogen, lower alkyl, hydroxy, lower alkylthio, amino optionally substituted with lower alkyl, or lower alkoxy optionally substituted with a substituent selected from the group consisting of hydroxy, lower alkoxy, amino, lower alkylamino and aryl optionally substituted with lower alkoxy,
$R^7$ is hydrogen or lower alkyl,
A is lower alkylene, and
Q is O or $N-R^9$ is hydrogen or acyl,
provided that $R^3$ is not hydrogen when $X^1$ is $C-R^6$, in which $R^6$ is hydrogen, and
pharmaceutically acceptable salts thereof.

7 Claims, No Drawings

8-SUBSTITUTED QUINAZOLINES, QUINOXALINES AND BENZOPYRIDAZINES

This is a Division of application Ser. No. 08/660,393 filed on Jun. 7, 1996, now U.S. Pat. No. 5,708,173 which is a division of application Ser. No. 08/233,771, filed on Apr. 26, 1994, now U.S. Pat. No. 5,563,162.

This invention relates to new heterocyclic compounds and pharmaceutically acceptable salts thereof.

More particularly, it relates to new heterocyclic compounds and pharmaceutically acceptable salts thereof which have activities as bradykinin antagonists, to processes for preparation thereof, to a pharmaceutical composition comprising the same, and to methods of using the same therapeutically in the prevention and/or the treatment of bradykinin or its analogues mediated diseases such as allergy, inflammation, autoimmune disease, shock, pain, or the like, in human being or animals.

One object of this invention is to provide new and useful heterocyclic compounds and pharmaceutically acceptable salts thereof which possess activities as bradykinin antagonists.

Another object of this invention is to provide processes for the preparation of said compounds and salts thereof.

A further object of this invention is to provide a pharmaceutical composition comprising, as an active ingredient, said heterocyclic compounds and pharmaceutically acceptable salts thereof.

Still further object of this invention is to provide a therapeutical method for the prevention and/or the treatment of bradykinin or its analogues mediated diseases such as allergy, inflammation, autoimmune disease, shock, pain, or the like, using said heterocyclic compounds and pharmaceutically acceptable salts thereof.

Some heterocyclic compounds have been known as described, for example, in EP-A-224,086, EP-A-261,539, Chemical Abstracts 90:34849g (1979), or Chemical Abstracts 97:18948c (1982). However, it is not known that said compounds have activities as bradykinin antagonists.

The object heterocyclic compounds of this invention are new and can be represented by the following general formula [I]:

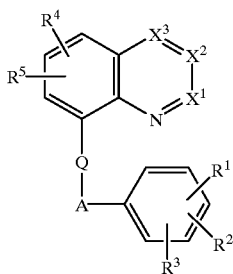

[I]

wherein $X^1$ is N or C—$R^6$,
$X^2$ is N or C—$R^7$,
$X^3$ is N or C—$R^8$,
$R^1$ is hydrogen or halogen,
$R^2$ is halogen,
$R^3$ is hydrogen nitro, amino, optionally having suitable substituent(s) or a heterocyclic group optionally having suitable substituent(s),
$R^4$ and $R^5$ are each hydrogen or halogen,
$R^6$ and $R^8$ are each hydrogen, halogen, lower alkyl, hydroxy, lower alkylthio, amino optionally substituted with lower alkyl, or lower alkoxy optionally substituted with a substituent selected from the group consisting of hydroxy, lower alkoxy, amino, lower alkylamino and aryl optionally substituted with lower alkoxy,
$R^7$ is hydrogen or lower alkyl,
A is lower alkylene, and
Q is O or N—$R^9$, in which $R^9$ is hydrogen or acyl,
provided that $R^3$ is not hydrogen when $X^1$ is C—$R^6_1$, in which $R^6$ is hydrogen.

The object compound [I] or its salt can be prepared by processes as illustrated in the following reaction schemes.

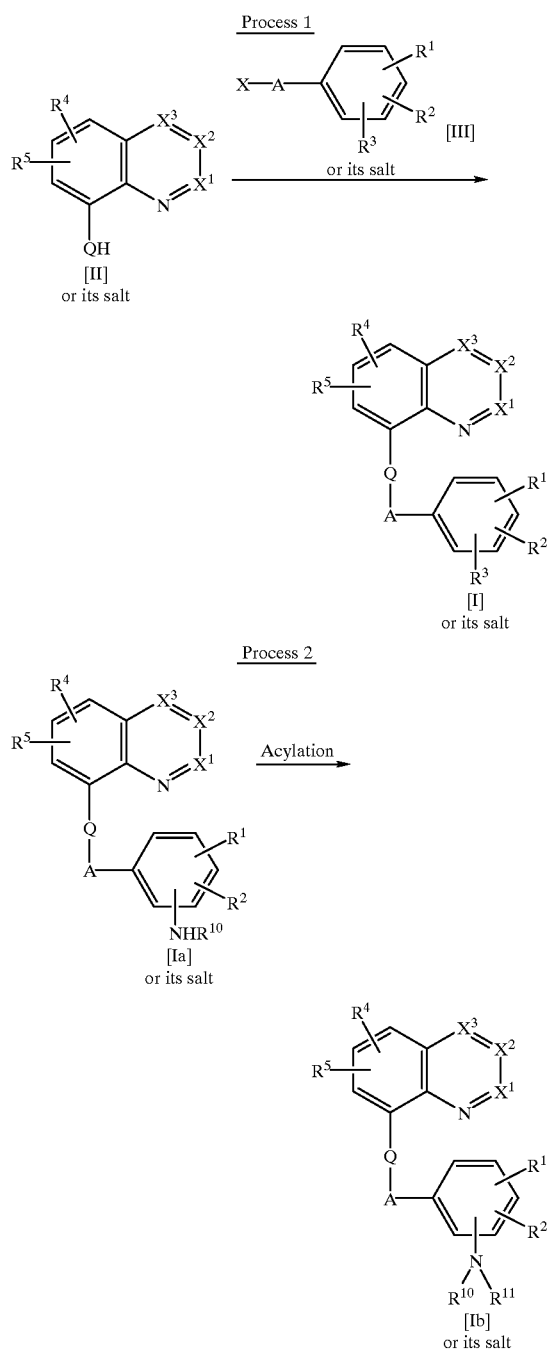

Process 3

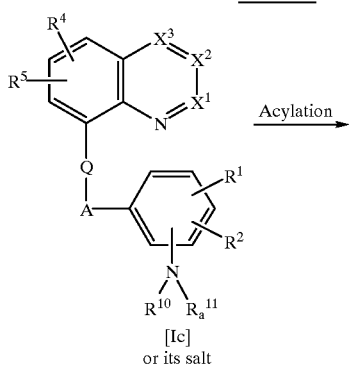

[Ic]
or its salt

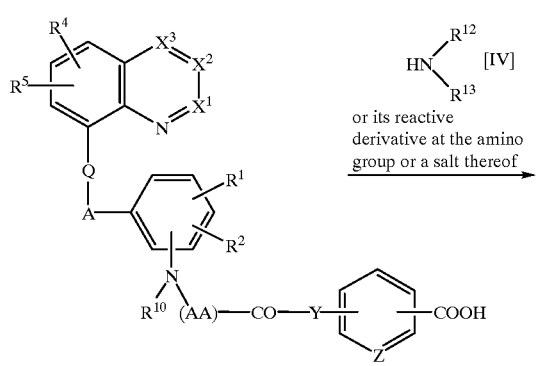

[Id]
or its salt

Process 4

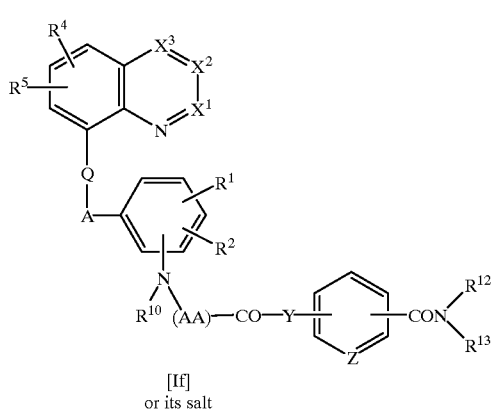

[If]
or its salt wherein $R^{10}$ is hydrogen or lower alkyl,
$R^{11}$ is acyl,
$R_a^{11}$ is acyl having amino,
$R_b^{11}$ is acyl having acylamino,
$R^{12}$ R is hydrogen, lower alkyl, lower alkoxy(lower)alkyl, lower alkylamino(lower)alkyl, heterocyclic(lower)alkyl, a heterocyclic group, lower alkenyl, lower alkynyl, lower alkylcarbamoyloxy(lower)alkyl, lower alkoxycarbonyl(lower)alkyl, carboxy(lower)alkyl, lower alkylcarbamoyl(lower)alkyl, lower alkoxycarbonyl-ar(lower)alkyl, carboxy-ar(lower)alkyl, lower alkylcarbamoyl-ar(lower)alkyl, protected or unprotected hydroxy(lower)alkyl or aryl optionally substituted with lower alkylamino, and
$R^{13}$ is hydrogen, lower alkyl, lower alkoxy(lower)alkyl or protected or unprotected hydroxy(lower)alkyl, or
$R^{12}$ and $R^{13}$ are taken together with the attached nitrogen atom to form a heterocyclic group optionally having suitable substituent(s),
(AA) is amino acid residue,
X is a leaving group,
Y is NH or lower alkenylene,
Z is CH or N, and
$R^1$, $R^2$, $R^3$, $R^4$, $R^5$, $X^1$, $X^2$, $X^3$, Q and A are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenyl moiety, lower alkynyl moiety and ar(lower)alkenyl moiety in the various definitions is intended to mean a group having 2 to 6 carbon atoms.

Further, the term "lower" in lower alkenoyl moiety, lower alkynoyl moiety, cyclo(lower)alkyl moiety, cyclo(lower)alkenyl moiety, ar(lower)alkenoyl moiety, ar(lower)alkynoyl moiety and heterocyclic(lower)alkenoyl moiety in the various definitions is intended to mean a group having 3 to 6 carbon atoms.

Suitable "halogen" may be fluorine, chlorine, bromine and iodine.

Suitable "aryl" and aryl moiety in the term "ar(lower)alkenoyl" may be phenyl, naphthyl, phenyl substituted with lower alkyl [e.g. tolyl, xylyl, mesityl, cumenyl, di(tert-butyl) phenyl, etc.] and the like, in which preferable one is phenyl, naphthyl and tolyl.

Suitable "lower alkyl" and lower alkyl moiety in the terms "heterocyclic(lower)alkyl", "lower alkylthio" and "lower alkylamino" may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "lower alkoxy" may be straight or branched one such as methoxy, ethoxy, propoxy, isopropoxy, butoxy, isobutoxy, tert-butoxy, pentyloxy, hexyloxy or the like, in which preferable one is $C_1$–$C_4$ alkoxy such as methoxy, ethoxy or isopropoxy.

Suitable "lower alkenylene" may be a straight or branched $C_2$–$C_6$ alkenylene such as vinylene, methylvinylene, propenylene, 1,3-butadienylene or the like, in which the most preferable one is vinylene.

Suitable "acyl" may be substituted or unsubstituted alkanoyl such as alkanoyl [e.g. formyl, acetyl, propionyl, butyryl, isobutyryl, valeryl, isovaleryl, pivaloyl, hexanoyl, heptanoyl, 3,3-dimethylbutyryl, etc.], halo(lower)alkanoyl [e.g. chloroacetyl, trifluoroacetyl, bromoacetyl, bromobutyryl, heptafluorobutyryl, etc.], hydroxy(lower) alkanoyl [e.g. glycoloyl, lactoyl, 3-hydroxypropionyl, glyceroyl, etc.], lower alkylsulfonyloxy(lower)alkanoyl [e.g. mesyloxyacetyl, ethylsulfonyloxyacetyl, mesyloxypropionyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkylthio(lower)alkanoyl [e.g. methylthioacetyl, ethylthioacetyl, methylthiopropionyl, ethylthiopropionyl, propylthiopropionyl, methylthiobutyryl, etc.], lower alkanoyloxy(lower)alkanoyl [e.g. acetyloxyacetyl, acetyloxypropionyl, propionyloxyacetyl, etc.], aryloxy (lower)alkanoyl [e.g. phenyloxyacetyl, phenyloxypropionyl, tolyloxyacetyl, naphthyloxyacetyl, etc.), aroyl(lower) alkanoyl [e.g. phenyloxalyl, benzoylacetyl, benzoylpropionyl, etc.], carboxy(lower)alkanoyl [e.g. oxalo, carboxyacetyl, 3-carboxypropionyl, 3-carboxybutyryl, 4-carboxybutyryl, 4-carboxyvaleryl, etc.], esterified carboxy (lower)alkanoyl, for example, lower alkoxycarbonyl(lower) alkanoyl [e.g. methoxycarbonylacetyl, ethoxycarbonylacetyl, methoxycarbonylpropionyl, ethoxycarbonylpropionyl, etc.], carbamoyl(lower)alkanoyl [e.g. carbamoylacetyl, carbamoylpropionyl, etc.], lower alkylcarbamoyl(lower)alkanoyl [e.g. methylcarbamoylacetyl, methylcarbamoylpropionyl, ethylcarbamoylpropionyl, dimethylcarbamoylpropionyl, (N-methyl-N-ethylcarbamoyl)propionyl, etc.], ar(lower) alkanoyl [e.g. phenylacetyl, tolylacetyl, naphthylacetyl, 2-phenylpropionyl, 3-phenylpropionyl, 4-phenylbutyryl, tritylcarbonyl, etc.], optionally substituted heterocyclic (lower)alkanoyl [e.g. morpholinoacetyl, thiomorpholinoacetyl, morpholinopropionyl, thiomorpholinopropionyl, piperidinopropionyl, piperazinylpropionyl, pyridylacetyl, pyrrolidinylpropionyl, imidazolidinylpropionyl, piperidinoacetyl, pyrrolidinylacetyl, hexamethyleneiminoacetyl, hexamethyleneiminopropionyl, imidazolylacetyl, furylacetyl, thienylacetyl, methylpiperazinylacetyl, pyridylpiperazinylacetyl, etc.], heterocyclicthio(lower) alkanoyl [e.g. pyridylthioacetyl, pyrimidinylthioacetyl, imidazolylthiopropionyl, etc.], etc., lower alkenoyl [e.g. acryloyl, crotonoyl, isocrotonoyl, 3-butenoyl, 3-pentenoyl, 4-pentenoyl, methacryloyl, etc.], lower alkynoyl [e.g. propioloyl, 2-butynoyl, 3-butynoyl, etc.], cyclo(lower) alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], etc., substituted or unsubstituted aroyl such as aroyl [e.g. benzoyl, toluoyl, xyloyl, naphthoyl, etc.], lower alkoxyaroyl [e.g. methoxybenzoyl, etc.], haloaroyl [e.g. chlorobenzoyl, fluorobenzoyl, etc.], acylaroyl, for example, lower alkoxycarbonylaroyl [e.g. methoxycarbonylbenzoyl, etc.], etc., substituted or unsubstituted ar(lower)alkenoyl such as ar(lower)alkenoyl [e.g. cinnamoyl, allocinnamoyl, α-methylcinnamoyl, 4-methylcinnamoyl, etc.], lower alkoxy-ar(lower)alkenoyl [e.g. methoxycinnamoyl, ethoxycinnamoyl, dimethoxycinnamoyl, etc.], lower alkylenedioxy-ar(lower)alkenoyl [e.g. methylenedioxycinnamoyl, ethylenedioxycinnamoyl, etc.], nitro-ar(lower)alkenoyl [e.g. nitrocinnamoyl, etc.], cyano-ar (lower)alkenoyl [e.g. cyanocinnamoyl, etc.],. halo-ar(lower) alkenoyl [e.g. chlorocinnamoyl, fluorocinnamoyl, etc.], hydroxy-ar(lower)alkenoyl [e.g. hydroxycinnamoyl, etc.], hydroxy(lower)alkoxy-ar(lower)alkenoyl [e.g. hydroxymethoxycinnamoyl, hydroxyethoxycinnamoyl, etc.], amino(lower)alkoxy-ar(lower)alkenoyl [e.g. aminoethoxycinnamoyl, etc.], lower alkylamino(lower) alkoxy-ar(lower)alkenoyl [e.g. methylaminomethoxycinnamoyl, dimethylaminoethoxycinnamoyl, etc.], heterocyclic(lower)alkoxy-ar(lower)alkenoyl [e.g. pyridylmethoxycinnamoyl, etc.], optionally substituted heterocyclic-ar(lower)alkenoyl [e.g. morpholinocinnamoyl, methylpiperazinylcinnamoyl, pyrrolidinylcinnamoyl, oxopyrrolidinylcinnamoyl, oxopiperidinocinnamoyl, dioxopyrrolidinylcinnamoyl, oxooxazolidinylcinnamoyl, pyrrolylcinnamoyl, tetrazolylcinnamoyl, etc.], amino-ar (lower)alkenoyl [e.g. aminocinnamoyl, etc.], lower alkylamino-ar (lower)alkenoyl [e.g. methylaminocinnamoyl, dimethylaminocinnamoyl, etc.], acylamino-ar (lower)alkenoyl, for example, lower alkanoylamino-ar (lower)alkenoyl [e.g. acetylaminocinnamoyl, propionylaminocinnamoyl, isobutyrylaminocinnamoyl, etc.], cycloalkyl(lower)alkanoylamino-ar(lower)alkenoyl [e.g. cyclopentylacetylaminocinnamoyl, cyclohexylacetylaminocinnamoyl, adamantylacetylaminocinnamoyl, etc.], cycloalkylcarbonylamino-ar(lower)alkenoyl [e.g. cyclopropylcarbonylaminocinnamoyl, cyclopentylcarbonylaminocinnamoyl, cyclohexylcarbonylaminocinnamoyl, adamantylcarbonylaminocinnamoyl, etc.], lower alkenoylamino-ar(lower)alkenoyl [e.g. acryloylaminocinnamoyl, crotonoylaminocinnamoyl, etc.], lower alkoxycarbonylamino-ar(lower)alkenoyl [e.g. methoxycarbonylaminocinnamoyl, ethoxycarbonylaminocinnamoyl, etc.], hydroxy(lower)alkanoylanmino-ar(lower) alkenoyl [e.g. hydroxyacetylaminocinnamoyl, hydroxypropionylaminocinnamoyl, etc.], lower alkoxy (lower)alkanoylamino-ar(lower)alkenoyl [e.g. methoxyacetylaminocinnamoyl, methoxypropionylaminocinnamoyl, etc.], halo(lower)alkanoylamino-ar(lower) alkenoyl [e.g. chloroacetylaminocinnamoyl, bromobutyrylaminocinnamoyl, trifluoroacetylaminocinnamoyl, etc.], amino(lower)alkanoylamino-ar(lower) alkenoyl [e.g. aminoacetylaminocinnamoyl, amino propionylaminocinnamoyl, etc.], lower alkylamino(lower) alkanoylamino-ar(lower)alkenoyl [e.g. methylaminoacetylaminocinnamoyl, dimethylaminoacetylaminocinnamoyl, etc.], lower alkanoylamino(lower)alkanoylamino-ar(lower) alkenoyl [e.g. acetylaminoacetylaminocinnamoyl, acetylaminopropionylaminocinnamoyl, etc.], carboxy (lower)alkanoylamino-ar(lower)alkenoyl [e.g. carboxyacetylaminocinnamoyl, carboxypropionylaminocinnamoyl, etc.], lower alkoxycarbonyl(lower) alkanoylamino-ar(lower)alkenoyl [e.g. ethoxycarbonylacetylaminocinnamoyl, ethoxycarbonylpropionylaminocinnamoyl, etc.], lower alkoxycarbonyl(lower)alkenoylamino-ar(lower)alkenoyl [e.g. ethoxycarbonylacryloylaminocinnamoyl, etc.], halo (lower)alkoxycarbonylamino-ar(lower)alkenoyl [e.g. chloroethoxycarbonylaminocinnamoyl, etc.], optionally substituted heterocyclic(lower)alkanoylamino-ar(lower) alkenoyl [e.g. pyridylacetylaminocinnamoyl, thienylacetylaminocinnamoyl, methylpyrrolylacetylaminocinnamoyl, etc.], aroylamino-ar(lower)alkenoyl [e.g. benzoylaminocinnamoyl, etc.], optionally substituted heterocycliccarbonylamino-ar(lower)alkenoyl [e.g. pyridylcarbonylaminocinnamoyl, morpholinocarbonylaminocinnamoyl, furylcarbonylaminocinnamoyl, thienylcarbonylaminocinnamoyl, oxazolylcarbonylaminocinnamoyl, methyloxazolylcarbonylaminocinnamoyl, dimethylisoxazolylcarbonylaminocinnamoyl, imidazolylcarbonylaminocinnamoyl, methylimidazolylcarbonylaminocinnamoyl, piperidylcarbonylaminocinnamoyl, ethylpiperidylcarbonylaminocinnamoyl, acetylpiperidylcarbonylaminocinnamoyl, pyrrolidinylcarbonylaminocinnamoyl, acetylpyrrolidinylcarbonylaminocinnamoyl, tert-butoxycarbonylpyrrolidinylcarbonylaminocinnamoyl, etc.], lower alkylsulfonylamino-ar(lower)alkenoyl [e.g. mesylaminocinnamoyl, ethylsulfonylaminocinnamoyl, etc.], etc., N-(lower alkanoyl)-N-(lower alkyl) amino-ar(lower)alkenoyl [e.g. N-acetyl-N-methylaminocinnamoyl, N-acetyl-N-ethylaminocinnamoyl, N-propionyl-N-methylaminocinnamoyl, etc.], N-[lower alkoxy(lower)-alkanoyl]-N-(lower alkyl)-amino-ar(lower)alkenoyl [e.g. N-methoxyacetyl-N-methylaminocinnamoyl, N-methoxypropionyl-N-methylaminocinnamoyl, etc.], N-(lower alkanoyl)-N-[heterocyclic(lower)alkyl]amino-ar(lower)alkenoyl [e.g. N-acetyl-N-pyridylmethylaminocinnamoyl, etc.], N-(lower alkanoyl)-N-[lower alkoxy(lower)alkyl]amino-ar(lower)alkenoyl [e.g. N-acetyl-N-methoxyethylaminocinnamoyl, N-acetyl-N-methoxymethylaminocinnamoyl, N-propionyl-N-methoxyethylaminocinnamoyl, etc.], N-(lower alkanoyl)-N-[lower alkoxycarbonyl(lower)alkyl]amino-ar(lower)alkenoyl [e.g. N-acetyl-N-tert-butoxycarbonylmethylaminocinnamoyl, N-acetyl- N-tert-butoxycarbonylethylaminocinnamoyl, N-propionyl-N-tert-butoxycarbonylmethylaminocinnamoyl, etc.], N-(lower alkanoyl)-N-[carboxy(lower)alkyl]amino-ar(lower)alkenoyl [e.g. N-acetyl-N-carboxymethylaminocinnamoyl, N-acetyl-N-carboxyethylaminocinnamoyl, N-propionyl-N-carboxymethylaminocinnamoyl, etc.], N-[lower alkoxy(lower)alkanoyl]-N-[heterocyclic(lower)alkyl]amino-ar(lower)alkenoyl [e.g. N-methoxyacetyl-N-pyridylmethylaminocinnamoyl, N-methoxypropionyl-N-pyridylmethylaminocinnamoyl, etc.], N-[heterocycliccarbonyl]-N-[lower alkoxy(lower)alkyl]amino-ar(lower)alkenoyl [e.g. N-pyridylcarbonyl-N-methoxymethylaminocinnamoyl, N-pyridylcarbonyl-N-methoxyethylaminocinnamoyl, N-thienylcarbonyl-N-methoxyethylaminocinnamoyl, etc.], ureido-ar(lower)alkenoyl [e.g. ureidocinnamoyl, etc.], lower alkylureido-ar(lower)alkenoyl [e.g. methylureidocinnamoyl, ethylureidocinnamoyl, dimethylureidocinnamoyl, etc.], heterocyclicureido-ar(lower)alkenoyl [e.g. pyridylureidocinnamoyl, pyrimidinylureidocinnamoyl, thienylureidocinnamoyl, etc.], acyl-ar(lower)alkenoyl, for example, lower alkanoyl-ar(lower)alkenoyl [e.g. formylcinnamoyl, acetylcinnamoyl, propionylcinnamoyl, etc.], carboxy-ar(lower)alkenoyl [e.g. carboxycinnamoyl, etc.], lower alkoxycarbonyl-ar(lower)alkenoyl [e.g. methoxycarbonylcinnamoyl, ethoxycarbonylcinnamoyl, etc.], carbamoyl-ar(lower)alkenoyl [e.g. carbamoylcinnamoyl, etc.], lower alkylcarbamoyl-ar(lower)alkenoyl [e.g. methyLcarbamoylcinnamoyl, ethylcarbamoylcinnamoyl, dimethylcarbamoylcinnamoyl, propylcarbamoylcinnamoyl, isopropylcarbamoylcinnamoyl, diethylcarbamoylcinnamoyl, N-methyl-N-ethylcarbamoylcinnamoyl, etc.], hydroxy(lower) alkylcarbamoyl-ar(lower)alkenoyl [e.g. hydroxyethylcarbamoylcinnamoyl, bis(hydroxyethyl)carbamoylcinnamoyl, etc.], N-[hydroxy(lower)alkyl]-N-(lower alkyl) carbamoyl-ar(lower)alkenoyl [e.g. N-hydroxyethyl-N-methylcarbamoylcinnamoyl, etc.], lower alkoxy(lower)alkylcarbamoyl-ar(lower)alkenoyl [e.g. methoxymethylcarbamoylcinnamoyl, methoxyethylcarbamoylcinnamoyl, bis(methoxyethyl)carbamoylcinnamoyl, ethoxyethylcarbamoylcinnamoyl, methoxypropylcarbamoylcinnamoyl, bis(ethoxyethyl)carbamoylcinnamoyl, etc.], N-[lower alkoxy(lower)alkyl]-N-(lower alkyl)carbamoyl-ar(lower)alkenoyl [e.g. N-methoxyethyl-N-methylcarbamoylcinnamoyl, N-ethoxyethyl-N-methylcarbamoylcinnamoyl, etc.], heterocyclic(lower)alkylcarbamoyl-ar(lower)alkenoyl [e.g. pyridylmethylcarbamoylcinnamoyl, furylmethylcarbamoylcinnamoyl, thienylmethylcarbamoylcinnamoyl, etc.], N-[heterocyclic(lower)alkyl]-N-(lower alkyl) carbamoyl-ar(lower)alkenoyl [e.g. N-pyridylmethyl-N-methylcarbamoylcinnamoyl, etc.], heterocycliccarbamoyl-ar(lower)alkenoyl [e.g. morpholinylcarbamoylcinnamoyl, thienylcarbamoylcinnamoyl, pyridylcarbamoylcinnamoyl, pyrimidinylcarbamoylcinnamoyl, tetrazolylcarbamoylcinnamoyl, etc.], optionally substituted heterocycliccarbonyl-ar(lower)alkenoyl [e.g. morpholinocarbonylcinnamoyl, pyrrolidinylcarbonylcinnamoyl, piperidinocarbonylcinn amoyl, tetrahydropyridylcarbonylcinnamoyl, methylpiperazinylcarbonylcinnamoyl, etc.], lower alkenylcarbamoyl-ar(lower)alkenoyl [e.g. vinylcarbamoylcinnamoyl, allylcarbamoylcinnamoyl, methylpropenylcarbamoylcinnamoyl, etc.], lower alkynylcarbamoyl-ar(lower)alkenoyl [e.g. ethynylcarbamoylcinnamoyl, propynylcarbamoylcinnamoyl, etc.], amino(lower)alkylcarbamoyl-ar(lower)alkenoyl [e.g. aminomethylcarbamoylcinnamoyl, aminoethylcarbamoylcinnamoyl, etc.], lower alkylamino(lower)alkylcarbamoyl-ar(lower)alkenoyl [e.g. methylaminomethylcarbamoylcinnamoyl, methylaminoethylcarbamoylcinnamoyl, ethylaminoethylcarbamoylcinnamoyl, dimethylaminoethylcarbamoylcinnamoyl, etc.], lower alkylcarbamoyloxy(lower)alkylcarbamoyl-ar(lower)alkenoyl [e.g. methylcarbamoyloxymethylcarbamoylcinnamoyl, methylcarbamoyloxyethylcarbamoylcinnamoyl, ethylcarbamoyloxyethylcarbamoylcinnamoyl, dimethylcarbamoyloxyethylcarbamoylcinnamoyl, etc.], lower alkylcarbamoyl(lower)alkylcarbamoyl-ar(lower)alkenoyl [e.g. methylcarbamoylmethylcarbamoylcinnamoyl, methylcarbamoylethylcarbamoylcinnamoyl, ethylcarbamoylethylcarbamoylcinnamoyl, dimethylcarbamoylethylcarbamoylcinnamoyl, etc.], lower alkoxycarbonyl(lower)alkylcarbamoyl-ar (lower)alkenoyl [e.g. methoxycarbonylmethylcarbamoylcinnamoyl, methoxycarbonylethylcarbamoylcinnamoyl, ethoxycarbonylmethylcarbamoylcinnamoyl, ethoxycarbonylethylcarbamoylcinnamoyl, etc.], carboxy(lower)alkylcarbamoyl-ar(lower)alkenoyl [e.g. carboxymethylcarbamoylcinnamoyl, carboxyethylcarbamoylcinnamoyl, etc.], [lower alkylcarbamoyl-ar(lower)alkyl]carbamoyl-ar(lower)alkenoyl [e.g. (methylcarbamoyl-phenethyl)carbamoylcinnamoyl, (ethylcarbamoyl-phenethyl)carbamoylcinnamoyl, etc.], [lower alkoxycarbonyl-ar(lower)alkyl]carbamoyl-ar(lower)alkenoyl [e.g. (methoxycarbonyl-phenethyl)carbamoylcinnamoyl, (ethoxycarbonyl-phenethyl)carbamoylcinnamoyl, etc.], [carboxy-ar(lower)alkyl]

carbamoyl-ar(lower)alkenoyl [e.g. carboxy-phenethyl) carbamoylcinnamoyl, etc.], N-[lower alkylcarbamoyl (lower) alkyl]-N-(lower alkyl)carbamoyl-ar(lower)alkenoyl [e.g. N-(methylcarbamoylmethyl)-N-methylcarbamoylcinnamoyl, N-(methylcarbamoylethyl)-N-methylcarbamoylcinnamoyl, N-(ethylcarbamoylethyl)-N-methylcarbamoylcinnamoyl, N-(dimethylcarbamoylethyl)-N-methylcarbamoylcinnamoyl, etc.], N-[lower alkoxycarbonyl(lower)alkyl]-N-(lower alkyl)carbamoyl-ar(lower)alkenoyl [e.g. N-methoxycarbonylmethyl-N-methylcarbamoylcinnamoyl, N-methoxycarbonylethyl-N-methylcarbamoylcinnamoyl, N-ethoxycarbonylmethyl-N-methylcarbamoylcinnamoyl, N-ethoxycarbonylethyl-N-methylcarbamoylcinnamoyl, etc.], N-[carboxy(lower) alkyl]-N-(lower alkyl)carbamoyl-ar(lower)alkenoyl [e.g. N-carboxymethyl-N-methylcarbamoylcinnamoyl, N-carboxyethyl-N-methylcarbamoylcinnamoyl, etc.], arylcarbamoyl-ar(lower)alkenoyl [e.g. phenylcarbamoylcinnamoyl, naphthylcarbamoylcinnamoyl, etc.], etc., etc., ar(lower)alkynoyl [e.g. phenylpropioloyl, etc.], substituted or unsubstituted heterocyclic(lower)alkenoyl such as heterocyclic(lower)alkenoyl [e.g. morpholinylacryloyl, pyridylacryloyl, thienylacryloyl, etc.], amino-heterocyclic (lower)alkenoyl [e.g. aminopyridylacryloyl, etc.], lower alkylamino-heterocyclic(lower)alkenoyl [e.g. methylaminopyridylacryloyI, dimethylaminopyridylacryloyl, etc.], acylamino-heterocyclic(lower)alkenoyl, for example, lower alkanoylamino-heterocyclic(lower)alkenoyl [e.g. acetylaminopyridylacryloyl, propionylaminopyridylacryloyl, etc.], lower alkenoylamino-heterocyclic (lower)alkenoyl [e.g. acryloylaminopyridylacryloyl, crotonoylaminopyridylacryloyl, etc.], heterocyclic(lower) alkanoylamino-heterocyclic(lower)alkenoyl [e.g. pyridylacetylaminopyridylacryloyl, thienylacetylaminopyridylacryloyl, etc.], heterocycliccarbonylamino-heterocyclic(lower)alkenoyl [e.g. pyridylcarbonyl-aminopyridylacryloyl, furylcarbonylaminopyridylacryloyl, etc.], lower alkanoylamino(lower)alkanoylamino-heterocyclic(lower)alkenoyl [e.g. acetylaminoacetyl-aminopyridylacryloyl, acetylaminopropionylaminopyridylacryloyl, etc.], lower alkoxycarbonyl(lower) alkanoylamino-heterocyclic(lower)alkenoyl [e.g. ethoxycarbonylacetylaminopyridylacryloyl, ethoxycarbonylpropionylaminopyridylacryloyl, etc.], lower alkoxy(lower)alkanoylamino-heterocyclic(lower)alkenoyl [e.g. methoxyacetylaminopyridylacryloyl, methoxypropionyl-aminopyridylacryloyl, ethoxypropionylaminopyridylacryloyl, etc.], etc., lower alkylureido-heterocyclic lower)alkenoyl [e.g. methylureidopyridylacryloyl, etc.], acyl-heterocyclic(lower) alkenoyl, for example, carboxyheterocyclic(lower)alkenoyl [e.g. carboxypyridylacryloyl, etc.], lower alkoxycarbonyl-heterocyclic(lower)alkenoyl [e.g. ethoxycarbonyl-pyridylacryloyl, etc.], lower alkylcarbamoyl-heterocyclic (lower)alkenoyl [e.g. methylcarbamoylpyridylacryloyl, ethylcarbamoylpyridylacryloyl, direthylcarbamoyl-pyridylacryloyl, diethylcarbamoylpyridylacryloyl, isopropylcarbamoylpyridylacryloyl, N-ethyl-N-methylcarbamoylpyridylacryloyl, etc.], lower alkoxy(lower) alkylcarbamoyl-heterocyclic (lower) alkenoyl [e.g. methoxymethylcarbamoylpyridylacryloyl, methoxyethyl-carbam oylpyridylacryloyl, methoxypropylcarbamoyl-pyridylacryloyl, ethoxyethylcarbamoylpyridylacryloyl, bis (methoxyethyl)carbamoylpyridylacryloyl, etc.], hydroxy (lower) alkylcarbamoyl-heterocyclic(lower)alkenoyl [e.g. hydroxymethylcarbamoylpyridylacryloyl, hydroxyethylcarbamoylpyridylacryloyl, bis(hydroxyethyl) carbamoylpyridylacryloyl, etc.], heterocycliccarbamoyl-heterocyclic (lower)alkenoyl [e.g. pyridylcarbamoylpyridylacryloyl, morpholinylcarbamoyl-pyridylacryloyl, thienylcarbamoylpyridylacryloyl, pyrimidinylcarbamoylpyridylacryloyl, etc.], heterocyclic (lower)alkylcarbamoyl-heterocyclic(lower)alkenoyl [e.g. pyridylmethylcarbamoylpyridylacryloyl, furylmethylcarbamoylpyridylacryloyl, thienylmethylcarbamoylpyridylacryloyl, etc.], heterocycliccarbonyl-heterocyclic(lower)alkenoyl [e.g. morpholinocarbonylpyridylacryloyl, pyrrolidinylcarbonylpyridylacryloyl, piperidinocarbonylpyridylacryloyl, etc.], lower alkenylcarbamoyl-heterocyclic(lower)alkenoyl [e.g. vinylcarbamoylpyridylacryloyl, allylcarbamoylpyridylacryloyl, etc.], lower alkynylcarbamoyl-heterocyclic (lower)alkenoyl [e.g. ethynylcarbamoylpyridylacryloyl, propynylcarbamoylpyridylacryloyl, etc.], etc., etc., heterocycliccarbonyl which may be substituted with substituent [e.g. furoyl, thenoyl, nicotinoyl, isonicotinoyl, morpholinocarbonyl, piperidinocarbonyl, 4-methyl-1-piperazinylcarbonyl, 4-ethyl-1-piperazinylcarbonyl, dimethylaminopiperidinocarbonyl, 4-methylcarbamoyl-l-piperazinylcarbonyl, 1,2,3,6-tetrahydropyridylcarbonyl, pyrrolidinylcarbonyl, indolylcarbonyl, etc.], aryloxycarbonyl which may be substituted with nitro [e.g. phenyloxycarbonyl, nitrophenyloxycarbonyl, etc.], ar(lower)alkoxycarbonyl which may be substituted with nitro [e.g. benzyloxycarbonyl, nitrobenzyloxycarbonyl, etc.], substituted or unsubstituted carbamoyl or thiocarbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], carboxy(lower)alkylcarbamoyl [e.g. carboxymethylcarbamoyl, carboxyethylcarbamoyl, etc.], esterified carboxy(lower)alkylcarbamoyl, for example, lower alkoxycarbonyl(lower)alkylcarbamoyl [e.g. methoxycarbonylmethylcarbamoyl, ethoxycarbonylmethylcarbamoyl, ethoxycarbonylethylcarbamoyl, etc.], lower alkenylcarbamoyl [e.g. vinylcarbamoyl, allylcarbamoyl, etc.], cyclo(lower)alkylcarbamoyl [e.g. cyclopropylcarbamoyl, cyclobutylcarbamoyl, cyclopentylcarbamoyl, cyclohexylcarbamoyl, etc.], halo (lower)alkanoylcarbamoyl [e.g. trichloroacetylcarbamoyl, etc.], substituted or unsubstituted arylcarbamoyl, for example, arylcarbamoyl [e.g. phenylcarbamoyl, tolylcarbamoyl, xylylcarbamoyl, naphthylcarbamoyl, ethylphenylcarbamoyl, etc.], arylthiocarbamoyl [e.g. phenylthiocarbamoyl, etc.], lower alkoxy-arylcarbamoyl [e.g. methoxyphenylcarbamoyl, etc.], halo-arylcarbamoyl [e.g. fluorophenylcarbamoyl, chlorophenylcarbamoyl, etc.], halo(lower)alkyl-arylcarbamoyl [e.g. trifluoromethylphenylcarbamoyl, etc.], nitro-arylcarbamoyl [e.g. nitrophenylcarbamoyl, etc.], cyano-arylcarbamoyl [e.g. cyanophenylcarbamoyl, etc.], hydroxy(lower)alkyl-arylcarbamoyl [e.g. hydroxymethylphenylcarbamoyl, hydroxyethylphenylcarbamoyl, etc.], amino-arylcarbamoyl [e.g. aminophenylcarbamoyl, etc.], lower alkylamino-arylcarbamoyl [e.g. methylaminophenylcarbamoyl, ethylaminophenylcarbamoyl, dimethylaminophenylcarbamoyl, etc.], lower alkanoylami-noarylcarbamoyl [e.g. acetylaminophenylcarbamoyl, propionylaminophenylcarbamoyl, etc.], N-(lower alkanoyl)-N-(lower alkyl)amino-arylcarbamoyl [e.g. N-acetyl-N-methylaminophenylcarbamoyl, N-propionyl-N-methylaminophenylcarbamoyl, etc.], lower alkoxy(lower)

alkanoylamino-arylcarbamoyl [e.g. methoxyacetylaminophenylcarbamoyl, methoxypropionylaminophenylcarbamoyl, etc.], lower alkoxycarbonyl(lower)alkanoylamino-arylcarbamoyl [e.g. ethoxycarbonylacetylaminophenylcarbamoyl, methoxycarbonylpropionylaminophenylcarbamoyl, etc.], carboxyamino-arylcarbamoyl [e.g. carboxyaminophenylcarbamoyl, etc.], lower alkoxycarbonylamino-arylcarbamoyl [e.g. ethoxycarbonylaminophenylcarbamoyl, etc.], aroylamino-arylcarbamoyl [e.g. benzoylaminophenylcarbamoyl, etc.], heterocycliccarbonylamino-arylcarbamoyl [e.g. pyridylcarbonylaminophenylcarbamoyl, furylcarbonylaminophenylcarbamoyl, morpholinocarbonylaminophenylcarbamoyl, etc.], heterocyclic(lower)alkanoylamino-arylcarbamoyl [e.g. pyridylacetylaminophenylcarbamoyl, thienylacetylaminophenylcarbamoyl, etc.], ureido-arylcarbamoyl [e.g. ureidophenylcarbamoyl, etc.], lower alkylureido-arylcarbamoyl [e.g. methylureidophenylcarbamoyl, ethylureidophenylcarbamoyl, etc.], hydroxyimino(lower)alkyl-arylcarbamoyl [e.g. hydroxyiminoethylphenylcarbamoyl, etc.], lower alkoxyimino(lower)alkyl-arylcarbamoyl [e.g. methoxyiminoethylphenylcarbamoyl, etc.], lower alkylhydrazono(lower)alkyl-arylcarbamoyl [e.g. methylhydrazonoethylphenylcarbamoyl, dimethylhydrazonoethylphenylcarbamoyl, etc.], optionally substituted heterocyclic-arylcarbamoyl [e.g. oxopyrrolidinylphenylcarbamoyl, oxopiperidinophenylcarbamoyl, dioxopyrrolidinylphenylcarbamoyl, oxooxazolidinylphenylcarbamoyl, pyrrolylphenylcarbamoyl, etc.], acyl-arylcarbamoyl, for example, carboxy-arylcarbamoyl [e.g. carboxyphenylcarbamoyl, etc.], lower alkoxycarbonyl-arylcarbamoyl [e.g. ethoxycarbonylphenylcarbamoyl, etc.], heterocycliccarbonyl-arylcarbamoyl [e.g. morpholinocarbonylphenylcarbamoyl, pyrrolidinylcarbonylphenylcarbamoyl, piperidinocarbonylphenylcarbamoyl, 1,2,3,6-tetrahydropyridylcarbonylphenylcarbamoyl, piperazinylcarbonylphenylcarbamoyl, thiomorpholinocarbonylphenylcarbamoyl, etc.], heterocycliccarbonyl-arylcarbamoyl substituted with lower alkyl [e.g. methylpiperazinylcarbonylphenylcarbamoyl, ethylpiperazinylcarbonylphenylcarbamoyl, etc.], heterocycliccarbonyl-arylcarbamoyl substituted with aryl [e.g. phenylpiperazinylcarbonylphenylcarbamoyl, etc.], heterocycliccarbonyl-arylcarbamoyl substituted with a heterocyclic group [e.g. pyridylpiperazinylcarbonylphenylcarbamoyl, etc.], heterocycliccarbonyl-arylcarbamoyl substituted with lower alkanoyl [e.g. acetylpiperazinylcarbonylphenylcarbamoyl, etc.], heterocycliccarbonylarylcarbamoyl substituted with lower alkoxycarbonyl [e.g. ethoxycarbonylpiperazinylcarbonylphenylcarbamoyl, etc.], heterocycliccarbonyl-arylcarbamoyl substituted with lower alkylamino [e.g. methylaminopiperazinylcarbonylphenylcarbamoyl, dimethylaminopiperidinocarbonylphenylcarbamoyl, etc.], heterocycliccarbonyl-arylcarbamoyl substituted with lower alkylcarbamoyl [e.g. methylcarbamoylpiperazinylcarbonylphenylcarbamoyl, etc.], carbamoyl-arylcarbamoyl [e.g. carbamoylphenylcarbamoyl, etc.], lower alkylcarbamoyl-arylcarbamoyl [e.g. methylcarbamoylphenylcarbamoyl, ethylcarbamoylphenylcarbamoyl, propylcarbamoylphenylcarbamoyl, dimethylcarbamoyl-phenylcarbamoyl, diethylcarbamoyl- phenylcarbamoyl, N-ethyl-N-methylcarbamoylphenylcarbamoyl, N-isopropyl-N-methylcarbamoylphenylcarbamoyl, etc.], hydroxy(lower)alkylcarbamoyl-arylcarbamoyl [e.g. hydroxymethylcarbamoylphenylcarbamoyl, hydroxyethylcarbamoylphenylcarbamoyl, bis(hydroxyethyl)carbamoylphenylcarbamoyl, etc.], N-[hydroxy(lower)alkyl]-N-(lower alkyl)carbamoyl-arylcarbamoyl [e.g. N-(hydroxyethyl)-N-methylcarbamoylphenylcarbamoyl, etc.], lower alkoxy(lower)alkylcarbamoyl-arylcarbamoyl [e.g. methoxymethylcarbamoylphenylcarbamoyl, methoxyethylcarbamoylphenylcarbamoyl, ethoxyethylcarbamoylphenylcarbamoyl, bis(methoxyethyl)carbamoylphenylcarbamoyl, bis(ethoxyethyl)carbamoylphenylcarbamoyl, etc.], N-[lower alkoxy(lower)alkyl]-N-(lower alkyl)carbamoyl-arylcarbamoyl [e.g. N-(methoxyethyl)-N-methylcarbamoylphenylcarbamoyl, N-(methoxypropyl)-N-methylcarbamoylphenylcarbamoyl, etc.], lower alkylamino(lower)alkylcarbamoyl-arylcarbamoyl [e.g. methylaminoethylcarbamoylphenylcarbamoyl, dimethylaminoethylcarbamoylphenylcarbamoyl, etc.], N-[lower alkylamino(lower)alkyl]-N-(lower alkyl)carbamoylarylcarbamoyl [e.g. N-(dimethylaminoethyl)-N-methylcarbamoylphenylcarbamoyl, N-(dimethylaminopropyl)-N-methylcarbamoylphenylcarbamoyl, etc.], heterocycliccarbamoyl-arylcarbamoyl [e.g. morpholinylcarbamoylphenylcarbamoyl, thienylcarbamoylphenylcarbamoyl, pyridylcarbamoylphenylcarbamoyl, pyrimidinylcarbamoylphenylcarbamoyl, etc.], N-(heterocyclic)-N-(lower alkyl)carbamoyl-arylcarbamoyl [e.g. N-pyridyl-N-methylcarbamoylphenylcarbamoyl, etc.], heterocyclic(lower)alkylcarbamoyl-arylcarbamoyl [e.g. pyridylmethylcarbamoylphenylcarbamoyl, pyridylethylcarbamoylphenylcarbamoyl, thienylmethylcarbamoylphenylcarbamoyl, etc.], N-[heterocyclic(lower)alkyl]-N-(lower alkyl)carbamoylarylcarbamoyl [e.g. N-pyridylmethyl-N-methylcarbamoylphenylcarbamoyl, etc.], N-[heterocyclic(lower)alkyl]-N-[lower alkoxy(lower)alkyl]carbamoylarylcarbamoyl [e.g. N-pyridylmethyl-N-methoxyethylcarbamoylphenylcarbamoyl, etc.] arylcarbamoyl-arylcarbamoyl [e.g. phenylcarbamoylphenylcarbamoyl, etc.], lower alkylamino-arylcarbamoyl-arylcarbamoyl [e.g. dimethylaminophenylcarbamoylphenylcarbamoyl, etc.], lower alkanoyl-arylcarbamoyl [e.g. acetylphenylcarbamoyl, propionylphenylcarbamoyl, etc.], etc., etc., ar(lower)alkylcarbamoyl [e.g. benzylcarbamoyl, phenethylcarbamoyl, etc.], heterocycliccarbamoyl [e.g. furylcarbamoyl, thienylcarbamoyl, pyridylcarbamoyl, quinolylcarbamoyl, isoquinolylcarbamoyl, pyrimidinylcarbamoyl, pyrazolylcarbamoyl, etc.], heterocyclic(lower)alkylcarbamoyl [e.g. pyridylmethylcarbamoyl, pyridylethylcarbamoyl, furylmethylcarbamoyl, thienylmethylcarbamoyl, etc.], arylaminocarbamoyl [e.g. phenylaminocarbamoyl, etc.], aroylcarbamoyl [e.g. benzoylcarbamoyl, etc.], etc., lower alkylsulfonyl (e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], ar(lower)alkylsulf onyl [e.g. benzylsulfonyl, phenethylsulfonyl, etc.], ar(lower)alkenrylsulfonyl [e.g. styrylsulfonyl, cinnamoylsulfonyl, etc.], phthaloyl, substituted or unsubstituted amino acid residue mentioned below, or the like.

Suitable "amino acid residue" may include natural or artificial ones, and such amino acid may be glycine, sarcosine, alanine, β-alanine, valine, norvaline, leucine, isoleucine, norleucine, serine, threonine, cysteine, methionine, phenylalanine, phenylglycine, tryptophan, tyrosine, proline, hydroxyproline, glutamic acid, aspartic acid, glutamine, asparagine, lysine, arginine, histidine, ornithine, or the like, in which more preferable one is glycine, sarcosine, alanine, β-alanine and proline, and the most preferable one is glycine. And said amino acid residue may be substituted with suitable substituent(s) such as the above-mentioned lower alkyl, the above-mentioned aryl, the above-mentioned acyl, ar(lower)alkyl [e.g. benzyl, phenethyl, trityl, etc.], cycloalkyl [e.g. cyclopropyl, cyclobutyl, cyclopentyl, cyclohexyl, cycloheptyl, cyclooctyl, adamantyl, etc.], a heterocyclic group mentioned below, heterocyclic(lower)alkyl [e.g. pyridylmethyl, pyridylethyl, imidazolylmethyl, furylmethyl, thienylmethyl, morpholinomethyl, piperidinomethyl, etc.], substituted or unsubstituted amidino [e.g. amidino, methylamidino, N-ethyl-N'-cyanoamidino, etc.], or the like.

Preferred example of said amino acid residue substituted with suitable substituent(s) may be amino acid residue substituted with lower alkyl [e.g. ethylglycyl, isopropylglycyl, dimethylglycyl, diethylglycyl, ethylsarcosyl, isopropylsarcosyl, methylalanyl, methyl-β-alanyl, dimetnyl-β-alanyl, etc.], amino acid residue substituted with aryl [e.g. N-phenylglycyl, N-tolylglycyl, N-phenylalanyl, N-phenylsarcosyl, etc.], amino acid residue substituted with ar(lower)alkyl [e.g. benzylglycyl, tritylglycyl, phenethylglycyl, benzylsarcosyl, benzylalanyl, etc.], amino acid residue substituted with a heterocyclic group [e.g. morpholinoglycyl, piperidinoglycyl, pyridylglycyl, etc.], amino acid residue substituted with heterocyclic(lower)alkyl [e.g. pyridylmethylglycyl, imidazolylmethylglycyl, furylmethylglycyl, thienylmethylglycyl, etc.], amino acid residue substituted with cycloalkyl [e.g. cyclopropylglycyl, cyclobutylglycyl, cyclopentylglycyl, cyclohexylglycyl, cycloheptylglycyl, cyclooctylglycyl, adamantylglycyl, cyclohexylsarcosyl, cycloheptylsarcosyl, cyclohexylalanyl, etc.], amino acid residue substituted with optionally substituted amidino [e.g. amidinoglycyl, methylamidinoglycyl, N-ethyl-N'-cyanoamidinoglycyl, etc.], amino acid residue substituted with acyl such as amino acid residue substituted with alkanoyl [e.g. formylglycyl, acetylglycyl, acetylsarcosyl, acetylalanyl, acetyl-β-alanyl, propionylglycyl, butyrylglycyl, isobutyrylglycyl, valerylglycyl, isovalerylglycyl, pivaloylglycyl, hexanoylglycyl, heptanoylglycyl, etc.], amino acid residue substituted with halo(lower)alkanoyl [e.g. trifluoroacetylglycyl, trifluoroacetylsarcosyl, trifluoroacetylalanyl, bromoacetylglycyl, heptafluorobutyrylglycyl, etc.], amino acid residue substituted with hydroxy(lower)alkanoyl [e.g. glycoloylglycyl, glycoloylsarcosyl, lactoylglycyl, lactoylalanyl, etc.], amino acid residue substituted with lower alkylsulfonyloxy(lower)alkanoyl [e.g. mesyloxyacetylglycyl, ethylsulfonyloxyacetylglycyl, mesyloxyacetylsarcosyl, etc.], amino acid residue substituted with lower alkoxy(lower)alkanoyl [e.g. methoxyacetylglycyl, ethoxyacetylglycyl, methoxyacetylsarcosyl, methoxypropionylalanyl, etc.], amino acid residue substituted with aryloxy(lower)alkanoyl [e.g. phenyloxyacetylglycyl, phenyloxypropionylglycyl, phenyloxyacetylsarcosyl, etc.], amino acid residue substituted with lower alkylthio(lower)alkanoyl [e.g. methylthioacetylglycyl, methylthiopropionylglycyl, etc.], amino acid residue substituted with lower alkylcarbamoyl (lower)alkanoyl [e.g. methylcarbamoylpropionylglycyl, methylcarbamoylpropionylalanyl, etc.], amino acid residue substituted with lower alkanoyloxy(lower)alkanoyl [e.g. acetyloxyacetylglycyl, acetyloxyacetylsarcosyl, propionyloxyacetylglycyl, acetyloxypropionylalanyl, etc.], amino acid residue substituted with carboxy(lower)alkanoyl [e.g. carboxyacetylglycyl, carboxypropionylglycyl, carboxypropionylsarcosyl,. carboxyacetylalanyl, etc.], amino acid residue substituted with lower alkoxycarbonyl (lower)alkanoyl [e.g. methoxycarbonylacetylglycyl, ethoxycarbonylpropionylglycyl, methoxycarbonylacetylsarcosyl, etc.], amino acid residue substituted with ar(lower)alkanoyl [e.g. phenylacetylglycyl, phenylacetylsarcosyl, phenylpropionylalanyl, phenylpropionylglycyl, naphthylacetylglycyl, phenylbutyrylglycyl, etc.], amino acid residue substituted with optionally substituted heterocyclic(lower)alkanoyl [e.g. morpholinoacetylglycyl, thiomorpholinoacetylglycyl, its oxide or dioxide, pyridylacetylglycyl, morpholinopropionylalanyl, imidazolylacetylglycyl, piperidinoacetylglycyl, pyrrolidinylacetylglycyl, hexamethyleneiminoacetylglycyl, methylpiperazinylacetylglycyl, pyridylpiperazinylacetylglycyl, etc.], amino acid residue substituted with lower alkenoyl [e.g. acryloylglycyl, crotonoylglycyl, 3-pentendylglycyl, 3-butenoylglycyl, 4-pentenoylglycyl, 3-butenoylsarcosyl, etc.], amino acid residue substituted with ar(lower)alkenoyl [e.g. cinnamoylglycyl, allocinnamoylglycyl, α-methylcinnamoylglycyl, 4-methylcinnamoylglycyl, cinnamoylsarcosyl, etc.], amino acid residue substituted with lower alkoxy-ar(lower)alkenoyl [e.g. methoxycinnamoylglycyl, ethoxycinnamoylglycyl, dimethoxycinnamoylglycyl, etc.], amino acid residue substituted with lower alkylenedioxy-ar(lower)alkenoyl [e.g. methylenedioxycinnamoylglycyl, ethylenedioxycinnamoylglycyl, etc.], amino acid residue substituted with nitro-ar(lower)alkenoyl [e.g. nitrocinnamoylglycyl, etc.], amino acid residue substituted with cyano-ar(lower)alkenoyl [e.g. cyanocinnamoylglycyl, etc.], amino acid residue substituted with halo-ar(lower)alkenoyl [e.g. chlorocinnamoylglycyl, fluorocinnamoylglycyl, etc.], amino acid residue substituted with hydroxy-ar(lower)alkenoyl [e.g. hydroxycinnamoylglycyl, etc.], amino acid residue substituted with hydroxy(lower)alkoxy-ar(lower)alkenoyl [e.g. hydroxymethoxycinnamoylglycyl, hydroxyethoxycinnamoylglycyl, etc.], amino acid residue substituted with amino(lower)alkoxy-ar(lower)alkenoyl [e.g. aminoethoxycinnamoylglycyl, etc.], amino acid residue substituted with lower alkylamino(lower)alkoxy-ar (lower)alkenoyl [e.g. methylaminomethoxycinnamoylglycyl, dimethylaminoethoxycinnamoylglycyl, etc.], amino acid residue substituted with heterocyclic (lower)alkoxy-ar(lower)alkenoyl [e.g. pyridylmethoxycinnamoylglycyl, etc.], amino acid residue substituted with optionally substituted heterocyclic-ar(lower)alkenoyl [e.g. morpholinocinnamoylglycyl, methylpiperazinyl-cinnamoylglycyl, pyrrolidinylcinnamoylglycyl, oxopyrrolidinylcinnamoylglycyl, oxopiperidinocinnamoylglycyl, dioxopyrrolidinylcinnamoylglycyl, oxooxazolidinylcinnamoylglycyl, pyrrolylcinnamoylglycyl, tetrazolylcinnamoylglycyl, etc.], amino acid residue substituted with amino-ar(lower)alkenoyl [e.g. aminocinnamoylglycyl, etc.], amino acid residue substituted with lower alkylamino-ar(lower)alkenoyl [e.g. methylaminocinnamoylglycyl, dimethylaminocinnamoylglycyl, etc.], amino acid residue substituted with acylamino-ar(lower)alkenoyl, for example, amino acid residue substituted with lower alkanoylamino-ar(lower) alkenoyl [e.g. acetylaminocinnamoylglycyl, propionylaminocinnamoylglycyl, isobutyrylaminocinnamoylglycyl, etc.], amino acid residue substituted with cycloalkyl(lower)alkanoylamino-ar(lower)alkenoyl [e.g. cyclopentylacetylaminocinnamoylglycyl, cyclohexylacetylaminocinnamoylglycyl, adamantylacetylaminocinnamoylglycyl, etc.], amino acid residue substituted with cycloalkylcarbonylamino-ar(lower)alkenoyl [e.g. cyclopropylcarbonylaminocirnamoylglycyl, cyclopentylcarbonylaminocinnamoylglycyl, cyclohexylcarbonylaminocinnamoylglycyl, adamantylcarbonylaminocinnamoylglycyl, etc.], amino acid residue substituted with lower alkenoylamino-ar(lower)alkenoyl [e.g. acryloylaminocinnamoylglycyl, crotonoylaminocinnamoylglycyl, etc.], amino acid residue substituted with lower alkoxycarbonylamino-ar(lower)alkenoyl [e.g. methoxycarbonylaminocinnamoylglycyl, ethoxycarbonylaminocinnamoylglycyl, etc.], amino acid residue substituted with hydroxy(lower)alkanoylamino-ar(lower)alkenoyl [e.g. hydroxyacetylaminocinnamoylglycyl, hydroxypropionylaminocinnamoylglycyl, etc.], amino acid residue substituted with lower alkoxy(lower)alkanoylamino-ar(lower)alkenoyl [e.g. methoxyacetylaminocinnamoylglycyl, methoxypropionylaminocinnamoylglycyl, etc.], amino acid residue substituted with halo(lower)alkanoylamino-ar(lower)alkenoyl [e.g. chloroacetylaminocinnamoylglycyl, trifluoroacetylaminocinnamoylglycyl, bromobutyrylaminocinnamoylglycyl, etc.], amino acid residue substituted with amino(lower)alkanoylamino-ar(lower)alkenoyl [e.g. aminoacetylaminocinnamoylglycyl, aminopropionylaminocinnamoylglycyl, etc.], amino acid residue substituted with lower alkylamino(lower)alkanoylamino-ar(lower)alkenoyl [e.g. methylaminoacetylaminocinnamoylglycyl, dimethylaminoacetylaminocinnamoylglycyl, etc.], amino acid residue substituted with lower alkanoylamino(lower)alkanoylamino-ar(lower)alkenoyl [e.g. acetylaminoacetylaminocinnamoylglycyl, acetylaminopropionylaminocinnamoylglycyl, etc.], amino acid residue substituted with carboxy(lower)alkanoylamino-ar(lower)alkenoyl [e.g. carboxyacetylaminocinnamoylglycyl, carboxypropionylaminocinnamoylglycyl, etc.], amino acid residue substituted with lower alkoxycarbonyl(lower)alkanoylamino-ar(lower)alkenoyl [e.g. ethoxycarbonylacetylaminocinnamoylglycyl, ethoxycarbonylpropionylaminocinnamoylglycyl, etc.], amino acid residue substituted with lower alkoxycarbonyl(lower)alkenoylamino-ar(lower)alkenoyl [e.g. ethoxycarbonylacryloylaminocinnamoylglycyl, etc.], amino acid residue substituted with halo(lower)alkoxycarbonylamino-ar(lower)alkenoyl [e.g. chloroethoxycarbonylaminocinnamoylglycyl, etc.], amino acid residue substituted with optionally substituted heterocyclic(lower)alkanoylamino-ar(lower)alkenoyl [e.g. pyridylacetylaminocinnamoylglycyl, thienylacetylaminocinnamoylglycyl, methylpyrrolylacetylaminocinnamoylglycyl, etc.], amino acid residue substituted with aroylamino-ar(lower)alkenoyl [e.g. benzoylaminocinnamoylglycyl, etc.], amino acid residue substituted with optionally substituted heterocycliccarbonylamino-ar(lower)alkenoyl [e.g. pyridylcarbonylaminocinnamoylglycyl, morpholinocarbonylaminocinnamoylglycyl, furylcarbonylaminocinnamoylglycyl, thienylcarbonylaminocinnamoylglycyl, oxazolylcarbonylaminocinnamoylglycyl, methyloxazolylcarbonylaminocinnamoylglycyl, dimethylisoxazolylcarbonylaminocinnamoylglycyl, imidazolylcarbonylaminocinnamoylglycyl, methylimidazolylcarbonylaminocinnamoylglycyl, piperidylcarbonylaminocinnamoylglycyl, ethylpiperidylcarbonylaminocinnamoylglycyl, acetylpiperidylcarbonylaminocinnamoylglycyl, pyrrolidinylcarbonylaminocinnamoylglycyl, acetylpyrrolidinylcarbonylaminocinnamoylglycyl, tert-butoxycarbonylpyrrolidinylcarbonylaminocinnamoylglycyl, etc.], amino acid residue substituted with lower alkylsulfonylamino-ar(lower)alkenoyl [e.g. mesylaminocinnamoylglycyl, ethylsulfonylaminocinnamoylglycyl, etc.], etc., amino acid residue substituted with N-(lower alkanoyl)-N-(lower alkyl)amino-ar(lower)alkenoyl [e.g. N-acetyl-N-methylaminocinnamoylglycyl, N-acetyl-N-ethylaminocinnamoylglycyl, N-propionyl-N-methylaminocinnamoylglycyl, etc.], amino acid resieue substituted with N-[lower alkoxy(lower)alkanoyl]-N-(lower alkyl)amino-ar(lower)alkenoyl [e.g. N-methoxyacetyl-N-methylaminocinnamoylglycyl, N-methoxypropionyl-N-methylaminocinnamoylglycyl, etc.], amino acid residue substituted with N-(lower alkanoyl)-N-[heterocyclic(lower)alkyl]amino-ar(lower)alkenoyl [e.g. N-acetyl-N-pyridylmethylaminocinnamoylglycyl, etc.], amino acid residue substituted with N-(lower alkanoyl)-N-[lower alkoxy(lower)alkyl]amino-ar(lower)alkenoyl [e.g. N-acetyl-N-methoxyethylaminocinnamoylglycyl, N-acetyl-N-methoxymethylaminocinnamoylglycyl, N-propionyl-N-methoxyethylaminocinnamoylglycyl, etc.], amino acid residue substituted with N-(lower alkanoyl)-N-[lower alkoxycarbonyl(lower)alkyl]amino-ar(lower)alkenoyl [e.g. N-acetyl-N-tert-butoxycarbonylmethylaminocinnamoylglycyl, N-acetyl-N-tert-butoxycarbonylethylaminocinnamoylglycyl, N-propionyl-N-tert-butoxycarbonylmethylaminocinnamoylglycyl, etc.], amino acid residue substituted with N-(lower alkanoyl)-N-[carboxy(lower)alkyl]amino-ar(lower)alkenoyl [e.g. N-acetyl-N-carboxymethylaminocinnamoylglycyl, N-acetyl-N-carboxyethylaminocinnamoylglycyl, N-propionyl-N-carboxymethylaminocinnamoylglycyl, etc.], amino acid residue substituted with N-[lower alkoxy(lower)alkanoyl]-N-[heterocyclic(lower)alkyl]amino-ar(lower)alkenoyl [e.g. N-methoxyacetyl-N-pyridylmethylaminocinnamoylglycyl, N-methoxypropionyl-N-pyridylmethylaminocinnamoylglycyl, etc.], amino acid residue substituted with N-[heterocicccarbonyl]-N-[lower alkoxy(lower)alkyl]amino-ar(lower)alkenoyl [e.g. N-pyridylcarbonyl-N-methoxyethylaminocinnamoylglycyl, N-pyridylcarbonyl-N-methoxyethylaminocinnamoylglycyl, N-thienylcarbonyl-N-methoxyethylaminocinnamoylglycyl, etc.], amino acid residue substituted with ureido-ar(lower)alkenoyl [e.g. ureidocinnamoylglycyl, etc.], amino acid residue substituted with lower alkylureido-ar(lower)alkenoyl [e.g. methylureidocinnamoylglycyl, ethylureidocinnamoylglycyl, dimethylureidocinnamoylglycyl, etc.], amino acid residue substituted with heterocyclicureido-ar(lower)alkenoyl [e.g. pyridylureidocinnamoylglycyl, pyrimidinylureidocinnamoylglycyl, thienylureidocinnamoylglycyl, etc.], amino acid residue substituted with acyl-ar(lower)alkenoyl, for example, amino acid residue substituted with lower alkanoyl-ar(lower)alkenoyl [e.g. formylcinnamoylglycyl, acetylcinnamoylglycyl, propionylcinnamoylglycyl, etc.], amino acid residue substituted with carboxy-ar(lower)alkenoyl [e.g. carboxycinnamoylglycyl, etc.], amino acid residue substituted with lower alkoxycarbonyl-ar(lower)alkenoyl [e.g. methoxycarbonylcinnamoylglycyl, ethoxycarbonylcinnamoylglycyl, etc.], amino acid residue substituted with carbamoyl-ar(lower)alkenoyl [e.g. carbamoylcinnamoylglycyl, etc.], amino acid residue substituted with lower alkylcarbamoyl-ar(lower)alkenoyl [e.g. methylcarbamoylcinnamoylglycyl, ethylcarbamoylcinnamoylglycyl, dimethylcarbamoylci.amoylglycyl, propylcarbamoylcinnamoylglycyl, isopropylcarbamoylcinnamoylglycyl, diethylcarbamoylcinnamoylglycyl, N-methyl-N-ethylcarbamoylcinnamoylglycyl, etc.], amino acid residue substituted with hydroxy(lower) alkylcarbamoyl-ar(lower) alkenoyl [e.g. hydroxyethylcarbamoylcinnamoylglycyl, bis(hydroxyethyl) carbamoylcinnamoylglycyl, etc.], amino acid residue substituted with N-[hydroxy(lower)alkyl]-N-(lower alkyl) carbamoyl-ar(lower)alkenoyl [e.g. N-hydroxyethyl-N-methylcarbamoylcinnamoylglycyl, etc.], amino acid residue substituted with lower alkoxy(lower)alkylcarbamoyl-ar (lower)alkenoyl [e.g. methoxymethylcarbamoyl cinnamoylglycyl, methoxyethylcarbamoylcinnamoylglycyl, bis(methoxyethyl)carbamoylcinnamoylglycyl, ethoxyethylcarbamoylcinnamoylglycyl, methoxypropylcarbamoylcinnamoylglycyl, bis (ethoxyethyl)carbamoylcinnamoylglycyl, etc.], amino acid residue substituted with N-[lower alkoxy(lower)alkyl]-N-(lower alkyl)carbamoyl-ar(lower)alkenoyl [e.g. N-methoxyethyl-N-methylcarbamoylcinnamoylglycyl, N-ethoxyethyl-N-methylcarbamoylcinnamoylglycyl, etc.], amino acid residue substituted with heterocyclic(lower) alkylcarbamoyl-ar(lower)alkenoyl [e.g. pyridylmethylcarbamoylcinnamoylglycyl, furylmethylcarbamoylcinnamoylglycyl, thienylmethylcarbamoylcinnamoylglycyl, etc.], amino acid residue substituted with N-[heterocyclic(lower)alkyl]-N-(lower alkyl)carbamoyl-ar(lower)alkenoyl [e.g. N-pyridylmethyl-N-methylcarbamoylcinnamoylglycyl, etc.], amino acid residue substituted with heterocycliccarbamoyl-ar lower)alkenoyl [e.g. morpholinylcarbamoylcinnamoylglycyl, thienylcarbamoylcizmamoylglycyl, pyridylcarbamoylcinnamoylglycyl, pyrimidinylcarbamoylcinnamoylglycyl, tetrazolylcarbamoylcinnamoylglycyl, etc.], amino acid residue substituted with optionally substituted heterocycliccarbonyl-ar(lower)alkenoyl [e.g. morpholinocarbonylcinnamoylglycyl, pyrrolidinylcarbonylcinnamoylglycyl, piperidinocarbonylcinnamoylglycyl, tetrahydropyridyl-carbonylcinnamoylglycyl, methylpiperazinyl-carbonylcinnamoylglycyl, etc.], amino acid residue substituted with lower alkenylcarbamoyl-ar(lower)alkenoyl [e.g. vinylcarbamoylcinnamoylglycyl, allylcarbamoylcinnamoylglycyl, methylpropenylcarbamoylcinnamoylglycyl, etc.], amino acid residue substituted with lower alkynylcarbamoyl-ar(lower)alkenoyl [e.g. ethynylcarbamoylcinnamoylglycyl, propynylcarbamoylcinnamoylglycyl, etc.], amino acid residue substituted with amino(lower)alkylcarbamoyl-ar(lower) alkenoyl [e.g. aminomethylcarbamoylcinnamoylglycyl, aminoethylcarbamoylcinnamoylglycyl, etc.], amino acid residue substituted with lower alkylamino(lower) alkylcarbamoyl-ar(lower)alkenoyl [e.g. methylaminomethylcarbamoylcinnamoylglycyl, methylaminoethylcarbamoylcinnamoylglycyl, ethylaminoethylcarbamoylcinnamoylglycyl, dimethylaminoethylcarbamoylcinnamoylglycyl, etc.], amino acid residue substituted with lower alkylcarbamoyloxy(lower)alkylcarbamoyl-ar(lower) alkenoyl [e.g. methylcarbamoyloxymethylcarbamoylcinnamoylglycyl, methylcarbamoyloxyethylcarbamoylcinnamoylglycyl, ethylcarbamoyloxyethylcarbamoylcinnamoylglycyl, dirmethylcarbamoyloxyethylcarbamoylcinnamoylglycyl, etc.], amino acid residue substituted with lower alkylcarbamoyl(lower) alkylcarbamoyl-ar(lower)alkenoyl [e.g. methylcarbamoylmethylcarbamoylcinnamoylglycyl, methylcarbamoylethylcarbamoylcinnamoylglycyl, ethylcarbamoylethylcarbamoylcinnamoylglycyl, dimethylcarbamoylethylcarbamoylcinnamoylglycyl, etc.], amino acid residue substituted with lower alkoxycarbonyl (lower)alkylcarbamoyl-ar(lower)alkenoyl [e.g. methoxycarbonylmethylcarbamoylcinnamoylglycyl, methoxycarbonylethylcarbamoylcinnamoylglycyl, ethoxycarbonylmethylcarbamoylcinnamoylglycyl, ethoxycarbonylethylcarbamoylcinnamoylglycyl, etc.], amino acid residue substituted with carboxy(lower) alkylcarbamoyl-ar(lower)alkenoyl [e.g. carboxymethylcarbamoylcinnamoylglycyl, carboxyethylcarbamoylcinnamoylglycyl, etc.], amino acid residue substituted with [lower alkylcarbamoyl-ar(lower) alkyl)carbamoyl-ar(lower)alkenoyl [e.g. (methylcarbamoyl-phenethyl)carbamoylcinnamoylglycyl, (ethylcarbamoyl-phenethyl)carbamoylcinnamoylglycyl, etc.], amino acid residue substituted with [lower alkoxycarbonyl-ar(lower) alkyllcarbamoyl-ar(lower)alkenoyl [e.g. (methoxycarbonyl-phenethyl)carbamoylcinnamoylglycyl, (ethoxycarbonyl-phenethyl)carbamoylcinnamoylglycyl, etc.], amino acid residue substituted with [carboxy-ar(lower)alkyl] carbamoyl-ar(lower)alkenoyl [e.g. (carboxy-phenethyl) carbamoylcinnamoylglycyl, etc.], amino acid residue substituted with N-[lower alkylcarbamoyl(lower)alkyl]-N-(lower alkyl)carbamoyl-ar(lower)alkenoyl [e.g. N-(methyl-carbamoylmethyl)-N-methylcarbamoylcinnamoylglycyl, N-(methylcarbamoylethyl)-N-methylcarbamoyl-cinnamoylglycyl, N-(ethylcarbamoylethyl)-N-methylcarbamoylcinnamoylglycyl, N-(dimethyl-carbamoylethyl)-N-methylcarbamoylcinnamoylglycyl, etc.], amino acid residue substituted with N-[lower alkoxycarbonyl(lower)alkyl]-N-(lower alkyl)carbamoyl-ar (lower)alkenoyl [e.g. N-methoxycarbonylmethyl-N-methylcarbamoylcinnamoylglycyl, N-methoxy-carbonylethyl-N-methylcarbamoylcinnamoylglycyl, N-ethoxycarbonylmethyl-N-methylcarbamoyl-cinnamoylglycyl, N-ethoxycarbonylethyl-N-methylcarbamoylcinnamoylglycyl, etc.], amino acid residue substituted with N-[carboxy(lower)alkyl]-N-(lower alkyl) carbamoyl-ar(lower)alkenoyl [e.g. N-carboxymethyl-N-methylcarbamoylcinnamoylglycyl, N-carboxyethyl-N-methylcarbamoylcinnamoylglycyl, etc.], amino acid residue substituted with arylcarbamoyl-ar(lower)alkenoyl [e.g. phenylcarbamoylcinnamoylglycyl, naphthylcarbamoylcinnamoylglycyl, etc.], etc., amino acid residue substituted with ar(lower)alkynoyl [e.g. phenylpropioloylglycyl, etc.], amino acid residue substituted with heterocyclic(lower) alkenoyl [e.g. morpholinylacryloylglycyl, pyridylacryloylglycyl, thienylacryloylglycyl, etc.], amino acid residue substituted with amino-heterocyclic(lower) alkenoyl [e.g. aminopyridylacryloylglycyl, etc.], amino acid residue substituted with lower alkylamino-heterocyclic (lower)alkenoyl [e.g. methylaminopyridylacryloylglycyl, dimethylaminopyridylacryloylglycyl, etc.], amino acid residue substituted with acylamino-heterocyclic(lower) alkenoyl, for example, amino acid residue substituted with lower alkanoylamino-heterocyclic(lower)alkenoyl [e.g. acetylaminopyridylacryloylglycyl, propionyl-aminopyridylacryloylglycyl, etc.], amino acid residue substituted with lower alkenoylamino-heterocyclic(lower) alkenoyl [e.g. acryloylaminopyridylacryloylglycyl, crotonoylaminopyridylacryloylglycyl, etc.], amino acid residue substituted with heterocyclic(lower)alkanoylamino-heterocyclic(lower)alkenoyl [e.g. pyridyl-acetylaminopyridylacryloylglycyl, thienylacetyl-aminopyridylacryloylglycyl, etc.], amino acid residue substituted with heterocycliccarbonylamino-heterocyclic(lower)alkenoyl [e.g. pyridylcarbonylamino-pyridylacryloylglycyl, furylcarbamoylaminopyridylacryloylglycyl, etc.], amino acid residue substituted with lower alkanoylamino(lower)alkanoylamino-heterocyclic(lower)alkenoyl [e.g. acetylaminoacetylamino-pyridylacryloylglycyl, acetylaminopropionylamino-pyridylacryloylglycyl, etc.], amino acid residue substituted with lower alkoxycarbonyl(lower)alkanoylamino-heterocyclic(lower)alkenoyl [e.g. ethoxycarbonylacet-ylaminopyridylacryloylglycyl, ethoxycarbonylpro-pionylaminopyridylacryloylglycyl, etc.], amino acid residue substituted with lower alkoxy(lower)alkanoylamino-heterocyclic(lower)alkenoyl [e.g. methoxyacetyl-aminopyridylacryloylglycyl, methoxypropionyl-aminopyridylacryloylglycyl, ethoxypropionylamino-pyridylacryloylglycyl, etc.], etc., amino acid residue substituted with lower alkylureido-heterocyclic(lower)alkenoyl [e.g. methylureidopyridylacryloylglycyl, etc.], amino acid residue substituted with acyl-heterocyclic(lower)alkenoyl, for example, amino acid residue substituted with carboxy-heterocyclic(lower)alkenoyl [e.g. carboxypyridyl-acryloylglycyl, etc.], amino acid residue substituted with lower alkoxycarbonyl-heterocyclic(lower)alkenoyl [e.g. ethoxycarbonylpyridylacryloylglycyl, etc.], amino acid residue substituted with lower alkylcarbamoyl-heterocyclic(lower)alkenoyl [e.g. methylcarbamoylpyridyl-acryloylglycyl, ethylcarbamoylpyridylacryloylglycyl, dimethylcarbamoylpyridylacryloylglycyl, diethylcarbamoylpyridylacryloylglycyl, isopropylcarbamoylpyridylacryloylglycyl, N-ethyl-N-methylcarbamoylpyridylacryloylglycyl , etc.], amino acid residue substituted with lower alkoxy(lower)alkylcarbamoyl-heterocyclic(lower)alkenoyl [e.g. methoxymethylcarbamoylpyridylacryloylglycyl, methoxyethylcarbamoylpyridylacryloylglycyl, methoxypropylcarbamoylpyridylacryloylglycyl, ethoxyethylcarbamoylpyridylacryloylglycyl, bis(methoxyethyl)carbamoylpyridylacryloylglycyl, etc.], amino acid residue substituted with hydroxy(lower)alkylcarbamoyl-heterocyclic(lower)alkenoyl [e.g. hydroxymethylcarbamoylpyridylacryloylglycyl, hydroxyethylcarbamoylpyridylacryloylglycyl, bis(hydroxyethyl)carbamoylpyridylacryloylglycyl, etc.], amino acid residue substituted with heterocycliccarbamoylheterocyclic(lower)alkenoyl [e.g. pyridylcarbamoylpyridylacryloylglycyl, morpholinylcarbamoylpyridylacryloylgyycyl, thienylcarbamoylpyridylacryloylglycyl, pyrimidinylcarbamoylpyridylacryloylglycyl, etc.], amino acid residue substituted with heterocyclic(lower)alkylcarbamoyl-heterocyclic(lower)alkenoyl [e.g. pyridylmethylcarbamoylpyridylacryloylglycyl, furylmethylcarbamoylpyridylacryloylglycyl, thienylmethylcarbamoylpyridylacryloylglycyl, etc.], amino acid residue substituted with heterocycliccar-bonylheterocyclic(lower)alkenoyl [e.g. morpholinocarbonylpyridylacryloylglycyl, pyrrolidinylcarbonylpyridylacryloylglycyl, piperidinocarbonylpyridylacryloylglycyl, etc.], amino acid residue substituted with lower alkenylcarbamoyl-heterocyclic(lower)alkenoyl [e.g. vinylcarbamo-ylpyridylacryloylglycyl, allylcarbamoylpyridylacrylo-ylglycyl, etc.], amino acid residue substituted with lower alkynylcarbamoyl-heterocyclic(lower)alkenoyl [e.g. ethynylcarbamoylpyridylacryloylglycyl, propynylcarbamoylpyridylacryloylglycyl, etc.], etc., amino acid residue substituted with heterocyclicthio(lower)alkanoyl [e.g. pyridylthioacetylglycyl, pyrimidinylthioacetylglycyl, imidazolylthiopropion-ylglycyl, etc.], amino acid residue substituted with optionally substituted heterocycliccarbonyl [e.g. morpholinocarbonylglycyl, indolylcarbonylglycyl, 4-methyl-1-piperazinylcarbonylglycyl, etc.], amino acid residue substituted with cyclo(lower)alkylcarbonyl [e.g. cyclopropylcarbonylglycyl, cyclopentylcarbonylglycyl, cyclohexylcarbonylglycyl, cyclohexylcarbonylsarcosyl, etc.], amino acid residue substituted with lower alkoxycar-bonyl [e.g. methoxycarbonylglycyl, tert-butoxycarbonylglycyl, tert-butoxycarbonylsarcosyl, tert-butoxycarbonylalanyl, etc.], amino acid residue substituted with aryloxycarbonyl [e.g. phenoxycarbonylglycyl, etc.], amino acid residue substituted with aroyl(lower)alkanoyl [e.g. phenyloxalylglycyl, benzoylpropionylglycyl, etc.], amino acid residue substituted with aroyl [e.g. benzoylglycyl, naphthoylglycyl, benzoylsarcosyl, benzoylalanyl, etc.], amino acid residue substituted with nitro-aryloxycarbonyl [e.g. nitrophenyloxycarbonylglycyl, etc.], amino acid residue substituted with carbamoyl [e.g. carbamoylglycyl, carbamoylalanyl, carbamoylsarcosyl, carbamoyl-β-alanyl, etc.], amino acid residue substituted with lower alkylcarbamoyl [e.g. methylcarbamoylglycyl, ethylcarbamoylglycyl, propylcarbamoylglycyl, isopropylcarbamoylglycyl, methylcarbamoylsarcosyl, ethylcarbamoylalanyl, isopropylcarbamoyl-β-alanyl, pentylcarbamoylglycyl, etc.], amino acid residue substituted with lower alkoxycarbonyl(lower)alkylcarbamoyl [e.g. methoxycarbonylmethylcarbamoylglycyl, ethoxycarbonylmethylcarbamoylglycyl, etc.], amino acid residue substituted with lower alkenylcarbamoyl [e.g. vinylcarbamoylglycyl, allylcarbamoylglycyl, allylcarbamoylsarcosyl, etc.], amino acid residue substituted with cyclo(lower)alkylcarbamoyl [e.g. cyclopropylcarbamoylglycyl, cyclohexylcarbamoylglycyl, cyclohexylcarbamoylsarcosyl, etc.], amino acid residue substituted with arylcarbamoyl [e.g. phenylcarbamoylglycyl, naphthylcarbamoylglycyl, tolylcarbamoylglycyl, ethylphenylcarbamoylglycyl, phenylcarbamoylalanyl, phenylcarbamoylsarcosyl, etc.], amino acid residue substituted with lower alkoxy-arylcarbamoyl [e.g. methoxyphenylcarbamoylglycyl, ethoxyphenyl-carbamoylglycyl, methoxyphenylcarbamoylalanyl, etc.], amino acid residue substituted with halo(lower)alkyl-arylcarbamoyl [e.g. trifluoromethylphenylcarbamoylglycyl, trifluoromethylphenylcarbamoylalanyl, trifluoromethylphenylcarbamoylsarcosyl, etc.], amino acid residue substituted with halo-arylcarbamoyl [e.g. chlorophenylcarbamoylglycyl, fluorophenylcar-bamoylglycyl, fluorophenylcarbamoylalanyl, etc.], amino acid residue substituted with hydroxy(lower)alkyl-arylcarbamoyl [e.g. hydroxymethylphenylcarbamoylglycyl, hydroxyethylphenylcarbamoylglycyl, hydroxy-ethylphenylcarbamoylalanyl, etc.], amino acid residue substituted with nitro-arylcarbamoyl [e.g. nitrophenylcarbamoylglycyl, etc.], amino acid residue substituted with cyano-arylcarbamoyl [e.g. cyanophenylcarbamoylglycyl, etc.], amino acid residue substituted with amino-arylcarbamoyl [e.g. aminophenylcarbamoylglycyl, etc.], amino acid residue substituted with lower alkylamino-arylcarbamoyl [e.g. methylaminophenylcarbamoylglycyl, ethylaminophenylcarbamoylglycyl, dimethylaminophenylcarbamoylglycyl, etc.], amino acid residue substituted with lower alkanoylamino-arylcarbamoyl [e.g. acetylaminophenylcarbamoylglycyl, propionylaminophenylcarbamoylglycyl, etc.], amino acid residue substituted with N-(lower alkanoyl)-N-(lower alkyl) amino-arylcarbamoyl [e.g. N-acetyl-N-methylaminophenylcarbamoylglycyl, N-propionyl-N-methylaminophenylcarbamoylglycyl, etc.], amino acid residue substituted with lower alkoxy(lower) alkanoylamino-arylcarbamoyl [e.g. methoxyacetylaminophenylcarbamoylglycyl, methoxypropionylaminophenylcarbamoylglycyl, etc.], amino acid residue substituted with lower alkoxycarbonyl (lower)alkanoylamino-arylcarbamoyl [e.g. ethoxycarbonylacetylaminophenylcarbamoylglycyl, methoxycarbonylpropionylaminophenylcarbamoylglycyl, etc.], amino acid residue substituted with carboxyamino-arylcarbamoyl [e.g. carboxyaminophenylcarbamoylglycyl, etc.], amino acid residue substituted with lower alkoxycarbonylamino-arylcarbamoyl [e.g. ethoxycarbonylaminophenylcarbamoylglycyl, etc.], amino acid residue substituted with aroylamino-arylcarbamoyl [e.g. benzoylaminophenylcarbamoylglycyl, etc.], amino acid residue substituted with heterocycliccarbonylaminoarylcarbamoyl [e.g. pyridylcarbonylaminophenylcarbamoylglycyl, furylcarbonylaminophenylcarbamoylglycyl, morpholinocarbonylaminophenylcarbamoylglycyl, etc.], amino acid residue substituted with heterocyclic(lower)alkanoylamino-arylcarbamoyl [e.g. pyridylacetylaminophenylcarbamoylglycyl, thienylacetylaminophenylcarbamoylglycyl, etc.], amino acid residue substituted with ureido-arylcarbamoyl [e.g. ureidophenylcarbamoylglycyl, etc.], amino acid residue substituted with lower alkylureido-arylcarbamoyl [e.g. methylureidophenylcarbamoylglycyl, ethylureidophenylcarbamoylglycyl, etc.], amino acid residue substituted with hydroxyimino(lower)alkyl-arylcarbamoyl [e.g. hydroxyiminoethylphenylcarbamoylglycyl, etc.], amino acid residue substituted with lower alkoxyimino(lower)alkylarylcarbamoyl [e.g. methoxyiminoethylphenylcarbamoylglycyl, etc.], amino acid residue substituted with lower alkylhydrazono(lower) alkyl-arylcarbamoyl [e.g. methylhydrazonoethylphenylcarbamoylglycyl, dimethylhydrazonoethylphenylcarbamoylglycyl, etc.], amino acid residue substituted with optionally substituted heterocyclic-arylcarbamoyl [e.g. oxopyrrolidinylphenylcarbamoylglycyl, oxopiperidinophenylcarbamoylglycyl, dioxopyrrolidinylphenylcarbamoylglycyl, oxooxazolidinylphenylcarbamoylglycyl, pyrrolylphenylcarbamoylglycyl, etc.], amino acid residue substituted with acyl-arylcarbamoyl, for example, amino acid residue substituted with lower alkanoyl-arylcarbamoyl [e.g. acetylphenylcarbamoylglycyl, propionylphenylcarbamoylglycyl, etc.], amino acid residue substituted with heterocycliccarbonyl-arylcarbamoyl [e.g. morpholinocarbonylphenylcarbamoylglycyl, piperidinocarbonylphenylcarbamoylglycyl, piperazinylcarbonylphenylcarbamoylglycyl, thiomorpholinocarbonylphenylcarbamoylalanyl, pyrrolidinylcarbonylphenylcarbamoylglycyl, 1,2,3,6-tetrahydropyridylcarbonylphenylcarbamoylglycyl, etc.], amino acid residue substituted with carboxy-arylcarbamoyl [e.g. carboxyphenylcarbamoylglycyl, etc.], amino acid residue substituted with lower alkoxycarbonyl-arylcarbamoyl [e.g. methoxycarbonylphenylcarbamoyiglycyl, ethoxycarbonylphenylcarbamoylglycyl, etc.], amino acid residue substituted with carbamoyl-arylcarbamoyl [e.g. carbamoylphenylcarbamoylglycyl, etc.], amino acid residue substituted with lower alkylcarbamoyl-arylcarbamoyl [e.g. methylcarbamoylphenylcarbamoylglycyl, ethylcarbamoylphenylcarbamoylglycyl, propylcarbamoylphenylcarbamoylglycyl, dimethylcarbamoylphenylcarbamoylglycyl, diethylcarbamoylphenylcarbamoylglycyl, N-ethyl-N-methylcarbamoylphenylcarbamoylglycyl, N-isopropyl-N-methylcarbamoylphenylcarbamoylglycyl, etc.], amino acid residue substituted with heterocycliccarbonyl-arylcarbamoyl having lower alkyl [e.g. methylpiperazinylcarbonylphenylcarbamoylglycyl, ethylpiperazinylcarbonylphenylcarbamoylglycyl, etc.], amino acid residue substituted with heterocycliccarbonyl-arylcarbamoyl having aryl [e.g. phenylpiperazinylcarbonylphenylcarbamoylglycyl, etc.], amino acid residue substituted with heterocycliccarbonyl-arylcarbamoyl having a heterocyclic group [e.g. pyridylpiperazinylcarbonylphenylcarbamoylglycyl, etc.], amino acid-residue substituted with heterocycliccarbonyl-arylcarbamoyl having lower alkanoyl [e.g. acetylpiperazinylcarbonylphenylcarbamoylglycyl, etc.], amino acid residue substituted with heterocycliccarbonyl-arylcarbamoyl having lower alkoxycarbonyl [e.g. ethoxycarbonylpiperazinylcarbonylphenylcarbamoylglycyl, etc.], amino acid residue substituted with heterocycliccarbonyl-arylcarbamoyl having lower alkylamino [e.g. methylaminopiperazinylcarbonylphenylcarbamoylglycyl, dimethylaminopiperidinocarbonylphenylcarbamoylglycyl, etc.], amino acid residue substituted with heterocycliccarbonylarylcarbamoyl having lower alkylcarbamoyl [e.g. methylcarbamoylpiperazinylcarbonylphenylcarbamoylglycyl, etc.], amino acid residue substituted with hydroxy(lower)alkylcarbamoyl-arylcarbamoyl [e.g. hydroxymethylcarbamoylphenylcarbamoylglycyl, hydroxyethylcarbamoylphenylcarbamoylglycyl, bis (hydroxyethyl)carbamoylphenylcarbamoylglycyl, etc.], amino acid residue substituted with N-hydroxy(lower) alkyl-N-(lower alkyl)carbamoylarylcarbamoyl [e.g. N-(hydroxyethyl)-N-methylcarbamoylphenylcarbamoyl-glycyl, etc.], amino acid residue substituted with lower alkoxy(lower)alkylcarbamoyl-arylcarbamoyl [e.g. methoxymethylcarbamoylphenylcarbamoylglycyl, methoxyethylcarbamoylphenylcarbamoylglycyl, ethoxyethylcarbamoylphenylcarbamoylglycyl, bis (methoxyethyl)carbamoylphenylcarbamoylglycyl, bis (ethoxyethyl)carbamoylphenylcarbamoylglycyl, etc.], amino acid residue substituted with N-[lower alkoxy(lower) alkyl]-N-(lower alkyl)carbamoyl-arylcarbamoyl [e.g. N-(methoxyethyl)-N-methylcarbamoylphenyl-carbamoylglycyl, N-(methoxypropyl)-N-methylcarbamoylphenylcarbamoylglycyl, etc.], amino acid residue substituted with lower alkylamino(lower) alkylcarbamoyl-arylcarbamoyl [e.g. methylaminoethylcarbamoylphenylcarbamoylglycyl, dimethylaminoethylcarbamoylphenylcarbamoylglycyl, etc.], amino acid residue substituted with N-[lower alkylamino(lower)alkyl]-N-(lower alkyl)carbamoylarylcarbamoyl [e.g. N-(dimethylaminoethyl)-N-methylcarbamoylphenylcarbamoylglycyl, N-(dimethylaminopropyl)-N-methylcarbamoylphenylcarbamoylglycyl, etc.], amino acid residue substituted with heterocycliccarbamoyl-arylcarbamoyl [e.g.

morpholinylcarbamoylphenylcarbamoylglycyl, thienylcarbamoylphenylcarbamoylglycyl, pyridylcarbamoylphenylcarbamoylglycyl, pyrimidinylcarbamoylphenylcarbamoylglycyl, etc.], amino acid residue substituted with N-(heterocyclic)-N-(lower alkyl)carbamoyl-arylcarbamoyl [e.g. N-pyridyl-N-methylcarbamoylphenylcarbamoylglycyl, etc.], amino acid residue substituted with heterocyclic(lower)alkylcarbamoyl-arylcarbamoyl [e.g. pyridylmethylcarbamoylphenylcarbamoylglycyl, pyridylethylcarbamoylphenylcarbamoylglycyl, thienylmethylcarbamoylphenylcarbamoylglycyl, etc.], amino acid residue substituted with N-[heterocyclic(lower)alkyl-N-(lower alkyl)carbamoylarylcarbamoyl [e.g. N-pyridylmethyl-N-methylcarbamoylphenylcarbamoylglycyl, etc.], amino acid residue substituted with N-[heterocyclic(lower)alkyl]-N-[lower alkoxy(lower)alkyl]carbamoyl-arylcarbamoyl [e.g. N-pyridylmethyl-N-methoxyethylcarbamoylphenylcarbamoylglycyl, etc.], amino acid residue substituted with arylcarbamoyl-arylcarbamoyl [e.g. phenylcarbamoyl-phenylcarbamoylglycyl, etc.], amino acid residue substituted with lower alkylaminoarylcarbamoyl-arylcarbamoyl [e.g. dimethylaminophenylcarbamoylphenylcarbamoylglycyl, etc.], etc., amino acid residue substituted with arylthiocarbamoyl [e.g. phenylthiocarbamoylglycyl, naphthylthiocarbamoylglycyl, phenylthiocarbamoylalanyl, phenylthiocarbamoylsarcosyl, etc.], amino acid residue substituted with ar(lower)alkylcarbamoyl [e.g. benzylcarbamoylglycyl, benzylcarbamoylsarcosyl, benzylcarbamoylalanyl, etc.], amino acid residue substituted with aroylcarbamoyl [e.g. benzoylcarbamoylglycyl, etc.], amino acid residue substituted with heterocycliccarbamoyl [e.g. pyridylcarbamoylglycyl, pyridylcarbamoylalanyl, pyridylcarbamoylsarcosyl, thienylcarbamoylglycyl, pyrazolylcarbamoylglycyl, pyrimidinylcarbamoylglycyl, quinolylcarbamoylglycyl, isoquinolylcarbamoylglycyl, etc.], amino acid residue substituted with heterocyclic(lower)alkylcarbamoyl [e.g. pyridylmethylcarbamoylglycyl, pyridylethylcarbamoylglycyl, thienylmethylcarbamoylglycyl, etc.], amino acid residue substituted with arylaminocarbamoyl [e.g. phenylaminocarbamoylglycyl, etc.], amino acid residue substituted with ar(lower) alkenylsulfonyl [e.g. styrylsulfonylglycyl, cinnamoylsulfonylglycyl, etc.], amino acid residue substituted with lower alkylsulfonyl [e.g. mesylglycyl, ethylsulfonylglycyl, mesylsarcosyl, mesylalanyl, etc.], amino acid residue substituted with phthaloyl [e.g. phthaloylglycyl, phthaloylalanyl, phthaloyl-β-alanyl, etc.], amino acid residue having unsubstituted amino acid residue [e.g. glycylglycyl, alanylglycyl, sarcosylglycyl, prolylglycyl, glycylsarcosyl, prolylsarcosyl, etc.], amino acid residue having substituted amino acid residue [e.g. amino acid residue having amino acid residue substituted with lower alkyl (e.g. dimethylglycylglycyl, diethylglycylglycyl, dimethylglycylsarcosyl, ethylsarcosylglycyl, isopropylsarcosylglycyl, ethylglycylglycyl, propylglycylglycyl, isopropylglycylglycyl, ethylglycylalanyl, dimethylglycylalanyl, dimethylalanylglycyl, dimethyl-β-alanylglycyl, etc.), amino acid residue having amino acid residue substituted with a heterocyclic group (e.g. morpholinoglycylglycyl, piperidinoglycylglycyl, pyridylglycylglycyl, piperidinosarcosylglycyl, etc.), amino acid residue having amino acid residue substituted with heterocyclic(lower)alkyl (e.g. pyridylmethylglycylglycyl, imidazolylmethylglycylglycyl, furylmethylglycylglycyl, thienylmethylsarcosylglycyl, etc.), amino acid residue having amino acid residue substituted with cycloalkyl (e.g. cyclopropylglycylglycyl, cyclobutylglycylglycyl, cyclopentylglycylglycyl, cyclohexylglycylglycyl, cycloheptylglycylglycyl, cyclooctylglycylglycyl, adamantylglycylglycyl, cyclohexylsarcosylglycyl, cycloheptylsarcosylglycyl, cyclohexylglycylsarcosyl, cyclohexylglycylalanyl, etc.), amino acid residue having amino acid residue substituted with aryl (e.g. phenylglycylglycyl, phenylsarcosyiglycyl, etc.), amino acid residue having amino acid residue substituted with acyl {e.g. amino acid residue having amino acid residue substituted with alkanoyl (e.g. acetylglycylglycyl, acetylprolylglycyl, propionylglycylglycyl, acetylalanylglycyl, etc.), amino acid residue having amino acid residue substituted with lower alkoxycarbonyl e.g. tert-butoxycarbonylglycylglycyl, tert-butoxycarbonylprolylglycyl, etc., amino acid residue having amino acid residue substituted with phthaloyl (e.g. phthaloylglycylglycyl, etc.), etc.}, amino acid residue having amino acid residue substituted with ar(lower)alkyl (e.g. benzylglycylglycyl, etc.), etc.], etc., or the like.

Groups of the formulas of the compounds [Ie] and [If]:

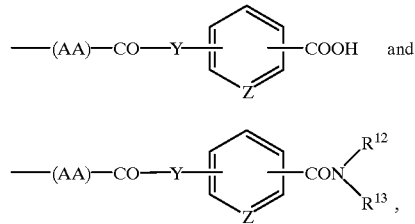

wherein $R^{12}$, $R^{13}$, (AA), Y and Z are each as defined above, are also included within "acyl".

Suitable "acyl having amino" may be unsubstituted amino acid residue, amino acid residue having unsubstituted amino acid residue, or the like, and preferred examples thereof can be referred to those exemplified above.

Suitable "acyl having acylamino" may be amino acid residue substituted with acyl, amino acid residue having amino acid residue substituted with acyl, or the like, and preferred examples thereof can be referred to those exemplified above.

Suitable substituents in the term "amino optionally having suitable substituent(s)" may be the above-mentioned lower alkyl, the above-mentioned acyl, ar(lower)alkyl [e.g. benzyl, phenethyl, trityl, etc.], carboxy(lower)alkyl [e.g. carboxymethyl, carboxyethyl, carboxypropyl, etc.], lower alkoxycarbonyl(lower)alkyl [e.g. methoxycarbonylmethyl, ethoxycarbonylmethyl, methoxycarbonylethyl, ethoxycarbonylpropyl, etc.], heterocyclic(lower)alkyl [e.g. pyridylmethyl, pyridylethyl, etc.], or the like.

Suitable "protected or unprotected hydroxy(lower)alkyl" may be hydroxymethyl, hydroxyethyl, hydroxypropyl, benzyloxymethyl, tert-butyldiphenylsilyloxyethyl or the like.

Suitable "lower alkoxy(lower)alkyl" may be methoxymethyl, methoxyethyl, methoxypropyl, ethoxymethyl, ethoxyethyl, or the like.

Suitable "lower alkylamino(lower)alkyl" may be methylaminomethyl, methylaminoethyl, methylaminopropyl, dimethylaminomethyl, dimethylaminoethyl, dimethylaminopropyl, diethylaminoethyl, or the like.

Suitable "lower alkenyl" may be vinyl, allyl, methylpropenyl, butenyl, pentenyl or the like.

Suitable "lower alkynyl" may be ethynyl, propynyl, butynyl, pentynyl or the like.

Suitable "lower alkylcarbamoyloxy(lower)alkyl" may be methylcarbamoyloxymethyl, methylcarbamoyloxyethyl, ethylcarbamoyloxyethyl, dimethylcarbamoyloxyethyl or the like.

Suitable "lower alkoxycarbonyl(lower)alkyl" may be methoxycarbonylmethyl, methoxycarbonylethyl, ethoxycarbonylmethyl, ethoxycarbonylethyl or the like.

Suitable "carboxy(lower)alkyl" may be carboxymethyl, carboxyethyl, carboxypropyl or the like.

Suitable "lower alkylcarbamoyl(lower)alkyl" may be methylcarbamoylmethyl, methylcarbamoylethyl, ethylcarbamoylethyl, dimethylcarbamoylethyl or the like.

Suitable "lower alkoxycarbonyl-ar(lower)alkyl" may be methoxycarbonyl-benzyl, methoxycarbonyl-phenethyl, ethoxycarbonyl-phenethyl or the like.

Suitable "carboxy-ar(lower)alkyl" may be carboxy-benzyl, carboxy-phenethyl or the like.

Suitable "lower alkylcarbamoyl-ar(lower)alkyl" may be methylcarbamoyl-benzyl, methylcarbamoyl-phenethyl, ethylcarbamoyl-phenethyl or the like.

Suitable "heterocyclic group" and all heterocyclic moieties in the various definitions mentioned in this specification and claims such as in the term "heterocyclic(lower) alkyl", "heterocyclic(lower)alkenoyl", etc., may include saturated or unsaturated, monocyclic or polycyclic one containing at least one hetero atom such as nitrogen atom, oxygen atom or sulfur atom, preferably N, O and/or S containing 5 or 6 membered heterocyclic group, in which preferable ones may be morpholinyl, piperazinyl, pyridyl, tetrahydropyridyl, pyrimidinyl, piperidyl, thienyl, furyl, oxazolyl, isoxazolyl, thiazolyl, tetrazolyl, imidazolyl, pyrrolidinyl, pyrrolyl, or the like.

Suitable substituents in the term "heterocyclic group optionally having suitable substituent(s)" may be the above-mentioned halogen, the above-mentioned lower alkyl, the above-mentioned acyl, the above-mentioned aryl, oxo, nitro, amino, ar(lower)alkyl [e.g. benzyl, phenethyl, trityl, etc.], lower alkoxycarbonyl(lower)alkyl [e.g. methoxycarbonylmethyl, ethoxycarbonylmethyl, methoxycarbonylethyl, ethoxycarbonylpropyl, etc.], or the like.

Suitable "heterocyclic group" formed by $R^{12}$, $R^{13}$ and the attached nitrogen atom may be morpholino, thiomorpholino, pyrrolidin-1-yl, piperidino, 1,2,3,6-tetrahydropyridin-1-yl, piperazin-1-yl, or the like. And said heterocyclic group may be substituted with suitable substituent(s) such as the above-mentioned lower alkyl, the above-mentioned heterocyclic group, the above-mentioned acyl, lower alkylamino, the above-mentioned aryl, or the like.

Preferred examples of "heterocyclic(lower)alkyl" may be morpholinomethyl, morpholinoethyl, pyridylmethyl, pyridylethyl, thienylmethyl, piperidinomethyl, pyrrolylmethyl, imidazolylmethyl, furylmethyl, or the like. Particularly, the preferred embodiments of $X^1$, $X^2$, $X^3$, $R^1$, $R^2$, $R^3$, $R^4$, $R^5$, Q and A are as follows:

A group of the formula: $-X^3=X^2-X^1=N-$ is a group of the formula

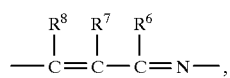

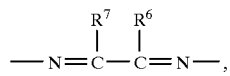

-continued

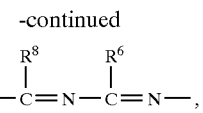

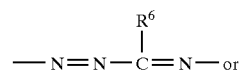

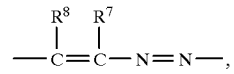

in which
$R^6$ and $R^8$ are each hydrogen; halogen such as fluorine, chlorine, bromine and iodine; lower alkyl such as methyl, ethyl, propyl, isopropyl, butyl, isobutyl, tert-butyl, pentyl and hexyl; hydroxy; lower alkylthio such as methylthio, ethylthio, propylthio, isopropylthio and butylthio; amino; lower alkylamino such as methylamino, ethylamino, propylamino, dimethylamino and diethylamino; lower alkoxy such as methoxy, ethoxy, propoxy, isopropoxy and butoxy; lower alkoxy(lower)alkoxy such as methoxymethoxy and methoxyethoxy; lower alkylamino(lower)alkoxy such as methylaminoethoxy and dimethylaminoethoxy; or ar(lower)alkoxy substituted with lower alkoxy such as dimethoxybenzyloxy;

$R^7$ is hydrogen; or lower alkyl such as methyl, ethyl, propyl, isopropyl and butyl;

$R^1$ is hydrogen; or halogen such as fluorine, chlorine, bromine and iodine;

$R^2$ is halogen such as fluorine, chlorine, bromine and iodine;

$R^3$ is hydrogen; nitro; a group of the formula

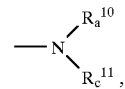

in which
$R_a^{10}$ is hydrogen; lower alkyl such as methyl, ethyl, propyl and butyl; carboxy(lower)alkyl such as carboxymethyl and carboxyethyl; lower alkoxycarbonyl (lower)alkyl such as methoxycarbonylmethyl, methoxycarbonylethyl and ethoxycarbonylmethyl; ar(lower)alkyl such as benzyl and phenethyl; and acyl such as lower alkanoyl [e.g. formyl, acetyl, propionyl, etc.], carboxy and esterified carboxy [e.g. lower alkoxycarbonyl (e.g. methoxycarbonyl, ethoxycarbonyl, tert-butoxycarbonyl, etc.), etc.], $R_c^{11}$ is hydrogen; lower alkyl such as methyl, ethyl, propyl, isopropyl and butyl; ar(lower)alkyl such as benzyl; heterocyclic(lower)alkyl such as pyridyl (lower)alkyl [e.g. pyridylmethyl, pyridylethyl, etc.]; and acyl such as lower alkanoyl [e.g. formyl, acetyl, propionyl, butyryl, isobutyryl, etc.], halo(lower) alkanoyl [e.g. trifluoroacetyl, etc.], carboxy, esterified carboxy [e.g. lower alkoxycarbonyl (e.g. methoxycarbonyl, ethoxycarbonyl, tert-butoxycarbonyl, etc.), etc.], hydroxy(lower)alkanoyl [e.g. glycoloyl, lactoyl, 3-hydroxypropionyl, etc.], lower alkanoyloxy(lower)alkanoyl [e.g. acetyloxyacetyl, acetyloxypropionyl, etc.], lower alkoxy(lower)alkanoyl [e.g. methoxyacetyl, methoxypropionyl, etc.], benzoyl, toluoyl, benzoyl substituted with lower alkoxy [e.g. methoxybenzoyl, etc.], benzoyl substituted with esterified carboxy [e.g. lower alkoxycarbonylbenzoyl (e.g. methoxycarbonylbenzoyl, tert-butoxycarbonylbenzoyl, etc.), etc.], benzoyl substituted with halogen [e.g. chlorobenzoyl, fluorobenzoyl, etc.], phenoxycarbonyl optionally substituted with nitro, lower alkylsulfonyl [e.g. mesyl, ethylsulfonyl, etc.], carbamoyl, lower alkylcarbamoyl [e.g. methylcarbamoyl, ethylcarbamoyl, isopropylcarbamoyl, etc.], halo(lower) alkanoylcarbamoyl [e.g. trichloroacetylcarbamoyl, etc.], phenylcarbamoyl, unsubstituted amino acid residue [e.g. glycyl, sarcosyl, alanyl, β-alanyl, etc.] and substituted amino acid residue [e.g. amino acid residue substituted with lower alkyl (e.g. ethylglycyl, isopropylglycyl, dimethylglycyl, diethylglycyl, ethylsarcosyl, isopropylsarcosyl, methylalanyl, methyl-β-alanyl, etc.)], amino acid residue substituted with optionally substituted amidino (e.g. amidinoglycyl, N-ethyl-N'-cyanoamidinoglycyl, etc.), amino acid residue substituted with acyl {e.g. amino acid residue substituted with alkanoyl (e.g. formylglycyl, acetylglycyl, acetylsarcosyl, acetylalanyl, acetyl-β-alanyl, propionylglycyl, butyrylglycyl, isobutyrylglycyl, valerylglycyl, isovalerylglycyl, pivaloylglycyl, hexanoylglycyl, heptanoylglycyl, etc.), amino acid residue substituted with halo(lower)alkanoyl (e.g. trifluoroacetylglycyl, trifluoroacetylsarcosyl, trifluoroacetylalanyl, bromoacetylglycyl, heptafluorobutyrylglycyl, etc.), amino acid residue substituted with hydroxy(lower) alkanoyl (e.g. glycoloylglycyl, glycoloylsarcosyl, lactoylglycyl, lactoylalanyl, etc.), amino acid residue substituted with lower alkylsulfonyloxy(lower) alkanoyl (e.g. mesyloxyacetylglycyl, ethylsulfonyloxyacetylglycyl, mesyloxyacetylsarcosyl, etc.), amino acid residue substituted with lower alkoxy (lower)alkanoyl (e.g. methoxyacetylglycyl, ethoxyacetylglycyl, methoxyacetylsarcosyl, methoxypropionylalanyl, etc.), amino acid residue substituted with aryloxy(lower)alkanoyl (e.g. phenyloxyacetylglycyl, phenyloxypropionylglycyl, phenyloxyacetylsarcosyl, etc.), amino acid residue substituted with lower alkylthio(lower)alkanoyl (e.g. methylthioacetylglycyl, methylthiopropionylglycyl, etc.), amino acid residue substituted with lower alkylcarbamoyl(lower)alkanoyl (e.g. methylcarbamoylpropionylglycyl, methylcarbamoylpropionylalanyl, etc.), amino acid residue substituted with lower alkanoyloxy(lower) alkanoyl (e.g. acetyloxyacetylglycyl, acetyloxyacetylsarcosyl, propionyloxyacetylglycyl, acetyloxypropionylalanyl, etc.), amino acid residue substituted with carboxy(lower)alkanoyl (e.g. carboxyacetylglycyl, carboxypropionylglycyl, carboxypropionylsarcosyl, carboxyacetylalanyl, etc.), amino acid residue substituted with lower alkoxycarbonyl(lower)alkanoyl (e.g. methoxycarbonylacetylglycyl, ethoxycarbonylpropionylglycyl, methoxycarbonylacetylsarcosyl, etc.), amino acid residue substituted with ar(lower)alkanoyl (e.g. phenylacetylglycyl, phenylpropionylglycyl, phenylbutyrylglycyl, phenylacetylsarcosyl, phenylpropionylalanyl, naphthylacetylglycyl, etc.), amino acid residue substituted with optionally substituted heterocyclic(lower) alkanoyl (e.g. morpholinoacetylglycyl, pyridylacetylglycyl, morpholinopropionylalanyl, imidazolylacetylglycyl, piperidinoacetylglycyl, pyrrolidinylacetylglycyl, hexamethyleneiminoacetylglycyl, methylpiperazinylacetylglycyl, pyridylpiperazinylacetylglycyl, thiomorpholinoacetylglycyl, its oxide or dioxide, etc.), amino acid residue substituted with lower alkenoyl (e.g. acryloylglycyl, crotonoylglycyl, 3-pentenoylglycyl, 3-butenoylglycyl, 4-pentenoylglycyl, 3-butenoylsarcosyl, etc.), amino acid residue substituted with ar(lower)alkenoyl (e.g. cinnamoylglycyl, α-methylcinnamoylglycyl, 4-methylcinnamoylglycyl, etc.), amino acid residue substituted with lower alkoxy-ar(lower)alkenoyl (e.g. methoxycinnamoylglycyl, ethoxycinnamoylglycyl, dimethoxycinnamoylglycyl, etc.), amino acid residue substituted with lower alkylenedioxy-ar(lower)alkenoyl (e.g. methylenedioxycinnamoylglycyl, ethylenedioxycinnamoylglycyl, etc.), amino acid residue substituted with nitro-ar(lower)alkenoyl (e.g. nitrocinnamoylglycyl, etc.), amino acid residue substituted with cyano-ar(lower)alkenoyl (e.g. cyanocinnamoylglycyl, etc.), amino acid residue substituted with halo-ar(lower)alkenoyl (e.g. chlorocinnamoylglycyl, fluorocinnamoylglycyl, etc.), amino acid residue substituted with hydroxy-ar(lower) alkenoyl (e.g. hydroxycinnamoylglycyl, etc.), amino acid residue substituted with hydroxy(lower)alkoxy-ar (lower)alkenoyl (e.g. hydroxymethoxycinnamoylglycyl, hydroxyethoxycinnamoylglycyl, etc.), amino acid residue substituted with amino(lower) alkoxy-ar(lower)alkenoyl (e.g. aminoethoxycinnamoylglycyl, etc.), amino acid residue substituted with lower alkylamino(lower)alkoxy-ar(lower) alkenoyl (e.g. methylaminomethoxycinnamoylglycyl, dimethylaminoethoxycinnamoylglycyl, etc.), amino acid residue substituted with heterocyclic(lower) alkoxy-ar(lower)alkenoyl (e.g. pyridylmethoxycinnamoylglycyl, etc.), amino acid residue substituted with optionally substituted heterocyclic-ar(lower) alkenoyl (e.g. morpholinocinnamoylglycyl, methylpiperazinylcinnamoylglycyl, pyrrolidinylcinnamoylglycyl, oxopyrrolidinylcinnamoylglycyl, oxopiperidinocinnamoylglycyl, dioxopyrrolidinylcinnamoylglycyl, oxooxazolidinylcinnamoylglycyl, pyrrolylcinnamoylglycyl, tetrazolylcinnamoylglycyl, etc.), amino acid residue substituted with amino-ar(lower)alkenoyl (e.g. aminocinnamoylglycyl, etc.), amino acid residue substituted with lower alkylamino-ar(lower)alkenoyl (e.g. methylaminocinnamoylglycyl, dimethylaminocinnamoylglycyl, etc.), amino acid residue substituted with lower alkanoylamino-ar(lower)alkenoyl (e.g. acetylaminocinnamoylglycyl, propionylaminocinnamoylglycyl, isobutyrylaminocinnamoylglycyl, etc.), amino acid residue substituted with cycloalkyl(lower)alkanoylamino-ar(lower)alkenoyl (e.g. cyclopentylacetylaminocinnamoylglycyl, cyclohexylacetylaminocinnamoylglycyl, adamantylacetylaminocinnamoylglycyl, etc.), amino acid residue substituted with cycloalkylcarbonylamino-ar(lower)alkenoyl (e.g. cyclopropylcarbonylaminocinnamoylglycyl, cyclopentylcarbonylaminocinnamoylglycyl, cyclohexylcarbonylaminocinnamoylglycyl, adamantylcarbonylaminocinnamoylglycyl, etc.), amino acid residue substituted with lower alkenoylamino-ar(lower)alkenoyl (e.g. acryloylaminocinnamoylglycyl, crotonoylaminocinnamoylglycyl, etc.) amino acid residue substituted with lower alkoxycarbonylamino-ar(lower)alkenoyl (e.g. methoxycarbonylaminocinnamoylglycyl, ethoxycarbonylaminocinnamoylglycyl, etc.), amino acid residue substituted with hydroxy(lower)alkanoylamino-ar(lower)alkenoyl (e.g. hydroxyacetylaminocinnamoylglycyl, hydroxypropionylaminocinnamoylglycyl, etc.), amino acid residue substituted with lower alkoxy(lower)alkanoylamino-ar(lower)alkenoyl (e.g. methoxyacetylaminocinnamoylglycyl, methoxypropionylaminocinnamoylglycyl, etc.), amino acid residue substituted with halo(lower)alkanoylamino-ar(lower)alkenoyl (e.g. chloroacetylaminocinnamoylglycyl, trifluoroacetylaminocinnamoylglycyl, bromobutyrylaminocinnamoylglycyl, etc.), amino acid residue substituted with amino(lower)alkanoylamino-ar(lower)alkenoyl (e.g. aminoacetylaminocinnamoylglycyl, aminopropionylaminocinnamoylglycyl, etc.), amino acid residue substituted with lower alkylamino(lower)alkanoylamino-ar(lower)alkenoyl (e.g. methylaminoacetylaminocinnamoylglycyl, dimethylaminoacetylaminocinnamoylglycyl, etc.), amino acid residue substituted with lower alkanoylamino(lower)alkanoylamino-ar(lower)alkenoyl (e.g. acetylaminoacetylaminocinnamoylglycyl, acetylaminopropionylaminocinnamoylglycyl, etc.), amino acid residue substituted with carboxy(lower)alkanoylamino-ar(lower)alkenoyl (e.g. carboxyacetylaminocinnamoylglycyl, carboxypropionylaminocinnamoylglycyl, etc.), amino acid residue substituted with lower alkoxycarbonyl(lower)alkanoylamino-ar(lower)alkenoyl (e.g. ethoxycarbonylacetylaminocinnamoylglycyl, ethoxycarbonylpropionylaminocinnamoylglycyl, etc.), amino acid residue substituted with lower alkoxycarbonyl(lower)alkenoylamino-ar(lower)alkenoyl (e.g. ethoxycarbonylacryloylaminocinnamoylglycyl, etc.), amino acid residue substituted with halo(lower)alkoxycarbonylamino-ar(lower)alkenoyl (e.g. chloroethoxycarbonylaminocinnamoylglycyl, etc.), amino acid residue substituted with optionally substituted heterocyclic(lower)alkanoylamino-ar(lower)alkenoyl (e.g. pyridylacetylaminocinnamoylglycyl, thienylacetylaminocinnamoylglycyl, methylpyrrolylacetylaminocinnamoylglycyl, etc.), amino acid residue substituted with aroylamino-ar(lower)alkenoyl (e.g. benzoylaminocinnamoylglycyl, etc.), amino acid residue substituted with optionally substituted heterocycliccarbonylamino-ar(lower)alkenoyl (e.g. pyridylcarbonylaminocinnamoylglycyl, morpholinocarbonylaminocinnamoylglycyl, furylcarbonylaminocinnamoylglycyl, thienylcarbonylaminocinnamoylglycyl, oxazolylcarbonylaminocinnamoylglycyl, methyloxazolylcarbonylaminocinnamoylglycyl, dimethylisoxazolylcarbonylaminocinnamoylglycyl, imidazolylcarbonylaminocinnamoylglycyl, methylimidazolylcarbonylaminocinnamoylglycyl, piperidylcarbonylaminocinnamoylglycyl, ethylpiperidylcarbonylaminocinnamoylglycyl, acetylpiperidylcarbonylaminocinnamoylglycyl, pyrrolidinylcarbonylaminocinnamoylglycyl, acetylpyrrolidinylcarbonylaminocinnamoylglycyl, tert-butoxycarbonylpyrrolidinylcarbonylaminocinnamoylglycyl, etc.), amino acid residue substituted with lower alkylsulfonylamino-ar(lower)alkenoyl (e.g. mesylaminocinnamoylglycyl, ethylsulfonylaminocinnamoylglycyl, etc.), amino acid residue substituted with N-(lower alkanoyl)-N-(lower alkyl)amino-ar(lower)alkenoyl (e.g. N-acetyl-N-methylaminocinnamoylglyclyl, N-acetyl-N-ethylaminocinnamoylglycyl, N-propionyl-N-methylaminocinnamoylglycyl, etc.), amino acid residue substituted with N-[lower alkoxy(lower)alkanoyl]-N-(lower alkyl)amino-ar(lower)alkenoyl (e.g. N-methoxyacetyl-N-methylaminocinnamoylglycyl, N-methoxypropionyl-N-methylaminocinnamoylglycyl, etc.), amino acid residue substituted with N-(lower alkanoyl)-N-[heterocyclic(lower)alkyl]amino-ar(lower)alkenoyl (e.g. N-acetyl-N-pyridylmethylaminocinnamoylglycly, etc.), amino acid residue substituted with N-(lower alkanoyl)-N-[lower alkoxy(lower)alkyl]amino-ar(lower)alkenoyl (e.g. N-acetyl-N-methoxyethylaminocinnamoylglycyl, N-acetyl-N-methoxymethylaminocinnamoylglycyl, N-propionyl-N-methoxyethylaminocinnamoylglycyl, etc.), amino acid residue substituted with N-(lower alkanoyl)-N-[lower alkoxycarbonyl(lower)alkyl]amino-ar(lower)alkenoyl (e.g. N-acetyl-N-tert-butoxycarbonylmethylaminocinnamoylglycyl, N-acetyl-N-tert-butoxycarbonylethylaminocinnamoylglycyl, N-propionyl-N-tert-butoxycarbonylmethylaminocinnamoylglycyl, etc.), amino acid residue substituted with N-(lower alkanoyl)-N-[carboxy(lower)alkyl]amino-ar(lower)alkenoyl (e.g. N-acetyl-N-carboxymethylaminocinnamoylglycyl, N-acetyl-N-carboxyethylaminocinnamoylglycyl, N-propionyl-N-carboxymethylaminocinnamoylglycyl, etc.), amino acid residue substituted with N-[lower alkoxy(lower)alkanoyl]-N-[heterocyclic(lower)alkyllamino-ar(lower)alkenoyl (e.g. N-methoxyacetyl-N-pyridylmethylaminocinnamoylglycyl, N-methoxypropionyl-N-pyridylmethylaminocinnamoylglycyl, etc.), amino acid residue substituted with N-[heterocycliccarbonyl]-N-[lower alkoxy(lower)alkyl]amino-ar(lower)alkenoyl (e.g. N-pyridylcarbonyl-N-methoxymethylaminocinnamoylglycyl, N-pyridylcarbonyl-N-methoxyethylaminocinnamoylglycyl, N-thienylcarbonyl-N-methoxyethylaminocinnamoylglycyl, etc.), amino acid residue substituted with ureido-ar(lower)alkenoyl (e.g. ureidocinnamoylglycyl, etc.), amino acid residue substituted with lower alkylureido-ar(lower)alkenoyl (e.g. methylureidocinnamoylglycyl, ethylureidocinnamoylglycyl, dimethylureidocinnamoylglycyl, etc.), amino acid residue substituted with heterocyclicureido-ar(lower)alkenoyl (e.g. pyridylureidocinnamoylglycyl, pyrimidinylureidocinnamoylglycyl, thienylureidocinnamoylglycyl, etc.), amino acid residue substituted with lower alkanoyl-ar(lower)alkenoyl (e.g. formylcinnamoylglycyl, acetylcinnamoylglycyl, propionylcinnamoylglycyl, etc.), amino acid residue substituted with carboxy-ar(lower)alkenoyl (e.g. carboxycinnamoylglycyl, etc.), amino acid residue substituted with lower alkoxycarbonyl-ar(lower)alkenoyl (e.g. methoxycarbonylcinnamoylglycyl, ethoxycarbonylcinnamoylglycyl, etc.), amino acid residue substituted with carbamoyl-ar(lower)alkenoyl (e.g. carbamoylcinnamoylglycyl, etc.), amino acid residue substituted with lower alkylcarbamoyl-ar(lower)alkenoyl (e.g. methylcarbamoylcinnamoylglycyl, ethylcarbamoylcinnamoylglycyl, dimethylcarbamoylcinnamoylglycyl, propylcarbamoylcinnamoylglycyl, isopropylcarbamoylcinnamoylglycyl, diethylcarbamoylcinnamoylglycyl, N-methyl-N-ethylcarbamoylcinnamoylglycyl, etc.), amino acid residue substituted with hydroxy(lower)alkylcarbamoyl-ar(lower)alkenoyl (e.g. hydroxyethylcarbamoylcinnamoylglycyl, bis-(hydroxyethyl)carbamoylcinnamoylglycyl, etc.), amino acid residue substituted with N-[hydroxy(lower)alkyl]-N-(lower alkyl)carbamoyl-ar(lower)alkenoyl (e.g. N-hydroxyethyl-N-methylcarbamoylcinnamoylglycyl, etc.), amino acid residue substituted with lower alkoxy(lower)alkylcarbamoyl-ar(lower)alkenoyl (e.g. methoxymethylcarbamoylcinnamoylglycyl, methoxyethylcarbamoylcinnamoylglycyl, bis(methoxyethyl)carbamoylcinnamoylglycyl, ethoxyethylcarbamoylcinnamoylglycyl, methoxypropylcarbamoylcinnamoylglycyl, bis(ethoxyethyl)carbamoylcinnamoylglycyl, etc.), amino acid residue substituted with N-[lower alkoxy(lower)alkyl]-N-(lower alkyl)carbamoyl- ar(lower)alkenoyl (e.g. N-methoxyethyl-N-methylcarbamoylcinnamoylglycyl, N-ethoxyethyl-N-methylcarbamoylcinnamoylglycyl, etc.), amino acid residue substituted with heterocyclic(lower)alkylcarbamoyl-ar(lower)alkenoyl (e.g. pyridylmethylcarbamoylcinnamoylglycyl, furylmethylcarbamoylcinnamoylglycyl, thienylmethylcarbamoylcinnamoylglycyl, etc.), amino acid residue substituted with N-[heterocyclic(lower)alkyl]-N-(lower alkyl)carbamoyl-ar(lower)alkenoyl (e.g. N-pyridylmethyl-N-methylcarbamoylcinnamoylglycyl, etc.), amino acid residue substituted with heterocycliccarbamoyl-ar(lower)alkenoyl (e.g. morpholinylcarbamoylcinnamoylglycyl, thienylcarbamoylcinnamoylglycyl, pyridylcarbamoylcinnamoylglycyl, pyrimidinylcarbamoylcinnamoylglycyl, tetrazolylcarbamoylcinnamoylglycyl, etc.), amino acid residue substituted with optionally substituted heterocycliccarbonyl-ar(lower)alkenoyl (e.g. morpholinocarbonylcinnamoylglycyl, pyrrolidinylcarbonylcinnamoylglycyl, piperidinocarbonylcinnamoylglycyl, tetrahydropyridylcarbonylcinnamoylglycyl, methylpiperazinylcarbonylcinnamoylglycyl, etc.), amino acid residue substituted with lower alkenylcarbamoyl-ar(lower)alkenoyl (e.g. vinylcarbamoylcinnamoylglycyl, allylcarbamoylcinnamoylglycyl, methylpropenylcarbamoylcinnamoylglycyl, etc.), amino acid residue substituted with lower alkynylcarbamoyl-ar(lower)alkenoyl (e.g. ethynylcarbamoylcinnamoylglycyl, propynylcarbamoylcinnamoylglycyl, etc.), amino acid residue substituted with amino(lower)alkylcarbamoyl-ar(lower)alkenoyl (e.g. aminomethylcarbamoylcinnamoylglycyl, aminoethylcarbamoylcinnamoylglycyl, etc.), amino acid residue substituted with lower alkylamino(lower)alkylcarbamoyl-ar(lower)alkenoyl (e.g. methylaminomethylcarbamoylcinnamoylglycyl, methylaminoethylcarbamoylcinnamoylglycyl, ethylaminoethylcarbamoylcinnamoylglycyl, dimethylaminoethylcarbamoylcinnamoylglycyl, etc.), amino acid residue substituted with lower alkylcarbamoyloxy(lower)alkylcarbamoyl-ar(lower)alkenoyl (e.g. methylcarbamoyloxymethylcarbamoylcinnamoylglycyl, methylcarbamoyloxyethylcarbamoylcinnamoylglycyl, ethylcarbamoyloxyethylcarbamoylcinnamoylglycyl, dimethylcarbamoyloxyethylcarbamoylcinnamoylglycyl, etc.), amino acid residue substituted with lower alkylcarbamoyl(lower)alkylcarbamoyl-ar(lower)alkenoyl (e.g. methylcarbamoylmethylcarbamoylcinnamoylglycyl, methylcarbamoylethylcarbamoylcinnamoylglycyl, ethylcarbamoylethylcarbamoylcinnamoylglycyl, dimethylcarbamoylethylcarbamoylcinnamoylglycyl, etc.), amino acid residue substituted with lower alkoxycarbonyl(lower)alkylcarbamoyl-ar(lower)alkenoyl (e.g. methoxycarbonylmethylcarbamoylcinnamoylglycyl, methoxycarbonylethylcarbamoylcinnamoylglycyl, ethoxycarbonylmethylcarbamoylcinnamoylglycyl, ethoxycarbonylethylcarbamoylcinnamoylglycyl, etc.), amino acid residue substituted with carboxy(lower)alkylcarbamoyl-ar(lower)alkenoyl (e.g. carboxymethylcarbamoylcinnamoylglycyl, carboxyethylcarbamoylcinnamoylglycyl, etc.), amino acid residue substituted with [lower alkylcarbamoyl-ar(lower)alkyl]carbamoyl-ar(lower)alkenoyl (e.g. (methylcarbamoylphenethyl)carbamoylcinnamoylglycyl, (ethylcarbamoyl-phenethyl)carbamoylcinnamoylglycyl, etc.), amino acid residue substituted with [lower alkoxycarbonyl-ar(lower)alkyl]carbamoyl-ar(lower)alkenoyl (e.g. (methoxycarbonylphenethyl)carbamoylcinnamoylglycyl, (ethoxycarbonyl-phenethyl)carbamoylcinnamoylglycyl, etc.), amino acid residue substituted with [carboxy-ar(lower)alkyl]carbamoyl-ar(lower)alkenoyl (e.g. (carboxy-phenethyl)carbamoylcinnamoylglycyl, etc.), amino acid residue substituted with N-[lower alkylcarbamoyl(lower)alkyl]-N-(lower alkyl)carbamoyl-ar(lower)alkenoyl (e.g. N-(methylcarbamoylmethyl)-N-methylcarbamoylcinnamoylglycyl, N-(methylcarbamoylethyl)-N-methylcarbamoylcinnamoylglycyl, N-(ethylcarbamoylethyl)-N-methylcarbamoylcinnamoylglycyl, N-(dimethylcarbamoylethyl)-N-methylcarbamoylcinnamoylglycyl, etc.), amino acid residue substituted with N-[lower alkoxycarbonyl(lower)alkyl]-N-(lower alkyl)carbamoyl-ar(lower)alkenoyl (e.g. N-methoxycarbonylmethyl-N-methylcarbamoylcinnamoylglycyl, N-methoxycarbonylethyl-N-methylcarbamoylcinnamoylglycyl, N-ethoxycarbonylmethyl-N-methylcarbamoylcinnamoylglycyl, N-ethoxycarbonylethyl-N-methylcarbamoylcinnamoylglycyl, etc.), amino acid residue substituted with N-[carboxy(lower)alkyl]-N-(lower alkyl)carbamoyl-ar(lower)alkenoyl (e.g. N-carboxymethyl-N-methylcarbamoylcinnamoylglycyl, N-carboxyethyl-N-methylcarbamoylcinnamoylglycyl, etc.) amino acid residue substituted with arylcarbamoyl-ar(lower)alkenoyl (e.g. phenylcarbamoylcinnamoylglycyl, naphthylcarbamoylcinnamoylglycyl, etc.), amino acid residue substituted with ar(lower)alkynoyl (e.g. phenylpropioloylglycyl, etc.), amino acid residue substituted with heterocyclic(lower)alkenoyl (e.g.

morpholinylacryloylglycyl, pyridylacryloylglycyl, thienylacryloylglycyl, etc.), amino acid residue substituted with amino-heterocyclic(lower)alkenoyl (e.g. aminopyridylacryloylglycyl, etc.), amino acid residue substituted with lower alkylamino-heterocyclic(lower) alkenoyl (e.g. methylaminopyridylacryloylglycyl, dimethylaminopyridylacryloylglycyl, etc.), amino acid residue substituted with lower alkanoylamino-heterocyclic(lower)alkenoyl (e.g. acetylaminopyridylacryloylglycyl, propionylaminopyridylacryloylglycyl, etc.), amino acid residue substituted with lower alkenoylamino-heterocyclic(lower)alkenoyl (e.g. acryloylaminopyridylacryloylglycyl, crotonoylaminopyridylacryloylglycyl, etc.), amino acid residue substituted with heterocyclic(lower)alkanoylamino-heterocyclic(lower)alkenoyl (e.g. pyridylacetylaminopyridylacryloylglycyl, thienylacetylaminopyridylacryloylglycyl, etc.), amino acid residue substituted with heterocycliccarbonylamino-heterocyclic(lower)alkenoyl (e.g. pyridylcarbonylaminopyridylacryloylglycyl, furylcarbonylaminopyridylacryloylglycyl, etc.), amino acid residue substituted with lower alkanoylamino(lower)alkanoylamino-heterocyclic(lower)alkenoyl (e.g. acetylaminoacetylaminopyridylacryloylglycyl, acetylaminopropionylaminopyridylacryloylglycyl, etc.), amino acid residue substituted with lower alkoxycarbonyl(lower)alkanoylamino-heterocyclic(lower)alkenoyl (e.g. ethoxycarbonylacetylaminopyridylacryloylglycyl, ethoxycarbonylpropionylaminopyridylacryloylglycyl, etc.), amino acid residue substituted with lower alkoxy(lower)alkanoylaminoheterocyclic(lower)alkenoyl (e.g. methoxyacetylaminopyridylacryloylglycyl, methoxypropionylaminopyridylacryloylglycyl, ethoxypropionylaminopyridylacryloylglycyl,. etc.), amino acid residue substituted with lower alkylureido-heterocyclic(lower)alkenoyl (e.g. methylureidopyridylacryloylglycyl, etc.), amino acid residue substituted with carboxy-heterocyclic(lower)alkenoyl (e.g. carboxypyridylacryloylglycyl, etc.), amino acid residue substituted with lower alkoxycarbonyl-heterocyclic(lower)alkenoyl (e.g. ethoxycarbonylpyridylacryloylglycyl, etc.), amino acid residue substituted with lower alkylcarbamoyl-heterocyclic(lower)alkenoyl (e.g. methylcarbamoylpyridylacryloylglycyl, ethylcarbamoylpyridylacryloylglycyl, dimethylcarbamoylpyridylacryloylglycyl, diethylcarbamoylpyridylacryloylglycyl, isopropylcarbamoylpyridylacryloylglycyl, N-ethyl-N-methylcarbamoylpyridylacryloylglycyl, etc.), amino acid residue substituted with lower alkoxy(lower)alkylcarbamoylheterocyclic(lower)alkenoyl (e.g. methoxymethylcarbamoylpyridylacryloylglycyl, methoxyethylcarbamoylpyridylacryloylglycyl, methoxypropylcarbamoylpyridylacryloylglycyl, ethoxyethylcarbamoylpyridylacryloylglycyl, bis (methoxyethyl)carbamoylpyridylacryloylglycyl, etc.), amino acid residue substituted with hydroxy(lower)alkylcarbamoylheterocyclic(lower)alkenoyl (e.g. hydroxymethylcarbamoylpyridylacryloylglycyl, hydroxyethylcarbamoylpyridylacryloylglycyl, bis (hydroxyethyl)carbamoylpyridylacryloylglycyl, etc.), amino acid residue substituted with heterocycliccarbamoyl-heterocyclic(lower)alkenoyl (e.g. pyridylcarbamoylpyridylacryloylglycyl, morpholinylcarbamoylpyridylacryloylglycyl, thienylcarbamoylpyridylacryloylglycyl, pyrimidinylcarbamoylpyridylacryloylglycyl, etc.), amino acid residue substituted with heterocyclic(lower)alkylcarbamoylheterocyclic(lower)alkenoyl (e.g. pyridylmethylcarbamoylpyridylacryloylglycyl, furylmethylcarbamoylpyridylacryloylglycyl, thienylmethylcarbamoylpyridylacryloylglycyl, etc.), amino acid residue substituted with heterocycliccarbonylheterocyclic(lower)alkenoyl (e.g. morpholinocarbonylpyridylacryloylglycyl, pyrrolidinylcarbonylpyridylacryloylglycyl, piperidinocarbonylpyridylacryloylglycyl, etc.), amino acid residue substituted with lower alkenylcarbamoyl-heterocyclic(lower)alkenoyl (e.g. vinylcarbamoylpyridylacryloylglycyl, allylcarbamoylpyridylacryloylglycyl, etc.), amino acid residue substituted with lower alkynylcarbamoyl-heterocyclic(lower)alkenoyl (e.g. ethylcarbamoylpyridylacryloylglycyl, propynylcarbamoylpyridylacryloylglycyl, etc.), amino acid residue substituted with heterocyclicthio(lower)alkanoyl (e.g. pyridylthioacetylglycyl, pyrimidinylthioacetylglycyl, imidazolylthiopropionylglycyl, etc.), amino acid residue substituted with optionally substituted heterocycliccarbonyl (e.g. morpholinocarbonylglycyl, indolylcarbonylglycyl, 4-methyl-1-piperazinylcarbonylglycyl, etc.), amino acid residue substituted with cyclo(lower)alkylcarbonyl (e.g. cyclopropylcarbonylglycyl, cyclopentylcarbonylglycyl, cyclohexylcarbonylglycyl, cyclohexylcarbonylsarcosyl, etc.), amino acid residue substituted with lower alkoxycarbonyl (e.g. methoxycarbonylglycyl, tert-butoxycarbonylglycyl, tert-butoxycarbonylsarcosyl, tert-butoxycarbonylalanyl, etc.), amino acid residue substituted with aryloxycarbonyl (e.g. phenoxycarbonylglycyl, etc.), amino acid residue substituted with aroyl(lower)alkanoyl (e.g. phenyloxalylglycyl, benzoylpropionylglycyl, etc.), amino acid residue substituted with aroyl (e.g. benzoylglycyl, benzoylsarcosyl, naphthoylglycyl, benzoylalanyl, etc.), amino acid residue substituted with nitro-aryloxycarbonyl (e.g. nitrophenyloxycarbonylglycyl, etc.), amino acid residue substituted with carbamoyl (e.g. carbamoylglycyl, carbamoylalanyl, carbamoylsarcosyl, carbamoyl-β-alanyl, etc.), amino acid residue substituted with lower alkylcarbamoyl (e.g. methylcarbamoylglycyl, ethylcarbamoylglycyl, propylcarbamoylglycyl, isopropylcarbamoylglycyl, pentylcarbamoylglycyl, methylcarbamoylsarcosyl, ethylcarbamoylalanyl, isopropylcarbamoyl-β-alanyl, etc.), amino acid residue substituted with lower alkoxycarbonyl(lower)alkylcarbamoyl (e.g. methoxycarbonyl-methylcarbamoylglycyl, ethoxycarbonylmethylcarbamoylglycyl, etc.), amino acid residue substituted with lower alkenylcarbamoyl (e.g. vinylcarbamoylglycyl, allylcarbamoylglycyl, allylcarbamoylsarcosyl, etc.), amino acid residue substituted with cyclo(lower)alkylcarbamoyl (e.g. cyclopropylcarbamoylglycyl, cyclohexylcarbamoylglycyl, cyclohexylcarbamoylsarcosyl, etc.), amino acid residue substituted with arylcarbamoyl (e.g.

phenylcarbamoylglycyl, naphthylcarbamoylglycyl, tolylcarbamoylglycyl, ethylphenylcarbamoylglycyl, phenylcarbamoylalanyl, phenylcarbamoylsarcosyl, etc.), amino acid residue substituted with lower alkoxy-arylcarbamoyl (e.g. methoxyphenylcarbamoylglycyl, ethoxyphenylcarbamoylglycyl, methoxyphenylcarbamoylalanyl, etc.), amino acid residue substituted with halo(lower)alkyl-arylcarbamoyl (e.g. trifluoromethylphenylcarbamoylglycyl, trifluoromethylphenylcarbamoylalanyl, trifluoromethylphenylcarbamoylsarcosyl, etc.), amino acid residue substituted with halo-arylcarbamoyl (e.g. chlorophenylcarbamoylglycyl, fluorophenylcarbamoylglycyl, fluorophenylcarbamoylalanyl, etc.), amino acid residue substituted with lower alkanoyl-arylcarbamoyl (e.g. acetylphenylcarbamoylglycyl, propionylphenylcarbamoylalanyl, etc.), amino acid residue substituted with hydroxy(lower)alkyl-arylcarbamoyl (e.g. hydroxymethylphenylcarbamoylglycyl, hydroxyethylphenylcarbamoylglycyl, hydroxyethylphenylcarbamoylalanyl, etc.), amino acid residue substituted with heterocycliccarbonyl-arylcarbamoyl (e.g. morpholinocarbonylphenylcarbamoylglycyl, piperidinocarbonylphenylcarbamoylglycyl, thiomorpholinocarbonylphenylcarbamoylalanyl, piperazinylcarbonylphenylcarbamoylglycyl, pyrrolidinylcarbonylphenylcarbamoylglycyl, 1,2,3,6-tetrahydropyridylcarbonylphenylcarbamoylglycyl, etc.), amino acid residue substituted with carboxy-arylcarbamoyl (e.g. carboxyphenylcarbamoylglycyl, etc.), amino acid residue substituted with lower alkoxycarbonyl-arylcarbamoyl (e.g. methoxycarbonylphenylcarbamoylglycyl, ethoxycarbonylphenylcarbamoylglycyl, etc.), amino acid residue substituted with carbamoyl-arylcarbamoyl (e.g. carbamoylphenylcarbamoylglycyl, etc.), amino acid residue substituted with lower alkylcarbamoyl-arylcarbamoyl (e.g. methylcarbamoylphenylcarbamoylglycyl, ethylcarbamoylphenylcarbamoylglycyl, propylcarbamoylphenylcarbamoylglycyl, dimethylcarbamoylphenylcarbamoylglycyl, diethylcarbamoylphenylcarbamoylglycyl, N-ethyl-N-methylcarbamoylphenylcarbamoylglycyl, N-isopropyl-N-methylcarbamoylphenylcarbamoylglycyl, etc.), amino acid residue substituted with nitro-arylcarbamoyl (e.g. nitrophenylcarbamoylglycyl, etc.), amino acid residue substituted with cyano-arylcarbamoyl (e.g. cyanophenylcarbamoylglycyl, etc.), amino acid residue substituted with amino-arylcarbamoyl (e.g. aminophenylcarbamoylglycyl, etc.), amino acid residue substituted with lower alkylamino-arylcarbamoyl (e.g. methylaminophenylcarbamoylglycyl, ethylaminophenylcarbamoylglycyl, dimethylaminophenylcarbamoylglycyl, etc.), amino acid residue substituted with lower alkanoylamino-arylcarbamoyl (e.g. acetylaminophenylcarbamoylglycyl, propionylaminophenylcarbamoylglycyl, etc.), amino acid residue substituted with N-(lower alkanoyl)-N-(lower alkyl)amino-arylcarbamoyl (e.g. N-acetyl-N-methylaminophenylcarbamoylglycyl, N-propionyl-N-methylaminophenylcarbamoylglycyl, etc.), amino acid residue substituted with lower alkoxy(lower)alkanoylamino-arylcarbamoyl (e.g. methoxyacetylaminophenylcarbamoylglycyl, methoxypropionylaminophenylcarbamoylglycyl, etc.), amino acid residue substituted with lower alkoxycarbonyl(lower)alkanoylamino-arylcarbamoyl (e.g. ethoxycarbonylacetylaminophenylcarbamoylglycyl, methoxycarbonylpropionylaminophenylcarbamoylglycyl, etc.), amino acid residue substituted with carboxyamino-arylcarbamoyl (e.g. carboxyaminophenylcarbamoylglycyl, etc.), amino acid residue substituted with lower alkoxycarbonylamino-arylcarbamoyl (e.g. ethoxycarbonylaminophenylcarbamoylglycyl, etc.), amino acid residue substituted with aroylamino-arylcarbamoyl (e.g. benzoylaminophenylcarbamoylglycyl, etc.), amino acid residue substituted with heterocycliccarbonylamino-arylcarbamoyl (e.g. pyridylcarbonylaminophenylcarbamoylglycyl, furylcarbonylaminophenylcarbamoylglycyl, morpholinocarbonylaminophenylcarbamoylglycyl, etc.), amino acid residue substituted with heterocyclic(lower)alkanoylamino-arylcarbamoyl (e.g. pyridylacetylaminophenylcarbamoylglycyl, thienylacetylaminophenylcarbamoylglycyl, etc.), amino acid residue substituted with ureido-arylcarbamoyl (e.g. ureidophenylcarbamoylglycyl, etc.), amino acid residue substituted with lower alkylureido-arylcarbamoyl (e.g. methylureidophenylcarbamoylglycyl, ethylureidophenylcarbamoylglycyl, etc.), amino acid residue substituted with hydroxyimino(lower)alkyl-arylcarbamoyl (e.g. hydroxyiminoethylphenylcarbamoylglycyl, etc.), amino acid residue substituted with lower alkoxyimino(lower)alkyl-arylcarbamoyl (e.g. methoxyiminoethylphenylcarbamoylglycyl, etc.), amino acid residue substituted with lower alkylhydrazono(lower)alkyl-arylcarbamoyl (e.g. methylhydrazonoethylphenylcarbamoylglycyl, dimethylhydrazonoethylphenylcarbamoylglycyl, etc.), amino acid residue substituted with optionally substituted heterocyclic-arylcarbamoyl (e.g. oxopyrrolidinylphenylcarbamoylglycyl, oxopiperidinophenylcarbamoylglycyl, dioxopyrrolidinylphenylcarbamoylglycyl, oxooxazolidinylphenylcarbamoylglycyl, pyrrolylphenylcarbamoylglycyl, etc.), amino acid residue substituted with heterocycliccarbonyl-arylcarbamoyl having lower alkyl (e.g. methylpiperazinylcarbonylphenylcarbamoylglycyl, ethylpiperazinylcarbonylphenylcarbamoylglycyl, etc.), amino acid residue substituted with heterocycliccarbonyl-arylcarbamoyl having aryl (e.g. phenylpiperazinylcarbonylphenylcarbamoylglycyl, etc.), amino acid residue substituted with heterocycliccarbonyl-arylcarbamoyl having a heterocyclic group (e.g. pyridylpiperazinylcarbonylphenylcarbamoylglycyl, etc.), amino acid residue substituted with heterocycliccarbonyl-arylcarbamoyl having lower alkanoyl (e.g. acetylpiperazinylcarbonylphenylcarbamoylglycyl, etc.), amino acid residue substituted with heterocycliccarbonyl-arylcarbamoyl having lower alkoxycarbonyl (e.g. ethoxycarbonylpiperazinylcarbonylphenylcarbamoylglycyl, etc.), amino acid residue substituted with heterocycliccarbonyl-arylcarbamoyl having lower alkylamino (e.g. methylaminopiperazinylcarbonylphenylcarbamoylglycyl, dimethylaminopiperidinocarbonylphenylcarbamoylglycyl, etc.), amino acid residue substituted with heterocycliccarbonyl-arylcarbamoyl having lower alkylcarbamoyl (e.g. methylcarbamoylpiperazinylcarbonylphenylcarbamoylglycyl, etc.), amino acid residue substituted with hydroxy(lower)alkylcarbamoyl-arylcarbamoyl (e.g. hydroxymethylcarbamoylphenylcarbamoylglycyl, hydroxyethylcarbamoylphenylcarbamoylglycyl, bis(hydroxyethyl)carbamoylphenylcarbamoylglycyl, etc.), amino acid residue substituted with N-[hydroxy(lower)alkyl]-N-(lower alkyl)carbamoyl-arylcarbamoyl (e.g. N-(hydroxyethyl)-N-methylcarbamoylphenylcarbamoylglycyl, etc.), amino acid residue substituted with lower alkoxy(lower)alkylcarbamoyl-arylcarbamoyl (e.g. methoxymethylcarbamoylphenylcarbamoylglycyl, methoxyethylcarbamoylphenylcarbamoylglycyl, ethoxyethylcarbamoylphenylcarbamoylglycyl, bis(methoxyethyl)carbamoylphenylcarbamoylglycyl, bis(ethoxyethyl)carbamoylphenylcarbamoylglycyl etc.), amino acid residue substituted with N-[lower alkoxy(lower)alkyl]-N-(lower alkyl)carbamoylarylcarbamoyl (e.g. N-(methoxyethyl)-N-methylcarbamoylphenylcarbamoylglycyl, N-(methoxypropyl)-N-methylcarbamoylphenylcarbamoylglycyl, etc.), amino acid residue substituted with lower alkylamino(lower)alkylcarbamoyl-arylcarbamoyl (e.g. methylaminoethylcarbamoylphenylcarbamoylglycyl, dimethylaminoethylcarbamoylphenylcarbamoylglycyl, etc.), amino acid residue substituted with N-[lower alkylamino(lower)alkyl]-N-(lower alkyl)carbamoyl-arylcarbamoyl (e.g. N-(dimethylaminoethyl)-N-methylcarbamoylphenylcarbamoylglycyl, N-(dimethylaminopropyl)-N-methylcarbamoylphenylcarbamoylglycyl, etc.), amino acid residue substituted with heterocycliccarbamoyl-arylcarbamoyl (e.g. morpholinylcarbamoyl-phenylcarbamoylglycyl, thienylcarbamoyl-phenylcarbamoylglycyl, pyridylcarbamoyl-phenylcarbamoylglycyl, pyrimidinylcarbamoylphenylcarbamoylglycyl, etc.), amino acid residue substituted with N-(heterocyclic)-N-(lower alkyl)carbamoylarylcarbamoyl (e.g. N-pyridyl-N-methylcarbamoylphenylcarbamoylglycyl, etc.), amino acid residue substituted with heterocyclic(lower)alkylcarbamoyl-arylcarbamoyl (e.g. pyridylmethylcarbamoylphenylcarbamoylglycyl, pyridylethylcarbamoylphenylcarbamoylglycyl, thienylmethylcarbamoylphenylcarbamoylglycyl, etc.), amino acid residue substituted with N-[heterocyclic(lower)alkyl]-N-(lower alkyl)carbamoyl-arylcarbamoyl (e.g. N-pyridylmethyl-N-methylcarbamoylphenylcarbamoylglycyl, etc.), amino acid residue substituted with N-[heterocyclic(lower)alkyl]-N-[lower alkoxy(lower)alkyl]carbamoyl-arylcarbamoyl (e.g. N-pyridylmethyl-N-methoxyethylcarbamoylphenylcarbamoylglycyl, etc.), amino acid residue substituted with arylcarbamoyl-arylcarbamoyl (e.g. phenylcarbamoylphenylcarbamoylglycyl, etc.), amino acid residue substituted with lower alkylaminoarylcarbamoyl-arylcarbamoyl (e.g. dimethylaminophenylcarbamoylphenylcarbamoylglycyl, etc.), amino acid residue substituted with arylthiocarbamoyl (e.g. phenylthiocarbamoylglycyl, naphthylthiocarbamoylglycyl, phenylthiocarbamoylalanyl, phenylthiocarbamoylsarcosyl, etc.), amino acid residue substituted with ar(lower)alkylcarbamoyl (e.g. benzylcarbamoylglycyl, benzylcarbamoylsarcosyl, benzylcarbamoylalanyl, etc.), amino acid residue substituted with aroylcarbamoyl (e.g. benzoylcarbamoylglycyl, etc.), amino acid residue substituted with heterocycliccarbamoyl (e.g. pyridylcarbamoylglycyl, pyridylcarbamoylalanyl, pyridylcarbamoylsarcosyl, thienylcarbamoylglycyl, pyrazolylcarbamoylglycyl, pyrimidinylcarbamoylglycyl, quinolylcarbamoylglycyl, isoquinolylcarbamoylglycyl, etc.), amino acid residue substituted with heterocyclic (lower) alkylcarbamoyl (e.g. pyridylmethylcarbamoylglycyl, pyridylethylcarbamoylglycyl, thienylmethylcarbamoylglycyl, etc.), amino acid residue substituted with arylaminocarbamoyl (e.g. phenylaminocarbamoylglycyl, etc.), amino acid residue substituted with ar(lower)alkenylsulfonyl (e.g. styrylsulfonylglycyl, cinnamoylsulfonylglycyl, etc.), amino acid residue substituted with lower alkylsulfonyl (e.g. mesylglycyl, ethylsulfonylglycyl, mesylsarcosyl, mesylalanyl, etc.), amino acid residue substituted with phthaloyl (e.g. phthaloylglycyl, phthaloylalanyl, phthaloyl-β-alanyl, etc.), amino acid residue having unsubstituted amino acid residue (e.g. glycylglycyl, alanylglycyl, sarcosylglycyl, prolylglycyl, glycylsarcosyl, prolylsarcosyl, etc.), amino acid residue having substituted amino acid residue such as amino acid residue having amino acid residue substituted with lower alkyl (e.g. dimethylglycylglycyl, diethylglycylglycyl, dimethylglycylsarcosyl, ethylsarcosylglycyl, isopropylsarcosylglycyl, ethylglycylglycyl, propylglycylglycyl, isopropylglycylglycyl, ethylglycylalanyl, dimethylglycylalanyl, dimethylalanylglycyl, dimethyl-β-alanylglycyl, etc.), amino acid residue having amino acid residue substituted with a heterocyclic group (e.g. morpholinoglycylglycyl, piperidinoglycylglycyl, pyridylglycylglycyl, piperidinosarcosylglycyl, etc.), amino acid residue having amino acid residue substituted with heterocyclic(lower)alkyl (e.g. pyridylmethylglycylglycyl, imidazolylmethylglycylglycyl, furylmethylglycylglycyl, thienylmethylsarcosylglycyl, etc.), amino acid residue having amino acid residue substituted with cycloalkyl (e.g. cyclopropylglycylglycyl, cyclobutylglycylglycyl, cyclopentylglycylglycyl, cyclohexylglycylglycyl, cycloheptylglycylglycyl, cyclooctylglycylglycyl, adamantylglycylglycyl, cyclohexylsarcosylglycyl, cycloheptylsarcosylglycyl, cyclohexylglycylsarcosyl, cyclohexylglycylalanyl, etc.), amino acid residue having amino acid residue substituted with aryl (e.g. phenylglycylglycyl, phenylsarcosylglycyl, etc.), amino acid residue having amino acid residue substituted with lower alkanoyl (e.g. acetylglycylglycyl, acetylprolylglycyl, propionylglycylglycyl, acetylalanylglycyl, etc.), amino acid residue having amino acid residue substituted with lower alkoxycarbonyl (e.g. tert-butoxycarbonylglycylglycyl, tert-butoxycarbonylprolylglycyl, etc.), amino acid residue having amino acid residue substituted with ar(lower)alkyl (e.g. benzylglycylglycyl, etc.) and amino acid residue having amino acid residue substituted with phthaloyl (e.g. phthaloylglycylglycyl, etc.), etc.}, etc.];
or a heterocyclic group such as piperazinyl, which may be substituted with substituent(s) such as ar(lower)alkyl [e.g. benzyl, phenethyl, etc.], lower alkoxycarbonyl(lower)alkyl [e.g. methoxycarbonylmethyl, methoxycarbonylethyl ethoxycarbonylmethyl, etc.] and/or oxo;

$R^4$ and $R^5$ are each hydrogen; or halogen such as fluorine, chlorine, bromine and iodine;

Q is O or N-$R^9$, in which $R^9$ is hydrogen; or acyl such as lower alkanoyl [e.g. formyl, acetyl, propionyl, butyryl, etc.] and lower alkoxycarbonyl [e.g. tert-butoxycarbonyl, etc.];

A is lower alkylene such as methylene, ethylene, methylmethylene and propylene.

Suitable "a leaving group" may be a conventional acid residue such as halogen [e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] to [If] in the Processes 2 to 4, it is to be noted that these compounds are included within the scope of the compound [I], and accordingly the suitable examples of the salts of these compounds are to be referred to those as exemplified for the object compound [I].

The processes for preparing the object compound [I] are explained in detail in the following.

Process 1

The object compound [I] or its salt can be prepared by reacting a compound [II] or its salt with a compound [III] or its salt.

Suitable salts of the compounds [II] and [III] may be the same as those exemplified for the compound [I].

The reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like.

The reaction temperature is not critical, and the reaction is usually carried out under cooling to heating.

Process 2

The object compound [Ib] or its salt can be prepared by acylating a compound [Ia] or its salt.

The acylation is carried out in the presence of an acylating agent.

Suitable acylating agents are the corresponding carboxylic acid or sulfonic acid compounds, which are represented by the formula : R—OH wherein R is acyl, and reactive derivatives thereof, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as p-nitrophenyl ester and N-hydroxysuccinimide ester. The kind of such reactive derivatives can be selected depending on the kind of acyl group to be introduced.

The reaction is usually carried out in a conventional solvent, such as methylene chloride, chloroform, pyridine, dioxane, tetrahydrofuran, N,N-dimethylformamide, or the like. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 3

The object compound [Id] or its salt can be prepared by acylating a compound [Ic] or its salt.

This reaction can be carried out in substantially the same manner as Process 2, and therefore the reaction mode and reaction condition of this reaction are to be referred to those explained in Process 2.

Process 4

The object compound [If] or its salt can be prepared by reacting a compound [Ie] or its reactive derivative at the carboxy group or a salt thereof with a compound [IV] or its reactive derivative at the amino group or a salt thereof.

Suitable reactive derivative at the carboxy group of the compound [Ie] may include an acid halide, an acid anhydride, an activated amide, an activated ester, and the like. Suitable examples of the reactive derivatives may be an acid chloride; an acid azide; a mixed acid anhydride with an acid such as dialkylphosphoric acid, sulfuric acid aliphatic carboxylic acid or aromatic carboxylic acid; a symmetrical acid anhydride; an activated amide with imidazole; or an activated ester [e.g. p-nitrophenyl ester, etc.]. These reactive derivatives can optionally be selected from them according to the kind of the compound [Ie] to be used.

Suitable reactive derivative at the amino group of the compound [IV] may be a silyl derivative formed by the reaction of the compound [IV] with a silyl compound such as bis(trimethylsilyl)acetamide or mono(trimethylsilyl) acetamide, or the like.

Suitable salts of the compound [IV] and its reactive derivative can be referred to the organic or inorganic acid addition salts as exemplified for the compound [I].

This reaction can be carried out in substantially the same manner as Process 2, and therefore the reaction mode and reaction condition of this reaction are to be referred to those explained in Process 2.

The object compound [I] and the starting compounds can also be prepared by the methods of Examples and Preparations mentioned below or similar manners thereto or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scope of this invention.

The object compound [I] and pharmaceutically acceptable salts thereof possess strong activities as bradykinin antagonists, and are useful for the treatment and/or the prevention of bradykinin or its analogues mediated diseases such as allergy, inflammation, autoimmune disease, shock, pain, or the like, and more particularly for the prevention and/or the treatment of asthma, cough, bronchitis, rhinitis, rhinorrhea, obstructive pulmonary disease [e.g. pulmonary emphysema, etc.], expectoration, pneumonitis, systemic inflammatory response syndrome (SIRS), septic shock, endotoxin shock, anaphylactic shock, adult respiratory distress syndrome, disseminated intravascular coagulopathy, arthritis, rheumatism, osteoarthritis, lumbago, inflammation-induced bone resorption, conjunctivitis, vernal conjunctivitis, uveitis, iritis, iridocyclitis, headache, migraine, toothache, backache, superficial pain, cancerous pain, postoperative pain, tenalgia, trauma [e.g. wound, burn, etc.], rash, erythema, eczema or dermatitis [e.g. contact dermatitis, atopic dermatitis, etc.], urticaria, herpes, itching, psoriasis, lichen, inflammatory bowel disease [e.g. ulcerative colitis, Crohn's disease, etc.], diarrhea, hepatitis, pancreatitis, gastritis, esophagitis, food allergy, ulcer, irritable bowel syndrome, nephritis, angina, periodontitis, edema, hereditary angioneurotic edema, cerebral edema, low blood pressure, thrombosis, myocardial infarction, cerebral vasospasm, congestion, coagulation, gout, central nervous system injury, premature labor, arteriosclerosis, post-gastrectomy dumping syndrome, carcinoid syndrome, altered sperm mobility, diabetic neuropathy, neuralgia, graft rejection in transplantation, or the like, in human being or animals.

And further, it is known that bradykinin relates to the release of mediators such as prostaglandins, leukotrienes, tachykinins, histamine, thromboxanes, or the like, so the compound [I] is expected to be useful for the prevention and/or the treatment of such mediators mediated diseases.

In order to illustrate the usefulness of the object is compound [I], the pharmacological test data of some representative compounds of the compound [I] are shown in the following.

$^3$H-Bradykinin receptor binding (i) Test Method:

(a) Crude ileum membrane preparation

Male Hartly strain guinea pigs were sacrificed by decapitation. The ileum was removed and homogenized in buffer (50 mM trimethylaminoethanesulfonic acid (TES), 1 mM 1,10-phenanthroline pH 6.8). The homogenate was centrifuged (1000×g, 20 minutes) to remove tissue clumps and the supernatant was centrifuges (100,000×g, 60 minutes) to yield a pellet. The pellet was resuspended in buffer (50 mm TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at −80° C. until use.

(b) $^3$H-Bradykinin binding to the membrane

The frozen crude membrane suspension was thawed. In binding assays, $^3$H-Bradykinin (0.06 nM) and drug (1×10$^-$$^6$M) were incubated with 50 µl of the membrane suspension at room temperature for 60 minutes in a final volume of 250 µl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 µM Bradykinin. The radioactivity retained on rinsed filters was determined by a liquid-scintillation counter.

| Test Compound (Example No.) | Inhibition % of $^3$H-Bradykinin binding (concentration: 1 × 10$^{-6}$M) |
|---|---|
| 29-(36) | 98 |
| 34-(7) | 100 |
| 35-(3) | 99 |
| 41-(12) | 95 |
| 41-(53) | 99 |
| 41-(64) | 95 |
| 57 (hydrochloride) | 99 |
| 58-(11) (dihydrochloride) | 99 |

The effects of the compound [I] on bradykinin-induced bronchoconstriction and carrageenin-induced paw edema were measured according to similar manners described in British Journal of Pharmacology, 102, 774–777 (1991).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral such as intravenous, intramascular, subcutaneous or intraarticular, external such as topical, enteral, intrarectal, transvaginal, inhalant, ophthalmic, nasal or hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

The following Preparations and Examples are given for the purpose of illustrating this invention.

PREPARATION 1

2,6-Dichloro-3-(phthalimidoacetyl)aminotoluene was obtained according to a similar manner to that of Example 5 mentioned below. mp: 245–246° C.

NMR (CDCl$_3$, δ): 2.48 (3H, s), 4.59 (2H, s), 7.27 (1H, d, J=9 Hz), 7.70–7.96 (4H), 8.00 (1H, br s), 8.12 (1H, d, J=9 Hz)

PREPARATION 2

2,6-Dichloro-3-[N-(phthalimidoacetyl)-N-methylamino] toluene was obtained according to a similar manner to that of Example 7 mentioned below. mp: 193–194° C.

NMR (CDCl$_3$, δ): 2.58 (3H, s), 3.21 (3H, s), 4.10 (2H, s), 7.30 (1H, d, J=9 Hz), 7.42 (1H, d, J=9 Hz), 7.65–7.91 (4H)

PREPARATION 3

A mixture of 2,6-dichloro-3-[N-(phthalimidoacetyl)-N-methylamino]toluene (303 mg), N-bromosuccinimide (150 mg), 2,2'-azobis-(2,4-dimethyl-4-methoxyvaleronitrile) (30 mg) and dichloromethane (6 ml) was heated under reflux for 5 hours. N-Bromosuccinimide (75 mg) was added therein and the mixture was heated under reflux for additional 3 hours. The reaction mixture was washed with saturated sodium bicarbonate solution twice and brine, dried over magnesium sulfate and evaporated in vacuo. The residue was crystallized from diethyl ether to give 3-bromomethyl-2,4-dichloro-N-methyl-N-(phthalimidoacetyl)aniline (102 mg) as crystals. mp: 211° C. (dec.)

NMR (CDCl$_3$, δ): 3.24 (3H, s), 4.09 (2H, s), 4.81 (2H, s), 7.44 (1H, d, J=9 Hz), 7.51 (1H, d, J=9 Hz), 7.68–7.91 (4H)

PREPARATION 4

A mixture of o-anisidine (15.11 g), ethyl propionylacetate (17.69 g) and acetic acid (0.5 ml) in benzene (30 ml) was refluxed removing water for 24 hours. The solvent was removed in vacuo, and the residue was dissolved in toluene (30 ml). The reaction mixture was refluxed for an additional 8 hours. The solvent was removed in vacuo. The residue was purified by column chromatography (hexane—ethyl acetate) to give ethyl 3-(2-methoxyanilino)-2-pentenoate (15.11 g) as an oil.

NMR (CDCl$_3$, δ): 1.06 (3H, t, J=7 Hz), 1.30 (3H, t, J=7 Hz), 2.32 (2H, q, J=7 Hz), 3.85 (3H, s), 4.18 (2H, q, J=7 Hz), 4.74 (1H, s), 6.83–6.98 (2H), 7.06–7.20 (2H), 10.18 (1H, br s)

PREPARATION 5

To a mixture of diphenyl ether (30 ml) and biphenyl (30 g) was added ethyl 3-(2-methoxyanilino)-2-pentenoate (15.1 g) during which time the internal temperature was maintained 230–235° C. The mixture was stirred at 235° C. for 1 hour. To the reaction mixture was added hexane (150 ml). The precipitate was collected by vacuum filtration and washed with hexane to give 2-ethyl-4-hydroxy-8-methoxyquinoline (10.37 g) as crystals. mp: 190–92° C.

NMR (CDCl$_3$, δ): 1.38 (3H, t, J=7 Hz), 2.70 (2H, q, J=7 Hz), 4.00 (3H, s), 6.20 (1H, d, J=1 Hz), 7.02 (1H, dd, J=9, 1 Hz), 7.23 (1H, t, J=9 Hz), 7.90 (1H, d, J=9 Hz), 8.52 (1H, br s)

PREPARATION 6

To a solution of 2-ethyl-4-hydroxy-8-methoxyquinoline (9.96 g) in phosphoryl chloride (30 ml) was added N,N-dimethylaniline (12.44 ml) below 8° C. in an ice bath. After 10 minutes the mixture was stirred at ambient temperature for 1.5 hours. The solvent was removed in vacuo. The residue was partitioned into dichloromethane and saturated sodium bicarbonate solution. The organic layer was washed with brine and dried over magnesium sulfate. The organic layer was evaporated in vacuo. The residue was purified by column chromatography (hexane—ethyl acetate) and recrystallized from hexane to give 4-chloro-2-ethyl-8-methoxyquinoline (8.90 g) as crystals. mp: 80–81° C.

NMR (CDCl$_3$, δ): 1.40 (3H, t, J=7 Hz), 3.08 (2H, q, J=7 Hz), 4.09 (3H, s), 7.10 (1H, d, J=9 Hz), 7.43–7.54 (2H), 7.78 (1H, d, J=9 Hz)

PREPARATION 7

A solution of 4-chloro-2-ethyl-8-methoxyquinoline (4.0 g) in 48% hydrobromic acid (80 ml) was refluxed for 2 days. The mixture was adjusted to pH 12 with 28% ammonia solution. The precipitate was collected by vacuum filtration, and was washed with water and hexane to give 4-chloro-2-ethyl-8-hydroxyguinoline (3.13 g) as crystals. mp: 45–47° C.

NMR (CDCl$_3$, δ): 1.40 (3H, t, J=7 Hz), 2.98 (2H, q, J=7 Hz), 7.19 (1H, d, J=9 Hz), 7.39–7.66 (3H)

PREPARATION 8

To the solution of piperazine (3 g) in dichloromethane (30 ml) was addedmethyl isocyanate (2.16 ml) in an ice water bath with stirring. After 10 minutes the mixture was stirred at ambient temperature for 1 hour. The reaction mixture was evaporated in vacuo. The residue was diluted with acetonitrile (15 ml) and crystals were filtered off. The filtrate was evaporated in vacuo. To the residue was added xylene and the solvent was azeotropically removed in vacuo to give N-methyl-1-piperazinecarboxamide (2.43 g) as an oil.

NMR (CDCl$_3$-CD$_3$OD, δ): 2.80 (3H, s), 2.83–2.93 (4H), 3.32–3.44 (4H)

PREPARATION 9

Dimethylamine (50% aqueous solution, 3.6 ml) was stirred in an ice bath and a solution of 3-nitrobenzoyl chloride (1.8 g) in 1,4-dioxan (4 ml) was dropwise added thereto. The resulting mixture was stirred vigorously at ambient temperature for 2.5 hours. Ethyl acetate was added and organic layer was washed with water, 1N hydrochloric acid, 1N sodium hydroxide, water and saturated sodium chloride solution successively and dried over anhydrous magnesium sulfate. After filtration and concentration, the residue was recrystallized from benzene-n-hexane to afford N,N-dimethyl-3-nitrobenzamide (1.5 g) as a pale yellow prism. mp: 84.7–87.7° C.

NMR (CDCl$_3$, δ): 3.00 (3H, s), 3.15 (3H, s), 7.61 (1H, t, J=7.5 Hz), 7.78 (1H, d, J=7.5 Hz), 8.22–8.35 (2H, m)

PREPARATION 10

To a stirred solution of 2-methoxyethylamine (0.9 ml) in dichloromethane (20 ml) was added triethylamine (2.1 ml), and the mixture was cooled in an ice-cooling bath. A solution of 3-nitrobenzoyl chloride (1.8 g) in dichloromethane (10 ml) was dropwise added thereto and the resulting mixture was stirred for 1.5 hours at the same temperature. The mixture was washed with water and saturated sodium chloride solution, dried over anhydrous magnesium sulfate. After filtration, the solvent was removed in vacuo to afford N-(2-methoxyethyl)-3-nitrobenzamide (2.7 g) as a yellow oil.

NMR (CDCl$_3$, δ): 3.41 (3H, s), 3.53–3.63 (2H, m), 3.63–3.76 (2H, m), 6.62 (1H, br s), 7.65 (1H, dt, J=8 and 0.5 Hz), 8.16(1H, dt, J=8, 0.5 Hz), 8.38 (1H, dt, J=8, 0.5 Hz), 8.61 (1H, m)

PREPARATION 11

To a stirred two-phase solution of 3-nitrobenzoyl chloride (9.3 g) in a mixture of diethyl ether (50 ml) and saturated sodium bicarbonate solution (50 ml) was added 3-aminomethylpyridine (5.4 g) in an ice-cooled bath. The mixture was stirred vigorously at ambient temperature for 30 minutes. The reaction mixture was filtered, and the resulting solid was washed with water. The solid was further solidified with diisopropyl alcohol-water to afford 3-nitro-N-(3-pyridylmethyl)benzamide (5.91 g) as a pale yellow amorphous solid.

NMR (CDCl$_3$, δ): 4.70 (2H, d, J=5 Hz), 7.05 (1H, br s), 7.30 (1H, dd, J=7, 5 Hz), 7.68 (1H, t, J=9 Hz), 7.76 (1H, dt, J=8, 0.5 Hz), 8.22 (1H, d, J=8 Hz), 8.39 (1H, m), 8.54 (1H, dd, J=5, 0.5 Hz), 8.60 (1H, d, J=0.5 Hz), 8.65 (1H, t, J=0.5 Hz)

PREPARATION 12

The following compounds were obtained according to similar manners to those of Preparation 9 to 11.

(1) N-Methyl-3-nitro-N-(2-pyridyl)benzamide mp: 79–82° C.

NMR (CDCl$_3$, δ): 3.61 (3H, s), 6.92 (1H, d, J=9 Hz), 7.10 (1H, dd, J=7, 5 Hz), 7.41 (1H, dt, J=1, 7 Hz), 7.56 (1H, dt, J=1, 7 Hz), 7.67 (1H, dt, J=7,1 Hz), 8.11–8.21 (2H), 8.41 (1H, dt, J=5, 1 Hz)

(2) 3-Nitro-N-(4-pyridyl)benzamide mp: >250° C.

NMR (DMSO-d$_6$, δ): 7.80 (2H, d, J=6 Hz), 7.89 (1H, t, J=7 Hz), 8.38–8.58 (4H), 8.80 (1H, t, J=1 Hz)

(3) 4-Methyl-1-(3-nitrobenzoyl)piperazine mp: 97–98° C.

NMR (CDCl$_3$, δ): 2.31–2.66 (7H), 3.38–3.97 (4H), 7.62 (1H, dt, J=8, 1 Hz), 7.78 (1H, dt, J=1, 8 Hz), 8.25–8.34 (2H)

PREPARATION 13

To a stirred solution of 3-nitro-N-(3-pyridylmethyl)benzamide (2.00 g) in tetrahydrofuran (40 ml) was added potassium tert-butoxide (917 mg) in one portion in an ice-cooled bath. The stirring was continued for 40 minutes and then iodomethane (0.53 ml) was added thereto. The reaction mixture was stirred at 0° C. for one hour, then at ambient temperature for five hours. Saturated sodium bicarbonate solution was added thereto and the mixture was extracted with ethyl acetate. The organic layer was washed with water and saturated sodium chloride solution. After dried over anhydrous magnesium sulfate and filtered, the solvent was removed in vacuo and the residue was purified by flash chromatography (methanol-chloroform 3%, V/V) to afford 3-nitro-N-methyl-N-(3-pyridylmethyl)benzamide (1.8 g) as a yellow oil.

NMR (CDCl$_3$, δ): 2.80–3.22 (3H, m), 4.40–4.93 (2H, m), 7.30–7.42 (1H, m), 7.44–7.90 (3H, m), 8.24–8.37 (2H, m), 8.40–8.75 (2H, m)

PREPARATION 14

N-(2-Methoxyethyl)-N-methyl-3-nitrobenzamide was obtained according to a similar manner to that of Preparation 13.

NMR (CDCl$_3$, δ): 2.96–3.21 (3H, m), 3.25–3.90 (7H, m), 7.60 (1H, br t, J=8 Hz), 7.79 (1H, br d, J=8 Hz), 8.20–8.46 (2H, m)

PREPARATION 15

3-Amino-N,N-dimethylbenzamide was obtained from 3-nitro-N,N-dimethylbenzamide according to a similar manner to that of Example 3.

NMR (CDCl$_3$, δ): 2.96 (3H, br s), 3.09 (3H, br s), 3.74 (2H, br s), 6.62–6.82 (3H, m), 7.08–7.22 (1H, m)

PREPARATION 16

To a stirred solution of N-(2-methoxyethyl)-N-methyl-3-nitrobenzamide (840 mg) in ethyl acetate (8 ml) was added platinum dioxide (160 mg) and the resulting heterogeneous mixture was stirred under hydrogen atmosphere for 8 hours. The catalyst was removed by filtration and the filtrate was concentrated in vacuo. The residue was purified by flash chromatography eluting with ethyl acetate to give 3-amino-N-(2-methoxyethyl)-N-methylbenzamide (761 mg) as a brown viscous oil.

NMR (CDCl$_3$, δ): 2.90–3.17 (3H, m), 3.18–3.96 (9H, m), 6.56–6.83 (3H, m), 7.15 (1H, t, J=9 Hz)

PREPARATION 17

The following compounds were obtained according to similar manners to those of Preparations 15 or 16.

(1) 3-Amino-N-methyl-N-(3-pyridylmethyl)benzamide

NMR (CDCl$_3$, δ): 2.87 (3H, br s), 3.75 (1 or 2H, br s), 4.41–4.88 (2H, m), 6.55–6.84 (3H, m), 7.03–7.40 (2H, m), 7.42–7.84 (1H, m), 8.35–8.70 (2H, m)

(2) 3-Amino-N-methyl-N-(2-pyridyl)benzamide

NMR (CDCl$_3$, δ): 3.58 (3H, s), 3.66 (2H, br s), 6.55–6.68 (2H), 6.79 (1H, t, J=1 Hz), 6.81–7.09 (3H), 7.48 (1H, dt, J=7, 1 Hz), 8.45 (1H, d, J=5 Hz)

(3) 3-Amino-N-(4-pyridyl)benzamide mp: 232–234° C.

NMR (DMSO-d$_6$, δ): 5.39 (2H, br s), 6.79 (1H, br d, J=8 Hz), 7.02–7.11 (2H), 7.19 (1H, t, J=8 Hz), 7.78 (2H, d, J=7 Hz), 8.46 (2H, d, J=7 Hz)

(4) 1-(3-Aminobenzoyl)-4-methylpiperazine mp: 114–116° C.

NMR (CDCl$_3$, δ): 2.28–2.60 (7H), 3.38–3.90 (6H), 6.68–6.79 (3H), 7.68 (1H, t, J=8 Hz)

PREPARATION 18

To a stirred solution of 3-amino-N,N-dimethylbenzamide (1.3 g) in 1,4-dioxane(20 ml) was added 1N sodium hydroxide (23.4 ml) and phenyl chloroformate (1.5 ml) successively in an ice-cooled bath. The bath was removed and the reaction mixture was stirred vigorously for 3 hours during which time, phenyl chloroformate (0.7 ml) was further added. The mixture was extracted with ethyl acetate and the organic layer was washed with water and saturated sodium chloride solution. After dried over anhydrous magnesium sulfate and filtered, the solvent was removed in vacuo and the residual oil was purified by flash chromatography eluting with ethyl acetate—n-hexane (2:1, V/V) to give a solid, which was recrystallized from benzene—n-hexane (5:1, V/V) to afford phenyl 3-(dimethylcarbamoyl)phenylcarbamate (1.4 g) as a colorless powder. mp: 151.2–153.0° C.

NMR (CDCl$_3$, δ): 3.00 (3H, s), 3.10 (3H, s), 7.09–7.46 (6H, m), 7.49–7.65 (3H, m)

PREPARATION 19

To a stirred mixture of ethyl 3-aminobenzoate (1 g) and triethylamine (1.1 ml) in dichloromethane (10 ml) was dropwise added phenyl chloroformate (0.8 ml) in an ice-cooled bath. The ice-bath was removed and the resulting mixture was stirred at ambient temperature for 5 hours. The mixture was extracted with dichloromethane and washed with water and saturated sodium chloride. The organic layer was dried over anhydrous magnesium sulfate, filtered and concentrated in vacuo to give a pale yellow solid. The solid was purified by flash chromatography eluting with ethyl acetate—dichloromethane (1:9, V/V) to give a desired compound. Diisopropyl ether was added thereto and the resulting suspension was heated on a water-bath (90° C.) and then cooled to ambient temperature with stirring and filtered to afford phenyl 3-(ethoxycarbonyl)phenylcarbamate (0.7 g) as a colorless needle. mp: 138° C.

NMR (CDCl$_3$, δ): 1.39 (3H, t, J=7.5 Hz), 4.38 (2H, q, J=7.5 Hz), 7.04–7.33 (4H, m), 7.34–7.51 (3H, m), 7.73–7.88 (2H, m), 8.05 (1H, t, J=0.5 Hz)

PREPARATION 20

The following compounds were obtained according to similar manners to those of Preparations 18 or 19.

(1) Phenyl 3-[N-(4-pyridyl)carbamoyl]phenylcarbamate mp: 204–206° C.

NMR (DMSO-d$_6$, δ): 5.39 (1H, br s), 6.71–6.82 (2H), 7.02–7.33 (4H), 7.40–7.81 (4H), 8.09 (1H, br s), 8.41–8.51 (2H), 9.32 (1H, br s)

(2) Phenyl 3-(4-methyl-1-piperazinylcarbonyl) phenylcarbamate mp: 152–154° C.

NMR (CDCl$_3$, δ): 2.27–2.56 (7H), 3.38–3.91 (4H), 7.10–7.60 (9H)

PREPARATION 21

Benzyl 3-pyridylmethylcarbamate was obtained reacting 3-aminomethylpyridine with benzyl chloroformate according to a similar manner to that of Preparation 19. mp: 73.6–77.1° C.

NMR (CDCl$_3$, δ): 4.40 (2H, d, J=6 Hz), 5.64 (2H, s), 5.60–5.77 (1H, m), 7.19–7.45 (6H, m), 7.65 (1H, d, J=7 Hz), 8.46–8.60 (2H, m)

PREPARATION 22

Benzyl N-(2-methoxyethyl)-N-(3-pyridylmethyl) carbamate was obtained by reacting benzyl 3-pyridylmethylcarbamate with 2-methoxyethyl chloride according to a similar manner to that of Preparation 13.

NMR (CDCl$_3$, δ): 3.25–3.30 (3H, m), 3.33–3.63 (4H, m), 4.59 (2H, br s), 5.16 (2H, br s), 7.11–7.71 (7H, m), 8.49 (2H, br d, J=3 Hz)

PREPARATION 23

A mixture of benzyl N-(2-methoxyethyl)-N-(3-pyridylmethyl)carbamate (5.4 g) and 10% palladium on carbon (1.0 g) in ethanol (50 ml) was stirred under hydrogen atmosphere for 9 hours. The catalyst was removed by filtration, and the filtrate was concentrated under azeotropic condition with toluene and ethanol. The residue was dissolved in ethanol and diethyl ether was added thereto to give precipitates, which were collected by filtration to give N-(2-methoxyethyl)-N-(3-pyridylmethyl)amine (1.3 g). mp: 134–135° C.

NMR (CDCl$_3$, δ): 3.06 (2H, t, J=5 Hz), 3.39 (3H, s), 3.80 (2H, t, J=5 Hz), 4.26 (2H, s), 7.36 (1H, dd, J=8 and 5 Hz), 8.21 (1H, br d, J=8 Hz), 8.60 (1H, d, J=5 Hz), 8.74 (1H, br s)

PREPARATION 24

To a mixture of ethyl 4-aminocinnamate (300 mg), triethylamine (167 mg) and dichloromethane (3 ml) was added a solution of propionyl chloride (182 mg) in dichloromethane (1 ml) in an ice-water bath, and the mixture was stirred for 1 hour at the same temperature. To the reaction mixture was added 4 drops of N,N-dimethylpropanediamine, and the mixture was further stirred for 5 minutes. The reaction mixture was washed with water, dried over magnesium sulfate, and evaporated in vacua. The residue was crystallized from diisopropyl ether to give ethyl 4-propionamidocinnamate (341 mg) as a colorless powder. mp: 138° C.

NMR (CDCl$_3$, δ): 1.26 (3H, t, J=8 Hz), 1.34 (3H, t, J=8 Hz), 2.42 (2H, q, J=8 Hz), 4.26 (2H, q, J=8 Hz), 6.37 (1H, d, J=16 Hz), 7.21 (1H, br s), 7.49 (2H, d, J=8 Hz), 7.58 (2H, d, J=8 Hz), 7.68 (1H, d, J=16 Hz)

PREPARATION 25

To a suspension of sodium hydride (60% active, 31 mg) in dimethylformamide (1 ml) was added a solution of ethyl 4-propionamidocinnamate (160 mg) in dimethylformamide (2 ml) at ambient temperature under nitrogen atmosphere. The mixture was stirred for 1 hour at same temperature, and a solution of iodomethane (111 mg) in dimethylformamide (2 ml) was added thereto. The reaction mixture was stirred at same temperature for 2 hours, poured into water, and extracted with ethyl acetate. The organic layer was washed with water, dried over magnesium sulfate and evaporated in vacuo to give ethyl 4-(N-methylpropionamido)cinnamate (168 mg) as an oil.

NMR (CDCl$_3$, δ): 1.07 (3H, t, J=8 Hz), 1.35 (3H, t, J=8 Hz), 2.13 (2H, q, J=8 Hz), 3.27 (3H, s), 4.29 (2H, q, J=8 Hz), 6.44 (1H, d, J=16 Hz), 7.21 (2H, d, J=8 Hz), 7.57 (2H, d, J=8 Hz), 7.68 (1H, d, J=16 Hz)

PREPARATION 26

Ethyl 4-(N-ethylacetamido)cinnamate was obtained according to a similar manner to that of Preparation 25.

NMR (CDCl$_3$, δ): 1.13 (3H, t, J=7.5 Hz), 1.35 (3H, t, J=7.5 Hz), 1.86 (3H, br s), 3.77 (2H, q, J=7.5 Hz), 4.29 (2H, q, J=7.5 Hz), 6.45 (1H, d, J=16 Hz), 7.19 (2H, d, J=8 Hz), 7.58 (2H, d, J=8 Hz), 7.68 (1H, d, J=16 Hz)

PREPARATION 27

To a suspension of sodium hydride (60% active, 125 mg) in dimethylformamide (2 ml) at ambient temperature was added ethyl 4-hydroxycinnamate (250 mg) under nitrogen atmosphere, and the mixture was stirred for 1 hour. 2-Picolyl chloride hydrochloride (256 mg) was added to the mixture at the same temperature, and allowed to stand for 16 hours. The reaction mixture was poured into water, extracted with ethyl acetate. The organic layer was washed with water, dried over magnesium sulfate and evaporated in vacuo. The residue was crystallized from diisopropyl ether to give ethyl 4-(2-pyridylmethoxy)cinnamate (188 mg) as colorless powder. mp 95° C.

NMR (CDCl$_3$, δ): 1.33 (3H, t, J=7.5 Hz), 4.26 (2H, q, J=7.5 Hz), 5.22 (2H, s), 6.30 (1H, d, J=16 Hz), 7.00 (2H, d, J=8 Hz), 7.20–7.30 (1H, m), 7.42–7.56 (3H, m), 7.64 (1H, d, J=16 Hz), 7.73 (1H, td, J=8, 1 Hz), 8.61 (1H, dif-dd, J=5 Hz)

PREPARATION 28

The following compounds were obtained according to a similar manner to that of Preparation 27.

(1) Ethyl 4-[2-(N,N-dimethylamino)ethoxy]cinnamate

NMR (CDCl$_3$, δ): 1.33 (3H, t, J=7.5 Hz), 2.34 (6H, s), 2.74 (2H, t, J=6 Hz), 4.10 (2H, t, J=6 Hz), 4.26 (2H, q, J=7.5 Hz), 6.30 (1H, d, J=16 Hz), 6.92 (2H, d, J=8 Hz), 7.48 (2H, d, J=8 Hz), 7.64 (1H, d, J=16 Hz)

(2) Ethyl 4-(2-acetoxyethoky)cinnamate

NMR (CDCl$_3$, δ): 1.33 (3H, t, J=7.5 Hz), 2.11 (3H, s), 4.19 (2H, t, J=6 Hz), 4.25 (2H, q, J=7.5 Hz), 4.44 (2H, t, J=6 Hz), 6.31 (1H, d, J=16 Hz), 6.94 (2H, d, J=8 Hz), 7.49 (2H, d, J=8 Hz), 7.64 (1H, d, J=16 Hz)

PREPARATION 29

To a suspension of 4-formylbenzoic acid (1.00 g) in dry tetrahydrofuran (15 ml) was added methyl (triphenylphosphoranylidene)acetate (2.50 g) at ambient temperature under nitrogen atmosphere. The reaction mixture was stirred for 1 hour at the same temperature, poured into aqueous sodium bicarbonate solution, and washed with ethyl acetate. 1N-Hydrochloric acid was added to the aqueous layer until the layer was adjusted to pH 2. The aqueous layer was extracted with ethyl acetate. The organic layer was washed with water, dried over magnesium sulfate and evaporated in vacuo. The residue was crystallized from diisopropyl ether to give methyl 4-carboxycinnamate (1.21 g) as colorless powder. mp :243° C.

NMR (DMSO-d$_6$, δ): 3.74 (3H, s), 6.76 (1H, d, J=16 Hz), 7.73 (1H, d, J=16 Hz), 7.85 (2H, d, J=8 Hz), 7.96 (2H, d, J=8 Hz)

PREPARATION 30

To a solution of methyl 4-carboxycinnamate (160 mg) in methylene chloride was added methylamine hydrochloride (58 mg) and 1-ethyl-3-(3-dimethylaminopropyl) carbodiimide (140 mg) at ambient temperature, and the mixture was stirred for 2 hours. To this suspension was added 1-hydroxybenzotriazole (137 mg) and dimethylformamide (2 ml), and the mixture was stirred for 14 hours at same temperature. The reaction mixture was poured into water, and extracted with dichloromethane. The organic layer was washed with aqueous sodium bicarbonate solution and water, dried over magnesium sulfate, and evaporated in vacuo. The residue was crystallized from diisopropyl ether to give methyl 4-(methylcarbamoyl)cinnamate (82 mg) as a colorless powder. mp: 210.5° C.

NMR (DMSO-d$_6$, δ): 2.79 (3H, d, J=5 Hz), 3.74 (3H, s), 6.74 (1H, d, J=16 Hz), 7.69 (1H, d, J=16 Hz), 7.80 (2H, d, J=8 Hz), 7.87 (2H, d, J=8 Hz), 8.51 (1H, q-like)

PREPARATION 31

The following compounds were obtained according to a similar manner to that of Preparation 30.
(1) Methyl 4-(N,N-dimethylcarbamoyl)cinnamate mp: 130° C.

NMR (CDCl$_3$, δ): 3.00 (3H, s), 3.12 (3H, s), 3.83 (3H, s), 6.49 (1H, d, J=16 Hz), 7.45 (2H, d, J=8 Hz), 7.58 (2H, d, J=8 Hz), 7.70 (1H, d, J=16 Hz)
(2) Methyl 4-[N-(2-methoxyethyl)carbamoyl]cinnamate mp: 122–124° C.

NMR (CDCl$_3$, δ): 3.40 (3H, s), 3.53–3.72 (4H), 3.83 (3H, s), 6.45–6.60 (3H), 7.58 (2H, d, J=8 Hz), 7.71 (1H, d, J=15 Hz), 7.80 (2H, d, J=8 Hz)
(3) Methyl 4-[N,N-bis(2-methoxyethyl)carbamoyl]cinnamate NMR (CDCl$_3$, δ): 3.21–3.86 (17H), 6.48 (1H, d, J=15 Hz), 7.44 (1H, d, J=9 Hz), 7.57 (1H, d, J=9 Hz), 7.70 (1H, d, J=15 Hz)

PREPARATION 32

Ethyl 4-(3-methylureido)cinnamate was obtained by reacting ethyl 4-aminocinnamate with methyl isocyanate according to a similar manner to that of Preparation 8. mp: 166° C.

NMR (DMSO-d$_6$, δ): 1.25 (3H, t, J=7.5 Hz), 2.64 (3H, d, J=5 Hz), 4.17 (2H, q, J=7.5 Hz), 6.12 (1H, q, J=5 Hz), 6.43 (1H, d, J=16 Hz), 7.45 (2H, d, J=8 Hz), 7.56 (1H, d, J=16 Hz), 7.59 (2H, d, J=8 Hz), 8.81 (1H, s)

PREPARATION 33

To a solution of ethyl 4-propionamidocinnamate (160 mg) in ethanol (5 ml) was added 1N aqueous sodium hydroxide solution (1.5 ml) at ambient temperature. The mixture was stirred at same temperature for 14 hours, and then at 40° C. for 2 hours. 1N-hydrochloric acid (1.5 ml) was added to the reaction mixture and evaporated in vacuo. The residue was diluted with 10% methanol-dichloromethane, washed with water, dried over magnesium sulfate and evaporated in vacuo. The residue was crystallized from diisopropyl ether to give 4-propionamidocinnamic acid (115 mg) as a colorless powder. mp: 243° C.

NMR (DMSO-d$_6$, δ): 1.08 (3H, t, J=8 Hz), 2.34 (2H, q, J=8 Hz), 6.39 (1H, d, J=16 Hz), 7.51 (1H, d, J=16 Hz), 7.62 (4H, s-like), 10.07 (1H, s)

PREPARATION 34

The following compounds were obtained according to a similar manner to that of Preparation 33.
(1) 4-(N-Methylpropionamido)cinnamic acid mp: 168° C.

NMR (DMSO-d$_6$, δ): 0.93 (3H, t, J=8 Hz), 2.11 (2H, dif-q), 3.16 (3H, s), 6.55 (1H, d, J=16 Hz), 7.37 (2H, d, J=8 Hz), 7.61 (1H, d, J=16 Hz), 7.76 (2H, d, J=8 Hz)
(2) 4-(N-Ethylacetamido)cinnamic acid mp: 203.5° C.

NMR (DMSO-d$_6$, δ): 1.01 (3H, t, J=7.5 Hz), 1.78 (3H, br s), 3.67 (2H, q, J=7.5 Hz), 6.57 (1H, d, J=16 Hz), 7.33 (2H, d, J=8 Hz), 7.62 (1H, d, J=16 Hz), 7.78 (2H, d, J=8 Hz)
(3) 4-(2-Pyridylmethoxy)cinnamic acid mp: 208° C.

NMR (DMSO-d$_6$, δ): 5.23 (2H, s), 6.38 (1H, d, J=16 Hz), 7.06 (2H, d, J=8 Hz), 7.35 (1H, dd, J=8, 5 Hz), 7.51 (1H, d, J=8 Hz), 7.53 (1H, d, J=16 Hz), 7.64 (2H, d, J=8 Hz), 7.83 (1H, td, J=8, 1 Hz), 8.58 (1H, dif-dd, J=5 Hz)
(4) 4-[2-(N,N-Dimethylamino)ethoxy]cinnamic acid mp: 187° C.

NMR (DMSO-d$_6$, δ): 2.23 (6H, s), 2.66 (2H, t, J=6 Hz), 4.12 (2H, t, J=6 Hz), 6.38 (1H, d, J=16 Hz), 6.97 (2H, d, J=8 Hz), 7.51 (1H, d, J=16 Hz), 7.62 (1H, d, J=8 Hz)
(5) 4-(2-Hydroxyethoxy)cinnamic acid mp: 194° C.

NMR (DMSO-d$_6$, δ): 3.64–3.79 (2H, br peak), 4.02 (2H, t, J=6 Hz), 4.90 (1H, br peak), 6.37 (1H, d, J=16 Hz), 6.98 (2H, d, J=8 Hz), 7.54 (1H, d, J=16 Hz), 7.63 (2H, d, J=8 Hz)
(6) 4-(Methylcarbamoyl)cinnamic acid mp: >250° C.

NMR (DMSO-d$_6$, δ): 2.78 (3H, d, J=5 Hz), 6.62 (1H, d, J=16 Hz), 7.61 (1H, d, J=16 Hz), 7.77 (2H, d, J=8 Hz), 7.85 (2H, d, J=8 Hz), 8.51 (1H, q-like)
(7) 4-(N,N-Dimethylcarbamoyl)cinnamic acid mp: 82° C.

NMR (DMSO-d$_6$, δ): 2.93 (3H, s), 2.97 (3H, s), 6.59 (1H, d, J=16 Hz), 7.43 (2H, d, J=8 Hz), 7.61 (1H, d, J=16 Hz), 7.75 (2H, d, J=8 Hz)
(8) 4-(3-Methylureido)cinnamic acid mp: 234° C.

NMR (DMSO-d$_6$, δ): 2.64 (3H, d, J=5 Hz), 6.12 (1H, q, J=5 Hz), 6.33 (1H, d, J=16 Hz), 7.44 (2H, d, J=8 Hz), 7.51 (1H, d, J=16 Hz), 7.55 (2H, d, J=8 Hz), 8.78 (1H, s)
(9) 4-[N-(2-Methoxyethyl)carbambyl]cinnamic acid mp: 207–209° C.

NMR (DMSO-d$_6$, δ): 3.20–3.50 (7H), 6.63 (1H, d, J=15 Hz), 7.62 (1H, d, J=15 Hz), 7.79 (2H, d, J=8 Hz), 7.89 (2H, d, J=8 Hz), 8.61 (1H, br s)
(10) 4-[N,N-Bis(2-methoxyethyl)carbamoyl]cinnamic acid NMR (CDCl$_3$, δ): 3.21–3.86 (17H), 6.48 (1H, d, J=15 Hz), 7.44 (2H, d, J=9 Hz), 7.57 (2H, d, J=9 Hz), 7.70 (1H, d, J=15 Hz)

PREPARATION 35

To a solution of ethyl 4-aminocinnamate (150 mg) and triethylamine (94 mg) in methylene chloride (3 ml) was added mesyl chloride (0.08 ml) under ice-cooling under nitrogen atmosphere, and the mixture was stirred at ambient temperature for 2 hours. The reaction mixture was poured into water, and extracted with methylene chloride twice. The combined organic layer was washed with water, dried over magnesium sulfate and concentrated to give a residue including ethyl 4-mesylaminocinnamate and ethyl 4-(N,N-dimesylamino)cinnamate. The residue was dissolved in ethanol, and 1N aqueous sodium hydroxide solution (1.5 ml) was added thereto at 40° C. The mixture was stirred at ambient temperature for 2 days, and 1N hydrochloric acid (1.5 ml) was added thereto. The mixture was concentrated in vacuo, and the residue was partitioned between 10% methanol-methylene chloride and water. The organic layer was washed with water, dried over magnesium sulfate and concentrated in vacuo. The residue was purified by preparative thin-layer chromatography (methylene chloride—methanol, 10:1, V/V) to give 4-mesylaminocinnamic acid (49.3 mg). mp: 218° C.

NMR (DMSO-d$_6$, δ): 3.05 (3H, s), 6.44 (1H, d, J=16 Hz), 7.21 (2H, d, J=8 Hz), 7.53 (1H, d, J=16 Hz), 7.66 (2H, d, J=8 Hz)

PREPARATION 36

To a solution of N-methylethanolamine (600 mg), in N,N-dimethylformamide were added imidazole (1.13 g) and tert-butyldiphenylsilyl chloride (2.20 g) at ambient temperature with stirring. After 8 hours, the mixture was diluted with water (60 ml) and was extracted with ethyl acetate (20 ml) twice. The organic layer was washed with water three times and brine, dried over magnesium sulfate. The solvent was removed in vacuo. The residue was purified by column chromatography eluting with dichloromethane-methanol to give N-(2-tert-butyldiphenylsilyloxyethyl)-N-methylamine (780 mg) as an oil.

NMR (CDCl$_3$, δ): 1.06 (9H, s), 2.45 (3H, s), 2.72 (2H, t, J=5 Hz), 3.78 (2H, t, J=5 Hz), 7.32–7.49 (6H), 7.61–7.71 (4H)

PREPARATION 37

A mixture of 4-chloro-8-(2,6-dichloro-3-nitrobenzyloxy)-2-methylquinoline (200 mg) and N,N-dimethylformamide (3 ml) was heated under reflux for 18 hours. The reaction mixture was partitioned into ethyl acetate and saturated aqueous solution of sodium bicarbonate. The organic layer was washed with water, dried over magnesium sulfate and evaporated in vacuo. The residue was purified by preparative thin-layer chromatography (dichloromethane-methanol) to give 8-hydroxy-2-methyl-4-dimethylaminoquinoline (26 mg) as a brownish powder.

NMR (CDCl$_3$, δ): 2.62 (3H, s), 3.03 (6H, s), 5.29 (1H, br s), 6.63 (1H, s), 7.07 (1H, d, J=8 Hz), 7.28 (1H, t, J=8 Hz), 7.46 (1H, d, J=8 Hz)

PREPARATION 38

To a stirred solution of 3,4-dimethoxybenzyl alcohol (1.68 g) in 1,3-dimethyl-2-imidazolidinone (10 ml) was added sodium hydride (60% in oil, 400 mg) portionwise in an ice-water bath under a nitrogen atmosphere. The mixture was stirred for 30 minutes and then 4-chloro-8-hydroxy-2-methylguinoline (770 mg) was added thereto. The reaction mixture was stirred at 150° C. for 3 hours and cooled to ambient temperature followed by partition into ethyl acetate and water. The organic layer was washed with water twice, dried over magnesium sulfate and evaporated in vacuo. The residue was washed with diethyl ether to give a pale yellow powder (812 mg) of 8-hydroxy-4-(3,4-dimethoxybenzyloxy)-2-methylquinoline. mp: 129–131°0 C.

NMR (CDCl$_3$, δ): 2.67 (3H, s), 3.91 (6H, s), 5.20 (2H, s), 6.71 (1H, s), 6.91 (1H, d, J=8 Hz), 7.02 (1H, s), 7.06 (1H, d, J=8 Hz), 7.12 (1H, d, J=8 Hz), 7.32 (1H, t, J=8 Hz), 7.60 (1H, d, J=8 Hz)

PREPARATION 39

A mixture of 4-chloro-8-hydroxy-2-methylguinoline (9 g), 1,3-dimethyl-2-imidazolidinone (100 ml) and 28% solution of sodium methoxide in methanol (135 ml) was stirred at 150° C. for 4 hours. The reaction mixture was cooled to ambient temperature followed by partition into ethyl acetate and water. The organic layer was washed with water and brine, dried over magnesium sulfate and concentrated in vacuo. The crystalline residue was washed with n-hexane to give 8-hydroxy-4-methoxy-2-methylquinoline (5.57 g). mp: 110.5–112° C.

NMR (CDCl$_3$, δ): 2.67 (3H, s), 4.01 (3H, s), 6.63 (1H, s), 7.11 (1H, d, J=8 Hz), 7.31 (1H, t, J=8 Hz), 7.56 (1H, d, J=8 Hz)

PREPARATION 40

The following compounds were obtained according to similar manners to those of Preparations 38 or 39.

(1) 4-Ethoxy-8-hydroxy-2-methylquinoline mp: 85–86° C.

NMR (CDCl$_3$, δ): 1.56 (3H, t, J=6 Hz), 2.66 (3H, s), 4.23 (2H, q, J=6 Hz), 6.60 (1H, s), 7.10 (1H, d, J=8 Hz), 7.31 (1H, t, J=8 Hz), 7.60 (1H, d, J=8 Hz)

(2) 8-Hydroxy-2-methyl-4-methylthioquinoline mp: 98–99° C.

NMR (CDCl$_3$, δ): 2.60 (3H, s), 2.70 (3H, s), 7.00 (1H, s), 7.13 (1H, d, J=8 Hz), 7.38 (1H, t, J=8 Hz), 7.50 (1H, d, J=8 Hz)

(3) 8-Hydroxy-4-(2-methoxyethoxy)-2-methylquinoline

NMR (CDCl$_3$, δ): 2.40 (3H, s), 3.52 (3H, s), 3.91 (2H, t, J=6 Hz), 4.32 (2H, t, J=6 Hz), 6.64 (1H, s), 7.12 (1H, d, J=8 Hz), 7.32 (1H, t, J=8 Hz), 7.62 (1H, d, J=8 Hz)

(4) 8-Hydroxy-2-methyl-4-(2-dimethylaminoethoxy) quinoline mp: 94–96° C.

NMR (CDCl$_3$, δ): 2.40 (6H, s), 2.67 (3H, s), 2.91 (2H, t, J=6 Hz), 4.29 (2H, t, J=6 Hz), 6.63 (1H, s), 7.12 (1H, d, J=8 Hz), 7.31 (1H, t, J=8 Hz), 7.59 (1H, d, J=8 Hz)

PREPARATION 41

8-Hydroxy-2-methoxyguinoline was obtained reacting 2-chloro-8-hydroxyquinoline with sodium methoxide according to a similar manner to that of Preparation 39. mp: 40–41° C.

NMR (CDCl$_3$, δ): 4.09 (3H, s), 6.94 (1H, d, J=8 Hz), 7.17 (1H, dd, J=8, 3 Hz), 7.20–7.36 (2H), 7.60 (1H, s), 8.00 (1H, d, J=8 Hz)

EXAMPLE 1

To a mixture of sodium hydride (40% in oil, 24 mg) and N,N-dimethylformamide (1 ml) was added 8-hydroxy-2-methylquinoline (80 mg) in an ice-water bath. The mixture was stirred for 30 minutes at the same temperature and then 2,6-dichlorobenzyl bromide (120 mg) was added therein. The reaction mixture was stirred at ambient temperature for 1 hour. To this mixture was added water (0.5 ml) in an ice-water bath. The precipitates were corrected by vacuum filtration and washed with water (3 ml) to give 8-(2,6-dichlorobenzyloxy)-2-methylquinoline (117 mg) as a white powder.

NMR (CDCl$_3$, δ): 2.76 (3H, s), 5.62 (2H, s), 7.18–7.47 (7H), 8.01 (1H, d, J=8 Hz)

EXAMPLE 2

The following compounds were obtained according to a similar manner to that of Example 1.

(1) 8-(2,6-Dichloro-3-nitrobenzyloxy)-2-methylquinoline

NMR (CDCl$_3$, δ): 2.76 (3H, s), 5.70 (2H, s), 7.21–7.57 (5H), 7.76 (1H, d, J=8 Hz), 8.02 (1H, d, J=8 Hz)

(2) 4-Chloro-8-(2,6-dichloro-3-nitrobenzyloxy)-2-methylquinoline

NMR (CDCl$_3$, δ): 2.70 (3H, s), 5.67 (2H, s), 7.23–7.92 (6H)

(3) 2-Ethyl-4-chloro-8-[2,6-dichloro-3-[N-methyl-N-(phthalimidoacetyl)amino]benzyloxy]quinoline mp: 109–110° C.

NMR (CDCl$_3$, δ): 1.40 (3H, t, J=7 Hz), 3.00 (2H, q, J=7 Hz), 3.24 (3H, s), 4.04 (2H, s), 5.72 (2H, s), 7.31–7.58 (5H), 7.69–7.91 (5H)

(4) 2-Ethyl-8-[2,6-dichloro-3-[N-methyl-N-(phthalimidoacetyl)amino]benzyloxy]quinoline mp: 115–116° C.

NMR (CDCl$_3$, δ): 1.40 (3H, t, J=7 Hz), 3.01 (2H, q, J=7 Hz), 3.22 (3H, s), 4.04 (2H, s), 5.78 (2H, s), 7.25–7.59 (6H), 7.70–7.91 (4H), 8.06 (1H, d, J=9 Hz)

EXAMPLE 3

To a mixture of 8-(2,6-dichloro-3-nitrobenzyloxy)-2-methylquinoline (1.0 g), concentrated hydrochloric acid (5.2 ml) and methanol (5.2 ml) was added iron powder (666 mg). The mixture was heated under reflux for 2 hours and stirred in an ice-water bath for 1 hour. The precipitate was collected by vacuum filtration and washed with 1N hydrochloric acid and water to give 8-(3-amino-2,6-dichlorobenzyloxy)-2-methylquinoline dihydrochloride (635 mg) as a brownish powder.

NMR (DMSO-d$_6$, δ): 2.93 (3H, s), 5.50 (2H, s), 6.98 (1H, d, J=8 Hz), 7.23 (1H, d, J=8 Hz), 7.80–8.02 (4H), 9.03 (1H, d, J=8 Hz)

EXAMPLE 4

8-(3-Amino-2,6-dichlorobenzyloxy)-4-chloro-2-methylquinoline dihydrochloride was obtained according to a similar manner to that of Example 3.

NMR (DMSO-d$_6$, δ): 2.61 (3H, s), 5.30–5.45 (2H), 6.80–7.26 (2H), 7.50–7.95 (4H)

EXAMPLE 5

To a mixture of 8-(3-amino-2,6-dichlorobenzyloxy)-2-methylquinoline dihydrochloride (4.06 g), 4-dimethylaminopyridine (120 mg), N-methylpyrrolidone (30 ml) and pyridine (10 ml) was added phthalimidoacetyl chloride (3.35 g) at ambient temperature. The mixture was stirred at 50° C. for 1.5 hours and cooled in an ice-water bath. Water (40 ml) was added therein and the mixture was stirred for 30 minutes in an ice water bath. The precipitate was collected by vacuum filtration and washed with water and ethyl acetate to give 8-[2,6-dichloro-3-(phthalimidoacetylamino)benzyloxy]-2-methylguinoline (4.45 g) as a yellowish powder.

NMR (CDCl$_3$, δ): 2.86 (3H, s), 4.74 (2H, s), 5.51 (2H, s), 7.20–7.50 (5H), 7.63–7.93 (4H), 8.03 (1H, d, J=8 Hz), 8.29 (1H, d, J=8 Hz)

EXAMPLE 6

4-Chloro-8-[2,6-dichloro-3-(phthalimidoacetylamino)benzyloxy]-2-methylquinoline was obtained according to a similar manner to that of Example 5.

NMR (DMSO-d$_6$, δ): 2.60 (3H, s), 4.56 (2H, s), 5.48 (2H, s), 7.48–8.02 (10H)

EXAMPLE 7

To a mixture of 8-[2,6-dichloro-3-(phthalimidoacetylamino)benzyloxy]-2-methylquinoline (4.44 g) and N,N-dimethylformamide (44 ml) was added sodium hydride (60% in oil, 375 mg) in an ice-water bath. After stirring for 30 minutes in an ice-water bath, methyl iodide (0.6 ml) was added thereto and the mixture was stirred at ambient temperature for 1 hour. To this mixture was added water (88 ml) in an ice-water bath and the mixture was stirred at the same temperature for 1.5 hours. The precipitate was collected by vacuum filtration and washed with water and methanol to give 8-[2,6-dichloro-3-[N-(phthalimidoacetyl)-N-methylamino]benzyloxy]-2-methylquinoline (3.99 g) as a yellow powder.

NMR (CDCl$_3$, δ): 2.76 (3H, s), 3.23 (3H, s), 4.08 (2H, s), 5.68 (1H, d, J=12 Hz), 5.75 (1H, d, J=12 Hz), 7.24–7.59 (6H), 7.66–7.91 (4H), 8.03 (1H, d, J=8 Hz)

EXAMPLE 8

4-Chloro-8-[2,6-dichloro-3-[N-(phthalimidoacetyl)-N-methylamino]benzyloxy]-2-methylquinoline was obtained according to a similar manner to that of Example 7.

NMR (CDCl$_3$, δ): 2.72 (3H, s), 3.23 (3H, s), 4.06 (2H, s), 5.66 (1H, d, J=12 Hz); 5.73 (1H, d, J=12 Hz), 7.30–7.92 (10H)

EXAMPLE 9

A mixture of 8-[2,6-dichloro-3-[N-(phthalimidoacetyl)-N-methylamino]benzyloxy]-2-methylquinoline (3.98 g), hydrazine monohydrate (0.72 ml) and ethanol (40 ml) was heated under reflux for 1 hour. The precipitate was removed by vacuum filtration and the filtrate was evaporated in vacuo. The residue was dissolved with dichloromethane and the precipitate was removed by vacuum filtration. The filtrate was evaporated in vacuo to give 8-[3-(N-glycyl-N-methylamino)-2,6-dichlorobenzyloxy]-2-methylquinoline (2.99 g) as a yellow amorphous powder.

NMR (CDCl$_3$, δ): 2.76 (3H, s), 2.96 (1H, d, J=16 Hz), 3.10 (1H, d, J=16 Hz), 3.21 (3H, s), 5.66 (2H, s), 7.20–7.50 (6H), 8.02 (1H, d, J=8 Hz)

EXAMPLE 10

The following compounds were obtained according to a similar manner to that of Example 9.

(1) 8-[3-(N-Glycyl-N-methylamino)-2,6-dichlorobenzyloxy]-4-chloro-2-methylquinoline NMR (CDCl$_3$, δ): 2.72 (3H, s), 2.96 (1H, d, J=16 Hz), 3.15 (1H, d, J=16 Hz), 3.21 (3H, s), 5.63 (2H, s), 7.22–7.55 (5H), 7.88 (1H, d, J=8 Hz)

(2) 8-[3-(N-Glycyl-N-methylamino)-2,6-dichlorobenzyloxy]-4-chloro-2-ethylquinoline mp: 161–164° C.

NMR (CDCl$_3$, δ): 1.40 (3H, t, J=7 Hz), 2.89–3.09 (4H), 3.20 (3H, s), 5.70 (2H, s), 7.19–7.52 (5H), 7.88 (1H, t, J=9 Hz)

(3) 8-[3-(N-Glycyl-N-methylamino)-2,6-dichlorobenzyloxy]-2-ethylguinoline mp: 125–128° C.

NMR (CDCl$_3$, δ): 1.40 (3H, t, J=7 Hz), 2.89–3.14 (4H), 3.20 (3H, s), 5.71 (2H, s), 7.20–7.51 (6H), 8.06 (1H, d, J=9 Hz)

EXAMPLE 11

To a solution of 8-[3-(N-glycyl-N-methylamino)-2,6-dichlorobenzyloxy]-2-methylguinoline (100 mg) in dichloromethane (2 ml) was added ethyl isocyanate (0.04 ml) in an ice-water bath. The mixture was stirred at the same temperature for 30 minutes and then evaporated in vacuo. The residue was purified by preparative thin layer chromatography (ethyl acetate-methanol) to give 8-[2,6-dichloro-3-[N-(N'-ethylureidoacetyl)-N-methylamino]benzyloxy]-2-methylquinoline (115 mg) as a white amorphous powder.

NMR (CDCl$_3$, δ): 1.02 (3H, t, J=7 Hz), 2.69 (3H, s), 3.10 (2H, m), 3.23 (3H, s), 3.82 (2H, t, J=4 Hz), 5.18 (1H, m), 5.52 (1H, d, J=12 Hz), 5.68 (1H, d, J=12 Hz), 7.20–7.50 (6H), 8.04 (1H, d, J=8 Hz)

EXAMPLE 12

To a stirred solution of N,N'-carbonyldiimidazole (78.2 mg) in 1,4-dioxane (1 ml) was added a solution of 3-acetamidoaniline (72 mg) in 1,4-dioxane (2 ml) at ambient temperature and the solution was stirred at the same temperature for 21 hours. 8-[2,6-Dichloro-3-(N-glycyl-N-methylamino)benzyloxy]-2-methylquinoline (150 mg) was added thereto at ambient temperature and the resulting mixture was heated at 110° C. for 6.5 hours. Dimethylsulfoxide (0.5 ml) was added thereto and the resulting solution was stirred at 110° C. for 5 hours. After cooling, the mixture was concentrated in vacuo and the residue was purified by preparative thin-layer chromatography (methanol-chloroform, 10%, V/V) to afford 8-[2,6-dichloro-3-[N-[N'-(3-acetamidophenyl)ureidoacetyl]N-methylamino]benzyloxy]-2-methylguinoline (75 mg) as a pale yellow amorphous solid.

NMR (CDCl$_3$, δ): 1.99 (3H, s), 2.62 (3H, s), 3.16 (3H, s), 3.79 (1H, dd, J=20, 4 Hz), 3.91 (1H, dd, J=20, 5 Hz), 5.22 (2H, s), 6.07 (1H, br t), 6.93–7.13 (2H, m), 7.16–7.37 (5H, m), 7.39–7.56 (3H, m), 8.06 (1H, d, J=9 Hz), 8.40 (1H, br s), 9.00 (1H, br s)

EXAMPLE 13

To a stirred mixture of 8-[3-(N-glycyl-N-methylamino)-2,6-dichlorobenzyloxy]-2-methylguinoline (100 mg) and triethylamine (68 μl) in dichloromethane (2 ml) was added 4-nitrophenyl chloroformate (55 mg) at ambient temperature and the mixture was stirred at the same temperature for 2.5 hours. The mixture was diluted with chloroform and washed with saturated sodium bicarbonate solution. After dried with magnesium sulfate, the solvent was removed in vacuo to afford a yellow amorphous solid a including 8-[2,6-dichloro-3-[N-methyl-N-(4-nitrophenoxycarbonylglycyl)amino]benzyloxy]-2-methylguinoline. This solid was dissolved in anhydrous dioxane (2 ml) and to the solution was added ethyl 3-aminobenzoate (45 mg) at ambient temperature. The mixture was stirred at 100° C. for 18 hours. After cooled and concentrated in vacuo, the residue was purified by flash chromatography eluting with ethyl acetate-hexane (2:1 then 4:1, V/V) to give 8-[2,6-dichloro-3-[N-[N'-(3-ethoxycarbonylphenyl)ureidoacetyl]-N-methylamino]benzyloxy]-2-methylquinoline (107 mg) as an amorphous solid.

NMR (CDCl$_3$, δ): 1.24 (3H, t, J=7.5 Hz), 2.60 (3H, s), 3.23 (3H, s), 3.81 (1H, dd, J=17.5, 5 Hz), 4.24 (2H, q, J=7.5 Hz), 4.34 (1H, dd, J=17.5, and 7 Hz), 5.43 (1H, d, J=10 Hz), 5.56 (1H, dd, J=7, 5 Hz), 5.62 (1H, d, J=10 Hz), 7.12–7.37 (5H, m), 7.41–7.54 (3H, m), 7.60 (1H, dt, J=7.5, 0.5 Hz), 7.82 (1H, t, J=0.5 Hz), 8.09 (1H, d, J=7.5 Hz), 8.55 (1H, br s)

EXAMPLE 14

The following compounds were obtained according to similar manners to those of Examples 11 to 13.

(1) 8-[3-[N-[N'-(3-Acetylphenyl)ureidoacetyl]-N-methylamino]-2,6-dichlorobenzyloxy]-2-methylquinoline NMR (CDCl$_3$, δ): 2.40 (3H, s), 2.62 (3H, s), 3.23 (3H, s), 3.83 (1H, dd, J=17, 4 Hz), 4.37 (1H, dd, J=17, 6 Hz), 5.47 (1H, d, J=12 Hz), 5.60 (1H, m), 5.65 (1H, d, J=12 Hz), 7.17–7.58 (9H), 7.82 (1H, t, J=1 Hz), 8.10 (1H, d, J=8 Hz), 8.71 (1H, s)

(2) 8-[3-[N-[N'-(3-Acetylphenyl)ureidoacetyl]-N-methylamino]-2,6-dichlorobenzyloxy]-4-chloro-2-methylquinoline NNR (CDCl$_3$, δ): 2.46 (3H, s), 2.62 (3H, s), 3.23 (3H, s), 3.82 (1H, dd, J=17, 4 Hz), 4.26 (1H, dd, J=17, 6 Hz), 5.49 (1H, d, J=12 Hz), 5.56 (1H, m), 5.65 (1H, d, J=12 Hz), 7.17–7.64 (9H), 7.84 (1H, t, J=1 Hz), 7.90 (1H, d, J=8 Hz), 8.32 (1H, s)

(3) 8-[3-[N-(N'-Benzoylureidoacetyl)-N-methylamino]-2,6-dichlorobenzyloxy]-2-methylquinoline mp: 220–221° C.

NMR (CDCl$_3$, δ): 2.70 (3H, s), 3.26 (3H, s), 3.70 (1H, dd, J=16, 4 Hz), 4.00 (1H, dd, J=16, 4 Hz), 5.63 (2H, s), 7.20–7.60 (9H), 7.83 (2H, d, J=8 Hz), 8.01 (1H, d, J=8 Hz), 8.87 (1H, s), 9.20 (1H, t like)

(4) 8-[2,6-Dichloro-3-[N-(N'-pentylureidoacetyl)-N-methylamino]benzyloxy]-2-methylquinoline NMR (CDCl$_3$, δ): 0.80 (3H, t, J=7.5 Hz), 1.05–1.60 (6H, m), 2.70 (3H, s), 3.07 (2H, m), 3.25 (3H, s), 3.80 (2H, d, J=5 Hz), 5.03–5.28 (2H, m), 5.53 (1H, d, J=9 Hz), 5.67 (1H, d, J=9 Hz), 7.16–7.56 (6H, m), 8.03 (1H, d, J=8 Hz)

(5) 8-[2,6-Dichloro-3-[N-[N'-[3-(N-methyl-N-acetylamino)phenyl]ureidoacetyl]-N-methylamino]benzyloxy]-2-methylquinoline NMR (CDCl$_3$, δ): 1.81 (3H, s), 2.59 (3H, s), 3.13 (3H, s), 3.23 (3H, s), 3.27 (1H, dd, J=18, 4 Hz), 4.49 (1H, dd, J=18, 7 Hz), 5.42 (1H, d, J=10 Hz), 5.45 (1H, m), 5.63 (1H, dd, J=10 Hz), 6.69 (1H, dt, J=6, 1 Hz), 7.00–7.16 (2H, m), 7.17–7.42 (5H, m), 7.43–7.56 (2H, m), 8.11 (1H, d, J=8 Hz), 8.90 (1H, br s)

(6) 8-[2,6-Dichloro-3-[N-[N'-(3-dimethylaminophenyl)ureidoacetyl]-N-methylamino]benzyloxy]-2-methylquinoline NMR (CDCl$_3$, δ): 2.66 (3H, s), 2.82 (6H, s), 3.22 (3H, s), 3.81 (1H, dd, J=17, 5 Hz), 4.05 (1H, dd, J=17, 5 Hz), 5.51 (1H, d, J=10 Hz), 5.61–5.70 (2H), 6.89 (1H, dd, J=9, 1 Hz), 6.51 (1H, d, J=9 Hz), 6.74 (1H, t, J=1 Hz), 7.05 (1H, t, J=9 Hz), 7.20–7.49 (6H), 7.56 (1H, s), 8.06 (1H, d, J=9 Hz)

(7) 8-[2,6-Dichloro-3-[N-[N'-[3-(N'-methylureido)phenyl]ureidoacetyl]-N-methylamino]benzyloxy]-2-methylquinoline NMR (CDCl$_3$—CD$_3$OD, δ): 2.63 (3H, s), 2.71 (3H, s), 3.19 (3H, s), 3.68 (1H, d, J=17 Hz), 3.89 (1H, d, J=17 Hz), 5.51 (2H, s), 6.82 (1H, d, J=7 Hz), 6.96–7.50 (9H), 8.07 (1H, d, J=9 Hz)

(9) 8-[2,6-Dichloro-3-[N-methyl-N-[N'-(3-nitrophenyl)ureidoacetyl]amino]benzyloxy]-2-methylquinoline NMR (CDCl$_3$, δ): 2.60 (3H, s), 3.22 (3H, s), 3.81 (1H, dd, J=17, 5 Hz), 4.43 (1H, dd, J=17, 8 Hz), 5.42 (1H, d, J=10 Hz), 5.56–5.69 (2H), 7.13–7.57 (8H), 7.71 (1H, dd, J=8, 1 Hz), 8.12 (1H, d, J=8 Hz), 8.20 (1H, t, J=1 Hz), 9.33 (1H, br s)

(9) 8-[3-[N-[N'-(4-Acetylphenyl)ureidoacetyl]-N-methylamino]-2,6-dichlorobenzyloxy]-2-methylquinoline NMR (CDCl$_3$, δ): 2.50 (3H, s), 2.59 (3H, s), 3.22 (3H, s), 3.80 (1H, dd, J=17, 4 Hz), 4.42 (1H, dd, J=17, 8 Hz), 5.45 (1H, d, J=10 Hz), 5.56–5.69 (2H), 7.20–7.40 (6H), 7.46–7.59 (2H), 7.73 (2H, d, J=9 Hz), 8.12 (1H, d, J=9 Hz), 9.09 (1H, s)

(10) 8-[2,6-Dichloro-3-[N-methyl-N-(N'-phenylureidoacetyl)amino]benzyloxy]-2-methylquinoline NMR (CDCl$_3$, δ): 2.62 (3H, s), 3.21 (3H, s), 3.80 (1H, dd, J=17, 5 Hz), 4.20 (1H, dd, J=17, 6 Hz), 5.48 (1H, d, J=10 Hz), 5.56–5.69 (2H), 6.91 (1H, t, J=7 Hz), 7.10–7.37 (8H), 7.48 (2H, d, J=5 Hz), 8.09 (1H, d, J=9 Hz), 8.12 (1H, s)

(11) 8-[3-[N-(N'-Benzylureidoacetyl)-N-methylamino]-2,6-dichlorobenzyloxy]-2-methylquinoline.

NMR (CDCl$_3$, δ): 2.61 (3H, s), 3.17 (3H, s), 3.81 (2H, d, J=5 Hz), 4.19 (1H, dd, J=17, 5 Hz), 4.84 (1H, dd, J=17, 5 Hz), 5.31 (1H, br t, J=5 Hz), 5.52 (1H, d, J=9 Hz), 5.60–5.73 (2H), 7.10–7.52 (11H), 8.01 (1H, d, J=9 Hz)

(12) 8-[2,6-Dichloro-3-[N-[N'-(3-ethoxycarbonylaminophenyl)ureidoacetyl]-N-methylamino]benzyloxy]-2-methylquinoline mp: 233–235° C.

NMR (CDCl$_3$—CD$_3$OD, δ): 1.30 (3H, t, J=7 Hz), 2.69 (3H, s), 3.25 (3H, s), 3.64 (1H, d, J=17 Hz), 3.90 (1H, d, J=17 Hz), 4.19 (2H, q, J=7 Hz), 5.56 (2H, s), 6.01 (1/3H, t, J=5 Hz), 6.89 (1H, d, J=8 Hz), 7.06–7.56 (9H), 7.97 (1/3H, br s), 8.09 (1H, d, J=9 Hz)

(13) 8-[2,6-Dichloro-3-[N-[N'-(1-naphthyl)ureidoacety]-N-methylamino]benzyloxy]-2-methylquinoline NMR (CDCl$_3$, δ): 2.70 (3H, s), 3.17 (3H, s), 3.68 (1H, dd, J=17, 5 Hz), 3.89 (1H, dd, J=17, 5 Hz), 5.54 (1H, d, J=10 Hz), 5.62 (1H, d, J=10 Hz), 5.93 (1H, br t, J=5 Hz), 7.12–7.52 (10H), 7.70 (2H, d, J=9 Hz), 7.83 (1H, d, J=9 Hz), 7.91–8.08 (2H)

(14) 8-[3-[N-[N'-(3-Acetylphenyl)ureidoacetyl]-N-methylamino]-2,6-dichlorobenzyloxy]-4-chloro-2-ethylquinoline NMR (CDCl$_3$, δ): 1.27 (3H, t, J=7 Hz), 2.47 (3H, s), 2.89 (2H, q, J=7 Hz), 3.24 (3H, s), 3.82 (1H, dd, J=17, 5 Hz), 4.12 (1H, dd, J=17, 6 Hz), 5.52 (1H, d, J=10 Hz), 5.61–5.72 (2H), 7.18–7.69 (8H), 7.81–7.93 (2H), 8.19 (1H, br s)

(15) 8-[3-[N-[N'-(3-Acetylphenyl)ureidoacetyl]-N-methylamino]-2,6-dichlorobenzyloxy]-2-ethylquinoline NMR (CDCl$_3$, δ): 1.21 (3H, t, J=7 Hz), 2.40 (3H, s), 2.90 (2H, q, J=7 Hz), 3.22 (3H, s), 3.82 (1H, dd, J=17, 5 Hz), 4.31 (1H, dd, J=17, 6 Hz), 5.50 (1H, d, J=10 Hz), 5.58 (1H, m), 5.69 (1H, d, J=10 Hz), 7.15–7.54 (9H), 7.82 (1H, t, J=1 Hz), 8.12 (1H, d, J=9 Hz), 8.51 (1H, s)

EXAMPLE 15

To a mixture of 8-[3-(N-glycyl-N-methylamino)-2,6-dichlorobenzyloxy]-2-methylquinoline (100 mg), triethylamine (50 mg) and dichloromethane (2.0 ml) was added heptanoyl chloride (0.05 ml) in an ice-water bath. The mixture was stirred at the same temperature for 30 minutes and washed with water. The organic layer was collected and dried over magnesium sulfate and evaporated in vacuo. The residue was purified by preparative thin layer chromatography (dichloromethane—methanol) to give 8-[2,6-dichloro-3-[N-(heptanoylglycyl)-N-methylamino]benzyloxy]-2-methylquinoline (130 mg) as a pale yellow oil.

NMR (CDCl$_3$, δ): 0.88 (3H, t, J=7 Hz), 1.20–1.40 (4H), 1.53–1.80 (4H), 2.22 (2H, t, J=7 Hz), 2.76 (3H, s), 3.26 (3H, s), 3.50 (1H, dd, J=17, 4 Hz), 3.83 (1H, dd, J=17, 6 Hz), 5.64 (2H, s), 6.41 (1H, t-like), 7.22–7.52 (6H), 8.03 (1H, d, J=8 Hz)

EXAMPLE 16

To a mixture of 8-[3-(N-glycyl-N-methylamino)-2,6-dichlorobenzyloxy]-2-methylquinoline (81 mg), 4-phenylbutyric acid (40 mg) and dimethylformamide (2 ml) were added 1-ethyl-3-(3-dimethylaminopropyl) carbodiimide hydrochloride (50 mg) and 1-hydroxybenzotriazole (41 mg). After being stirred for an hour at ambient temperature, the mixture was poured into water and extracted with ethyl acetate. The organic layer was separated, washed with water, dried over magnesium sulfate and evaporated in vacuo. The residue was purified by preparative thin-layer chromatography (dichloromethane—methanol) to give 8-[2,6-dichloro-3-[N-methyl-N-(4-phenylbutyrylglycyl)amino]benzyloxy]-2-methylquinoline (105 mg) as a colorless glass.

NMR (CDCl$_3$, δ): 1.95 (2H, m), 2.23 (2H, t, J=7 Hz), 2.64 (2H, t, J=7 Hz), 2.74 (3H, s), 3.23 (3H, s), 3.48 (1H, dd, J=18, 4 Hz), 3.82 (1H, dd, J=18, 4 Hz), 5.63 (2H, s), 6.39 (1H, t-like), 7.11–7.51 (11H), 8.03 (1H, d, J=8 Hz)

EXAMPLE 17

The following compounds were obtained according to similar manners to those of Examples 15 or 16.

(1) 8-[2,6-Dichloro-3-[N-methyl-N-(phenylacetylglycyl)amino]benzyloxy]-2-methylquinoline NMR (CDCl$_3$, δ): 2.72 (3H, s), 3.20 (3H, s), 3.43 (1H, dd, J=17, 4 Hz), 3.59 (2H, s), 3.80 (1H, dd, J=17, 5 Hz), 5.63 (2H, s), 6.38 (1H, t-like), 7.18–7.50 (11H), 8.01 (1H, d, J=8 Hz)

(2) 8-[2,6-Dichloro-3-[N-methyl-N-(3-phenylpropionylglycyl)amino]benzyloxy]-2-methylquinoline NMR (CDCl$_3$, δ): 2.53 (2H, t, J=7 Hz), 2.73 (3H, s), 2.94 (2H, t, J=7 Hz), 3.23 (3H, s), 3.46 (1H, dd, J=17, 4 Hz), 3.80 (1H, dd, J=17, 5 Hz), 5.66 (2H, s), 6.38 (1H, t-like), 7.12–7.52 (11H), 8.03 (1H, d, J=8 Hz)

(3) 8-[2,6-Dichloro-3-[N-methyl-N-(phenoxyacetylglycyl)amino]benzyloxy]-2-methylquinoline NMR (CDCl$_3$, δ): 2.73 (3H, s), 3.26 (3H, s), 3.58 (1H, dd, J=17, 4 Hz), 3.90 (1H, dd, J=17, 5 Hz), 4.50 (2H, s), 5.66 (2H, s), 6.89–7.08 (3H), 7.20–7.58 (9H), 8.03 (1H, d, J=8 Hz)

(4) 8-1 2,6-Dichloro-3-[N-methyl-N-(2-naphthoylglycyl)amino]benzyloxy]-2-methylquinoline NMR (CDCl$_3$, δ): 2.75 (3H, s), 3.30 (3H, s), 3.77 (1H, dd, J=16, 4 Hz), 4.08 (1H, dd, J=16, 5 Hz), 5.68 (2H, s), 7.23–7.63 (9H), 7.82–7.98 (4H), 8.03 (1H, d, J=8 Hz), 8.33 (1H, s)

(5) 8-[3-[N-(Cinnamoylglycyl)-N-methylamino]-2,6-dichlorobenzyloxy]-2-methylquinoline NMR (CDCl$_3$, δ): 2.73 (3H, s), 3.26 (3H, s), 3.65 (1H, dd, J=17.5, 4 Hz), 3.85 (1H, dd, J=17.5, 5 Hz), 5.65 (2H, s), 6.48 (1H, d, J=20 Hz), 6.65 (1H, br t), 7.19–7.53 (11H, m), 7.57 (1H, d, J=20 Hz), 8.02 (1H, d, J=8 Hz)

(6) 8-[2,6-Dichloro-3-[N-methyl-N-[(E)-3-(2-thienyl)acryloylglycyl]amino]benzyloxy]-2-methylquinoline NMR (CDCl$_3$, δ): 2.74 (3H, s), 3.27 (3H, s), 3.63 (1H, dd, J=16, 4 Hz), 3.94 (1H, dd, J=16, 5 Hz), 5.64 (2H, s), 6.29 (1H, d, J=15 Hz), 6.59 (1H, t-like), 7.02 (1H, dd, J=5, 4 Hz), 7.16–7.54 (8H), 7.70 (1H, d, J=15 Hz), 8.03 (1H, d, J=8 Hz)

(7) 8-[2,6-Dichloro-3-[N-methyl-N-[(E)-3-(3-thienyl)acryloylglycyl]amino]benzyloxy]-2-methylquinoline NMR (CDCl$_3$, δ): 2.72 (3H, s), 3.24 (3H, s), 3.63 (1H, dd, J=18, 4 Hz), 3.95 (1H, dd, J=18, 5 Hz), 5.63 (2H, s), 6.30 (1H, d, J=15 Hz), 6.60 (1H, t-like), 7.18–7.63 (10 H), 8.02 (1H, d, J=8 Hz)

(8) 8-[2,6-Dichloro-3-[N-methyl-N-[(E)-3-(3-pyridyl)acryloylglycyl]amino]benzyloxy]-2-methylquinoline NMR (CDCl$_3$, δ) 2.72 (3H, s), 3.27 (3H, s), 3.67 (1H, dd, J=17, 4 Hz), 3.95 (1H, dd, J=17, 5 Hz), 5.65 (2H, s), 6.57 (1H, d, J=15 Hz), 6.77 (1H, t-like), 7.21–7.64 (8H), 7.80 (1H, dt, J=8, 1 Hz), 8.03 (1H, d, J=8 Hz), 8.57 (1H, dd, J=5, 1 Hz), 8.72 (1H, d, J=1 Hz)

(9) 8-[2,6-Dichloro-3-[N-methyl-N-(phenyloxalylglycyl)amino]benzyloxy]-2-methylquinoline NMR (CDCl$_3$, δ): 2.77 (3H, s), 3.29 (3H, s), 3.63 (1H, dd, J=17, 4 Hz), 3.94 (1H, dd, J=17, 5 Hz), 5.68 (2H, s), 7.21–7.68 (9H), 7.78 (1H, t-like), 8.04 (1H, d, J=8 Hz), 8.23–8.35 (2H)

(10) 8-[2,6-Dichloro-3-[N-methyl-N-(N-phenylglycylglycyl)amino]benzyloxy]-2-methylquinoline NMR (CDCl$_3$, δ): 2.66 (3H, s), 3.20 (3H, s), 3.61 (1H, dd, J=17, 5 Hz), 3.73–3.86 (2H), 3.89 (1H, dd, J=17, 5 Hz), 4.58 (1H, t-like), 5.62 (2H, s), 6.58 (1H, d, J=8 Hz), 6.78 (1H, t, J=8 Hz), 7.11–7.53 (9H), 8.02 (1H, d, J=8 Hz)

(11) 8-[2,6-Dichloro-3-[N-methyl-N-(1-naphthylacetylglycyl)amino]benzyloxy]-2-methylquinoline NMR (CDCl$_3$, δ): 2.70 (3H, s), 3.13 (3H, s), 3.35 (1H, dd, J=16, 4 Hz), 3.74 (1H, dd, J=16, 5 Hz), 4.03 (2H, s), 5.61 (2H, s), 6.29 (1H, t-like), 7.16–7.59 (10H), 7.77–8.03 (4H)

(12) 8-[2,6-Dichloro-3-[N-methyl-N-(2-naphthylacetylglycyl)amino]benzyloxy]-2-methylquinoline NMR (CDCl$_3$, δ): 2.71 (3H, s), 3.17 (3H, s), 3.43 (1H, dd, J=16, 4 Hz), 3.73 (2H, s), 3.81 (1H, dd, J=16, 5 Hz), 5.62 (2H, s), 6.41 (1H, t-like), 7.14–7.55 (9H), 7.70–7.90 (4H), 8.00 (1H, d, J=8 Hz)

(13) 8-[2,6-Dichloro-3-[N-methyl-N-(phenoxycarbonylglycyl)amino]benzyloxy]-2-methylquinoline NMR (CDCl$_3$, δ): 2.73 (3H, s), 3.26 (3H, s), 3.52 (1H, dd, J=17, 4 Hz), 3.83 (1H, dd, J=17, 5 Hz), 5.66 (2H, s), 5.90 (1H, t-like), 7.05–7.54 (11H), 8.03 (1H, d, J=8 Hz)

(14) 8-[2,6-Dichloro-3-[N-methyl-N-(2-nitrocinnamoylglycyl)amino]benzyloxy]-2-methylquinoline NMR (CDCl$_3$, δ): 2.74 (3H, s), 3.28 (3H, s), 3.67 (1H, dd, J=16, 4 Hz), 3.95 (1H, dd, J=16, 5 Hz), 5.65 (2H, s), 6.42 (1H, d, J=15 Hz), 6.79 (1H, t-like), 7.20–7.67 (9H), 7.92–8.08 (3H)

(15) 8-[2,6-Dichloro-3-[N-methyl-N-(3-nitrocinnamoylglycylamino]benzyloxy]-2-methylquinoline NMR (CDCl$_3$, δ): 2.72 (3H, s), 3.28 (3H, s), 3.69 (1H, dd, J=16, 4 Hz), 3.97 (1H, dd, J=16, 5 Hz), 5.66 (2H, s), 6.63 (1H, d, J=15 Hz), 6.80 (1H, t-like), 7.22–7.57 (7H), 7.62 (1H, d, J=15 Hz), 7.79 (1H, d, J=8 Hz), 8.04 (1H, d, J=8 Hz), 8.20 (1H, d, J=8 Hz), 8.36 (1H, t, J=1 Hz)

(16) 8-[2,6-Dichloro-3-[N-methyl-N-(4-nitrocinnamoylglycyl)amino]benzyloxy]-2-methylquinoline NMR (CDCl$_3$, δ): 2.73 (3H, s), 3.28 (3H, s), 3.70 (1H, dd, J=16, 4 Hz), 3.97 (1H, dd, J=16, 15 Hz), 5.66 (2H, s), 6.62 (1H, d, J=15 Hz), 6.82 (1H, t-like), 7.21–7.70 (9H), 8.03 (1H, d, J=8 Hz), 8.21 (2H, d, J=8 Hz)

(17) 8-[2,6-Dichloro-3-[N-(2-methoxycinnamoylglycyl)-N-methylamino]benzyloxy]-2-methylquinoline NMR (CDCl$_3$, δ): 2.74 (3H, s), 3.27 (3H, s), 3.63 (1H, dd, J=16, 4 Hz), 3.87 (3H, s), 3.96 (1H, dd, J=16, 4 Hz), 5.65 (2H, s), 6.61 (1H, d, J=15 Hz), 6.62 (1H, t-like), 6.87–7.01 (2H), 7.21–7.55 (8H), 7.81 (1H, d, J=15 Hz), 8.03 (1H, d, J=8 Hz)

(18) 8-[2,6-Dichloro-3-[N-(3-methoxycinnamoylglycyl)-N-methylamino]benzyloxy]-2-methylquinoline NMR (CDCl$_3$, δ): 2.73 (3H, s), 3.26 (3H, s), 3.66 (1H, dd, J=16, 4 Hz), 3.81 (3H, s), 3.96 (1H, dd, J=16, 4 Hz), 5.66 (2H, s), 6.48 (1H, d, J=15 Hz), 6.67 (1H, t-like), 6.90 (1H, dd, J=8, 2 Hz), 7.10 (1H, s), 7.10 (1H, d, J=8 Hz), 7.20–7.61 (8H), 8.03 (1H, d, J=8 Hz)

(19) 8-[2,6-Dichloro-3-[N-(4-methoxycinnamoylglycyl)-N-methylamino]benzyloxy]-2-methylquinoline NMR (CDCl$_3$, δ): 2.74 (3H, s), 3.27 (3H, s), 3.64 (1H, dd, J=16, 4 Hz), 3.82 (3H, s), 3.96 (1H, dd, J=16, 5 Hz), 5.66 (2H, s), 6.36 (1H, d, J=15 Hz), 6.60 (1H, t-like), 6.83–6.94 (2H), 7.18–7.60 (9H), 8.04 (1H, d, J=8 Hz)

EXAMPLE 18

A mixture of phenylhydrazine (54 mg), N,N'-carbonyldiimidazole (81 mg) and 1,4-dioxane (3 ml) was stirred at ambient temperature for 3 days under nitrogen atmosphere. To this mixture was added 8-[3-(N-glycyl-N-methylamino)-2,6-dichlorobenzyloxy]-2-methylquinoline (121 mg). The mixture was heated under reflux for 1 hour. After being cooled to ambient temperature, the mixture was poured into water and extracted with dichloromethane. The organic layer was dried over magnesium sulfate and evaporated in vacuo. The residue was purified by preparative thin-layer chromatography (dichloromethane—methanol) to give 8-[2,6-dichloro-3-[N-methyl-N-(N'-anilinoureidoacetyl)amino]benzyloxy]-2-methylquinoline (143 mg) as an amorphous powder.

NMR (CDCl$_3$, δ): 2.60 (3H, s), 3.20 (3H, s), 3.72 (1H, dd, J=16, 5 Hz), 3.88 (1H, dd, J=16, 5 Hz), 5.62 (2H, s), 5.98 (1H, s), 6.34 (1H, t-like), 6.46 (1H, s), 6.68–7.52 (11H), 8.00 (1H, d, J=8 Hz)

EXAMPLE 19

To a solution of 8-[3-(N-glycyl-N-methylamino)-2,6-dichlorobenzyloxy]-2-methylquinoline (81 mg) and triethylamine (0.04 ml) in dichloromethane (2 ml) was added a solution of (E)-styrenesulfonyl chloride (48 mg) in dichloromethane (1 ml) in an ice-water bath. After being stirred for 30 minutes under ice-cooling, the reaction mixture was partitioned into dichloromethane and water. The organic layer was dried over magnesium sulfate and evaporated in vacua. The residue was purified by preparative thin-layer chromatography (dichloromethane—methanol) to give 8-[2,6-dichloro-3-[N-methyl-N-((E)-styrylsulfonylglycyl)amino]benzyloxy]-2-methylquinoline (78 mg) as an amorphous powder.

NMR (CDCl$_3$, δ): 2.73 (3H, s), 3.18 (3H, s), 3.38 (1H, dd, J=16, 5 Hz), 3.54 (1H, dd, J=16, 5 Hz), 5.35 (1H, t like), 5.60 (2H, s), 6.70 (1H, d, J=15 Hz), 7.11–7.52 (12H), 8.03 (1H, d, J=8 Hz)

EXAMPLE 20

To a solution of 8-[2,6-dichloro-3-[N-[N'-(3-ethoxycarbonylphenyl)ureidoacetyl]-N-methylamino]-benzyloxy]-2-methylquinoline (97 mg) in ethanol (1 ml) was added 1N sodium hydroxide solution (0.179 ml) at ambient temperature. The mixture was stirred for 3 hours at the same temperature and for 3 hours at 50° C. The reaction mixture was adjusted to pH 5 with 1N hydrochloric acid and water (1 ml) was added therein. The precipitate was collected by vacuum filtration and washed with water and acetonitrile to give 8-[3-[N-[N'-(3-carboxyphenyl)ureidoacetyl]-N-methylamino]-2,6-dichlorobenzyloxy]-2-methylquinoline (62 mg) as crystals. mp: 240–241° C.

NMR (DMSO-d$_6$, δ): 2.63 (3H, s), 3.18 (3H, s), 3.43 (1H, dd, J=17, 5 Hz), 3.69 (1H, dd, J=17, 5 Hz), 5.49 (11H, d, J=10 Hz), 5.58 (1H, d, J=10 Hz), 7.27–7.72 (8H), 7.30 (2H, s), 8.02 (1H, s), 8.29 (1H, br s), 9.09 (1H, s)

EXAMPLE 21

To a mixture of 8-[3-[N-[N'-(3-carboxyphenyl)ureidoacetyl]-N-methylamino]-2,6-dichlorobenzyloxy)-2-methylquinoline (130 mg), morpholine (22 µl) and N,N-dimethylformamide (1.5 ml) were added 1-ethyl-3-(3-dimethylaminopropyl)carbodiimide hydrochloride (58 mg) and 1-hydroxybenzotriazole (41 mg), and the mixture was stirred for 1 hour at ambient temperature. The reaction mixture was diluted with a mixture of methanol and chloroform (1:10, V/V), washed with saturated sodium bicarbonate solution and brine, dried over magnesium sulfate, and concentrated in vacuo. The residue was purified by flash chromatography (chloroform—methanol) to give 8-[2,6-dichloro-3-[N-methyl-N-[N'-[3-(morpholinocarbonyl)phenyl]ureidoacetyl]amino]benzyloxy]-2-methylquinoline (137 mg) as colorless amorphous solid.

NMR (CDCl$_3$, δ): 2.60 (3H, s), 3.20 (3H, s), 3.25–3.88 (8H, m), 3.78 (1H, dd, J=17.5, 5 Hz), 4.27 (1H, dd, J=17.5,

7 Hz), 5.44 (1H, d, J=10 Hz), 5.51–5.66 (1H, m), 5.60 (1H, d, J=10 Hz), 6.95 (1H, dt, J=7.5, 0.5 Hz), 7.16 (1H, t, J=7.5 Hz), 7.18–7.37 (6H, m), 7.44–7.54 (2H, m), 8.09 (1H, d, J=8 Hz), 8.69 (1H, br s)

EXAMPLE 22

The following compounds were obtained according to a similar manner to that of Example 21.

(1) 8-[2,6-Dichloro-3-[N-methyl-N-[N'[3-(4-methyl-1-piperazinylcarbonyl)phenyl]ureidoacetyl]amino]-benzyloxy]-2-methylquinoline NMR (CDCl$_3$, δ): 2.06–2.50 (4H, m), 2.23 (3H, s), 2.61 (3H, s), 3.21 (3H, s), 3.23–3.81 (4H, m), 3.76 (1H, dd, J=17.5, 5 Hz), 4.80 (1H, dd, J=17.5, 7 Hz), 5.45 (1H, d, J=10 Hz), 5.56 (1H, dd, J=7, 5 Hz), 5.62 (1H, d, J=10 Hz), 6.95 (1H, br d, J=7.5 Hz), 7.16 (1H, t, J=7.5 Hz), 7.18–7.39 (6H, m), 7.44–7.55 (2H, m), 8.09 (1H, d, J=8 Hz), 8.68 (1H, br s)

(2) 8-[2,6-Dichloro-3-[N-[N'-[3-(2-methoxyethylcarbamoyl)phenyl]ureidoacetyl]-N-methylamino]-benzyloxy]-2-methylquinoline NMR (CDCl$_3$, δ): 2.62 (3H, s), 3.20 (3H, s), 3.33 (3H, s), 3.45–3.66 (4H, m), 3.83 (1H, dd, J=17.5, 4 Hz), 4.11 (1H, dd, J=17.5, 6 Hz), 5.50 (1H, d, J=10 Hz), 5.65 (1H, d, J=10 Hz), 5.82 (1H, br t, J=4 Hz), 6.70 (1H, m), 7.05–7.53 (9H, m), 7.61 (1H, br s), 8.07 (1H, d, J=9 Hz), 8.55 (1H, br s)

(3) 8-[2,6-Dichloro-3-[N-[N'-[3-[N-[2-(N,N-dimethylamino)ethyl]-N-methylcarbamoyl]phenyl]ureidoacetyl]-N-methylamino]benzyloxy]-2-methylquinoline NMR (CDCl$_3$, δ): 1.73–2.58 (10H, m), 2.60 (3H, s), 2.79–3.10 (3H, m), 3.22 (3H, s), 3.58 (1H, m), 3.78 (1H, dd, J=17, 5 Hz), 4.20 (1H, m), 5.47 (1H, d, J=10 Hz), 5.63 (1H, d, J=10 Hz), 5.64 (1H, m), 6.95 (1H, d, J=6 Hz), 7.07–7.54 (6H, m), 7.99 (1H, d, J=8 Hz), 8.60 (1H, m)

(4) 8-[2,6-Dichloro-3-[N-[N'-(3-methylcarbamoylphenyl)ureidoacetyl]-N-methylamino]benzyloxy]-2-methylquinoline mp: 157–161° C. (dec.).

NMR (CDCl$_3$, δ): 2.62 (3H, s), 2.90 (3H, d, J=5 Hz), 3.20 (3H, s), 3.82 (1H, dd, J=18, 5 Hz), 4.00 (1H, dd, J=18, 5 Hz), 5.52 (1H, d, J=10 Hz), 5.64 (1H, d, J=10 Hz), 5.99 (1H, br s), 6.68 (1H, br s), 7.07–7.51 (9H, m), 7.59 (1H, br s), 8.09 (1H, d, J=9 Hz), 8.56 (1H, br s)

(5) 8-[3-[N-[N'-(3-Dimethylcarbamoylpherxyl)ureidoacetyl]-N-methylamino]-2,6-dichlorobenzyloxy]-2-methylquinoline NMR (CDCl$_{3, 6}$): 2.61 (3H, s), 2.90 (3H, br s), 3.04 (3H, br s), 3.22 (3H, s), 3.79 (1H, dd, J=18, 5 Hz), 4.20 (1H, dd, J=18, 6 Hz), 5.48 (1H, d, J=10 Hz), 5.59–5.70 (2H, m), 6.95 (1H, d, J=7 Hz), 7.09–7.51 (9H, m), 8.09 (1H, d, J=9 Hz), 8.59 (1H, s)

(6) 8-[2,6-Dichloro-3-[N-[N'-[3-(3-pyridylmethylcarbamoyl)phenyl]ureidoacetyl]-N-methylamino]-benzyloxy]-2-methylquinoline mp: 204–206° C.

NMR (CDCl$_3$—CD$_3$OD, δ): 2.66 (3H, s), 3.26 (3H, s), 3.68 (1H, d, J=17 Hz), 3.90 (1H, d, J=17 Hz), 4.60 (2H, s), 5.56 (2H, s), 7.20–7.56 (10H), 7.72–7.82 (2H), 8.09 (1H, d, J=9 Hz), 8.45 (1H, dd, J=5, 1 Hz), 8.53 (1H, d, J=1 Hz)

(7) 8-[2,6-Dichloro-3-[N-methyl-N-[N'-[3-[4-(4-pyridyl)-1-piperazinylcarbonyl)phenyl]ureidoacetyl]amino]-benzyloxy]-2-methylquinoline NMR (CDCl$_3$, δ): 2.61 (3H, s), 3.08–3.91 (12H), 4.28 (1H, dd, J=17.6 Hz), 5.46 (1H, d, J=10 Hz), 5.58–5.70 (2H), 6.61 (2H, br d, J=6 Hz), 6.99 (1H, d, J=7 Hz), 7.12–7.50 (9H), 8.08 (1H, d, J=9 Hz), 8.30 (2H, br d, J=6 Hz), 8.81 (1H, s)

(8) 8-[3-[N-[N'-[3-(4-Acetyl-1-piperazinylcarbonyl)phenyl]ureidoacetyl]-N-methylamino]-2,6-dichlorobenzyloxy]-2-methylquinoline NMR (CDCl$_3$, δ): 2.10 (3H, s), 2.60 (3H, s), 3.21 (3H, s), 3.23–3.87 (9H), 4.30 (1H, dd, J=17, 6 Hz), 5.45 (1H, d, J=10 Hz), 5.51–5.69 (2H), 6.94 (1H, d, J=8 Hz), 7.10–7.54 (9H), 8.10 (1H, d, J=9 Hz), 8.79 (1H, br s)

(9) 8-[2,6-Dichloro-3-[N-[N'-[3-(3-pyridylcarbamoyl)phenyl]ureidoacetyl]-N-methylamino]benzyloxy]-2-methylquinoline mp: 156–160° C. (broad).

NMR (CDCl$_3$, δ): 2.68 (3H, s), 3.21 (3H, s), 3.77–4.05 (2H), 5.41 (1H, d, J=10 Hz), 5.57 (1H, d, J=10 Hz), 6.39 (1H, br t, J=5 Hz), 6.96–7.52 (11H), 8.03 (1H, d, J=9 Hz), 8.32 (1H, d, J=5 Hz), 8.39–8.50 (2H), 9.01 (1H, d, J=1 Hz), 9.56 (1H, br s)

(10) 8-[2,6-Dichloro-3-[N-[N'-[3-(2-pyridylmethylcarbamoyl)phenyl]ureidoacetyl]-N-methylamino]-benzyloxy]-2-methylquinoline NMR (CDCl$_3$, δ): 2.62 (3H, s), 3.21 (3H, s), 3.81 (1H, dd, J=17, 5 Hz), 4.11 (1H, dd, J=17, 6 Hz), 4.70 (2H, d, J=5 Hz), 5.50 (1H, d, J=10 Hz), 5.65 (1H, d, J=10 Hz), 5.81 (1H, br t, J=5 Hz), 7.10–7.73 (13H), 8.06 (1H, d, J=9 Hz), 8.50 (1H, d, J=5 Hz), 8.60 (1H, s)

(11) 8-[2,6-Dichloro-3-[N-[N'-[3-(4-pyridylmethylcarbamoyl)phenyl]ureidoacetyl]-N-methylamino]-benzyloxy]-2-methylquinoline NMR (CDCl$_3$, δ): 2.61 (3H, s), 3.19 (3H, s), 3.81 (1H, dd, J=17, 5 Hz), 4.03 (1H, dd, J=17, 6 Hz), 4.52 (2H, d, J=6 Hz), 5.51 (1H, d, J=10 Hz), 5.61 (1H, d, J=10 Hz), 5.90 (1H, br t, J=5 Hz), 7.07–7.50 (12H), 7.58 (1H, s), 8.08 (1H, d, J=9 Hz), 8.50 (2H, d, J=6 Hz), 8.60 (1H, s)

(12) 8-[2,6-Dichloro-3-[N-methyl-N-[N'-[3-(1-piperazinylcarbonyl)phenyl]ureidoacetyl]amino]-benzyloxy]-2-methylquinoline NMR (CDCl$_3$, δ): 2.53–2.98 (4H, m), 2.62 (3H,s), 3.14–3.86 (5H, m), 3.78 (1H, dd, J=16, 5 Hz), 4.18 (1H, dd, J=16, 7 Hz), 5.25 (1H, d, J=10 Hz), 5.61 (1H, d, J=10 Hz), 5.71 (1H, br t, J=5 Hz), 6.94 (1H, br d, J=7.5 Hz), 7.08–7.40 (6H, m), 7.15 (1H, t, J=7.5 Hz), 7.48 (2H, d, J=5 Hz), 8.08 (1H, d, J=9 Hz), 8.70 (1H, br s)

(13) 8-[2,6-Dichloro-3-[N-methyl-N-[N'-[3-(4-phenyl-1-piperazinylcarbonyl)phenyl]ureidoacetyl]amino]-benzyloxy]-2-methylquinoline NMR (CDCl$_3$, δ): 2.60 (3H, s), 2.64–4.11 (8H, m), 3.21 (3H, s), 3.79 (1H, dd, J=17, 4 Hz), 4.30 (1H, dd, J=17, 7 Hz), 5.44 (1H, d, J=9 Hz), 5.57 (1H, m), 5.61 (1H, d, J=9 Hz), 6.81–7.05 (4H, m), 7.11–7.53 (10H, m), 8.03 (1H, d, J=9 Hz), 8.71 (1H, br s)

(14) 8-[2,6-Dichloro-3-[N-[N'-[3-(4-ethoxycarbonyl-1-piperazinylcarbonyl)phenyl]ureidoacetyl]-N-methylamino]benzyloxy]-2-methylquinoline NMR (CDCl$_3$, δ): 1.28 (3H, t, J=7.5 Hz), 2.60 (3H, s), 3.10–4.16 (8H, m), 3.79 (1H, dd, J=17.5, 7.5 Hz), 4.17 (2H, q, J=7.5 Hz), 4.31 (1H, dd, J=17.5, 7.5 Hz), 5.45 (1H, d, J=9 Hz), 5.55 (1H, dd, J=7.5, 5 Hz), 5.63 (1H, d, J=9 Hz), 6.93 (1H, d, J=7 Hz), 7.10–7.39 (6H, m), 7.40–7.56 (2H, m), 8.10 (2H, m), 8.73 (1H, br s)

(15) 8-[2,6-Dichloro-3-[N-[N'-[3-[2-(N,N-dimethylamino)ethylcarbamoyl]phenyl]ureidoacetyl]-N-methylamino]benzyloxy]-2-methylquirioline NMR (CDCl$_3$, δ): 2.40 (6H, s), 2.64 (3H, s), 2.70 (2H, t, J=7 Hz), 3.20 (3H, s), 3.37–3.69 (3H, m), 3.80 (1H, dd, J=16, 4 Hz), 4.04 (1H, dd, J=16, and 6 Hz), 5.50 (1H, d, J=10 Hz), 5.64 (1H, d, J=10 Hz), 5.87 (1H, br t, J=5 Hz), 7.15 (1H, t, J=7.5 Hz), 7.20–7.50 (8H, m), 7.66 (1H, br s), 8.06 (1H, d, J=9 Hz), 8.64 (1H, br s)

EXAMPLE 23

To a mixture of 8-[3-(N-glycyl-N-methylamino)-2,6-dichlorobenzyloxy]-2-methylquinoline (150 ml), triethylamine (0.077 ml) and dichloromethane (1.5 ml) was added bromoacetyl chloride (0.034 ml) in a dry ice-acetone bath. After 30 minutes, to the mixture was added N-methyl-N-cycloheptylamine (236 mg). The mixture was stirred for 3 hours at ambient temperature. The reaction mixture was washed with aqueous sodium bicarbonate solution, water and brine. The organic layer was dried over magnesium sulfate and evaporated in vacuo. The residue was purified .by a silica gel column chromatography (dichloromethane—methanol) to yield 8-[3-[N-[(N-cycloheptyl-N-methylglycyl)glycyl]-N-methylamino]-2,6-dichlorobenzyloxy]-2-methylquinoline (151 mg) as amorphous.

NMR (CDCl$_3$, δ) 1.29–1.96 (12H), 2.30 (3H, s), 2.58 (1H, m), 2.75 (3H, s), 3.01 (2H, s), 3.26 (3H, s), 3.50 (1H, dd, J=18, 4 Hz), 3.89 (1H, dd, J=18, 5 Hz), 5.63 (2H, s), 7.19–7.52 (6H), 8.02 (1H, d, J=8 Hz), 8.13 (1H, br t, J=5 Hz)

EXAMPLE 24

8-[2,6-Dichloro-3-[N-methyl-N-[[[4-(4-pyridyl)-1-piperazinyl]acetyl]glycyl]amino]benzyloxy]-2-methylquinoline was obtained according to a similar manner to that of Example 23.

NMR (CDCl$_3$, δ): 2.60–2.80 (7H), 3.10 (2H, s), 3.24 (3H, s), 3.38–3.61 (5H), 3.91 (1H, dd, J=18, 5 Hz), 5.65 (2H, s), 6.70 (2H, d, J=6 Hz), 7.22–7.55 (6H), 7.89 (1H, br t, J=5 Hz), 8.03 (1H, d, J=8 Hz), 8.28 (2H, d, J=6 Hz)

EXAMPLE 25

A mixture of 8-[3-[N-[N'-(3-acetylphenyl)-ureidoacetyl]-N-methylamino]-2,6-dichlorobenzyloxy]-2-methylquinoline (200 mg), methoxyamine hydrochloride (58.5 mg) and pyridine (71 μl) in ethanol (3 ml) was stirred at ambient temperature for one hour and then at 70° C. for two hours. After being cooled, the mixture was diluted with chloroform and washed with saturated sodium bicarbonate solution. The organic phase was dried over anhydrous magnesium sulfate and concentrated in vacuo. The residue was crystallized from ethyl acetate and filtered to give 8-[2,6-dichloro-3-[N-[N'-[3-(1-methoxyiminoethyl)phenyl]ureidoacetyl]-N-methylamino]benzyloxy]-2-methylquinoline (161 mg) as a colorless powder. mp: 218–224° C.

NMR (DMSO-d$_6$, δ): 2.12 (3H, s), 2.60 (3H, s), 3.15 (3H, s), 3.43 (1H, dd, J=17.5, 5 Hz), 3.66 (1H, dd, J=17.5, 4 Hz), 3.89 (3H, s), 5.46 (1H, d, J=9 Hz), 5.53 (1H, d, J=9 Hz), 6.37 (1H, br t), 7.11–7.30 (2H, m), 7.32–7.60 (5H, m), 7.70 (1H, m), 7.80 (2H, s), 8.20 (1H, d, J=9 Hz), 8.92–9.08 (1H, m)

EXAMPLE 26

8-[2,6-Dichloro-3-[N-[N'-[3-(1-hydroxyiminoethyl) phenyl]ureidoacetyl]-N-methylamino]3benzyloxy]-2-methylquinoline was obtained according to a similar manner to that of Example 25.

NMR (CDCl$_3$, δ): 2.10 (3H, s), 2.64 (3H, s), 3.17 (3H, s), 3.81 (2H, br d, J=5 Hz), 5.45 (1H, d, J=10 Hz), 5.59 (1H, d, J=10 Hz), 6.03 (1H, br t, J=5 Hz), 7.09–7.52 (10H), 8.03 (1H, d, J=9 Hz), 8.51 (1H, s), 9.23 (1H, br s)

EXAMPLE 27

A mixture of 8-[3-[N-[N'-(3-acetylphenyl)ureidoacetyl]-N-methylamino]-2,6-dichlorobenzyloxy]-2-methylquinoline (200 mg) and N,N-dimethylhydrazine (35 μl) in ethanol (2 ml) was heated at 50° C. for one hour and then at 90° C. for 6 hours. Then the mixture was heated at 100° C. for 15 hours during which time an additional N,N-dimethylhydrazine (108 μl) and acetic acid (0.5 ml) was added therein. The mixture was concentrated in vacua and the residue was diluted with ethyl acetate. The organic phase was washed with saturated sodium bicarbonate solution and brine and then dried over anhydrous magnesium sulfate. The organic layer was concentrated in vacua and the residue was purified by flash chromatography eluting with ethyl acetate. The desired fraction was concentrated and the residue was powderized with diethyl ether and filtered to afford 8-[2,6-dichloro-3-[N-[N'-[3-(1-dimethylhydrazonoethyl)phenyl]ureidoacetyl]-N-methylamino]benzyloxy]-2-methylquinoline (50 mg) as a colorless powder.

NMR (CDCl$_3$, δ): 2.16 (3H, s), 2.50 (6H, s), 2.63 (3H, s), 3.22 (3H, s), 3.82 (1H, dd, J=16, 4 Hz), 4.20 (1H, dd, J=16, 6 Hz), 5.48 (1H, d, J=18 Hz), 5.62 (1H, m), 5.66 (1H, d, J=18 Hz), 7.08–7.37 (6H, m), 7.40–7.53 (3H, m), 7.57 (1H, m), 8.06 (1H, d, J=8 Hz), 8.18 (1H, br s)

EXAMPLE 28

To a solution of 8-[2,6-dichloro-3-[N-(N'-ethylureidoacetyl)-N-methylamino]benzyloxy]-2-methylguinoline (111 mg) in ethanol (3 ml) was added 10% solution of hydrogen chloride in methanol (0.5 ml). The mixture was evaporated in vacua to give a pale yellow glass which was washed with ether to give 8-[2,6-dichloro-3-[N-(N'-ethylureidoacetyl)-N-methylamino]benzyloxy]-2-methylquinoline hydrochloride (112 mg) as a pale yellow amorphous powder.

NMR (DMSO-d$_6$, δ): 0.94 (3H, t, J=7 Hz), 2.94 (3H, s), 2.95 (2H, q, J=7 Hz), 3.13 (3H, s), 3.39 (1H, d, J=16 Hz), 3.70 (1H, d, J=16 Hz), 5.65 (2H, s), 7.55–8.06 (6H), 9.05 (1H, d, J=8 Hz)

EXAMPLE 29

The following compounds were obtained according to a similar manner to that of Example 28.
(1) 8-[3-[N-[N'-(3-Acetylphenyl)ureidoacetyl]-N-methylamino]-2,6-dichlorobenzyloxy]-2-methylquinoline hydrochloride mp: 168–170° C.

NMR (DMSO-d$_6$, δ): 2.51 (3H, s), 2.90 (3H, s), 3.17 (3H, s), 3.52 (1H, d, J=16 Hz), 3.76 (1H, d, J=16 Hz), 5.62 (2H, s), 6.56 (1H, br s), 7.31–8.06 (10H), 8.90 (1H, d like), 9.32 (1H, s)
(2) 8-[3-[N-[N'-(3-Acetylphenyl)ureidoacetyl]-N-methylamino]-2,6-dichlorobenzyloxy]-4-chloro-2-methylquinoline hydrochloride NMR (DMSO-d$_6$, δ): 2.53 (3H, s), 2.68 (3H, s), 3.16 (3H, s), 3.46 (1H, d, J=16 Hz), 3.70 (1H, d, J=16 Hz), 5.52 (1H, d, J=12 Hz), 5.61 (1H, d, J=12 Hz), 6.50 (1H, br s), 7.31–7.93 (9H), 8.00 (1H, t, J=1 Hz), 9.20 (1H, s)
(3) 8-[2,6-Dichloro-3-[N-(heptanoylglycyl)-N-methylamino]benzyloxy]-2-methylquinoline hydrochloride NMR (DMSO-d$_6$, δ): 0.86 (3H, t, J=7 Hz), 1.11–1.54 (8H), 2.09 (2H, t, J=7 Hz), 2.90 (3H, s), 3.11 (3H, s), 3.40 (1H, dd, J=16, 4 Hz), 3.72 (1H, dd, J=16, 6 Hz), 5.58 (1H, d, J=12 Hz), 5.67 (1H, d, J=12 Hz), 7.50–8.10 (6H), 8.94 (1H, d, J=8 Hz)
(4) 8-[3-[N-(Cinnamoylglycyl)-N-methylamino]-2,6-dichlorobenzyloxy]-2-methylquinoline hydrochloride NMR (CDCl$_3$—CD$_3$OD 4:1 V/V, δ): 3.09 (3H, s), 3.21 (3H, s), 3.91 (2H, s), 5.59 (1H, d, J=10 Hz), 5.79 (1H, d, J=10 Hz), 6.59 (1H, d, J=20 Hz), 7.28–7.66 (6H, m), 7.58 (1H, d, J=20 Hz), 7.61 (1H, d, J=14 Hz), 7.72 (1H, br d, J=6 Hz), 7.81–8.03 (3H, m), 8.98 (1H, d, J=6 Hz)

(5) 8-[2,6-Dichloro-3-[N-[N'-(3-ethoxycarbonylphenyl)ureidoacetyl]-N-methylamino]benzyloxy]-2-methylquinoline hydrochloride NMR (CDCl$_3$—CD$_3$OD, δ): 1.37 (3H, t, J=7 Hz), 3.01 (3H, s), 3.31 (3H, s), 3.89 (2H, br s), 4.30 (2H, q, J=7 Hz), 5.61 (1H, d, J=10 Hz), 5.82 (1H, d, J=10 Hz), 7.26–7.47 (2H), 7.58–8.00 (7H), 8.09 (1H, t, J=1 Hz), 8.96 (1H, d, J=9 Hz)

(6) 8-[2,6-Dichloro-3-[N-(N'-pentylureidoacetyl)-N-methylamino]benzyloxy]-2-methylquinoline hydrochloride NMR (DMSO-d$_6$, δ): 0.85 (3H, t, J=7.5 Hz), 1.10–1.44 (6H, m), 2.50 (3H, s), 3.11 (3H, s), 2.85–2.95 (2H, m), 3.38 (1H, d, J=17.5 Hz), 3.68 (1H, d, J=17.5 Hz), 5.61 (2H, s), 7.79 (2H, br s), 7.90 (3H, br s), 7.98 (1H, d, J=7.5 Hz), 9.01 (1H, d, J=8 Hz)

(7) 8-[2,6-Dichloro-3-[N-[N'-(3-acetamidophenyl)ureidoacetyl]-N-methylamino]benzyloxy]-2-methylquinoline hydrochloride NNR (CDCl$_3$—CD$_3$OD 3:1 V/V, δ): 2.07 (3H, s), 2.86 (3H, br s), 3.29 (3H, s), 3.89 (2H, s), 5.58 (1H, br d, J=8 Hz), 5.79 (1H, br d, J=8 Hz), 6.91–7.23 (3H, m), 7.26–8.03 (7H, m), 8.90 (1H, br d, J=6 Hz)

(8) 8-[2,6-Dichloro-3-[N-[N'-[3-(N-methyl-N-acetylamino)phenyl]ureidoacetyl]-N-methylamino]benzyloxy]-2-methylquinoline hydrochloride NNR (CDCl$_3$—CD$_3$OD 3:1 V/V, δ): 1.81 (3H, s), 3.04 (3H, br s), 3.11 (3H, s), 3.27 (3H, s), 3.84 (1H, d, J=17 Hz), 3.96 (1H, d, J=17 Hz), 5.59 (1H, d, J=8 Hz), 5.75 (1H, d, J=8 Hz), 6.75 (1H, m), 7.17–8.02 (9H, m), 8.91 (1H, m)

(9) 8-[2,6-Dichloro-3-[N-[N'-[3-(N,N-dimethylamino)phenyl]ureidoacetyl]-N-methylamino]benzyloxy]-2-methylquinoline dihydrochloride NMR (CDCl$_3$—CD$_3$OD, δ): 3.08 (3H, s), 3.22 (6H, s), 3.30 (3H, s), 3.81 (2H, s), 5.61 (1H, d, J=10 Hz), 5.80 (1H, d, J=10 Hz), 7.25 (1H, d, J=7 Hz), 7.33–7.52 (2H, m), 7.60 (1H, d, J=9 Hz), 7.68 (1H, d, J=9 Hz), 7.76–7.98 (5H), 8.96 (1H, d, J=9 Hz)

(10) 8-[2,6-Dichloro-3-[N-[N'-[3-(N'-methylureido)phenyl]-ureidoacetyl]-N-methylamino]benzyloxy]-2-methylquinoline hydrochloride NMR (CDCl$_3$—CD$_3$OD, δ): 2.75 (3H, s), 2.90 (3H, s), 3.30 (3H, s), 3.80 (1H, d, J=17 Hz), 3.92 (1H, d, J=17 Hz), 5.61 (1H, d, J=10 Hz), 5.81 (1H, d, J=10 Hz), 6.80–7.00 (3H), 7.32 (1H, s), 7.56 (1H, d, J=9 Hz), 7.64 (1H, d, J=9 Hz), 7.70–8.00 (4H), 8.90 (1H, d, J=9 Hz)

(11) 8-[3-[N-[N'-(3-Carboxyphenyl)ureidoacetyl]-N-methylamino]-2,6-dichlorobenzyloxy]-2-methylquinoline hydrochloride NMR (CDCl$_3$—CD$_3$OD, δ): 3.00 (3H, s), 3.31 (3H, s), 3.81 (1H, d, J=18 Hz), 3.95 (1H, d, J=18 Hz), 5.60 (1H, d, J=10 Hz), 5.82 (1H, d, J=10 Hz), 7.23–7.40 (2H), 7.56–8.02 (7H), 8.11 (1H, s), 8.94 (1H, d, J=9 Hz)

(12) 8-[2,6-Dichloro-3-[N-methyl-N-[N'-(3-(morpholinocarbonyl)phenyl]ureidoacetyl]amino]benzyloxy]-2-methylquinoline hydrochloride NMR (CDCl$_3$—CD$_3$OD 3:1 V/V, δ): 2.93 (3H, s), 3.20–3.44 (8H, m), 3.29 (3H, s), 3.80 (1H, d, J=17 Hz), 3.97 (1H, d, J=17 Hz), 5.58 (1H, d, J=10 Hz), 5.79 (1H, d, J=10 Hz), 6.91 (1H, br d J=7.5 Hz), 7.16–8.01 (9H, m), 8.89 (1H, d, J=9 Hz)

(13) 8-[2,6-Dichloro-3-[N-methyl-N-[N'-[3-(4-methyl-1-piperazinylcarbonyl)phenyl]ureidoacetyl]amino]-benzyloxy]-2-methylquinoline dihydrochloride NMR (CDCl$_3$—CD$_3$OD 3:1 V/V, δ): 2.84–3.96 (8H, m), 2.90 (3H, s), 2.98 (3H, s), 3.30 (3H, s), 3.84 (2H, br s), 5.60 (1H, d, J=10 Hz), 5.82 (1H, d, J=10 Hz), 7.01 (1H, br d, J=6 Hz), 7.28 (1H, t, J=7.5 Hz), 7.36 (1H, br t, J=7 Hz), 7.43–8.03 (7H, n), 8.94 (1H, d, J=9 Hz)

(14) 8-[2,6-Dichloro-3-[N-[N'-[3-(2-methoxyethylcarbamoyl)phenyl]ureidoacetyl]-N-methylamino]benzyloxy]-2-methylquinoline hydrochloride NMR (CDCJ$_3$—CD$_3$OD 3:1 V/V, δ): 2.92 (3H, s), 3.27 (3H, s), 3.36 (3H, s), 3.44–3.60 (4H, m), 3.85 (1H, d, J=17 Hz), 3.96 (1H, d, J=17 Hz), 5.58 (1H, d, J=9 Hz), 5.80 (1H, d, J=9 Hz), 7.20 (1H, t, J=7 Hz), 7.30–7.50 (2H, m), 7.53–7.99 (7H, m), 8.90 (1H, d, J=9 Hz)

(15) 8-[2,6-Dichloro-3-[N-[N'-[3-[N-(2-dimethylaminoethyl)-N-methylcarbamoyl]phenyl]ureidoacetyl]-N-methylamino]benzyloxy]-2-methylquinoline dihydrochloride NMR (CDCl$_3$—CD$_3$OD 3:1 V/V, δ): 2.99 (9H, br s), 3.08 (3H, s), 3.25 (3H, s), 3.30–3.54 (4H, m), 3.91 (2H, m), 5.61 (1H, d, J=10 Hz), 5.81 (1H, d, J=10 Hz), 7.08 (1H, d, J=7 Hz), 7.28 (1H, t, J=8 Hz), 7.40–7.55 (1H, m), 7.59 (1H, d, J=9 Hz), 7.66 (1H, d, J=9 Hz), 7.78 (1H, d, J=7 Hz), 7.82–8.02 (4H, m), 8.96 (1H, d, J=9 Hz)

(16) 8-[2,6-Dichloro-3-[N-[N'-(3-methylcarbamoylphenyl)ureidoacetyl]-N-methylamino]benzyloxy]-2-methylquinoline hydrochloride NMR (CDCl$_3$—CD$_3$OD, δ): 2.91 (3H, s), 3.00 (3H, s), 3.31 (3H, s), 3.79 (1H, d, J=18 Hz), 3.91 (1H, d, J=18 Hz), 5.60 (1H, d, J=10 Hz), 5.82 (1H, d, J=10 Hz), 7.20–7.46 (3H), 7.60 (1H, d, J=9 Hz), 7.69 (1H, d, J=9 Hz), 7.74–8.00 (5H), 8.95 (1H, d, J=9 Hz)

(17) 8-[3-[N-[N'-(3-Dimethylcarbamoylphenyl)ureidoacetyl]-N-methylamino]-2,6-dichlorobenzyloxy]-2-methylquinoline hydrochloride NMR (CDCl$_3$—CD$_3$OD, δ): 2.99 (6H, s), 3.06 (3H, s), 3.30 (3H, s), 3.85 (2H, s), 5.60 (1H, d, J=10 Hz), 5.82 (1H, d, J=10 Hz), 6.98 (1H, d, J=6 Hz), 7.20–7.38 (2H), 7.43–8.02 (7H), 8.94 (1H, d, J=8 Hz)

(18) 8-[2,6-Dichloro-3-[N-[N'[3-(3-pyridylmethylcarbamoyl)phenyl]ureidoacetyl]-N-methylamino]benzyloxy]-2-methylquinoline dihydrochloride NMR (CDCl$_3$—CD$_3$OD, δ): 2.98 (3H, s), 3.30 (3H, s), 3.86 (2H, s), 4.74 (2H, s), 5.60 (1H, d, J=10 Hz), 5.81 (1H, d, J=10 Hz), 7.28 (1H, d, J=8 Hz), 7.48–8.09 (10H), 8.61–8.74 (2H), 8.88–9.01 (2H)

(19) 8-[2,6-Dichloro-3-[N-methyl-N-[N'-[3-[4-(4-pyridyl)-1-piperazinylcarbonyl]phenyl]ureidoacetyl]amino]-benzyloxy]-2-methylquinoline trihydrochloride NMR (CDCl$_3$—CD$_3$OD, δ): 2.99 (3H, s), 3.30 (3H, s), 3.64–4.00 (10H), 5.62 (1H, d, J=10 Hz), 5.82 (1H, d, J=10 Hz), 7.04 (1H, d, J=7 Hz), 7.13 (2H, br d, J=7 Hz), 7.30 (1H, t, J=8 Hz), 7.40–7.55 (2H), 7.60 (1H, d, J=9 Hz), 7.68 (1H, d, J=9 Hz), 7.78 (1H, d, J=7 Hz), 7.83–8.00 (3H), 8.16 (2H, br d, J=7 Hz), 8.95 (1H, d, J=9 Hz)

(20) 8-[3-[N-[N'-[3-(4-Acetyl-1-piperazinylcarhonyl)phenyl]ureidoacetyl]-N-methylamino]-2,6-dichlorobenzyloxy]-2-methylquinoline hydrochloride NMR (CDCl$_3$—CD$_3$OD, δ): 2.14 (3H, s), 2.98 (3H, s), 3.30 (3H, s), 3.35–3.90 (10H), 5.60 (1H, d, J=10 Hz), 5.81 (1H, d, J=10 Hz), 6.99 (1H, d, J=7 Hz), 7.22–7.53 (3H), 7.60 (1H, d, J=9 Hz), 7.68 (1H, d, J=9 Hz), 7.71–8.00 (4H), 8.93 (1H, d, J=9 Hz)

(21) 8-[2,6-Dichloro-3-[N-methyl-N-[N'-(3-nitrophenyl)ureidoacetyl]amino]benzyloxy]-2-methylquinoline hydrochloride NMR (CDCl$_3$—CD$_3$OD, δ): 3.10 (3H, s), 3.31 (3H, s), 3.82 (1H, d, J=17 Hz), 3.96 (1H, d, J=17 Hz), 5.61 (1H, d, J=10 Hz), 5.83 (1H, d, J=10 Hz), 7.33–7.48 (2H), 7.61 (1H, d, J=9 Hz), 7.19 (1H, d, J=9 Hz), 7.27–8.01 (5H), 8.61 (1H, br s), 8.99 (1H, d, J=9 Hz)

(22) 8-[3-[N-[N'-(4-Acetylphenyl)ureidoacetyl]-N-methylamino]-2,6-dichlorobenzyloxy]-2-methylquinoline hydrochloride mp: 173–176° C.

NMR (CDCl₃—CD₃OD, δ): 2.58 (3H, s), 3.03 (3H, s), 3.30 (3H, s), 3.79 (1H, d, J=18 Hz), 3.90 (1H, d, J=18 Hz), 5.62 (1H, d, J=10 Hz), 5.83 (1H, d, J=10 Hz), 7.45 (1H, d, J=9 Hz), 7.60 (1H, d, J=9 Hz), 7.68 (1H, d, J=9 Hz), 7.76–8.01 (7H), 8.99 (1H, d, J=9 Hz)

(23) 8-[2,6-Dichloro-3-[N-methyl-N-(N'-phenylureido acetyl)amino]benzyloxy]-2-methylquinoline hydrochloride NMR (CDCL₃—CD₃OD, δ): 2.91 (3H, s), 3.30 (3H, s), 3.88 (2H, s), 5.61 (1H, d, J=10 Hz), 5.84 (1H, d, J=10 Hz), 6.98 (1H, t, J=6 Hz), 7.12–7.31 (4H), 7.59 (1H, d, J=9 Hz), 7.68 (1H, d, J=9 Hz), 7.74–8.00 (4H), 8.93 (1H, d, J=9 Hz)

(24) 8-[3-[N-(N'-Benzylureidoacetyl)-N-methylamino]-2,6-dichlorobenzyloxy]-2-methylquinoline hydrochloride NMR (CDCl₃—CD₃OD, δ): 2.78 (3H, s), 3.29 (3H, s), 3.84 (2H, s), 4.19 (1H, d, J=16 Hz), 4.29 (1H, d, J=16 Hz), 5.59 (1H, d, J=10 Hz), 5.82 (1H, d, J=10 Hz), 7.11–7.31 (5H), 7.58 (1H, d, J=9 Hz), 7.68 (1H, d, J=9Hz), 7.71–8.00 (4H), 8.92 (1H, d, J=9 Hz)

(25) 8-[3-[N-[(N-Cycloheptyl-N-methylglycyl)glycyl]-N-methylamino]-2,6-dichlorobenzyloxy]-2-methylquinoline dihydrochloride NMR (CDCl₃—CD₃OD, δ): 1.40–2.68 (12H), 2.86 (3H, s), 3.23 (6H, s), 3.59 (1H, m), 3.70–4.13 (4H), 5.59 (1H, d, J=10 Hz), 5.71 (1H, d, J=10 Hz), 7.50–7.90 (6H), 8.75 (1H, d, J=9 Hz)

(26) 8-[2,6-Dichloro-3-[N-methyl-N-[[4-(4-pyridyl)-1-piperazinyl]acetylglycyl]amino]benzyloxy]-2-methylquinoline tetrahydrochloride NMR (CDCl₃—CD₃OD, δ): 3.10 (3H, s), 3.28 (3H, s), 3.60–3.75 (4H), 3.81 (2H, d, J=5 Hz), 4.00–4.30 (6H), 5.68 (1H, d, J=10 Hz), 5.79 (1H, d, J=10 Hz), 7.28 (2H, d, J=7 Hz), 7.58–8.00 (6H), 8.20 (2H, d, J=7 Hz), 8.95 (1H, d, J=9 Hz)

(27) 8-[2,6-Dichloro-3-[N-[N'-[3-(3-pyridylcarbamoyl) phenyl]ureidoacetyl]-N-methylamino]benzyloxy]-2-methylquinoline dihydrochloride NMR (CDCl₃—CD₃OD, δ): 3.03 (3H, s), 3.30 (3H, s), 3.89 (2H, s), 5.61 (1H, d, J=10 Hz), 5.82 (1H, d, J=10 Hz), 7.38 (1H, t, J=9 Hz), 7.46–8.11 (10H), 8.51 (1H, d, J=6 Hz), 8.94 (1H, dd, J=9, 1 Hz), 9.00 (1H, d, J=9 Hz), 9.61 (1H, d, J=1 Hz)

(28) 8-[2,6-Dichloro-3-[N-[N'-[3-(2-pyridylmethylcarbamoyl)phenyl]ureidoacetyl]-N-methylamino]-benzyloxy]-2-methylquinoline dihydrochloride NMR (CDCl₃—CD₃OD, δ): 3.00 (3H, s), 3.30 (3H, s), 3.78 (1H, d, J=17 Hz), 3.90 (1H, d, J=17 Hz), 4.93 (2H, s), 5.60 (1H, d, J=10 Hz), 5.82 (1H, d, J=10 Hz), 7.31 (1H, t, J=9 Hz), 7.50–8.01 (10H), 8.10 (1H, d, J=9 Hz), 8.52 (1H, t, J=9 Hz), 8.72 (1H, d, J=6 Hz), 8.97 (1H, d, J=9 Hz)

(29) 8-[2,6-Dichloro-3-[N-[N'-[3-(4-pyridylmethylcarbamoyl)phenyl]ureidoacetyl]-N-methylamino]-benzyloxy]-2-methylquinoline dihydrochloride NMR (CDCl₃—CD₃OD, δ): 2.97 (3H, s), 3.30 (3H, s), 3.86 (2H, s), 4.82 (2H, sl, 5.60 (1H, d, J=10 Hz), 5.81 (1H, d, J=10 Hz), 7.29 (1H, t, J=9 Hz), 7.50–8.00 (9H), 8.04 (2H, d, J=6 Hz), 8.71 (2H, d, J=6 Hz), 8.94 (1H, d, J=9 Hz)

(30) 8-[2,6-Dichloro-3-[N-methyl-N-[N'-[3-(1-piperazinylcarbonyl)phenyl]ureidoacetyl]amino] benzyloxy]-2-methylquinoline dihydrochloride NMR (CDCl₃—CD₃OD 3:1 V/V, δ): 2.96 (3H, s), 3.11–3.45 (8H, m), 3.29 (3H, s), 3.86 (2H, s), 5.58 (1H, d, J=10 Hz), 5.80 (1H, d, J=10 Hz), 6.99 (1H, d, J=7 Hz), 7.18–8.01 (9H, m), 8.91 (1H, d, J=9 Hz)

(31) 8-[2,6-Dichloro-3-[N-methyl-N-[N'-[3-(4-phenyl-1-piperazinylcarbonyl)phenyl]ureidoacetyl]amino]-benzyloxy]-2-methylquinoline dihydrochloride NMR (CDCl₃—CD₃OD 3:1 V/V, δ): 2.91 (3H, s), 3.23 (3H, s), 3.26–3.40 (4H, m), 3.60 (4H, br s), 3.72 (2H, br s), 5.52 (1H, d, J=10 Hz), 5.76 (1H, d, J=10 Hz), 7.00 (1H, br d, J=7 Hz), 7.15–7.37 (3H, m), 7.39–7.95 (11H, m), 8.86 (1H, d, J=9 Hz)

(32) 8-[2,6-Dichloro-3-[N-[N'-[3-(4-ethoxycarbonyl-1-piperazinylcarbonyl)phenyl]ureidoacetyl]-N-methylamino] benzyloxy]-2-methylquinoline hydrochloride NMR (CDCl₃—CD₃OD 3:1 V/V, δ): 1.28 (3H, t, J=7.5 Hz), 2.92 (3H, s), 3.20–3.83 (8H, m), 3.95 (2H, s), 4.16 (2H, g, J=7.5 Hz), 5.59 (1H, d, J=9 Hz), 5.79 (1H, d, J=9 Hz), 6.90 (1H, d, J=5 Hz), 7.22 (1H, t, J=7.5 Hz), 7.40–7.74 (6H, m), 7.75–7.98 (3H, m), 8.88 (1H, d, J=9 Hz)

(33) 8-[2,6-Dichloro-3-[N-[N'-[3-[2-(N,N-dimethylamino) ethylcarbamoyl]phenyl]ureidoacetyl]-N-methylamino]-benzyloxy]-2-methylquinoline dihydrochloride NMR (CDCl₃—CD₃OD 3:1 V/V, δ): 3.06 (6H, s), 3.08 (3H, s), 3.30 (3H, s), 3.33–3.46 (2H, m), 3.79 (2H, br t, J=6 Hz), 3.81 (1H, d, J=20 Hz), 3.89 (1H, d, J=20 Hz), 5.59 (1H, d, J=10 Hz), 5.80 (1H, d, J=10 Hz), 7.28 (1H, t, J=8 Hz), 7.45–8.00 (9H, m), 8.94 (1H, d, J=9 Hz)

(34) 8-[2,6-Dichloro-3-[N-[N'-(3-ethoxycarbonylaminophenyl)ureidoacetyl]-N-methylamino]benzyloxy]-2-methylquinoline hydrochloride NMR (CDCl₃—CD₃OD, δ): 1.28 (3H, t, J=7 Hz), 2.91 (3H, s), 3.30 (3H, s) 3.89 (2H, s), 4.09 (2H, q, J=7 Hz), 5.60 (1H, d, J=10 Hz), 5.81 (1H, d, J=10 Hz), 6.90–7.19 (3H), 7.39 (1H, br s), 7.58 (1H, d, J=9 Hz), 7.64 (1H, d, J=9 Hz), 7.70–8.00 (4H), 8.91 (1H, d, J=9 Hz)

(35) 8-[2,6-Dichloro-3-[N-[N'-(1-naphthyl)ureidoacetyl]-N-methylamino]benzyloxy]-2-methylquinoline hydrochloride NMR (CDCl₃—CD₃OD, δ): 2.50 (3H, s), 3.32 (3H, s), 3.99 (2H, s) 5.62 (1H, d, J=10 Hz), 5.80 (1H, d, J=10 Hz), 7.13 (1H, t, J=9 Hz), 7.35–8.07 (12H), 8.81 (1H, d, J=9 Hz)

(36) 8-[3-[N-[N'-(3-Acetylphenyl)ureidoacetyl]-N-methylamino]-2,6-dichlorobenzyloxy]-4-chloro-2-ethylquinoline hydrochloride NMR (CDCl₃—CD₃OD, δ): 1.35 (3H, t, J=7HZ), 2.52 (3H, s), 3.19–3.46 (5H), 3.85 (1H, d, J=17 Hz), 3.99 (1H, d, J=17 Hz), 5.60 (1H, d, J=10 Hz), 5.84 (1H, d, J=10 Hz), 7.29–7.63 (5H), 7.85 (1H, d, J=8 Hz), 7.98–8.19 (4H)

(37) 8-[3-[N-[N'-(3-Acetylphenyl)ureidoacetyl]-N-methylamino]-2,6-dichlorobenzyloxy]-2-ethylquinoline hydrochloride NMR (CDCl₃—CD₃OD, δ): 1.39 (3H, t, J=8 Hz), 2.54 (3H, s), 3.22–3.44 (5H), 3.89 (2H s) 5.60 (1H, d, J=10 Hz), 5.85 (1H, d, J=10 Hz), 7.30–7.70 (5H), 7.77–8.02 (5H), 9.00 (1H, d, J=9 Hz)

(38) 8-[2,6-Dichloro-3-[N-methyl-N-[(E)-3-(3-pyridyl) acryloylglycyl]amino]benzyloxy]-2-methylquinoline dihydrochloride NMR (DMSO-d₆, δ): 2.90 (3H, s), 3.15 (3H, s), 3.60 (1H, dd, J=16, 5 Hz), 3.92 (1H, dd, J=16, 5 Hz), 5.64 (2H, s) 7.08 (1H, d, J=15 Hz), 7.53 (1H, d, J=15 Hz), 7.77–8.00 (7H), 8.43–8.59 (2H), 8.77 (1H, d, J=8 Hz), 8.90–9.08 (2H)

(39) 8-[2,6-Dichloro-3-[N-methyl-N-(4-nitrocinnamoylglycyl)amino]benzyloxy]-2-methylquinoline hydrochloride NMR (DMSO-d₆, δ): 2.89 (3H, s), 3.17 (3H, s), 3.60 (1H, dd, J=16, 5 Hz), 3.90 (1H, dd, J=16, 4 Hz), 5.62 (2H, s), 7.02 (1H, d, J=15 Hz), 7.50 (1H, d, J=15 Hz), 7.65–7.97 (9H), 8.26 (1H, d, J=8 Hz), 8.52 (1H, t like), 8.88 (1H, br s)

EXAMPLE 30

The following compounds were obtained according to a similar manner to that of Example 1.

(1) 8-(2,6-Dichloro-3-nitrobenzyloxy)-2-methyl-4-dimethylaminoquinoline

NMR (CDCl$_3$, δ): 2.59 (3H, s), 3.18 (6H, s), 5.52 (2H, s), 6.61 (1H, s), 7.19–7.49 (3H), 7.67–7.78 (2H)

(2) 8-(2,6-Dichloro-3-nitrobenzyloxy)-2,4-dimethylquinoline mp: 218–219° C.

NMR (CDCl$_3$, δ): 2.66 (3H, s), 2.70 (3H, s), 5.70 (2H, s), 7.15 (1H, s), 7.26 (1H, d, J=8 Hz), 7.41 (1H, t, J=8 Hz), 7.52 (1H, d, J=8 Hz), 7.65 (1H, d, J=8 Hz), 7.77 (1H, d, J=8 Hz)

(3) 8-(2,6-Dichloro-3-nitrobenzyloxy)-4-(3,4-dimethoxybenzyloxy)-2-methylquinoline mp: 218–220° C.

NMR (CDCl$_3$, δ): 2.70 (3H, s), 3.91 (6H, s), 5.18 (2H, s), 5.68 (2H, s), 6.74 (1H, s), 6.92 (1H, d, J=8 Hz), 7.02 (1H, s), 7.06 (1H, d, J=8 Hz), 7.19–7.39 (2H), 7.50 (1H, d, J=8 Hz), 7.76 (1H, d, J=8 Hz), 7.88 (1H, d, J=8 Hz)

(4) 8-(2,6-Dichloro-3-nitrobenzyloxy)-4-methoxy-2-methylquinoline

NMR (CDCl$_3$, δ): 2.70 (3H, s), 4.02 (3H, s), 5.68 (2H, s), 6.67 (1H, s), 7.25 (1H, dd, J=8, 1 Hz), 7.34 (1H, t, J=8 Hz), 7.50 (1H, d, J=8 Hz), 7.75 (1H, d, J=8 Hz), 7.84 (1H, dd, J=8, 1 Hz)

(5) 8-(2,6-Dichloro-3-nitrobenzyloxy)-4-ethoxy-2-methylquinoline mp: 212–213° C.

NMR (CDCl$_3$, δ): 1.57 (3H, t, J=6 Hz), 2.69 (3H, s), 4.24 (2H, q, J=6 Hz), 5.68 (2H, s), 6.62 (1H, s), 7.23 (1H, d, J=8 Hz), 7.34 (1H, t, J=8 Hz), 7.50 (1H, d, J=8 Hz), 7.76 (1H, d, J=8 Hz), 7.87 (1H, d, J=8 Hz)

(6) 8-(2,6-Dichloro-3-nitrobenzyloxy)-2-methyl-4-methylthioquinoline mp: 225–226° C.

NMR (CDCl$_3$, δ): 2.61 (3H, s), 2.72 (3H, s), 5.69 (2H, s), 7.02 (1H, s), 7.26 (1H, d, J=8 Hz), 7.40 (1H, t, J=8 Hz), 7.50 (1H, d, J=8 Hz), 7.75 (1H, d, J=8 Hz), 7.76 (1H, d, J=8 Hz)

(7) 8-(2,6-Dichloro-3-nitrobenzyloxy)-4-(2-methoxyethoxy)-2-methylquinoline mp: 185–188° C.

NMR (CDCl$_3$, δ): 2.69 (3H, s), 3.51 (3H, s), 3.90 (2H, t, J=6 Hz), 4.32 (2H, t, J=6 Hz), 5.68 (2H, s), 6.66 (1H, s), 7.24 (1H, d, J=8 Hz), 7.34 (1H, t, J=8 Hz), 7.50 (1H, d, J=8 Hz), 7.76 (1H, d, J=8 Hz), 7.89 (1H, d, J=8 Hz)

(8) 8-(2,6-Dichloro-3-nitrobenzyloxy)-2-methyl-4-(2-dimethylaminoethoxy)quinoline mp: 144–146° C.

NMR (CDCl$_3$, δ): 2.41 (6H, s), 2.70 (3H, s), 2.90 (2H, t, J=6 Hz), 4.28 (2H, t, J=6 Hz), 5.68 (2H, s), 6.64 (1H, s), 7.23 (1H, d, J=8 Hz), 7.33 (1H, t, J=8 Hz), 7.50 (1H, d, J=8 Hz), 7.75 (1H, d, J=8 Hz), 7.85 (1H, d, J=8 Hz)

(9) 2-Chloro-8-(2,6-dichloro-3-nitrobenzyloxy)quinoline mp: 198–199° C.

NMR (CDCl$_3$, δ): 5.66 (2H, s), 7.27–7.58 (5H), 7.80 (1H, d, J=8 Hz), 8.10 (1H, d, J=8 Hz)

(10) 8-(2,6-Dichloro-3-nitrobenzyloxy)-2-methoxyquinoline mp: 137–138° C.

NMR (CDCl$_3$, δ): 4.10 (3H, s), 5.70 (2H, s), 6.95 (1H, d, J=8 Hz), 7.30 (1H, d, J=5 Hz), 7.47 (1H, dd, J=8, 5 Hz), 7.52 (1H, d, J=8 Hz), 7.77 (1H, d, J=8 Hz), 8.00 (1H, d, J=8 Hz)

EXAMPLE 31

A mixture of 8-(2,6-dichloro-3-nitrobenzyloxy)-4-(3,4-dimethoxybenzyloxy)-2-methylquinoline (106 mg), 2,3-dichloro-5,6-dicyano-1,4-benzoquinone (50 mg) and dichloromethane-water (18:1, V/V, 2.85 ml) was heated under reflux for 19 hours. The reaction mixture was partitioned into dichloromethane and saturated aqueous sodium hydrogen carbonate. The organic layer was washed with brine, dried over magnesium sulfate and evaporated in vacuo. The residue was purified by a preparative thin-layer chromatography (dichloromethane-methanol) followed by washing with ethanol to give a brownish powder (26 mg) of 8-(2,6-dichloro-3-nitrobenzyloxy)-4-hydroxy-2-methylquinoline. mp: 255–258° C.

NMR (DMSO-d$_6$, δ): 2.32 (3H, s), 5.47 (2H, s), 5.91 (1H, s), 7.27 (1H, t, J=8 Hz), 7.46 (1H, d, J=8 Hz), 7.69 (1H, d, J=8 Hz), 7.90 (1H, d, J=8 Hz), 8.20 (1H, d, J=8 Hz)

EXAMPLE 32

To a suspension of 8-[2,6-dichloro-3-[N-methyl-N-[N'-(3-nitrophenyl)ureidoacetyl]amino]benzyloxy]-2-methylquinoline (4.7 g) in ethanol (47 ml) was added tin(II) chloride (6.45 g) at ambient temperature. The mixture was refluxed for 2 hours. After cooling, the mixture was adjusted to pH 10 with 1N sodium hydroxide solution. To this mixture was added dichloromethane (50 ml) and the precipitate was removed by filtration. The filtrate was extracted with dichloromethane twice. The organic layer was washed with saturated sodium bicarbonate solution, water and brine. After dried over magnesium sulfate, the solvent was removed in vacuo. The residue was purified by column chromatography eluting with dichloromethane-methanol to give 8-[3-[N-[N'-( 3-aminophenyl)ureidoacetyl]-N-methylamino]-2,6-dichlorobenzyloxy]-2-methylquinoline (3.22 g) as amorphous.

NMR (CDCl$_3$, δ): 2.63 (3H, s), 3.20 (3H, s), 3.59 (2H, br s), 3.79 (1H, dd, J=17, 5 Hz), 4.03 (1H, dd, J=17, 6 Hz), 5.50 (1H, d, J=10 Hz), 5.59–5.75 (2H), 6.79 (1H, dd, J=8, 1 Hz), 6.48 (1H, d, J=8 Hz), 6.80 (1H, t, J=1 Hz), 6.91 (1H, t, J=8 Hz), 7.19–7.50 (6H), 7.82 (1H, br s), 8.06 (1H, d, J=9 Hz)

EXAMPLE 33

The following compounds were obtained according to similar manners to those of Example 11 to 13.

(1) 8-[2,6-Dichloro-3-[N-[N'-(3-methoxyphenyl)ureidoacetyl]-N-methylamino]benzyloxy]2-methylquinoline NMR (CDCl$_3$, δ): 2.63 (3H, s), 3.21 (3H, s), 3.68 (3H, s), 3.80 (1H, dd, J=17, 5 Hz), 4.20 (1H, dd, J=17, 6 Hz), 5.49 (1H, d, J=10 Hz), 5.57–5.70 (2H), 6.50 (1H, dd, J=8, 1 Hz), 6.71 (1H, d, J=8 Hz), 6.94–7.09 (2H), 7.21–7.50 (6H), 8.08 (1H, d, J=9 Hz), 8.15 (1H, br s)

(2) 8-[2,6-Dichloro-3-[N-[N'-(4-methoxyphenyl)ureidoacetyl]-N-methylamino]benzyloxy]-2-methylquinoline NMR (CDCl$_3$, δ): 2.64 (3H, s), 3.20 (3H, s), 3.70–3.88 (4H), 4.07 (1H, dd, J=17.5 Hz), 5.42–5.57 (2H), 5.67 (2H, d, J=10 Hz), 6.76 (2H, d, J=9 Hz), 7.10–7.50 (8H), 7.61 (1H, br s), 8.05 (1H, d, J=9 Hz)

(3) 8-[2,6-Dichloro-3-[N-[N'-(2-ethoxycarbonylphenyl)ureidoacetyl]-N-methylamino]benzyloxy]-2-methylquinoline NMR (CDCl$_3$, δ): 1.40 (3H, t, J=7 Hz), 2.75 (3H, s), 3.25 (3H, s), 3.52 (1H, dd, J=17, 4 Hz), 3.89 (1H, dd, J=17, 5 Hz), 4.35 (2H, q, J=7 Hz), 5.57–5.69 (3H), 6.95 (1H, t, J=7 Hz), 7.20–7.52 (8H), 7.93–8.06 (2H), 8.43 (1H, d, J=9 Hz)

(4) 8-[3-[N-[N'-(3-Cyanophenyl)ureidoacetyl]-N-methyl-amino]-2,6-dichlorobenzloxy]-2-methylquinoline NMR (CDCl$_3$, δ): 2.48 (3H, s), 3.21 (3H, s), 3.78 (1H, dd, J=17, 5 Hz), 4.40 (1H, dd, J=17, 7 Hz), 5.44 (1H, d, J=10 Hz), 5.56 (1H, dd, J=7, 5 Hz), 5.63 (1H, d, J=10 Hz), 7.15 (2H, d, J=5 Hz), 7.20–7.44 (5H, m), 7.45–7.58 (2H, m), 7.64 (1H, br s), 8.11 (1H, d, J=9 Hz), 9.23 (1H, br s)

(5) 8-[2,6-Dichloro-3-[N-methyl-N-[N'-(2-pyridylmethyl)ureidoacetyl]amino]benzyloxy]-2-methquinoline NMR (CDCl$_3$, δ): 2.70 (3H, s), 3.21 (3H, s), 3.68 (1H, dd, J=17,5 Hz), 3.85 (1H, dd, J=17,5 Hz), 4.42 (2H, t, J=5 Hz), 5.48–5.61 (2H), 5.68 (1H, d, J=10 Hz), 6.02 (1H, br t, J=5 Hz), 7.11 (1H, t, J=6 Hz), 7.20–7.50 (7H), 7.60 (1H, dt, J=6, 1 Hz), 8.02 (1H, d, J=9 Hz), 8.48 (1H, d, J=5 Hz)

(6) 8-[2,6-Dichloro-3-[N-methyl-N-[N'-(2-pyridyl)ureidoacetyl]amino]benzyloxyl]-2-methylquinoline NMR (CDCl$_3$, δ): 2.62 (3H, s), 3.26 (3H, s), 3.80 (1H, dd, J=17,5 Hz), 4.10 (1H, dd, J=17, 5 Hz), 5.58 (1H, *d, J=10

Hz), 5.63 (1H, d, J=10 Hz), 6.68 (1H, d, J=8 Hz), 6.86 (1H, dd, J=7, 6 Hz), 7.20–7.56 (7H), 7.96–8.08 (2H), 8.26 (1H, dd, J=5, 1 Hz), 9.80 (1H, br t, J=5 Hz)

(7) 8-[2,6-Dichloro-3-[N-[N'-(3-pyridylmethyl)ureidoacetyl]-N-methylamino]benzyloxy]-2-methylquinoline NMR (CDCl$_3$, δ): 2.56 (3H, s), 3.20 (3H, s), 3.79 (1H, dd, J=17, 4 Hz), 4.02 (1H, dd, J=17, 6 Hz), 4.12 (1H, dd, J=15, 5 Hz), 4.33 (1H, dd, J=15, 6 Hz), 5.28 (1H, br t, J=5 Hz), 5.49 (1H, d, J=10 Hz), 5.70 (1H, d, J=10 Hz), 6.24 (1H, br t, J=6 Hz), 7.08 (1H, dd, J=8, 5 Hz), 7.17–7.30 (3H, m), 7.31 (1H, d, J=9 Hz), 7.38–7.58 (4H, m), 8.01 (1H, d, J=8 Hz), 8.29–8.50 (2H, m)

(8) 8-[3-[N-[N'-(3-Aminophenyl)ureidoacetyl]-N-methylamino]-2,6-dichlorobenzloxy]-2-methylquinoline NMR (CDCl$_3$, δ): 2.64 (3H, s), 3.20 (31, s), 3.60 (2H, br s), 3.80 (1H, dd, J=17, 5 Hz), 4.06 (1H, dd, J=17, 6 Hz), 5.50 (1H, d, J=10 Hz), 5.63 (1H, d, J=10 Hz), 5.64 (1H, br s), 6.29 (1H, dd, J=8, 1 Hz), 6.46 (1H, br s, J=8 Hz), 6.80 (1H, t, J=1 Hz), 6.91 (1H, t, J=8 Hz), 7.17–7.55 (7H, m), 7.84 (1H, br s), 8.05 (1H, d, J=9 Hz)

(9) 8-[2,6-Dichloro-3-[N-[N'-(4-pyridyl)ureidoacetyl]-N-methyl-amino]benzyloxy]-2-methylquinoline NMR (CDCl$_3$, δ): 2.58 (3H, s), 3.20 (3H, s), 3.76 (1H, dd, J=17, 5 Hz), 4.41 (1H, dd, J=17, 7 Hz), 5.43 (1H, d, J=10 Hz), 5.61 (1H, d, J=10 Hz), 5.63 (1H, m), 7.11 (2H, dd, J=6, 1 Hz), 7.19–7.40 (4H, m), 7.43–7.60 (2H, m), 8.12 (1H, d, J=9 Hz), 8.23 (2H, dd, J=6, 0.5 Hz), 9.43 (1H, br s)

(10) 8-[2,6-Dichloro-3-[N-[N'-(4-pyridylmethyl)ureidoacetyl]-N-methylamino]benzyloxyl]-2-methylquinoline NMR (CDCl$_3$, δ): 2.59 (3H, s), 3.20 (3H, s), 3.80 (1H, dd, J=17, 4 Hz), 4.01 (11, dd, J=17, 6 Hz), 4.10 (1H, dd, J=16, 6 Hz), 4.31 (1H, dd, J=16, 6 Hz), 5.38 (1H, br t, J=5 Hz), 5.50 (1H, d, J=10 Hz), 5.69 (1H, d, J=10 Hz), 6.24 (1H, br t, J=6 Hz), 7.08 (2H, d, J=6 Hz), 7.16–7.36 (2H, m), 7.31 (1H, d, J=8 Hz), 7.45 (2H, d, J=4 Hz), 7.49 (1H, d, J=8 Hz), 8.01 (1H, d, J=8 Hz), 8.40 (2H, d, J=5 Hz)

(11) 8-[2,6-Dichloro-3-[N-[N'-(3-pyridyl)ureidoacetyl]-N-methylamino]benzyloxy]-2-methylquinoline NMR (CDCl$_3$, δ): 2.58 (3H, s), 3.22 (3H, s), 3.80 (1H, dd, J=18, 5 Hz), 4.51 (1H, dd, J=18, 8 Hz), 5.41 (1H, d, J=10 Hz), 5.50 (1H, br t, J=4 Hz), 5.63 (1H, d, J=10 Hz), 7.09 (1H, dd, J=8, 5 Hz), 7.18–7.39 (4H, m), 7.42–7.55 (2H, m), 7.90 (1H, dt, J=8, 0.5 Hz), 8.04–8.16 (2H, m), 8.20 (1H, d, J=2 Hz), 9.15 (1H, br s)

(12) 8-[2,6-Dichloro-3-[N-[N'-[3-[N-(2-methoxyethyl)-N-methylcarbamoyl]phenyl]ureidoacetyl]-N-methylamino]benzyloxy]-2-methylquinoline NMR (CDCl$_3$, δ): 2.61 (3H, s), 2.84–3.29 (7H, m), 3.20 (3H, s), 3.28 (1H, dd, J=17, 5 Hz), 4.20 (1H, dd, J=7, 17 Hz), 5.47 (1H, d, J=10 Hz), 5.63 (1H, d, J=10 Hz), 5.64 (1H, m), 6.94 (1H, d, J=7 Hz), 7.13 (1H, t, J=8 Hz), 7.15–7.56 (8H, m), 8.09 (1H, d, J=9 Hz), 8.60 (1H, m)

(13) 8-[2,6-Dichloro-3-[N-methyl-N-[N'-[3-[N-methyl-N-(3-pyridylmethyl)carbamoyl]phenyl]ureidoacetyl]amino]benzyloxy]-2-methylguinoline NMR (CDCl$_3$, δ): 2.59 (3H, s), 2.70–3.04 (3H, m), 3.21 (3H, s), 3.79 (1H, dd, J=16, 4 Hz), 4.25 (1H, dd, J=16, 6 Hz), 4.39–4.88 (2H, m), 5.46 (1H, d, J=10 Hz), 5.60 (1H, d, J=10 Hz), 5.62 (1H, m), 6.98 (1H, br d, J=6 Hz), 7.08–7.76 (10H, m), 8.10 (1H, d, J=10 Hz), 8.30–8.79 (3H, m)

(14) 8-[2,6-Dichloro-3-[N-methyl-N-[N'-[3-[N-methyl-N-(2-pyridyl)carbamoyl]phenyl]ureidoacetyl]amino]benzyloxy]-2-methylquinoline NMR (CDCl$_3$, δ): 2.59 (3H, s), 3.21 (3H, s), 3.50 (3H, s), 3.78 (1H, dd, J=17,5 Hz), 4.19 (1H, dd, J=17, 6 Hz), 5.48 (1H, d, J=10 Hz), 5.56–5.69 (2H), 6.77–7.02 (4H), 7.20–7.51 (9H), 8.09 (1H, d, J=8 Hz), 8.30 (1H, dd, J=5, 1 Hz), 8.39 (1H, br s)

(15) 8-[2,6-Dichloro-3-[N-(N'-ethylureidoacetyl)-N-methylamino]benzyloxy]-4-methoxy-2-methylquinoline NMR (CDCl$_3$, δ): 1.00 (3H, t, J=7 Hz), 2.62 (3H, s), 3.00–3.17 (2H), 3.21 (3H, s), 3.77 (1H, dd, J=17, 5 Hz), 3.91 (1H, dd, J=17, 6 Hz), 4.02 (3H, s), 5.69 (1H, br s), 5.85–5.02 (2H), 5.66 (1H, d, J=10 Hz), 6.67 (1H, s), 7.19–7.50 (4H), 7.80 (1H, dd, J=8, 1 Hz)

(16) 8-[2,6-Dichloro-3-[N-[N'-(3-dimethylcarbamoylphenyl)ureidoacetyl]-N-methylamino]benzyloxy]-4-methoxy-2-methylquinoline NMR (CDCl$_3$, δ): 2.54 (3H, s), 2.88 (3H, br s), 3.00 (3H, br s), 3.21 (3H, s), 3.79 (1H, dd, J=17, 5 Hz), 4.05 (3H, s), 4.31 (1H, dd, J=17, 6 Hz), 5.41 (1H, d, J=10 Hz), 5.60 (1H, d, J=10 Hz), 5.69 (1H, br s), 6.68 (1H, s), 6.94 (1H, d, J=8 Hz), 7.07–7.39 (6H), 7.45 (1H, t, J=8 Hz), 7.83 (1H, d, J=9 Hz), 8.89 (1H, br s)

(17) 8-[2,6-Dichloro-3-[N-methyl-N-[N'-[3-(4-pyridylcarbamoyl)phenyl]ureidoacetyl]amino]benzyloxy]-4-methoxy-2-methylquinoline NMR (CDCl$_3$, δ): 2.61 (3H, s), 3.21 (3H, s), 3.87–4.09 (5H), 5.41 (1H, d, J=10 Hz), 5.51 (1H, d, J=10 Hz), 6.32 (1H, br s), 6.63 (1H, s), 6.98–7.13 (2H), 7.20–7.50 (5H), 7.79–7.90 (3H), 8.50 (2H, d, J=6 Hz), 8.60 (1H, br s), 9.55 (1H, br s)

(18) 8-[2,6-Dichloro-3-[N-methyl-N-[N'-[3-(4-methyl-1-piperazinylcarbonyl)phenyl]ureidoacetyl]amino]benzyloxy]-4-methoxy-2-methylquinoline NMR (CDCl$_3$, δ): 2.03–2.48 (7H), 2.52 (3H, s), 3.15–3.87 (8H), 4.03 (3H, s), 4.45 (1H, dd, J=17, 8 Hz), 5.40 (1H, d, J=10 Hz), 5.49–5.62 (2H), 6.67 (1H, s), 6.91 (1H, d, J=7 Hz), 7.10–7.50 (9H), 7.82 (1H, d, J=8 Hz), 9.01 (1H, br s)

(19) 8-[3-[N-[N'-(3-Acetylphenyl)ureidoacetyl]-N-methylamino]-2,6-dichlorobenzyloxy]-4-methoxy-2-methylquinoline NMR (CDCl$_3$, δ): 2.38 (3H, s), 2.55 (3H, s), 3.22 (3H, s), 3.81 (1H, dd, J=17, 4 Hz), 4.05 (3H, s), 4.49 (1H, dd, J=17, 7 Hz), 5.40 (1H, d, J=10 Hz), 5.51–5.68 (2H), 6.69 (1H, s), 7.12–7.52 (8H), 7.79–7.89 (2H), 9.06 (1H, br s)

(20) 8-[2,6-Dichloro-3-[N-[N'-(2-methoxyphenyl)ureidoacetyl]-N-methylamino]benzyloxy]-2-methylquinoline NMR (CDCl$_3$, δ): 2.71 (3H, s), 3.24 (3H, s), 3.67 (3H, s), 3.69 (1H, dd, J=17, 5 Hz), 3.86 (1H, dd, J=17, 5 Hz), 5.58 (1H, d, J=10 Hz), 5.65 (1H, d, J=10 Hz), 5.89 (1H, br t, J=5 Hz), 6.72–6.84 (1H, m), 6.85–7.00 (2H, m), 7.16 (1H, br s), 7.20–7.51 (6H, m), 7.93–8.02 (1H, m), 8.02 (1H, d, J=10 Hz)

EXAMPLE 34

The following compounds were obtained according to a similar manner to that of Example 21.

(1) 8-[2,6-Dichloro-3-[N-[N'-[3-(N-ethyl-N-methylcarbamoyl)phenyl]ureidoacetyl]-N-methylamino]benzyloxyl]-2-methylquinoline NMR (CDCl$_3$, δ): 0.96–1.20 (3H), 2.62 (3H, s), 2.79–3.06 (3H), 3.13–3.30 (4H), 3.50 (1H, m), 3.79 (1H, dd, J=18, 5 Hz), 4.19 (1H, dd, J=18, 6 Hz), 5.48 (1H, d, J=10 Hz), 5.59–5.72 (2H), 6.91 (1H, d, J=8 Hz), 7.09–7.53 (9H), 8.09 (1H, d, J=9 Hz), 8.59 (1H, br s)

(2) 8-[2,6-Dichloro-3-[N-[N'-[3-(N-isopropyl-N-methylcarbamoyl)phenyl]ureidoacetyl]-N-methylamino]-benzyloxy]-2-methylquinoline NMR (CDCl$_3$, δ): 0.99–1.19 (6H), 2.59–2.92 (6H), 3.21 (3H, s), 3.79 (1H, dd, J=18, 5 Hz), 3.96 (1H, m), 4.20 (1H, dd, J=18, 6 Hz), 5.48 (1H, d, J=10 Hz), 5.59–5.70 (2H), 6.90 (1H, br d, J=7 Hz), 7.10–7.51 (9H), 8.09 (1H, d, J=9 Hz), 8.59 (1H, br s)

(3) 8-[2,6-Dichloro-3-[N-[N'-(3-diethylcarbamoylphenyl)ureidoacetyl]-N-methylamino]benzyloxy]-2-methylquinoline NMR (CDCl$_3$, δ): 0.86–1.31 (6H, m), 2.61 (3H, s), 3.04–3.63 (4H, m), 3.22 (3H, s), 3.80 (1H, dd, J=17, 5 Hz), 4.20 (1H, dd, J=17, 7 Hz), 5.47 (1H, d, J=10 Hz), 5.63 (1H, d, J=10 Hz), 5.65 (1H, m), 6.90 (1H, dt, J=7, 0.5 Hz), 7.09–7.38 (6H, m), 7.14 (1H, t, J=8 Hz), 7.43–7.51 (2H, m), 8.09 (1H, d, J=9 Hz), 8.58 (1H, br s)

(4) 8-[2,6-Dichloro-3-[N-methyl-N-[N'-[3-(2-pyridylcarbamoyl)phenyl]ureidoacetyl]amino]benzyloxyl]-2-methylquinoline NMR (CDCl$_3$, δ): 2.62 (3H, s), 3.22 (3H, s), 3.86 (1H, dd, J=17, 5 Hz), 4.22 (1H, dd, J=17, 6 Hz), 5.50 (1H, d, J=10 Hz), 5.66 (1H, d, J=10 Hz), 5.80 (1H, br t, J=6 Hz), 7.03 (1H, dd, J=7, 5 Hz), 7.16–7.50 (9H), 7.71 (1H, dt, J=8, 1 Hz), 7.80 (1H, br s), 8.09 (1H, d, J=9 Hz), 8.25–8.33 (2H), 8.68 (1H, br s), 8.71 (1H, br s)

(5) 8-[2,6-Dichloro-3-[N-methyl-N-[N'-[3-(4-pyridylcarbamoyl)phenyl]ureidoacetyl]amino]benzyloxy]-2-methylquinoline NMR (CDCl$_3$, δ): 2.69 (3H, s), 3.23 (3H, s), 3.89 (1H, dd, J=17, 5 Hz), 4.03 (1H, dd, J=17, 5 Hz), 5.42 (1H, d, J=10 Hz), 5.54 (1H, d, J=10 Hz), 6.45 (1H, br t, J=5 Hz), 6.96 (1H, br s), 7.02 (1H, t, J=9 Hz), 7.20–7.56 (9H), 7.89 (2H, d, J=6 Hz), 8.06 (1H, d, J=9 Hz), 8.44 (1H, s), 8.51 (2H, d, J=6 Hz), 9.61 (1H, br s)

(6) 8-[2,6-Dichloro-3-[N-methyl-N-[N'-[3-[N-methyl-N-(4-pyridyl)carbamoyl]phenyl]ureidoacety amino]benzyloxy]-2-methylquinoline NMR (CDCl$_3$, δ): 2.50 (3H, s), 3.21 (3H, s), 3.40 (3H, s), 3.73 (1H, dd, J=18, 5 Hz), 4.33 (1H, dd, J=18, 7 Hz), 5.39–5.50 (2H), 5.61 (1H, d, J=10 Hz), 6.80 (2H, d, J=5 Hz), 6.90 (1H, d, J=7 Hz), 7.02 (1H, t, J=8 Hz), 7.18–7.38 (6H), 7.45–7.58 (2H), 8.10 (1H, d, J=9 Hz), 8.31 (2H, br d, J=5 Hz), 8.61 (1H, br s)

(7) 8-[2,6-Dichloro-3-[N-methyl-N-[N'-[3-[N-methyl-N-(3-pyridyl)carbamoyl]phenyl]ureidoacetyl]amino]benzyloxy]-2-methylquinoline NMR (CDCl$_3$, δ): 2.56 (3H, s), 3.21 (3H, s), 3.40 (3H, s), 3.79 (1H, dd, J=17, 5 Hz), 4.25 (1H, dd, J=17, 6 Hz), 5.41–5.69 (3H), 6.80 (1H, d, J=7 Hz), 6.99 (1H, t, J=8 Hz), 7.04–7.54 (10H), 8.11 (1H, d, J=8 Hz), 8.22 (1H, d, J=2 Hz), 8.31 (1H, d, J=5 Hz), 8.50 (1H, br s)

(8) 8-(2,6-Dichloro-3-[N-methyl-N-[N'-[3-(5-pyrimidinylcarbamoyl)phenyl]ureidoacetyl]amino]benzyloxy]-2-methylquinoline NMR (CDCl$_3$, δ): 2.63 (3H, s), 3.21 (3H, s), 3.72–4.03 (2H), 5.49 (1H, d, J=10 Hz), 5.59 (1H, d, J=10 Hz), 6.36 (1H, br s), 6.98–7.51 (10H), 8.07 (1H, d, J=9 Hz), 8.50 (1H, br s), 8.95 (1H, s), 9.37 (2H, s), 9.85 (1H, br s)

(9) 8-[2,6-Dichloro-3-[N-[N'-[3-[3-(N,N-dimethylamino)phenylcarbamoyl]phenyl]ureidoacetyl]-N-methylamino]benzyloxy]-2-methylquinoline NMR (CDCl$_3$, δ): 2.70 (3H, s), 2.95 (6H, s), 3.22 (3H, s), 3.83 (1H, dd, J=17, 5 Hz), 4.02 (1H, dd, J=17, 6 Hz), 5.51 (2H, s), 6.79 (1H, br t, J=5 Hz), 6.55 (1H, dt, J=7.1 Hz), 6.99–7.10 (2H), 7.16–7.55 (11H), 8.06 (1H, d, J=9 Hz), 8.32 (1H, s), 9.04 (1H, br s)

(10) 8-[2,6-Dichloro-3-[N-[N'-[3-(4-ethyl-1-piperazinylcarbonyl)phenyl]ureidoacetyl]-N-methylamino]-benzyloxy]-2-methylquinoline NMR (CDCl$_3$, δ): 1.08 (3H, t, J=7 Hz), 2.13–2.48 (6H), 2.60 (3H, s), 3.28–3.43 (2H), 3.61–3.85 (3H), 4.39 (1H, dd, J=18, 8 Hz), 5.41–5.54 (2H), 5.62 (1H, d, J=10 Hz), 6.95 (1H, d, J=8 Hz), 7.11–7.39 (7H), 7.45–7.53 (2H), 8.10 (1H, d, J=9 Hz), 8.67 (1H, br s)

(11) 8-[2,6-Dichloro-3-[N-[N'-[3-[4-(methylcarbamnoyl)-1-pyperazinylcarbonyl]phenyl]ureidoacetyl]-N-methylamino]benzyloxy]-2-methylquinoline NMR (CDCl$_3$, δ): 2.61 (3H, s), 2.80 (3H, d, J=5 Hz), 3.16–3.77 (11H), 3.80 (1H, dd, J=17, 5 Hz), 4.15 (1H, dd, J=17, 6 Hz), 4.73 (1H, br d, J=5 Hz), 5.48 (1H, d, J=10 Hz), 5.62 (1H, d, J=10 Hz), 5.77 (1H, br t, J=5 Hz), 6.93 (1H, d, J=7 Hz), 7.10–7.52 (9H), 8.10 (1H, d, J=9 Hz), 8.77 (1H, br s)

(12) 8-[2,6-Dichloro-3-[N-[N'-[3-(4-dimnethylamnopiperidinocarbonyl)phenyl]ureidoacetyl]-N-methylamino]benzyloxy]-2-methylquinoline NMR (CDCl$_3$, δ): 1.10–2.10 (5H), 2.29 (6H, s), 2.39 (1H, m), 2.66 (3H, s), 2.92 (1H, m), 3.23 (3H, s), 3.75 (1H, d, J=17 Hz), 3.91 (1H, d, J=17 Hz), 4.70 (1H, m), 5.52 (1H, d, J=10 Hz), 5.60 (1H, d, J=10 Hz), 6.94 (1H, d, J=7 Hz), 7.18–7.52 (9H), 8.07 (1H, d, J=9 Hz)

(13) 8-[2,6-Dichloro-3-[N-methyl-N-[N'-[3-(1-pyrrolidinylcarbonyl)phenyl]ureidoacetyl]amino]benzyloxy]-2-methylquinoline NMR (CDCl$_3$, δ): 1.61–1.97 (4H), 2.62 (3H, s), 3.21 (3H, s), 3.30 (2H, t, J=6 Hz), 3.57 (2H, t, J=6 Hz), 3.80.(1H, dd, J=18, 5 Hz), 4.19 (1H, dd, J=18, 6 Hz), 5.48 (1H, d, J=10 Hz), 5.59–5.73 (2H), 7.02–7.52 (10H), 8.09 (1H, d, J=9 Hz), 8.62 (1H, br s)

(14) 8-[2,6-Dichloro-3-[N-methyl-N-[N'-[3-(1,2,3,6-tetrahydropyridin-1-ylcarbonyl)phenyl]ureidoacetyl]amino]benzyloxy]-2-methylquinoline NMR (CDCl$_3$, δ): 1.95–2.31 (2H, m), 2.60 (3H, s), 3.21 (3H, s), 3.32–3.52 (1H, m), 3.66–3.88 (2H, m), 3.77 (1H, dd, J=18, 5 Hz), 4.02–4.23 (1H, m), 4.17 (1H, dd, J=18, 6 Hz), 5.45 (1H, d, J=10 Hz), 5.56–5.88 (3H, m), 5.62 (1H, d, J=10 Hz), 6.96 (1H, br d, J=6 Hz), 7.11–7.40 (6H, m), 7.16 (1H, t, J=8 Hz), 7.42–7.52 (2H, m), 8.08 (1H, d, J=10 Hz), 8.59 (1H, br s)

(15) 8-[2,6-Dichloro-3-[N-[N'-[3-[N-[3-(dimethylamino)propyl]-N-methylcarbamoyl]phenyl]ureidoacetyl]-N-methylamino]benzyloxy]-2-methylquinoline NMR (CDCl$_3$, δ): 1.60–1.92 (2H), 2.09–2.68 (12H), 2.80–3.08 (2H), 3.13–3.31 (4H), 3.49 (1H, m), 3.78 (1H, dd, J=17, 5 Hz), 4.09 (1H, m), 5.49 (1H, d, J=10 Hz), 5.62 (1H, d, J=10 Hz), 5.73 (1H, br s), 6.90 (1H, d, J=7 Hz), 7.08–7.52 (9H), 8.08 (1H, d, J=9 Hz), 8.69 (1H, br s)

(16) 8-[2,6-Dichloro-3-[N-[N'-[3-[N-(3-methoxypropyl)-N-methylcarbamoyl]phenyl]ureidoacetyl]-N-methylaminolbenzyloxy]-2-methylquinoline NMR (CDCl$_3$, δ): 1.53–2.04 (4H, m), 2.60 (3H, s), 2.79–3.12 (3H, m), 3.14–3.64 (8H, m), 3.80 (1H, dd, J=17, 5 Hz), 4.09–4.32 (1H, m), 5.48 (1H, d, J=10 Hz), 5.58–5.74 (1H, m), 5.54 (1H, d, J=10 Hz), 6.94 (1H, br d, J=7 Hz), 7.14 (1H, d, J=8 Hz), 7.19–7.60 (8H, m), 8.09 (1H, d, J=9 Hz), 8.50–8.68 (1H, m)

(17) 8-[3-[N-[N'-[3-[N,N-Bis(2-methoxyethyl)carbamoyl]phenyl]ureidoacetyl]-N-methylamino]-2,6-dichlorobenzyloxy]-2-methylquinoline NMR (CDCl$_3$, δ): 2.61 (31, s), 3.12–3.87 (18H), 4.22 (1H, dd, J=18, 6 Hz), 5.48 (1H, d, J=10 Hz), 5.53–5.70 (2H), 6.93 (1H, d, J=7 Hz), 7.09–7.51 (9H), 8.09 (1H, d, J=9 Hz), 8.53 (1H, br s)

(18) 8-[3-[N-[N'-[3-[N,N-Bis(2-ethoxyethyl)carbamoyl]phenyl]ureidoacetyl]-N-methylamino]-2,6-dichlorobenzyloxy]-2-methylquinoline NMR (CDCl$_3$, δ): 1.00–1.28 (6H, m), 2.62 (3H, s), 3.21 (3H, s), 3.23–3.80 (12H, m), 3.77 (1H, dd, J=17.5, 5 Hz), 4.20 (1H, dd, J=17.5, 6 Hz), 5.46 (1H, d, J=10 Hz), 5.60 (1H, br t, J=5 Hz), 5.64 (1H, d, J=10 Hz), 6.94 (1H, br d, J=8 Hz), 7.14 (1H, t, J=7.5 Hz), 7.17–7.55 (8H, m), 8.08 (1H, d, J=8 Hz), 8.47 (1H, br s)

(19) 8-[3-[N-[N'-[3-[N-[2-(tert-Butyldiphenylsilyloxy) ethyl]-N-methylcarbamoyl]phenyl]ureidoacetyl]-N-methylamino]-2,6-dichlorobenzyloxy]-2-methylquinoline NMR (CDCl$_3$, δ): 1.03 (9H, br s), 2.60 (3H, s), 2.98 (3H, br d, J=6 Hz), 3.21 (3H, s), 3.27–3.92 (5H), 4.22 (1H, m), 5.45 (1H, d, J=10 Hz), 5.56 (1H, br s), 5.62 (1H, d, J=10 Hz), 6.91 (1H, br d, J=7 Hz), 7.02–7.72 (19H), 8.07 (1H, d, J=9 Hz), 8.29 (0.5H, br s), 8.48 (0.5H, br s)

(20) 8-[2,6-Dichloro-3-[N-methyl-N-[N'-[3-[N-methyl-N-(2-pyridylmethyl)carbamoyl]phenyl]ureidoacetyl]amino] benzyloxy]-2-methylquinoline NMR (CDCl$_3$, δ): 2.59 (3H, s), 2.80–3.09 (3H, m), 3.20 (3H, s), 3.78 (1H, br d, J=17 Hz), 4.19 (1H, dd, J=17 and 6 Hz), 4.49–4.89 (2H, m), 5.45 (1H, d, J=10 Hz), 5.53–5.71 (2H, m), 6.92–7.70 (13H, m), 8.09 (1H, d, J=9 Hz), 8.51 (1H, d, J=4 Hz), 8.60 (1H, m)

(21) 8-[2,6-Dichloro-3-[N-[N'-[3-[N-(2-methoxyethyl)-N-(3-pyridylmethyl)carbamoyl]phenyl]ureidoacetyl]-N-methylamino]benzyloxy]-2-methylquinoline NMR (CDCl$_3$, δ): 2.59 (3H, s), 3.04–3.70 (7H, m), 3.20 (3H, s), 3.28 (1H, dd, J=16, 5 Hz), 4.30 (1H, dd, J=16, 6 Hz), 4.51–4.88 (2H, m), 5.44 (1H, d, J=10 Hz), 5.49–5.69 (3H, m), 6.95 (1H, br d, J=6 Hz), 7.05–7.77 (11H, m), 8.08 (1H, d, J=8 Hz), 8.30–8.74 (3H, m)

EXAMPLE 35

The following compounds were obtained according to similar manners to those of Examples 15 or 16.

(1) 8-[2,6-Dichloro-3-[N-methyl-N-(3-phenylpropioloylglycyl)amino]benzyloxy]-2-methylquinoline NMR (CDCl$_3$, δ): 2.75 (3H, s), 3.26 (3H, s), 3.60 (1H, dd, J=18, 4 Hz), 3.90 (1H, dd, J=18, 4 Hz), 5.65 (2H, s), 6.95 (1H, br s), 7.20–7.61 (11H, m), 8.04 (1H, d, J=8 Hz)

(2) 8-[2,6-Dichloro-3-[N-(4-formylcinnamoylglycyl)-N-methylamino]benzyloxy]-2-methylquinoline NMR (CDCl$_3$, δ): 2.74 (3H, s), 3.28 (3H, s), 3.69 (1H, dd, J=18, 4 Hz), 3.96 (1H, dd, J=18, 4 Hz), 5.65 (2H, s), 6.61 (1H, d, J=16 Hz), 6.75 (1H, br s), 7.20–7.71 (9H, m), 7.88 (2H, d, J=8 Hz), 8.06 (1H, d, J=8 Hz), 10.01 (1H, s)

(3) 8-[3-[N-(4-Aminocinnamoylglycyl)-N-methylamino]-2,6-dichlorobenzyloxy]-2-methylquinoline NMR (CDCl$_3$, δ): 2.73 (3H, s), 3.25 (3H, s), 3.62 (1H, dd, J=18, 4 Hz), 3.94 (1H, dd, J=18, 5 Hz), 5.65 (2H, s), 6.28 (1H, d, J=15 Hz), 6.52 (1H, t-like), 6.63 (2H, d, J=8 Hz), 7.18–7.54 (9H), 8.03 (1H, d, J=8 Hz)

(4) 8-[2,6-Dichloro-3-[N-methyl-N-((E)-2-methyl-3-phenylacryloylglycyl)amino]benzyloxy]-2-methylquinoline NMR (CDCl$_3$, δ): 2.11 (3H, s), 2.74 (3H, s), 3.26 (3H, s), 3.61 (1H, dd, J=16 Hz, 5 Hz), 3.93 (1H, dd, J=16, 5 Hz), 5.63 (2H, s), 6.87 (1H, t-like), 7.20–7.54 (12H, m), 8.02 (1H, d, J=8 Hz)

(5) 8-[2,6-Dichloro-3-[N-methyl-N-[(E)-3-(4-pyridyl) acryloylglycyl]amino]benzyloxy]-2-methylquinoline mp: 111–114.5° C.

NMR (CDCl$_3$, δ): 2.73 (3H, s), 3.28 (3H, s), 3.72 (1H, dd, J=16, 5 Hz), 3.95 (1H, dd, J=16, 5 Hz), 5.63 (2H, s), 6.65 (1H, d, J=16 Hz), 6.87 (1H, t-like), 7.21–7.40 (5H, m), 7.40–7.57 (4H, m), 8.03 (1H, d, J=8 Hz), 8.60 (2H, d, J=6 Hz)

(6) 8-[2,6-Dichloro-3-[N-[4-(N,N-dimethylamino) cinnamoyl-glycyl]-N-methylamino]benzloxy]-2-methylquinoline NMR (CDCl$_3$, δ): 2.74 (3H, s), 3.00 (6H, s), 3.25 (3H, s), 3.60 (1H, dd, J=16, 5 Hz), 3.93 (1H, dd, J=16, 5 Hz), 5.62 (2H, s), 6.25 (1H, d, J=16 Hz), 6.47 (1H, t-like), 6.56–6.77 (2H, m), 7.14–7.60 (9H, m), 8.03 (1H, d, J=8 Hz)

(7) 8-[3-[N-(4-Chlorocinnamoylglycyl)-N-methylamino]-2,6-dichlorobenzyloxy]-2-methylquinoline NMR (CDCl$_3$, δ): 2.74 (3H, s), 3.26 (3H, s), 3.64 (1H, dd, J=17, 3 Hz), 3.94 (1H, dd, J=17, 3 Hz), 5.64 (1H, s), 6.45 (1H, d, J=16 Hz), 6.65 (1H, t-like), 7.20–7.60 (11H, m), 8.03 (1H, d, J=8 Hz)

(8) 8-[2,6-Dichloro-3-[N-methyl-N-(4-methylcinnamoylglycyl)amino]benzyloxy]-2-methylquinoline NMR (CDCl$_3$, δ): 2.36 (3H, s), 2.75 (3H, s), 3.26 (3H, s), 3.63 (1H, dd, J=4, 17 Hz), 3.94 (1H, dd, J=4, 17 Hz), 5.64 (2H, s), 6.42 (1H, d, J=16 Hz), 6.58 (1H, t-like), 7.16 (2H, d, J=8 Hz), 7.20–7.50 (8H, m), 7.53 (1H, d, J=16 Hz), 8.02 (1H, d, J=8 Hz)

(9) 8-[3-[N-[4-(Acetamido)cinnamoylglycyl]-N-methylamino]-2,6-dichlorobenzyloxy]-2-methylquinoline NMR (CDCl$_3$, δ): 2.10 (3H, s), 2.68 (3H, s), 3.23 (3H, s), 3.61 (1H, dd, J=16, 5 Hz), 3.87 (1H, dd, J=16, 5 Hz), 5.60 (2H, s), 6.38 (1H, d, J=16 Hz), 6.62 (1H, t-like), 7.15–7.65 (11H, m), 8.05 (1H, d, J=8 Hz), 8.44 (1H, s)

(10) 8-[2,6-Dichloro-3-[N-methyl-N-[4-(N-methylacetamida)cinnamoylglycyl]amino]benzyloxy]-2-methylquinoline NMR (CDCl$_3$, δ): 1.90 (3H, s), 2.75 (3H, s), 3.28 (6H, s), 3.66 (1H, dd, J=17, 3 Hz), 3.95 (1H, dd, J=17, 3 Hz), 5.66 (2H, s), 6.49 (1H, d, J=16 Hz), 6.67 (1H, t-like), 7.13–7.65 (11H, m), 8.03 (1H, d, J=8 Hz)

(11) 8-[2,6-Dichloro-3-[N-methyl-N-[4-(propionamido) cinnamoylglycyl]amino]benzyloxy]-2-methylquinoline NMR (CDCl$_3$, δ): 1.21 (3H, t, J=8 Hz), 2.35 (2H, q, J=8 Hz), 2.70 (3H, s), 3.25 (3H, s), 3.62 (1H, dd, J=4, 17 Hz), 3.90 (1H, dd, J=4, 17 Hz), 5.60 (2H, s), 6.40 (1H, d, J=16 Hz), 6.61 (1H, t-like), 7.13–7.61 (11H, m), 7.86 (1H, s), 8.04 (1H, d, J=8 Hz)

(12) 8-[2,6-Dichloro-3-[N-methyl-N-[4-(N-methylpropionamido)cinnamoylglycyl]amino]benzyloxy]-2-methylquinoline NMR (CDCl$_3$, δ): 1.06 (3H, t, J=8 Hz), 2.13 (2H, dif-q), 2.74 (3H, s), 3.18–3.29 (6H, m), 3.65 (1H, dd, J=17, 4 Hz), 3.95 (1H, dd, J=17, 4 Hz), 5.66 (2H, s), 6.48 (1H, d, J=16 Hz), 6.67 (1H, t-like), 7.07–7.64 (11H, m), 8.03 (1H, d, J=8 Hz)

(13) 8-[2,6-Dichloro-3-[N-[4-ethylacetamido) cinnamoylglycyl]-N-methylamino]benzyloxyl]-2-methylquinoline NMR (CDCl$_3$, δ): 1.10 (3H, t, J=7.5 Hz), 1.84 (3H, s), 2.74 (3H, s), 3.28 (3H, s), 3.65 (1H, dd, J=17, 4 Hz), 3.74 (2H, q, J=7.5 Hz), 3.95 (1H, dd, J=17, 4 Hz), 5.65 (2H, s), 6.48 (1H, d, J=16 Hz), 6.67 (1H, t-like), 7.15 (2H, d, J=8 Hz), 7.20–7.65 (9H, m), 8.03 (1H, d, J=8 Hz)

(14) 8-[2,6-Dichloro-3-[N-methyl-N-[4-(2-pyridylmethoxy) cinnamoylglycyl]amino]benzyloxy]-2-methylquinoline NMR (CDCl$_3$, δ): 2.73 (3H, s), 3.27 (3H, s), 3.63 (1H, dd, J=17, 3 Hz), 3.94 (1H, dd, J=17, 3 Hz), 5.23 (2H, s), 5.65 (2H, s), 6.35 (1H, d, J=16 Hz), 6.56 (1H, t-like), 6.98 (2H, d, J=8 Hz), 7.18–7.59 (11H, m), 7.73 (1H, td, J=8, 1 Hz), 8.02 (1H, d, J=8 Hz), 8.62 (1H, dif-dd, J=5 Hz)

(15) 8-[2,6-Dichloro-3-[N-[4-[2-(N,N-dimethylamino)-ethoxy]cinnamoylglycyl]-N-methylamino]benzyloxy]-2-methylquinoline NMR (CDCl$_3$, δ): 2.35 (6H, s), 2.67–2.81 (5H, m), 3.27 (3H, s), 3.62 (1H, dd, J=16, 4 Hz), 3.95 (1H, dd, J=16, 4 Hz), 4.10 (2H, t, J=6 Hz), 5.68 (2H, s), 6.35 (1H, d, J=16 Hz), 6.55 (1H, t-like), 6.92 (2H, d, J=8 Hz), 7.20–7.45 (3H, m), 7.45–7.58 (6H, m), 8.02 (1H, d, J=8 Hz)

(16) 8-[2,6-Dichloro-3-[N-[4-(2-hydroxyethoxy)cinnamoylglycyl]-N-methylamino]benzyloxy]-2-methylquinoline NMR (CDCl₃, δ): 2.01 (1H, t-like), 2.73 (3H, s), 3.27 (3H, s), 3.63 (1H, dd, J=18, 4 Hz), 3.86–4.04 (3H, m), 4.11 (2H, t, J=5 Hz), 5.65 (2H, s), 6.35 (1H, d, J=16 Hz), 6.58 (1H, t-like), 6.90 (2H, d, J=8 Hz), 7.21–7.48 (3H, m), 7.48–7.60 (6H, m), 8.03 (1H, d, J=8 Hz)

(17) 8-[2,6-Dichloro-3-[N-methyl-N-[4-(methylcarbamoyl)cinnamoylglycyl]amino]benzyloxy]-2-methylquinoline NMR (CDCl₃, δ): 2.73 (3H, s), 3.00 (3H, d, J=5 Hz), 3.26 (3H, s), 3.64 (1H, dd, J=4, 17 Hz), 3.93 (1H, dd, J=4, 17 Hz), 5.66 (2H, s), 6.28 (1H, q-like), 6.53 (1H, d, J=16 Hz), 6.69 (1H, t-like), 7.18–7.64 (9H, m), 7.75 (2H, d, J=8 Hz), 8.03 (1H, d, J=8 Hz)

(18) 8-[2,6-Dichloro-3-[N-[4-(dimethylcarbamoyl)cinnamoylglycyl]-N-methylamino]benzloxy]-2-methylguinoline NMR (CDCl₃, δ): 2.74 (3H, s), 2.99 (3H, s), 3.12 (3H, s), 3.28 (3H, s), 3.65 (1H, dd, J=17, 4 Hz), 3.95 (1H, dd, J=17, 4 Hz), 5.64 (2H, s), 6.52 (1H, d, J=16 Hz), 6.68 (1H, t-like), 7.20–7.66 (11H, m), 8.05 (1H, d, J=8 Hz)

(19) 8-[2,6-Dichloro-3-[N-methyl-N-[4-(3-methylureido)cinnamoylglycyl]amino benzyloxy]-2-methylquinoline NMR (CDCl₃, δ): 2.63 (3H, s), 2.71 (3H, d, J=5 Hz), 3.14 (3H, s), 3.62 (1H, dd, J=17, 4 Hz), 3.80 (1H, dd, J=17, 4 Hz), 5.32 (1H, q-like), 5.55 (2H, s), 6.32 (1H, d, J=16 Hz), 6.70 (1H, t-like), 7.18–7.38 (8H, m), 7.38–7.55 (3H, m), 8.02–8.14 (2H, m)

(20) 8-[2,6-Dichloro-3-[N-[4-(methanesulfonamido)cinnamoylglycyl]-N-methylamino]benzyloxy]-2-methylquinoline NMR (CDCl₃, δ): 2.74 (3H, s), 3.04 (3H, s), 3.28 (3H, s), 3.66 (1H, dd, J=18, 4 Hz), 3.95 (1H, dd, J=18, 4 Hz), 5.65 (2H, s), 6.41 (1H, d, J=16 Hz), 6.64 (1H, t-like), 6.78 (1H, br s), 7.13–7.59 (11H, m), 8.02 (1H, d, J=8 Hz)

(21) 8-[2,6-Dichloro-3-[N-methyl-N-(butyrylglycyl)amino]benzyloxy]-4-methoxy-2-methylquinoline NMR (CDCl₃, δ): 0.93 (3H, t, J=7 Hz), 1.54–1.80 (2H), 2.20 (2H, t, J=7 Hz), 2.71 (3H, s), 3.22 (3H, s), 3.49 (1H, dd, J=17, 4 Hz), 3.82 (1H, dd, J=17, 5 Hz), 4.01 (3H, s), 5.60 (2H, s), 6.41 (1H, br s), 6.65 (1H, s), 7.19–7.51 (4H), 7.81 (1H, dd, J=8, 1 Hz)

(22) 8-[2,6-Dichloro-3-[N-(heptanoylglycyl)-N-methylamino]benzyloxy]-4-methoxy-2-methylquinoline NMR (CDCl₃, δ): 0.81–0.99 (3H), 1.20–1.40 (6H), 1.52–1.80 (2H), 2.21 (2H, t, J=7 Hz), 2.70 (3H, s), 3.25 (3H, s), 3.48 (1H, dd, J=17, 4 Hz), 3.83 (1H, dd, J=17, 5 Hz), 4.01 (3H, s), 5.61 (2H, s), 6.40 (1H, br s), 6.67 (1H, s), 7.20–7.41 (3H), 7.49 (1H, d, J=9 Hz), 7.81 (1H, dd, J=8, 1 Hz)

(23) 8-(2,6-Dichloro-3-[N-methyl-N-[(E)-3-(3-pyridyl)-acryloylglycyl]amino]benzyloxy]-4-methoxy-2-methylquinoline NMR (CDCl₃, δ): 2.69 (3H, s), 3.28 (3H, s), 3.66 (1H, dd, J=17, 4 Hz), 3.89–4.04 (4H), 5.61 (2H, s), 6.57 (1H, d, J=15 Hz), 6.65 (1H, s), 6.75 (1H, m), 7.20–7.62 (4H), 7.74–7.88 (2H), 8.57 (1H, dd, J=5, 1 Hz), 8.71 (1H, d, J=1 Hz)

(24) 8-[2,6-Dichloro-3-[N-[4-(dimethylcarbamoyl)cinnamoylglycyl]-N-methylamino]benzyloxy]-4-methoxy-2-methylquinoline NMR (CDCl₃, δ): 2.69 (3H, s), 2.99 (3H, br s), 3.11 (3H, br s), 3.29 (3H, s), 3.67 (1H, dd, J=17, 4 Hz), 3.78–4.08 (4H), 5.61 (2H, s), 6.51 (1H, d, J=15 Hz), 6.67 (1H, s), 6.72 (1H, br s), 7.20–7.63 (8H), 7.82 (1H, dd, J=8, 1 Hz)

(25) 8-[2,6-Dichloro-3-[N-methyl-N-[4-(N-methylacetamido)cinnamoylglycyl]amino]benzyloxy]-4-methoxy-2-methylquinoline NMR (CDCl₃, δ): 1.91 (3H, br s), 2.70 (3H, s), 3.28 (6H, s), 3.68 (1H, dd, J=17, 4 Hz), 3.89–4.06 (4H), 5.62 (2H, s), 6.49 (1H, d, J=15 Hz), 6.67 (1H, s), 6.73 (1H, br s), 7.12–7.62 (9H), 7.82 (1H, d, J=8 Hz)

(26) 8-[2,6-Dichloro-3-[N-[4-[N-(2-methoxyethyl)carbamoyl]cinnamoylglycyl]-N-methylamino]benzyloxy]-2-methylquinoline NMR (CDCl₃, δ): 2.72 (3H, s), 3.28 (3H, s), 3.39 (3H, s), 3.51–3.76 (5H), 3.96 (1H, dd, J=18, 5 Hz), 5.64 (2H, s), 6.49–6.62 (2H), 6.75 (1H, br t, J=4 Hz), 7.21–7.66 (9H), 7.78 (2H, d, J=8 Hz), 8.03 (1H, d, J=8 Hz)

(27) 8-[3-[N-[4-[N,N-Bis(2-methoxyethyl)carbamoyl]-cinnamoylglycyl]-N-methylamino]-2,6-dichlorobenzyloxy]2-methylquinoline NMR (CDCl₃, δ): 2.73 (3H, s), 3.20–3.84, (18H), 3.96 (1H, dd, J=18, 5 Hz), 5.63 (2H, s), 6.50 (1H, d, J=15 Hz), 6.69 (1H, br t, J=4 Hz), 7.20–7.63 (11H), 8.02 (1H, d, J=8 Hz)

EXAMPLE 36

8-[2,6-Dichloro-3-[N-[4-(methoxyacetamido)cinnamoylglycyl]-N-methylamino]benzloxy]-2-methylquinoline was obtained by reacting 8-[2,6-dichloro-3-[N-(4-aminocinnamoylglycyl)-N-methylamino]benzloxy]-2-methylquinoline with methoxyacetic acid according to a similar manner to that of Example 16.

NMR (CDCl₃, δ): 2.74 (3H, s), 3.26 (3H, s), 3.51 (3H, s), 3.65 (1H, dd, J=18, 4 Hz), 3.86–4.07 (3H, m), 5.65 (2H, s), 6.43 (1H, d, J=16 Hz), 6.61 (1H, br peak), 7.22–7.40 (3H, m), 7.40–7.66 (8H, m), 8.03 (1H, d, J=8 Hz), 8.35 (1H, s)

EXAMPLE 37

The following compounds were obtained according to a similar manner to that of Example 36.

(1) 8-[2,6-Dichloro-3-[N-methyl-N-[4-(3-pyridylacetamido)cinnamoylglycyl]aminoabenzyloxy]-2-methylquinoline NMR (CDCl₃, δ): 2.64 (3H, s), 3.21 (3H, s), 3.51–3.70 (3H, m), 3.88 (1H, dd, J=18, 4 Hz), 5.60 (2H, s), 6.38 (1H, d, J=16 Hz), 6.62 (1H, t-like), 7.16–7.74 (13H, m), 8.07 (1H, d, J=8 Hz), 8.36 (1H, s), 8.47–8.60 (2H, m)

(2) 8-[2,6-Dichloro-3-[N-methyl-N-[4-(isonicotinoylamino)cinnamoylglycyl]amino]benzyloxy]-2-methylquinoline NMR (CDCl₃, δ): 2.62 (3H, s), 3.19 (3H, s), 3.60 (1H, dd, J=18, 4 Hz), 3.88 (1H, dd, J=18, 4 Hz), 5.60 (2H, s), 6.41 (1H, d, J=16 Hz), 6.65 (1H, t-like), 7.18–7.60 (9H, m), 7.64–7.80 (4H, m), 8.05 (1H, d, J=8 Hz), 8.68 (2H, d, J=5 Hz), 8.93 (1H, s)

(3) 8-3-[N-[4-(Benzamido)cinnamoylglycyl]-N-methylamino]-2,6-dichlorbenzyloxy-2-methylquinoline NMR (CDCl₃, δ): 2.70 (3H, s), 3.25 (3H, s), 3.63 (1H, dd, J=4, 18 Hz), 3.93 (1H, dd, J=4, 18 Hz), 5.64 (2H, s), 6.43 (1H, d, J=16 Hz), 6.63 (1H, t-like), 7.14–7.36 (4H, m), 7.36–7.62 (9H, m), 7.69 (2H, d, J=8 Hz), 7.89 (2H, d, J=8 Hz), 7.98–8.14 (2H, m)

(4) 8-[3-[N-[4-(4-Bromobutyramido)cinnamoylglycyl]-N-methylamino]-2,6-dichlorobenzyloxy]-2-methylquinoline NMR (CDCl₃, δ): 2.18 (3H, t, J=6 Hz), 2.55 (3H, t, J=6 Hz), 2.75 (3H, s), 3.26 (3H, s), 3.46–3.72 (4H, m), 3.94 (1H, dd, J=18, 4 Hz), 5.63 (2H, s), 6.40 (1H, d, J=16 Hz), 6.63 (1H, br peak), 7.18–7.37 (4H, m), 7.37–7.62 (7H, m), 7.68 (1H, s), 8.06 (1H, d, J=8 Hz)

EXAMPLE 38

To a solution of 8-[3-[N-[N'-[3-[N-[2-(tert-butyldiphenylsilyloxy)ethyl]-N-methylcarbamoyl]phenyl]

ureidoacetyl]-N-methylamino]-2,6-dichlorobenzyloxy]-2-methylquinoline (256 mg) in tetrahydrofuran (2.5 ml) was added 1M tetrabutylammonium fluoride in tetrahydrofuran (0.6 ml) at ambient temperature. The reaction mixture was stirred for 2 hours. The mixture was partitioned between dichloromethane and water. The organic layer was washed with water and brine, dried over magnesium sulfate and evaporated in vacuo. The residue was purified by column chromatography eluting with dichloromethane-methanol to give 8-[2,6-dichloro-3-[N-[N'-[3-[N-(2-hydroxyethyl)-N-methylcarbamoyl]phenyl]ureidoacetyl]-N-methylaminolbenzyloxy]-2-methylquinoline (148 mg) as amorphous.

NMR (CDCl$_3$, δ): 2.65 (3H, s), 2.91–3.14 (3H), 3.21 (3H, s), 3.32–4.09 (7H), 5.50 (1H, d, J=10 Hz), 5.63 (1H, d, J=10 Hz), 5.90 (1H, br t, J=5 Hz), 6.92–7.51 (10H), 8.09 (1H, d, J=9 Hz), 8.72 (1H, br s)

EXAMPLE 39

To a stirred solution of 8-[3-[N-[4-(bromobutyramido)cinnamoylglycyl]-N-methylamino]-2,6-dichlorobenzyloxy]-2-methylquinoline (50 mg) in N,N-dimethylformamide was added potassium carbonate (30 mg) at ambient temperature and the resulting mixture was stirred at the same temperature for 16 hours. The reaction mixture was poured into water and extracted with ethyl acetate. The organic layer was washed with water and brine, and dried over anhydrous magnesium sulfate. After filtration, the solvent was removed in vacuo and the residue was purified by preparative thin layer chromatography (methanol—ethyl acetate=1:12, V/V) to afford 8-[2,6-dichloro-3-[N-methyl-N-(4-(2-oxo-1-pyrrolidinyl)cinnamoylglycyl]amino]benzyloxy]-2 2-methylguinoline (33.4 mg) as an amorphous solid.

NMR (CDCl$_3$, δ): 2.18 (2H, quint., J=7.5 Hz), 2.64 (2H, t, J=7.5 Hz), 2.74 (3H, s), 3.27 (3H, s), 3.63 (1H, dd, J=18, 4 Hz), 3.80–4.04 (3H, m), 5.65 (2H, s), 6.44 (1H, d, J=16 Hz), 6.60 (1H, t-like), 7.15–7.56 (9H, m), 7.56–7.70 (2H, m), 8.02 (1H, d, J=8 Hz)

EXAMPLE 40

(1) 8-(3-Amino-2,6-dichlorobenzloxy]-4-methoxy-2-methylquinoline was obtained from 8-(2,6-dichloro-3-nitrobenzloxy]-4-methoxy-2-methylguinoline according to a similar manner to that of Example 32. mp: >250° C.

NMR (DMSO-d$_6$, δ): 2.58 (3H, s), 4.00 (3H, s), 5.31 (2H, s), 5.68 (2H, br s), 6.90 (1H, d, J=8 Hz), 7.23 (1H, d, J=8 Hz), 7.31–7.46 (2H), 7.68 (1H, dd, J=8, 2 Hz)

(2) 8-[2,6-Dichloro-3-(phthalimidoacetylamino)benzyloxy]-4-methoxy-2-methylquinoline was obtained according to a similar manner to that of Example 5. mp: 184–185° C.

NMR (CDCl$_3$, δ): 2.62 (3H, s), 4.27 (3H, s), 4.78–5.02 (2H), 5.10–5.79 (2H), 6.60 (1H, br d, J=9 Hz), 7.19–7.38 (2H), 7.58 (1H, t, J=9 Hz), 7.70–7.99 (7H)

(3) 8-(2,6-Dichloro-3-[N-(phthalimidoacetyl)-N-methylamino]benzyloxy-4-methoxy-2-methylquinoline was obtained according to a similar manner to that of Example 7. mp: 209–210° C.

NMR (CDCl$_3$, δ): 2.70 (3H, s), 3.22 (3H, s), 3.99 (3H, s), 4.02 (2H, s), 5.65 (1H, d, J=10 Hz), 5.72 (1H, d, J=10 Hz), 6.63 (1H, s), 7.21–7.40 (2H), 7.46 (1H, d, J=9 Hz), 7.53 (1H, d, J=9 Hz), 7.68–7.91 (5H)

(4) 8-[3-(N-Glycyl-N-methylamino]-2,6-dichlorobenzyloxy]-4-methoxy-2-methylquinoline was obtained according to a similar manner to that of Example 9.

NMR (CDCl$_3$, δ): 2.70 (3H, s), 2.95 (1H, d, J=17 Hz), 3.10 (1H, d, J=17 Hz), 3.21 (3H, s), 4.01 (3H, s), 5.62 (2H, s), 7.18–7.29 (2H), 7.33 (1H, t, J=8 Hz), 7.46 (1H, d, J=9 Hz), 7.32 (1H, d, J=8 Hz)

EXAMPLE 41

The following compounds were obtained according to a similar manner to that of Example 28.

(1) 8-[2,6-Dichloro-3-[N-(2-methoxycinnamoylglycyl)-N-methylamino]benzyloxy]-2-methylquinoline hydrochloride NMR (DMSO-d$_6$, δ): 2.88 (3H, s), 3.15 (3H, s), 3.60 (1H, dd, J=16, 5 Hz), 3.85 (3H, s), 3.86 (1H, dd, J=16, 4 Hz), 5.62 (2H, s), 6.80 (1H, d, J=15 Hz), 6.91–7.11 (2H), 7.38 (1H, t, J=8 Hz), 7.46–7.98 (8H), 8.34 (1H, t-like), 8.92 (1H, d-like)

(2) 8-[2,6-Dichloro-3-[N-(3-methoxycinnamoylglycyl)-N-methylamino]benzloxy]-2-methylquinoline hydrochloride NMR (DMSO-d$_6$, δ): 2.86 (3H, s), 3.13 (3H, s), 3.58 (1H, dd, J=16, 6 Hz), 3.78 (3H, s), 3.90 (1H, dd, J=16, 5 Hz), 5.63 (2H, s), 6.83 (1H, d, J=15 Hz), 6.98 (1H, dd, J=8, 3 Hz), 7.09–7.20 (2H), 7.28–7.42 (2H), 7.70–7.97 (6H), 8.32 (1H, t-like), 8.90 (1H, d-like)

(3) 8-[2,6-Dichloro-3-[N-(4-methoxycinnamoylglycyl)-N-methylamino]benzyloxy]-2-methylquinoline hydrochloride NMR (DMSO-d$_6$, δ): 2.91 (3H, s), 3.16 (3H, s), 3.59 (1H, dd, J=16, 5 Hz), 3.79 (3H, s), 3.89 (1H, dd, J=16, 6 Hz), 5.63 (2H, s), 6.66 (1H, d, J=15 Hz), 6.99 (2H, d, J=8 Hz), 7.34 (1H, d, J=15 Hz), 7.52 (2H, d, J=8 Hz), 7.74–7.99 (6H), 8.24 (1H, t-like), 8.96 (1H, d-like)

(4) 8-[2,6-Dichloro-3-[N-[N'-(2-methoxyphenyl)ureidoacetyl]-N-methylamino]benzloxy]-2-methylquinoline hydrochloride NMR (CDCl$_3$—CD$_3$OD, 3:1 V/V, δ): 2.93 (3H, s), 3.30 (3H, s), 3.86 (5H, s), 5.60 (1H, d, J=10 Hz), 5.83 (1H, d, J=10 Hz), 6.74 (1H, dt, J=7, 0.5 Hz), 6.82–7.02 (2H, m), 7.57 (1H, d, J=9 Hz), 7.65 (1H, d, J=9 Hz), 7.70–7.80 (2H, m), 7.81–8.01 (3H. m), 8.95 (1H, d, J=10 Hz)

(5) 8-[2,6-Dichloro-3-[N-[N'-(3-methoxyphenyl)ureidoacetyl]-N-methylamino]benzyloxy]-2-methylquinoline hydrochloride NMR (CDCl$_3$—CD$_3$OD, δ): 2.94 (3H, s), 3.30 (3H, s), 3.70 (3H, s), 3.88 (2H, s), 5.60 (1H, d, J=10 Hz), 5.82 (1H, d, J=10 Hz), 6.50 (1H, dd, J=8, 1 Hz), 6.80 (1H, dd, J=8, 1 Hz), 6.98 (1H, t, J=1 Hz), 7.09 (1H, t, J=7 Hz), 7.58 (1H, d, J=9 Hz), 7.66 (1H, d, J=9 Hz), 7.76 (1H, d, J=7 Hz), 7.81–8.00 (3H), 8.93 (1H, d, J=9 Hz)

(6) 8-[2,6-Dichloro-3-[N-[N'-(4-methoxyphenyl)ureidoacetyl]-N-methylamino]benzyloxy]-2-methylquinoline hydrochloride NMR (CDCl$_3$—CD$_3$OD, δ): 2.86 (3H, s), 3.29 (3H, s), 3.71 (3H, s), 3.82 (1H, d, J=16 Hz), 3.96 (1H, d, J=16 Hz), 5.60 (1H, d, J=10 Hz), 5.82 (1H, d, J=10 Hz), 6.68 (2H, d, J=10 Hz), 7.14 (2H, d, J=10 Hz), 7.58 (1H, d, J=9 Hz), 7.63 (1H, d, J=9 Hz), 7.70–8.00 (4H), 8.90 (1H, d, J=9 Hz)

(7) 8-[2,6-Dichloro-3-[N-[N'-(2-ethoxycarbonylphenyl)ureidoacetyl]-N-methylamino]benzloxy]-2-methylquinoline hydrochloride NMR (CDCl$_3$—CD$_3$OD, δ): 1.41 (3H, t, J=7 Hz), 2.99 (3H, s), 3.31 (3H, s), 3.79 (1H, d, J=17 Hz), 3.89 (1H, d, J=17 Hz), 4.39 (2H, q, J=7 Hz), 5.61 (1H, d, J=10 Hz), 5.81 (1H, d, J=10 Hz), 7.01 (1H, t, J=8 Hz), 7.40 (1H, dt, J=9, 1 Hz), 7.57 (1H, d, J=9 Hz), 7.66 (1H, d, J=9 Hz), 7.77 (1H, dd, J=8, 1 Hz), 7.84–8.05 (4H), 8.13 (1H, d, J=9 Hz), 8.98 (1H, J=9 Hz)

(8) 8-[3-[N-[N'-(3-Cyanophenyl)ureidoacetyl]-N-methylamino]-2,6-dichlorobenzyloxy]-2-methylquinoline hydrochloride NMR (CDCl$_3$—CD$_3$OD, 3:1 V/V, δ): 3.06 (3H, s), 3.30 (3H, s), 3.83 (1H, d, J=17 Hz), 3.92 (1H, d, J=17 Hz), 5.60 (1H, d, J=10 Hz), 5.83 (1H, d, J=10 Hz), 7.18–7.30 (1H, m), 7.31–7.41 (2H, m), 7.59 (1H, d, J=8 Hz), 7.65 (1H, d, J=8 Hz), 7.77 (1H, br d, J=7 Hz), 7.82–8.04 (4H, m), 8.95 (1H, d, J=9 Hz)

(9) 8-[2,6-Dichloro-3-[N-methyl-N-[N'-(2-pyridylmethyl)ureidoacetyl]amino]benzyloxy]-2-methylquinoline dihydrochloride NMR (CDCl$_3$, δ): 3.01 (3H, s), 3.28 (3H, s), 3.73 (2H, s), 4.76 (2H, br s), 5.62 (1H, d, J=10 Hz), 5.79 (1H, d, J=10 Hz), 7.58 (1H, d, J=9 Hz), 7.67 (1H, d, J=9 Hz), 7.75 (1H, dd, J=6, 1 Hz), 7.81–8.10 (5H), 8.54 (1H, dt, J=7, 1 Hz), 8.71 (1H, br d, J=6 Hz), 8.95 (1H, d, J=9 Hz)

(10) 8-[2,6-Dichloro-3-[N-methyl-N-[N'-(2-pyridyl)ureidoacetyl]amino]benzyloxy]-2-methylquinoline dihydrochloride NMR (CDCl$_3$—CD$_3$OD, δ): 3.10 (1H, s), 3.12 (2H, s), 3.29 (3H, s), 3.76 (0.8H, d, J=17 Hz), 3.92 (0.8H, d, J=17 Hz), 4.31 (0.2H, d, J=17 Hz), 4.51 (0.2H, d, J=17 Hz), 5.50 (0.3H, d, J=10 Hz), 5.68 (0.7H, d, J=10 Hz), 5.76 (0.7H, d, J=10 Hz), 5.89 (0.3H, d, J=10 Hz), 7.30–7.49 (8H), 8.20 (1H, br d, J=7 Hz), 8.30 (1H, br t, J=7 Hz), 8.92 (1H, d, J=9 Hz)

(11) 8-(2,6-Dichloro-3-[N-[N'-(3-pyridylmethyl)ureidoacetyl]-N-methylamino]benzyloxy]-2-methylquinoline dihydrochloride NMR (CDCl$_3$—CD$_3$OD, 3:1 V/V, δ): 3.01 (3H, s), 3.27 (3H, s), 3.75 (2H, s), 4.50 (2H, s), 5.60 (1H, d, J=10 Hz), 5.77 (1H, d, J=10 Hz), 7.55 (1H, d, J=9 Hz), 7.64 (1H, d, J=9 Hz), 7.73 (1H, d, J=7 Hz), 7.80–8.11 (4H, m), 8.58 (1H, br d, J=7 Hz), 8.70 (1H, d, J=6 Hz), 8.76 (1H, br s), 8.93 (1H, d, J=8 Hz)

(12) 8-[3-[N-[N'-(3-Aminophenyl)ureidoacetyl]-N-methylaminol-2,6-dichlorobenzyloxy]-2-methylquinoline dihydrochloride NMR (CDCl$_3$—CD$_3$OD, 3:1 V/V, δ): 3.05 (3H, s), 3.29 (3H, s), 3.83 (2H, s), 5.60 (1H, d, J=10 Hz), 5.81 (1H, d, J=10 Hz), 6.98 (1H, br d, J=9 Hz), 7.27 (1H, t, J=8 Hz), 7.31–7.54 (2H, m), 7.59 (1H, d, J=9 Hz), 7.65 (1H, d, J=9 Hz), 7.75 (1H, d, J=8 Hz), 7.80–8.04 (2H, m), 8.93 (1H, d, J=8 Hz)

(13) 8-[2,6-Dichloro-3-[N-methyl-N-[N'-(4-pyridyl)ureidoacetyl]amino benzyloxy]-2-methylquinoline dihydrochloride NMR (CDCl$_3$—CD$_3$OD, 3:1 V/V, δ): 3.08 (1H, s), 3.12 (2H, s), 3.28 (2H, s), 3.42 (1H, s), 3.80 (0.67H, d, J=15 Hz), 3.90 (0.67H, d, J=15 Hz), 4.29 (0.33H, d, J=17 Hz), 4.46 (0.33H, d, J=17 Hz), 5.49 (0.33H, d, J=9 Hz), 5.65 (0.67H, d, J=10 Hz), 5.75 (0.67H, d, J=10 Hz), 5.89 (0.33H, d, J=9 Hz), 7.41–8.04 (8H, m), 8.35 (0.67H, d, J=7 Hz), 8.48 (1.33H, d, J=7 Hz), 8.89 (0.33H, d, J=9 Hz), 9.05 (0.67H, d, J=9 Hz)

(14) 8-[2,6-Dichloro-3-[N-[N'-(4-pyridylmethyl)ureidoacetyl]-N-methylamino]benzyloxy]-2-methylquinoline dihydrochloride NMR (CDCl$_3$—CD$_3$OD, 3:1 V/V, δ): 2.93 (3H, s), 3.27 (3H, s), 3.74 (2H, s), 4.58 (2H, s), 5.60 (1H, d, J=10 Hz), 5.78 (1H, d, J=10 Hz), 7.57 (1H, d, J=9 Hz), 7.66 (1H, d, J=9 Hz), 7.76 (1H, d, J=7 Hz), 7.80–8.10 (5H, m), 8.65–8.81 (2H, m), 8.95 (1H, d, J=9 Hz)

(15) 8-[2,6-Dichloro-3-[N-[N'-(3-pyridyl)ureidoacetyl]-N-methylamino]benzyloxy]-2-methylquinoline dihydrochloride NMR (CDCl$_3$—CD$_3$OD, 3:1 V/V, δ): 3.08 (0.6H, s), 3.18 (2.4H, s), 3.29 (2.4H, s), 3.41 (0.6H, s), 3.36 (1.6H, s), 4.28 (0.2H, d, J=17 Hz), 4.41 (0.2H, d, J=7 Hz), 5.46 (0.2H, d, J=10 Hz), 5.60 (0.8H, d, J=10 Hz), 5.78 (0.8H, d, J=10 Hz), 5.90 (0.2H, d, J=10 Hz), 7.44–8.07 (7H, m), 8.23–8.44 (1.8H, m), 8.53 (0.2H, br d), 8.91 (0.2H, d, J=10 Hz), 8.93 (0.8H, d, J=10 Hz), 9.25 (0.8H, br s), 9.35 (0.2H, d, J=0.5 Hz)

(16) 8-[2,6-Dichloro-3-[N-[N'-r3-[N-(2-methoxyethyl)-N-methylcarbamoyl]phenyl]ureidoacetyl]-N-methylamino]benzyloxy]-2-methylquinoline hydrochloride NMR (CDCl$_3$—CD$_3$OD, 3:1 V/V, δ): 2.88–3.18 (6H, m), 3.21–3.55 (8H, m), 3.64 (2H, br s), 3.86 (2H, br s), 5.59 (1H, d, J=10 Hz), 5.83 (1H, d, J=10 Hz), 6.96 (1H, br d, J=6 Hz), 7.19–7.38 (2H, m), 7.46–8.04 (7H, m), 8.94 (1H, d, J=9 Hz)

(17) 8-[2,6-Dichloro-3-[N-methyl-N-[N'-[3-[N-methyl-N-(3-pyridylmethyl)carbamoyl]phenyl]ureidoacetyl]amino]benzyloxy]-2-methylquinoline dihydrochloride NMR (CDCl$_3$—CD$_3$OD, 3:1 V/V, δ): 2.94 (3H, s), 3.09 (3H, s), 3.29 (3H, s), 3.82 (1H, d, J=14 Hz), 3.91 (1H, d, J=14 Hz), 4.88 (2H, br s), 5.62 (1H, d, J=10 Hz), 5.80 (1H, d, J=10 Hz), 7.02 (1H, br d, J=6 Hz), 7.27 (1H, t, J=7 Hz), 7.35–8.22 (10H, m), 8.54–8.70 (1H, m), 8.81 (1H, d, J=10 Hz), 8.88–9.10 (2H, m)

(18) 8-[2,6-Dichloro-3-[N-methyl-N-(N'-[3-[N-methyl-N-(2-pyridyl)carbamoyl]phenyl]ureidoacetyl]amino]benzloxy]-2-methylquinoline dihydrochloride NMR (CDCl$_3$—CD$_3$OD, δ) 3.02 (3H, s), 3.29 (3H, s), 3.59 (3H, s), 3.83 (2H, s), 5.60 (1H, d, J=10 Hz), 5.81 (1H, d, J=10 Hz), 6.91 (1H, d, J=7 Hz), 7.14 (1H, t, J=8 Hz), 7.28–7.70 (6H), 7.75 (1H, d, J=7 Hz), 7.81–8.07 (4H), 8.53 (1H, d, J=6 Hz), 8.93 (1H, d, J=9 Hz)

(19) 8-[2,6-Dichloro-3-[N-[N'-[3-(N-ethyl-N-methylcarbamoyl)phenyl]ureidoacetyl]-N-methylamino]benzyloxy]-2-methylquinoline hydrochloride NMR (CDCl$_3$—CD$_3$OD, δ): 1.05–1.22 (3H), 2.82–3.09 (6H), 3.19–3.50 (5H), 3.78–4.12 (2H), 5.09 (1H, d, J=10 Hz), 5.80 (1H, d, J=10 Hz), 6.91 (1H, d, J=7 Hz), 7.17–8.00 (9H), 8.90 (1H, d, J=9 Hz)

(20) 8-[2,6-Dichloro-3-[N-[N'-[3-(N-isopropyl-N-methylcarbamoyl)phenyl]ureidoacetyl]-N-methylamino]benzloxy]-2-methylquinoline hydrochloride NMR (CDCl$_3$—CD$_3$OD, δ): 1.00 (6H, br d, J=6 Hz), 2.59–2.91 (6H), 3.18 (3H, s), 3.64–4.00 (3H), 5.47 (1H, d, J=10 Hz), 5.69 (1H, d, J=10 Hz), 6.77 (1H, d, J=7 Hz), 7.03–7.30 (3H), 7.43–7.86 (6H), 8.78 (1H, d, J=9 Hz)

(21) 8-[2,6-Dichloro-3-[N-[N'-(3-diethylcarbamoylphenyl)ureidoacetyl]-N-methylamino]benzyloxy]-2-methylquinoline hydrochloride NMR (CDCl$_3$—CD$_3$OD, 3:1 V/V, δ): 1.14 (6H, br q, J=9 Hz), 2.90 (3H, s), 3.11–3.61 (4H, m), 3.30 (3H, s), 3.83 (1H, d, J=14 Hz), 3.96 (1H, d, J=14 Hz), 5.58 (1H, d, J=10 Hz), 5.79 (1H, d, J=10 Hz), 6.90 (1H, m), 7.16–7.35 (2H, m), 7.38–7.77 (4H, m), 7.79–8.01 (3H, m), 8.90 (1H, d, J=9 Hz)

(22) 8-[2,6-Dichloro-3-[N-methyl-N-[N'-[3-(2-pyridylcarbamoyl)phenyl]ureidoacetyl]amino]benzyloxy]-2-methylquinoline dihydrochloride NMR (CDCl$_3$—CD$_3$OD, δ): 3.04 (3H, s), 3.30 (3H, s), 3.81 (1H, d, J=16 Hz), 3.93 (1H, d, J=16 Hz), 5.60 (1H, d, J=10 Hz), 5.81 (1H, d, J=10 Hz), 7.32–8.12 (11H), 8.41 (2H, br d, J=5 Hz), 8.53 (1H, br d, J=6 Hz), 8.96 (1H, d, J=9 Hz)

(23) 8-[2,6-Dichloro-3-[N-methyl-N-[N'-[3-(4-pyridylcarbamoyl)phenyl]ureidoacetyl]amino]benzyloxy]-2-methylquinoline dihydrochloride NMR (CDCl$_3$—CD$_3$OD, δ): 3.01 (3H, s), 3.30 (3H, s), 3.90 (2H, s), 5.61 (1H, d, J=10 Hz), 5.81 (1H, d, J=10 Hz), 7.38 (1H, t, J=9 Hz), 7.57–8.08 (9H), 8.48 (2H, d, J=7 Hz), 8.57 (2H, d, J=7 Hz), 8.96 (1H, d, J=9 Hz)

(24) 8-[2,6-Dichloro-3-[N-methyl-N-[N'-[3-[N-methyl-N-(4-pyridyl)carbamoyl]phenyl]ureidoacetyl]aminolbenzyloxy]-2-methylquinoline dihydrochloride NMR (CDCl$_3$—CD$_3$OD, δ): 3.02 (3H, s), 3.30 (3H, s), 3.60 (3H, s), 3.86 (2H, s), 5.62 (1H, d, J=10 Hz), 5.81 (1H, d, J=10 Hz), 7.10 (1H, d, J=8 Hz), 7.31 (1H, t, J=8 Hz), 7.49 (1H, m), 7.60 (1H, d, J=8 Hz), 7.67 (1H, d, J=8 Hz), 7.71–8.00 (7H), 8.58 (2H, d, J=6 Hz), 8.99 (1H, d, J=9 Hz)

(25) 8-[2,6-Dichloro-3-[N-methyl-N-[N'-[3-(5-pyrimidinylcarbamoyl)phenyl]ureidoacetyl]amino]benzyloxy]-2-methylquinoline dihydrochloride NMR (CDCl₃—CD₃OD, δ): 2.98 (3H, s), 3.29 (3H, s), 3.32–4.13 (2H), 5.59 (1H, d, J=10 Hz), 5.78 (1H, d, J=10 Hz), 7.30 (1H, t, J=8 Hz), 7.49 (1H, d, J=9 Hz), 7.58–8.04 (9H), 8.92 (1H, d, J=9 Hz), 9.10 (1H, br s), 9.52 (1H, br s)

(26) 8-[2,6-Dichloro-3-[N-[N'-[3-[3-(N,N-dimethylamino)phenylcarbamoyl]phenyl]ureidoacetyl]-N-methylamino]benzyloxy]-2-methylquinoline dihydrochloride NMR (CDCl₃—CD₃OD, δ) 3.00 (3H, s), 3.29 (6H, s), 3.31 (3H, s), 3.90 (2H, s), 5.60 (1H, d, J=10 Hz), 5.81 (1H, d, J=10 Hz), 7.31 (1H, t, J=8 Hz), 7.40–7.98 (12H), 8.24 (1H, br s), 8.91 (1H, d, J=9 Hz)

(27) 8-[2,6-Dichloro-3-[N-[N'-[3-(4-ethyl-1-piperazinylcarbonyl)phenyl]ureidoacetyl]-N-methylamino]benzloxy]-2-methylquinoline dihydrochloride NMR (CDCl₃—CD₃OD, δ): 1.46 (3H, t, J=7 Hz), 2.89–4.09 (18H), 5.59 (1H, d, J=10 Hz), 5.81 (1H, d, J=10 Hz), 6.99 (1H, d, J=7 Hz), 7.23 (1H, t, J=7 Hz), 7.31–7.62 (4H), 7.72 (1H, d, J=7 Hz), 7.79–8.00 (3H), 8.90 (1H, d, J=9 Hz)

(28) 8-[2,6-Dichloro-3-[N-[N'-[3-[4-(methylcarbamoyl)-1-piperazinylcarbonyl]phenyl]ureidoacetyl]-N-methylamino]benzyloxy]-2-methylquinoline hydrochloride NMR (CDCl₃—CD₃₀D, δ): 2.78 (3H, s), 2.99 (3H, s), 3.26–3.79 (11H), 3.85 (2H, s), 5.61 (1H, d, J=10 Hz), 5.82 (1H, d, J=10 Hz), 6.98 (1H, d, J=7 Hz), 7.22–7.53 (3H), 7.60 (1H, d, J=9 Hz), 7.69 (1H, d, J=9 Hz), 7.79 (1H, d, J=7 Hz), 7.81–8.01 (3H), 8.96 (1H, d, J=9 Hz)

(29) 8-[2,6-Dichloro-3-[N-[N'-[3-(4-dimethylaminopiperidinocarbonyl)phenyl]ureidoacetyl]-N-methylamino]benzyloxy]-2-methylquinoline dihydrochloride NMR (CDCl₃—CD₃OD, δ): 1.67–1.91 (2H), 2.02–2.48 (2H), 2.74–3.14 (10H), 3.29 (3H, s), 3.49 (1H, m), 3.80–4.02 (3H), 4.78 (1H, m), 5.59 (1H, d, J=10 Hz), 5.82 (1H, d, J=10 Hz), 6.99 (1H, d, J=7 Hz), 7.25 (1H, t, J=7 Hz), 7.33–7.49 (2H), 7.58 (1H, d, J=9 Hz), 7.66 (1H, d, J=9 Hz), 7.77 (1H, d, J=7 Hz), 7.81–8.00 (3H), 8.92 (1H, d, J=9 Hz)

(30) 8-[2,6-Dichloro-3-[N-methyl-N-[N'-[3-(1-pyrrolidinylcarbonyl)phenyl]ureidoacetyl]amino]benzyloxy]-2-methylquinoline hydrochloride NMR (CDCl₃—CD₃OD, δ): 1.81–2.08 (4H), 2.98 (3H, s), 3.30 (3H, s), 3.33–3.60 (4H), 3.87 (2H, s), 5.60 (1H, d, J=10 Hz), 5.81 (1H, d, J=10 Hz), 7.06 (1H, d, J=7 Hz), 7.20–7.39 (2H), 7.51–7.61 (2H), 7.66 (1H, d, J=9 Hz), 7.74 (1H, d, J=7 Hz), 7.81–8.00 (3H), 8.92 (1H, d, J=9 Hz)

(31) 8-[2,6-Dichloro-3-[N-methyl-N-[N'-[3-(1,2,3,6-tetrahydropyridin-1-yl-carbonyl)phenyl]ureidoacetyl]-amino]benzyloxy]-2-methylquinoline hydrochloride NMR (CDCl₃—CD₃OD, 3:1 V/V, δ): 2.18–2.32 (2H, m), 2.85–3.05 (3H, m), 3.29 (3H, m), 3.38–4.30 (6H, m), 5.56 (1H, d, J=10 Hz), 5.68–5.98 (2H, m), 5.81 (1H, d, J=10 Hz), 6.88–7.02 (1H, m), 7.19–7.38 (2H, m), 7.43–8.00 (7H, m), 8.90 (1H, d, J=9 Hz)

(32) 8-[2,6-Dichloro-3-[N-[N'-[3-[N-3-(dimethylamino)-propyl]-N-methylcarbamoyl]phenyl]ureidoacetyl]-N-methylamino]benzyloxy]-2-methylquinoline dihydrochloride NMR (CDCl₃—CD₃OD, δ): 2.07–2.30 (2H), 2.80–3.42 (17H), 3.50–4.01 (4H), 5.60 (1H, br d, J=10 Hz), 5.79 (1H, br d, J=10 Hz), 6.96 (1H, d, J=8 Hz), 7.10–7.49 (3H), 7.56 (1H, d, J=9 Hz), 7.62 (1H, d, J=9 Hz), 7.71 (1H, d, J=7 Hz), 7.80–8.00 (3H), 8.90 (l1H, m)

(33) 8-[2,6-Dichloro-3-rN-[N'-[3-[N-(3-methoxypropyl)-N-methylcarbamoyl]phenyl]ureidoacetyl]-N-methylaminolbenzyloxy]-2-methylquinoline hydrochloride NMR (CDCl₃—CD₃OD, 3:1 V/V, δ): 1.66–2.02 (2H, m), 2.94 (3H, s), 3.00 (3H, s), 3.13–3.66 (10H, m), 3.85 (2H, s), 5.59 (1H, d, J=8 Hz), 5.82 (1H, d, J=8 Hz), 6.92 (1H, d, J=5 Hz), 7.15–8.06 (9H, m), 8.92 (1H, br s)

(34) 8-[3-[N-[N'-[3-[N,N-Bis(2-methoxyethyl)carbamoyl]phenyl]ureidoacetyl]-N-methylamino]-2,6-dichlorobenzyloxy]-2-methylquinoline hydrochloride NMR (CDCl₃—CD₃OD, δ): 2.98 (3H, s), 3.21–3.97 (19H), 5.61 (1H, d, J=10 Hz), 5.85 (1H, d, J=10 Hz), 6.99 (1H, m), 7.21–7.34 (2H), 7.47 (1H, br s), 7.60 (1H, d, J=9 Hz), 7.69 (1H, d, J=9 Hz), 7.74–8.00 (4H), 8.95 (1H, d, J=9Hz)

(35) 8-[3-[N-[N'-[3-[N,N-Bis(2-ethoxyethyl)carbamoyl]phenyl]ureidoacetyl]-N-methylamino]-2,6-dichlorobenzyloxy]-2-methylquinoline hydrochloride NMR (CDCl₃—CD₃OD, 3:1 V/V, δ): 1.05–1.34 (6H, m), 2.93 (3H, s), 3.23–3.78 (12H, m), 3.29 (3H, s), 3.83 (2H, s), 5.59 (1H, d, J=10 Hz), 5.80 (1H, d, J=10 Hz), 6.98 (1H, d, J=7 Hz), 7.18–7.35 (2H, m), 7.39–7.52 (1H, m), 7.60 (1H, d, J=8 Hz), 7.68 (1H, d, J=8 Hz), 7.76 (1H, d, J=7 Hz), 7.80–8.00 (3H, m), 8.91 (1H, d, J=9 Hz)

(36) 8-[2,6-Dichloro-3-[N-[N'-[3-[N-(2-hydroxyethyl)-N-methylcarbamoyl]phenyl]ureidoacetyl]-N-methylamino]benzloxy]-2-methylquinoline hydrochloride NMR (CDCl₃—CD₃OD, δ): 2.95–3.13 (6H), 3.31 (3H, s), 3.58–3.90 (6H), 5.61 (1H, d, J=10 Hz), 5.85 (1H, d, J=10 Hz), 7.00 (1H, m), 7.21–7.35 (2H), 7.49 (1H, m), 7.60 (1H, d, J=9 Hz), 7.69 (1H, d, J=9 Hz), 7.76–7.99 (4H), 8.95 (1H, d, J=9 Hz)

(37) 8-[2,6-Dichloro-3-[N-methyl-N-[N'-[3-[N-methyl-N-(2-pyridylmethyl)carbamoyl]phenyl]ureiloacetyl]aminol]benzloxy]-2-methylquinoline dihydrochloride NMR (CDCl₃—CD₃OD, 3:1 V/V, δ): 2.98 (3H, s), 3.20 (3H, br s), 3.30 (3H, s), 3.86 (2H, s), 5.10 (2H, s), 5.60 (1H, d, J=10 Hz), 5.80 (1H, d, J=10 Hz), 7.01–7.17 (1H, m), 7.20–7.36 (1H, m), 7.37–7.50 (1H, m), 7.52–7.69 (2H, m), 7.76 (1H, d, J=7 Hz), 7.80–8.15 (6H, m), 8.50–8.68 (1H, m), 8.81 (1H, br d, J=5 Hz), 8.95 (1H, br d, J=9 Hz)

(38) 8-[2,6-Dichloro-3-[N-[N'-[3-[N-(2-methoxyethyl)-N-(3-pyridylmethyl)carbamoyl]phenyl]ureidoacetyl]-N-methylamino]benzyloxy]-2-methylguinoline dihydrochloride NMR (CDCl₃—CD₃OD, 3:1 V/V, δ): 2.93 (3H, s), 3.23 (3H, s), 3.29 (3H, s), 3.36–3.71 (4H, m), 3.80 (1H, d, J=16 Hz), 3.91 (1H, d, J=16 Hz), 4.30–5.02 (2H, m), 5.60 (1H, d, J=10 Hz), 5.80 (1H, d, J=10 Hz), 6.95–7.10 (1H, m), 7.25 (1H, br t, J=8 Hz), 7.34–8.14 (9H, m), 8.44–9.06 (4H, m)

(39) 8-[2,6-Dichloro-3-[N-methyl-N-(3-phenylpropioloylglycyl)amino]benzyloxyl]-2-methylquinoline hydrochloride NMR (CDCl₃—CD₃OD, δ): 3.14 (3H, s), 3.31 (3H, s), 3.89 (2H, s), 5.65 (1H, d, J=10 Hz), 5.74 (1H, d, J=10 Hz), 7.29–7.76 (8H, m), 7.76–7.98 (3H, m), 8.90 (1H, dif-d)

(40) 8-[2,6-Dichloro-3-[N-(4-formylcinnamoylglycyl)-N-methylamino]benzyloxy]-2-methylquinoline hydrochloride and its hydrate NMR (CDCl₃—CD₃OD, δ): 3.16 (15/8H, s), 3.18 (9/8H), 3.32 (3H, s), 3.80–4.10 (2H, m), 5.40 (5/8H, s), 5.61 (1H, d, J=10 Hz), 5.72 (3/8H, d, J=10 Hz), 5.75 (5J8H, d, J=10 Hz), 6.57 (5/8H, d, J=16 Hz), 6.75 (3/8H, d, J=16 Hz), 7.38–7.73 (7H, m), 7.73–7.96 (4H, m), 8.88 (3/8H, d, J=8 Hz), 8,91 (5/8H, d, J=8 Hz), 10.00 (3/5H, s)

(41) 8-[3-[N-(4-Aminocinnamoylglycyl)-N-methylamino]-2,6-dichlorobenzyloxy]-2-methylquinoline dihydrochloride NMR (CDCl₃—CD₃OD δ): 3.04 (3H, s), 3.23 (3H, s), 3.80 (1H, d, J=17 Hz), 3.98 (1H, d, J=l7 Hz), 5.51 (1H, d, J=10 Hz), 5.68 (1H, d, J=10 Hz), 6.51 (1H, d, J=16 Hz), 7.19–7.28 (1H, m), 7.28–7.56 (6H, m), 7.60 (1H, d, J=7.5 Hz), 7.68–7.92 (3H, m), 8.86 (1H, d, J=8 Hz)

(42) 8-[2,6-Dichloro-3-[N-methyl-N-((E)-2-methyl-3-phenylacryloylglycyl)amino]benzyloxy]-2-methylquinoline hydrochloride NMR (CDCl$_3$—CD$_3$OD, δ): 2.11 (3H, s), 3.16 (3H, s), 3.36 (3H, s), 3.88 (2H, s), 5.61 (1H, d, J=10 Hz), 5.74 (1H, d, J=10 Hz), 7.25–7.44 (5H, m), 7.44–7.72 (3H, m), 7.76–7.98 (3H, m), 8.93 (1H, d, J=8 Hz)

(43) 8-[2,6-Dichloro-3-[N-methyl-N-[(E)-3-(4-pyridyl)-acryloylglycyl]amino]benzyloxy]-2-methylquinoline dihydrochloride NMR (CDCl$_3$—CD$_3$OD, 3:1, δ): 3.90 (1H, d, J=15 Hz), 4.20 (1H, d, J=15 Hz), 5.58 (1H, d, J=10 Hz), 5.71 (1H, d, J=10 Hz), 7.30 (1H, d, J=16 Hz), 7.44–7.71 (4H, m), 7.71–7.97 (3H, m), 8.19 (2H, d, J=6 Hz), 8.77 (2H, d, J=6 Hz), 8.88 (1H, d, J=8 Hz)

(44) $^8$-[2,6-Dichloro-3-[N-[4-(N,N-dimethylamino) cinnamoylglycyl]-N-methylamino]benzyloxy]-2-methylquinoline dihydrochloride NMR (CDCl$_3$—CD$_3$OD, δ): 3.01 (3H, s), 3.83 (1H, d, J=17.5 Hz), 3.97 (1H, d, J=17.5 Hz), 5.67 (1H, d, J=11 Hz), 5.80 (1H, d, J=11 Hz), 6.68 (1H, d, J=16 Hz), 7.33–8.00 (11H, m), 9.00 (1H, d, J=8 Hz)

(45) 8-[3-[N-(4-Chlorocinnamoylglycyl)-N-methylamino]-2,6-dichlorobenzyloxy]-2-methylquinoline hydrochloride NMR (CDCl$_3$—CD$_3$OD, 3:1, δ): 3.26 (3H, s), 3.81 (1H, d, J=17 Hz), 3.93 (1H, d, J=17 Hz), 5.57 (1H, d, J=10 Hz), 5.68 (1H, d, J=10 Hz), 6.51 (1H, d, J=16 Hz), 7.25 (2H, d, J=8 Hz), 7.33–7.67 (6H, m), 7.71–7.91 (3I, m), 8.85 (1H, d, J=8 Hz)

(46) 8-[2,6-Dichloro-3-[N-methyl-N-(4-methylcinnamoylglycyl)amino]benzyloxy]-2-methylquinoline hydrochloride NMR (CDCl$_3$—CD$_3$OD, δ): 2.37 (3H, s), 3.14 (3H, s), 3.31 (3H, s), 3.86 (1H, d, J=17 Hz), 3.96 (1H, d, J=17 Hz), 5.60 (1H, d, J=10 Hz), 5.73 (1H, d, J=10 Hz), 6.51 (1H, d, J=16 Hz), 7.16 (2H, d, J=8 Hz), 7.35–7.71 (6H, m), 7.78–7.98 (3H, m), 8.93 (1H, d, J=8 Hz)

(47) 8-[3-[N-[4-(Acetamido)cinnamoylglycyl]-N-methylamino]-2,6-dichlorobenzloxy]-2-methylquinoline hydrochloride NMR (CDCl$_3$—CD$_3$OD, δ): 2.15 (3H, s), 3.07 (3H, s), 3.28 (3H, s), 3.87 (1H, d, J=16 Hz), 4.03 (1H, d, J=16 Hz), 5.58 (1H, d, J=10 Hz), 5.74 (1H, d, J=10 Hz), 6.44 (1H, d, J=16 Hz), 7.27–7.42 (2H, m), 7.42–7.71 (6H, m), 7.79–7.97 (3H, m), 8.92 (1H, d, J=8 Hz)

(48) 8-[2,6-Dichloro-3-[N-methyl-N-[4-(N-methylacetamido)cinnamoylglycyl]amino]benzyloxy]-2-methylquinoline hydrochloride NMR (CDCl$_3$—CD$_3$OD, δ): 1.89 (3H, s), 3.12 (3H, s), 3.27 (3H, s), 3.30 (3H, s), 5.61 (1H, d, J=10 Hz), 5.77 (1H, d, J=10 Hz), 6.62 (1H, d, J=16 Hz), 7.23 (1H, d, J=8 Hz), 7.41–7.77 (6H, m), 7.77–8.05 (3H, m), 8.95 (1H, d, J=8 Hz)

(49) 8-[2,6-Dichloro-3-[N-methyl-N-[4-(propionamido) cinnamoylglycyl]amino]benzyloxy]-2-methylguinoline hydrochloride NMR (CDCl$_3$—CD$_3$OD, δ) 1.17 (3H, t, J=8 Hz), 2.37 (3H, t, J=8 Hz), 3.03 (3H, s), 3.81 (1H, d, J=17 Hz), 3.97 (1H, d, J=17 Hz), 5.52 (1H, d, J=9 Hz), 5.69 (1H, d, J=9 Hz), 6.40 (1H, d, J=16 Hz), 7.20–7.39 (3H, m), 7.39–7.69 (5H, m), 7.69–7.95 (3H, m), 8.75–8.97 (1H, dif-d)

(50) 8-[2,6-Dichloro-3-[N-methyl-N-[4-(N-methylpropionamido)cinnamoylglycyl]amino]benzyloxy]-2-methylquinoline hydrochloride NMR (CDCl$_3$—CD$_3$OD, δ): 0.98 (3H, t, J=8 Hz), 1.93–2.14 (2H, dif-q), 3.03 (3H, s), 3.17 (3H, s), 3.23 (3H, s), 3.72–3.95 (2H, m), 5.52 (1H, d, J=10 Hz), 5.66 (1H, d, J=10 Hz), 6.52 (1H, d, J=16 Hz), 7.12 (2H, d, J=8 Hz), 7.33–7.65 (6H, m), 7.70–7.90 (3H, m), 8.86 (1H, d, J=8 Hz)

(51) 8-[2,6-Dichloro-3-[N-[4-(N-ethylacetamido) cinnamoylglycyl]-N-methylamino]benzyloxy]-2-methylquinoline hydrochloride NMR (CDCl$_3$—CD$_3$OD, δ): 1.16 (3H, t, J=7.5 Hz), 1.89 (3H, s), 3.17 (3H, s), 3.36 (3H, s), 3.91 (1H, d, J=17 Hz), 4.03 (1H, d, J=17 Hz), 5.67 (1H, d, J=10 Hz), 5.82 (1H, d, J=10 Hz), 6.68 (1H, d, J=16 Hz), 7.23 (2H, d, J=8 Hz), 7.49–7.80 (6H, m), 7.83–8.06 (3H, m), 9.00 (1H, d, J=8 Hz)

(52) 8-[2,6-Dichloro-3-[N-methyl-N-[4-(2-pyridylmethoxy) cinnamoylglycyl]amino]benzyloxy]-2-methylguinoline dihydrochloride NMR (CDCl$_3$—CD$_3$OD, δ): 3.04 (3H, s), 3.83 (1H, d, J=16 Hz), 3.98 (1H, d, J=16 Hz), 5.45–5.76 (4H, m), 6.42 (1H, d, J=16 Hz), 7.01 (2H, d, J=8 Hz), 7.21–7.67 (6H, m), 7.70–7.99 (4H, m), 8.16 (1H, d, J=8 Hz), 8.50 (1H, d, J=8 Hz), 8.77–8.99 (2H, m)

(53) 8-[2,6-Dichloro-3-[N-[4-[2-(N,N-dimethylamino) ethoxy]cinnamoylglycyl)-N-methylamino]benzloxy]-2-methylquinoline dihydrochloride NMR (CDCl$_3$—CD$_3$OD, δ): 2.94 (6H, s), 3.13 (3H, s), 3.30 (3H, s), 3.55 (2H, br peak), 3.87 (1H, d, J=16 Hz), 4.02 (1H, d, J=16 Hz), 4.47 (2H, br peak), 5.58 (1H, d, J=10 Hz), 5.73 (1H, d, J=10 Hz), 6.46 (1H, d, J=16 Hz), 6.91 (2H, d, J=8 Hz), 7.32–7.74 (6H, m), 7.74–8.00 (3H, m), 8.95 (1H, d, J=8 Hz)

(54) 8-[2,6-Dichloro-3-[N-[4-(2-hydroxyethoxy) cinnamoylglycyl]-N-methylamino]benzyloxy]-2-methylquinoline hydrochloride NMR (CDCl$_3$—CD$_3$OD, δ): 3.10 (3H, s), 3.33 (3H, s), 3.85–4.00 (4H, m), 4.11 (2H, t, J=5 Hz), 5.61 (1H, d, J=10 Hz), 5.78 (1H, d, J=10 Hz), 6.44 (1H, d, J=16 Hz), 6.93 (2H, d, J=8 Hz), 7.38–7.77 (6H, m), 7.77–8.03 (3H, m), 8.97 (1H, d, J=8 Hz)

(55) 8-[2,6-Dichloro-3-[N-methyl-N-[4-(methylcarbamoyl) cinnamoylglycyl]amino]benzyloxy]-2-methylquinoline hydrochloride NMR (CDCl$_3$—CD$_3$OD, δ): 2.98 (3H, s), 3.10 (3H, s), 3.31 (3H, s), 3.89 (1H, d, J=17 Hz), 4.05 (1H, d, J=17 Hz), 5.59 (1H, d, J=10 Hz), 5.75 (1H, d, J=10 Hz), 6.65 (1H, d, J=16 Hz), 7.37–7.73 (6H, m), 7.73–8.00 (5H, m), 8.92 (1H, d, J=8 Hz)

(56) 8–12,6-Dichloro-3-[N-[4-(dimethylcarbamoyl) cinnamoylglycyl]-N-methylamino]benzyloxy]-2-methylquinoline hydrochloride NMR (CDCl$_3$—CD$_3$OD, δ): 3.01 (3H, s), 3.10 (6H, s), 3.31 (3H, s), 3.84–4.05 (2H, m), 5.60 (1H, d, J=10 Hz), 5.77 (1H, d, J=10 Hz), 6.64 (1H, d, J=16 Hz), 7.34–7.59 (3H, m), 7.59–7.75 (5H, m), 7.81–8.02 (3H, m), 8.95 (1H, d, J=8 Hz)

(57) 8-[2,6-Dichloro-3-[N-methyl-N-[4-(3-methylureido) cinnamoylglycyl]amino]benzyloxy]-2-methylquinoline hydrochloride NMR (CDCl$_3$—CD$_3$OD, δ): 2.72 (3H, s), 2.96 (3H, s), 3.24 (3H, s), 3.91 (2H, s), 5.55 (1H, d, J=10 Hz), 5.68 (1H, d, J=10 Hz), 6.26 (1H, d, J=16 Hz), 7.11–7.22 (3H, m), 7.34 (2H, d, J=8 Hz), 7.41–7.55 (2H, m), 7.60 (1H, d, J=7.5 Hz), 7.71–7.90 (3H, m), 8.87 (1H, d, J=8 Hz)

(58) 8-[2,6-Dichloro-3-[N-[4-(methanesulfonamido) cinnamoylglycyl]-N-methylamino]benzyloxy]-2-methylquinoline hydrochloride NMR (CDCl$_3$—CD$_3$OD, δ): 2.94 (3H, s), 3.08 (3H, s), 3.25 (3H, s), 3.84 (1H, d, J=17.5 Hz), 4.00 (1H, d, J=17.5 Hz), 5.54 (1H, d, J=10 Hz), 5.68 (1H, d, J=10 Hz), 6.45 (1H, d, J=16 Hz), 7.16 (2H, d, J=8 Hz), 7.21–7.42 (3H, m), 7.42–7.65 (3H, m), 7.70–7.91 (3H, m), 8.85 (1H, d, J=8 Hz)

(59) 8-[2,6-Dichloro-3-[N-[4-(methoxyacetamido) cinnamoylglycyl]-N-methylamino]benzyloxy]-2-methylquinoline hydrochloride NMR (CDCl₃—CD₃OD, δ): 3.09 (3H, s), 3.52 (3H, s), 3.92 (2H, d, J=12.5 Hz), 4.03 (2H, s), 5.60 (1H, d, J=10 Hz), 5.76 (1H, d, J=10 Hz), 7.38–7.74 (8H, m), 7.80–7.98 (3H, m), 8.94 (1H, d, J=8 Hz)

(60) 8-[2,6-Dichloro-3-[N-methyl-N-[4-(3-pyridylacetamido)cinnamoylglycyl]amino]benzloxy]-2-methylquinoline dihydrochloride NMR (CDCl₃—CD₃OD, δ): 3.08 (3H, s), 3.30 (3H, s), 3.95 (2H, s), 4.10 (2H, s), 5.58 (1H, d, J=10 Hz), 5.77 (1H, d, J=10 Hz), 6.48 (1H, d, J=16 Hz), 7.28–7.44 (3H, m), 7.44–7.75 (5H, m), 7.80–8.03 (4H, m), 8.66–8.79 (2H, m), 8.96 (1H, d, J=8 Hz), 9.03 (1H, dif-d)

(61) 8-[2,6-Dichloro-3-[N-methyl-N-[4-(isonicotinoylamino)cinnamoylglycyl]amino]benzyloxy]-2-methylquinoline dihydrochloride NMR (CDCl₃—CD₃OD, δ): 3.10 (3H, s), 3.30 (3H, s), 3.96 (2H, d, J=2.5 Hz), 5.60 (1H, d, J=10 Hz), 5.78 (1H, d, J=10 Hz), 6.54 (1H, d, J=16 Hz), 7.28–7.41 (1H, m), 7.41–7.78 (5H, m), 7.78–8.02 (5H, m), 8.62 (2H, d, J=5 Hz), 8.86–9.04 (3H, m)

(62) 8-[3-[N-[4-(Benzamido)cinnamoylglycyl]-N-methylamino]-2,6-dichlorobenzyloxy]-2-methylquinoline hydrochloride NMR (CDCl₃—CD₃OD, δ): 3.11 (3H, s), 3.98 (1H, d, J=17.5 Hz), 4.05 (1H, d, J=17.5 Hz), 5.60 (1H, d, J=10 Hz), 5.75 (1H, d, J=10 Hz), 7.36–7.63 (8H, m), 7.63–7.80 (3H, m), 7.80–8.01 (5H, m), 8.94 (1H, d, J=8 Hz)

(63) 8-[2,6-Dichloro-3-[N-methyl-N-[4-(2-oxo-1-pyrrolidinyl)cinnamoylglycyl]amino]benzyloxy]-2-methylquinoline hydrochloride NMR (CDCl₃—CD₃OD, 3:1 V/V, δ): 2.14 (3H, quint, J=7.5 Hz), 2.59 (2H, t, J=7.5 Hz), 3.10 (3H, s), 3.25 (3H, s), 3.76–4.03 (4H, m), 5.56 (1H, d, J=10 Hz), 5.69 (1H, d, J=10 Hz), 6.48 (1H, d, J=16 Hz), 7.34–7.69 (8H, m), 7.70–7.91 (3H, m), 8.88 (1H, d, J=8 Hz)

(64) 8-[2,6-Dichloro-3-[N-(N'-ethylureidoacetyl)-N-methylamino]benzyloxy]-4-methoxy-2-methylquinoline hydrochloride NMR (CDCl₃—CD₃OD, δ): 0.93 (3H, t, J=7 Hz), 2.80 (3H, s), 2.96 (2H, q, J=7 Hz), 3.11 (3H, s), 3.64 (2H, s), 4.20 (3H, s), 5.36 (1H, d, J=10 Hz), 5.59 (1H, d, J=10 Hz), 7.11 (1H, s), 7.38 (1H, d, J=9 Hz), 7.42–7.52 (2H, m), 7.64 (1H, t, J=8 Hz), 7.83 (1H, d, J=8 Hz)

(65) 8-[2,6-Dichloro-3-[N-methyl-N-(butyrylglycyl)amino]benzloxy]-4-methoxy-2-methylquinoline hydrochloride NMR (CDCl₃—CD₃OD, δ): 0.94 (3H, t, J=7 Hz), 1.51–1.72 (2H), 2.21 (2H, t, J=7 Hz), 2.93 (3H, s), 3.30 (3H, s), 3.78 (2H, s), 4.38 (3H, s), 5.58 (1H, d, J=10 Hz), 5.77 (1H, d, J=10 Hz), 7.31 (1H, s), 7.56 (1H, d, J=9 Hz), 7.61–7.72 (2H), 7.81 (1H, t, J=8 Hz), 8.01 (1H, d, J=8 Hz)

(66) 8-[2,6-Dichloro-3-[N-(heptanoylglycyl)-N-methylamino]benzyloxy]-4-methoxy-2-methylquinoline hydrochloride NMR (CDCl₃—CD₃OD, δ): 0.80–0.95 (3H), 1.20–1.40 (6H), 1.49–1.68 (2H), 2.22 (2H, t, J=7 Hz), 2.94 (3H, s), 3.30 (3H, s), 3.69 (1H, d, J=17 Hz), 3.80 (1H, d, J=17 Hz), 4.37 (3H, s), 5.56 (1H, d, J=10 Hz), 5.74 (1H, d, J=10 Hz), 7.31 (1H, s), 7.52 (1H, d, J=8 Hz), 7.66 (2H, d, J=8 Hz), 7.80 (1H, t, J=8 Hz), 8.00 (1H, d, J=8Hz)

(67) 8-[2,6-Dichloro-3-[N-methyl-N-[(E)-3-(3-pyridyl) acryloylglycyl]amino]benzyloxy]-4-methoxy-2-methylquinoline dihydrochloride NMR (CDCl₃—CD₃OD, δ): 2.99 (3H, s), 3.31 (3H, s), 3.89 (1H, d, J=17 Hz), 4.03 (1H, d, J=17 Hz), 5.60 (1H, d, J=10 Hz), 5.78 (1H, d, J=10 Hz), 7.10 (1H, d, J=15 Hz), 7.40 (1H, s), 7.59–7.89 (5H), 7.98–8.14 (2H), 8.71–8.83 (2H), 9.16 (1H, br s)

(68) 8-[2,6-Dichloro-3-[N-[4-(dimethylcarbamoyl) cinnamoylglycyl]-N-methylamino]benzyloxy]-4-methoxy-2-methylquinoline hydrochloride NMR (CDCl₃—CD₃OD, δ): 2.98 (3H, s), 3.02 (3H, br s), 3.13 (3H, br s), 3.31 (3H, s), 3.93 (2H, s), 4.34 (2H, s), 5.59 (1H, d, J=10 Hz), 5.77 (1H, d, J=10 Hz), 6.68 (1H, d, J=15 Hz), 7.32 (1H, s), 7.40–7.73 (8H), 7.82 (1H, tr J=8 Hz), 8.01 (1H, d, J=8 Hz)

(69) 8-[2,6-Dichloro-3-[N-methyl-N-[4-(N-methylacetamido)cinnamoylglycyl]amino]benzyloxy]-4-methoxy-2-methylquinoline hydrochloride NMR (CDCl₃—CD₃OD, δ): 1.91 (3H, s), 2.98 (3H, s), 3.23–3.33 (6H), 3.89 (1H, d, J=17 Hz), 4.00 (1H, d, J=17 Hz), 4.36 (3H, s), 5.60 (1H, d, J=10 Hz), 5.79 (1H, d, J=10 Hz), 6.65 (1H, d, J=15 Hz), 7.21–7.37 (3H), 7.44–7.77 (6H), 7.82 (1H, t, J=8 Hz), 8.02 (1H, d, J=8 Hz)

(70) 8-[2,6-Dichloro-3-[N-[N'-(3-dimethylcarbamoylphenyl)ureidoacetyl]-N-methylamino] benzyloxy]-4-methoxy-2-methylquinoline hydrochloride NMR (CDCl₃—CD₃OD, δ): 2.83 (3H, s), 2.98 (3H, br s), 3.02 (3H, br s), 3.29 (3H, s), 3.87 (2H, s), 4.33 (3H, s), 5.52 (1H, d, J=10 Hz), 5.78 (1H, d, J=10 Hz), 6.95 (1H, d, J=7 Hz), 7.20–7.32 (3H), 7.49 (1H, s), 7.52–7.70 (3H), 7.80 (1H, t, J=8 Hz), 8.00 (1H, d, J=8 Hz)

(71) 8-[2,6-Dichloro-3-[N-methyl-N-[N'-[3-(4-pyridyl) carbamoylphenyl]ureidoacetyl]amino]benzyloxy]-4-methoxy-2-methylquinoline dihydrochloride NMR (CDCl₃—CD₃OD, δ): 2.88 (3H, s), 3.30 (3H, s), 3.81 (1H, d, J=17 Hz), 3.93 (1H, d, J=17 Hz), 4.30 3H, s), 5.57 (1H, d, J=10 Hz), 5.79 (1H, d, J=10 Hz), 7.25–7.48 (2H), 7.54–7.71 (6H), 7.80 (1H, t, J=8 Hz), 7.93–8.04 (2H), 8.45–8.61 (4H)

(72) 8-[2,6-Dichloro-3-[N-methyl-N-[N'-[3-(4-methyl-1-piperazinylcarbonyl)phenyl]ureidoacetyl]amino]benzloxy]-4-methoxy-2-methylquinoline dihydrochloride NMR (CDCl₃—CD₃OD, δ): 2.90 (3H, s), 2.92 (3H, s), 3.03–3.95 (13H), 4.36 (3H, s), 5.56 (1H, d, J=10 Hz), 5.80 (1H, d, J=10 Hz), 7.06 (1H, m), 7.27–7.77 (7H), 7.82 (1H, t, J=8 Hz), 8.00 (1H, d, J=8 Hz)

(73) 8-[3-[N-[N'-(3-Acetylphenyl)ureidoacetyl]-N-methylamino]-2,6-dichlorobenzyloxy]-4-methoxy-2-methylquinoline hydrochloride NMR (CDCl₃—CD₃OD, δ): 2.59 (3H, s), 2.95 (3H, s), 3.31 (3H, s), 3.80 (1H, d, J=17 Hz), 3.92 (1H, d, J=17 Hz), 4.34 (3H, s), 5.56 (1H, d, J=10 Hz), 5.79 (1H, d, J=10 Hz), 7.29 (1H, s), 7.32–7.48 (2H), 7.53–7.73 (4H), 7.81 (1H, t, J=8 Hz), 8.01 (1H, d, J=8 Hz), 8.09 (1H, br s)

(74) 8-[2,6-Dichloro-3-[N-[4-[N-(2-methoxyethyl) carbamoyl]cinnamoylglycyl]-N-methylamino]benzloxy]-2-methylquinoline hydrochloride NMR (CDCl₃—CD₃OD, δ): 3.10 (3H, s), 3.31 (3H, s), 3.41 (3H, s), 3.61 (4H, s), 3.95 (2H, s), 5.61 (1H, d, J=10 Hz), 5.80 (1H, d, J=10 Hz), 6.69 (1H, d, J=15 Hz), 7.40–8.01 (11H), 8.99 (1H, d, J=9 Hz)

(75) 8-[3-[N-[4-[N,N-Bis(2-methoxyethyl)carbamoyl] cinnamoylglycyl]-N-methylamino]-2,6-dichlorobenzyloxy]-2-methylquinoline hydrochloride NMR (CDCl₃—CD₃OD, δ): 3.09 (3H, s), 3.22–3.85 (17H), 3.95 (2H, s), 5.63 (1H, d, J=10 Hz), 5.82 (1H, d, J=10 Hz), 6.68 (1H, d, J=15 Hz), 7.40–7.71 (8H), 7.80 (1H, d, J=7 Hz), 7.87–8.02 (3H), 9.00 (1H, d, J=8 Hz)

PREPARATION 42

(1) Benzyl 2-ethoxyethylcarbamate was obtained by reacting 2-ethoxyethylamine with benzyl chloroformate according to a similar manner to that of Preparation 18.

NMR (CDCl₃, δ): 1.15 (3H, t, J=7.5 Hz), 3.38 (2H, q, J=6 Hz), 3.42–3.53 (4H, m), 5.10 (3H, s-like), 7.27–7.43 (5H, m)

(2) Benzyl N-(2-ethoxyethyl)-N-methylcarbamate was obtained by reacting benzyl 2-ethoxyethylcarbamate with iodomethane according to a similar manner to that of Preparation 13.

NMR (CDCl₃, δ): 1.10–1.24 (3H, m), 3.00 (3H, s), 3.35–3.62 (6H, m), 5.13 (2H, s), 7.24–7.44 (5H, m)

(3) N-(2-Ethoxyethyl)-N-methylamine hydrochloride was obtained according to a similar manner to that of Preparation 23.

NMR (CD₃OD, δ): 1.14–1.30 (3H, m), 2.70 (3H, s), 3.12–3.23 (2H, m), 3.50–3.63 (2H, m), 3.63–3.73 (2H, m)

PREPARATION 43

(1) To a solution of ethyl 4-aminocinnamate (3.00 g) in dichloromethane (21 ml) were added di-tert-butyl dicarbonate (3.77 g) and triethylamine (318 mg) in ice water bath and the mixture was stirred for 1 hour at 0° C. and at ambient temperature for 3 hours and heated to reflux for 12 hours. The reaction mixture was poured into water and extracted with dichloromethane. The precipitate was filtered off. The organic layer was separated, washed with water and brine, dried over magnesium sulfate and evaporated in vacuo. The residue was chromatographed on silica gel eluting with chloroform and recrystallized from a mixture of ethyl acetate and n-hexane to give ethyl 4-(tert-butoxycarbonylamino)cinnamate (2.38 g) as crystals. mp: 104.6–108.6° C.

NMR (CDCl₃, δ): 1.33 (3H, t, J=7.5 Hz), 4.52 (9H, s), 4.25 (2H, q, J=7.5 Hz), 6.33 (1H, d, J=16 Hz), 6.57 (1H, br s), 7.38 (2H, d, J=8 Hz), 7.46 (2H, d, J=8 Hz), 7.62 (1H, d, J=16 Hz)

(2) To a suspension of sodium hydride (60% dispersion in mineral oil, 165 mg) in N,N-dimethylformamide (1 ml) was added dropwise a solution of ethyl 4-(tert-butoxycarbonylamino)cinnamate (1.00 g) in N,N-dimethylformamide (5 ml) in ice water bath under nitrogen and stirred for 1 hour under same condition. To the mixture was added 2-bromoethyl methyl ether (602 mg) and stirred for 1 hour at same condition and at ambient temperature for 20 hours. The reaction mixture was poured into water and extracted with ethyl acetate. The organic layer was separated, washed with water and brine, dried over magnesium sulfate and evaporated in vacuo. The residue was chromatographed on silica gel eluting to a mixture of n-hexane and ethyl acetate (4:1) to give ethyl 4-[N-tert-butoxycarbonyl-N-(2-methoxyethyl)amino]cinnamate (935 mg) as an oil.

NMR (CDCl₃, δ): 1.34 (1H, t, J=7.5 Hz), 1.45 (9H, s), 3.33 (3H, s), 3.54 (2H, t, J=6 Hz), 3.80 (2H, t, J=6 Hz), 4.26 (2H, q, J=7.5 Hz), 6.39 (1H, d, J=16 Hz), 7.29 (2H, d, J=8 Hz), 7.48 (2H, d, J=8 Hz), 7.65 (1H, d, J=16 Hz)

(3) Trifluoroacetic acid (3 ml) was added to ethyl 4-[N-tert-butoxycarbonyl-N-(2-methoxyethyl)amino]cinnamate (932 mg) in ice water bath and stirred for 15 minutes at same temperature. The solvent was evaporated under reduced pressure. The residue was partitioned between ethyl acetate and aqueous sodium bicarbonate solution. The organic layer was washed with water and brine, dried over magnesium sulfate and evaporated in vacuo. The residue was chromatographed on silica gel eluting to a mixture of n-hexane and ethyl acetate (3:1) and recrystallized from a mixture of n-hexane and ethyl acetate to give ethyl 4-(2-methoxyethylamino)cinnamate (470 mg) as crystals. mp: 49.9–53.4° C.

NMR (CDCl₃, δ): 1.33 (3H, t, J=7.5 Hz), 3.32 (2H, q-like, J=6 Hz), 3.40 (3H, s), 3.60 (2H, t, J=6 Hz), 4.24 (2H, q, J=7.5 Hz), 4.35 (1H, t-like), 6.21 (1H, d, J=16 Hz), 6.60 (2H, d, J=8 Hz), 7.38 (2H, d, J=8 Hz), 7.60 (1H, d, J=16 Hz)

(4) Ethyl 4-[N-(2-methoxyethyl)-N-(isonicotinoyl)amino]cinnamate was obtained by reacting ethyl 4-(2-methoxyethylamino)cinnamate with isonicotinoyl chloride hydrochloride according to a similar manner to that of Preparation 24. mp: 98.4–102.3° C.

NMR (CDCl₃, δ): 1.31 (3H, t, J=7.5 Hz), 3.35 (3H, s), 3.65 (2H, t, J=6 Hz), 4.08 (2H, t, J=6 Hz), 4.25 (2H, q, J=7.5 Hz), 6.36 (1H, d, J=16 Hz), 7.06–7.20 (4H, m), 7.40 (2H, d, J=8 Hz), 7.57 (1H, d, J=16 Hz), 8.47 (2H, d, J=6 Hz)

PREPARATION 44

To a suspension of (E)-3-(6-acetylaminopyridin-3-yl)-acrylic acid (460 mg) in ethanol (5.4 ml) was added 1N sodium hydroxide (5.4 ml) at ambient temperature, and the mixture was stirred for 3 hours at 50° C. The reaction mixture was adjusted to pH 7, and the resulting precipitate was collected by filtration and dried to give (E)-(6-aminopyridin-3-yl)acrylic acid (295 mg). mp: 243.6–246.4° C.

NMR (DMSO-d₆, δ): 6.21 (1H, d, J=15 Hz), 6.45 (1H, d, J=8 Hz), 6.52 (2H, s), 7.42 (1H, d, J=15 Hz), 7.75 (1H, d, J=8 Hz), 8.11 (1H, s)

PREPARATION 45

(1) 1-(tert-Butyldiphenylsilyloxymethyl)-2,6-dichloro-3-nitrobenzene was obtained by reacting 2,6-dichloro-3-nitrobenzyl alcohol with tert-butyldiphenylsilyl chloride according to a similar manner to that of Preparation 36.

NMR (CDCl₃, δ): 1.05 (9H, s), 4.96 (2H, s), 7.27–7.51 (7H, m), 7.58–7.81 (5H, m)

(2) To a stirred mixture of 1-(tert-butyldiphenylsilyloxymethyl)-2,6-dichloro-3-nitrobenzene (433 mg), ferric chloride hexahydrate (17.5 mg) and activated carbon (17.5 mg) in a mixture of methanol (2.78 ml) and water (0.69 ml) was added hydrazine monohydrate (0.135 ml) dropwise at 60–70° C. After the addition was finished, the mixture was refluxed for half an hour. The mixture was allowed to cool and filtered. The filtrate was concentrated in vacuo. The residue was extracted with dichloromethane and the organic phase was dried over anhydrous magnesium sulfate. After being filtered, the filtrate was concentrated in vacuo and the resulting residue was washed with n-hexane to give 3-amino-1-(tert-butyldiphenylsilyloxymethyl)-2,6-dichlorobenzene (348 mg) as a white mass.

NMR (CDCl₃, δ): 1.05 (9H, s), 4.07 (2H, br s), 4.87 (2H, s), 6.66 (1H, d, J=9 Hz), 7.08 (1H, d, J=9 Hz), 7.30–7.50 (6H, m), 7.70–7.84 (4H, m)

(3) 1-(tert-Butyldiphenylsilyloxymethyl)-2,6-dichloro-3-(phthalimidoacetylamino)benzene was obtained according to a similar manner to that of Example 5. mp: 198.1° C.

NMR (CDCl₃, δ): 1.04 (9H, s), 4.57 (2H, s), 4.90 (2H, s), 7.25–7.50 (7H, m), 7.55–7.83 (6H, m), 7.85–8.07 (2H, m), 8.00 (1H, br s), 8.25 (1H, d, J=8 Hz)

(4) 1-(tert-Butyldiphenylsilyloxymethyl)-2,6-dichloro-3-[N-methyl-N-(phthalimidoacetyl)amino]benzene was obtained according to a similar manner to that of Example 7. mp: 167–172° C.

NMR (CDCl₃, δ): 1.06 (9H, s), 3.20 (3H, s), 4.04 (2H, s), 4.98 (2H, s), 7.31–7.51 (9H, m), 7.65–7.79 (6H, m), 7.80–7.92 (2H, m)

(5) 2,6-Dichloro-1-hydroxymethyl-3-[N-methyl-N-(phthalimidoacetyl)amino]benzene was obtained according to a similar manner to that of Example 38. mp: 236.2–240.8° C.

NMR (CDCl₃, δ): 2.24 (1H, t, J=7 Hz), 3.21 (3H, s), 4.09 (2H, s), 5.04 (2H, d, J=7 Hz), 7.43 (1H, d, J=8 Hz), 7.48 (1H, d, J=8 Hz), 7.67–7.75 (2H, m), 7.80–7.88 (2H, m)

(6) To a mixture of 2,6-dichloro-1-hydroxymethyl-3-[N-methyl-N-(phthalimidoacetyl)amino]benzene (399 mg) and triethylamine (0.17 ml) in methylene chloride (8 ml) was added methanesulfonyl chloride (0.086 ml) under −20° C., and the mixture was stirred for 1 hour. The mixture was washed with sodium bicarbonate solution and brine, dried over magnesium sulfate and concentrated in vacuo to give 2,6-dichloro-1-methylsulfonyloxymethyl-3-[N-methyl-N-(phthalimidoacetyl)amino]benzene (561 mg)

NMR (CDCl$_3$, δ): 3.15 (3H, s), 3.24 (3H, s), 4.09 (2H, s), 5.48 (2H, s), 7.56 (2H, s), 7.67–7.78 (2H, m), 7.80–7.93 (2H, m)

PREPARATION 46

To a suspension of 2,3-diaminophenol (2.93 g) in 2M aqueous acetic acid solution (47 ml) and 4M aqueous sodium acetate solution (29 ml) was added 40% aqueous pyruvic aldehyde solution (3.79 ml) at 60° C. The reaction mixture was stirred at 60° C. for 40 minutes. After cooling the reaction mixture was adjusted to pH 8 with saturated sodium hydrogen carbonate and extracted with dichloromethane (50 ml) twice. The organic layer was washed with saturated sodium hydrogen carbonate, water and brine. After dried over anhydrous magnesium sulfate, the solution was evaporated in vacuo. The residue was purified by flash column chromatography (silica gel 450 ml) eluting with n-hexane/ethyl acetate (5/1, V/V) to give 8-hydroxy-2-methylquinoxaline (the less polar product) as crystals and with n-hexane/ethyl acetate (3/1, V/V) to give 8-hydroxy-3-methylquinoxaline (the more polar product) as crystals. The former was washed with n-hexane to afford pale yellow crystals (1.27 g). The latter was washed with isopropyl ether to afford pale yellow crystals (1.30 g).

8-Hydroxy-2-methylquinoxaline mp: 83–84° C.

NMR (CDCl$_3$, δ): 2.78 (3H, s), 7.21 (1H, m), 7.60 (2H, d, J=5 Hz), 7.84 (1H, s), 8.79 (1H, s)

8-Hydroxy-3-methylquinoxaline mp: 104–105° C.

NMR (CDCl$_3$, δ): 2.80 (3H, s), 7.18 (1H, d, J=7.5 Hz), 7.55 (1H, d, J=7.5 Hz), 7.67 (1H, t, J=7.5 Hz), 7.79 (1H, s), 8.60 (1H, s)

PREPARATION 47

(1) 3-Amino-N-(2-methoxyethyl)benzamide was obtained from 3-nitro-N-(2-methoxyethyl)benzamide according to a similar manner to that of Preparation 16.

NMR (CDCl$_3$, δ): 3.39 (3H, s), 3.56 (2H, d, J=5 Hz), 3.62 (2H, d, J=5 Hz), 6.48 (1H, br s), 6.79 (1H, d, J=7.5 Hz), 7.06 (1H, d, J=7.5 Hz), 7.10–7.27 (3H)

(2) Phenyl 3-[(2-methoxyethyl)carbamoyl]phenylcarbamate was obtained according to a similar manner to that of Preparation 18. mp: 142.1–150.3° C.

NMR (CDCl$_3$, δ): 3.38 (3H, s), 3.52 (2H, d, J=5 Hz), 3.62–3.72 (2H), 6.59 (1H, br s), 7.16–7.29 (3H), 7.37–7.50 (4H), 7.65 (1H, br s), 7.80 (1H, br d, J=7.5 Hz), 7.95 (1H, s)

PREPARATION 48

(1) To a solution of 2-amino-3-methoxybenzoic acid (10.3 g), 4-dimethylaminopyridine (0.65 g) and triethylamine (34.3 ml) in N,N-dimethylformamide (60 ml) was added acetyl chloride (10.5 ml) at 3–15° C. for 20 minutes. Then the reaction mixture was heated at 90° C. After 3 hours, to the reaction mixture was added portionwise ammonium carbonate (17.7 g) for 10 minutes. The mixture was stirred at the same temperature for 1 hour. Cooling the mixture, water (300 ml) was added thereto. The precipitate was collected by filtration, washed with water and acetonitrile to give 8-methoxy-2-methyl-4-oxo-3,4-dihydroquinazoline (9.24 g) as colorless crystals. mp: 261–262° C.

NMR (CDCl$_3$, δ): 2.32 (3H, s), 3.88 (3H, s), 7.30 (1H, d, J=7.5 Hz), 7.38 (1H, t, J=7.5 Hz), 7.61 (1H, d, J=7.5 Hz)

(2) 4-Chloro-8-methoxy-2-methylquinazoline was obtained according to a similar manner to that of Preparation 6. mp: 101–102° C.

NMR (CDCl$_3$, δ): 2.91 (3H, s), 4.09 (3H, s), 7.27 (1H, d, J=7.5 Hz), 7.58 (1H, t, J=7.5 Hz), 7.80 (1H, d, J=7.5 Hz)

(3) A mixture of 4-chloro-8-methoxy-2-methylquinazoline (5.12 g), 10% palladium on carbon (512 mg) and triethylamine (3.72 g) in ethyl acetate (51 ml) was stirred under hydrogen atmosphere for 3 hours. The catalyst was removed by filtration, and the filtrate was concentrated. The residue was dissolved in methylene chloride, and the solution was washed with saturated sodium bicarbonate solution, water and brine, dried over magnesium sulfate, and concentrated. The residue was purified by silica gel column chromatography (methylene chloride-methanol) to give 8-methoxy-2-methylquinazoline (3.07 g). mp: 131–132° C.

NMR (CDCl$_3$, δ): 2.95 (3H, s), 4.09 (3H, s), 7.21 (1H, d, J=7.5 Hz), 7.48 (1H, d, J=7.5 Hz), 7.52 (1H, t, J=7.5 Hz), 9.30 (1H, s)

(4) To a solution of 8-methoxy-2-methylquinazoline (1.50 g) in dichloromethane (10 ml) was added 1M solution of boron tribromide in dichloromethane (12.9 ml) at 3–5° C. After 10 minutes, the reaction mixture was stirred at ambient temperature for 2 days. The mixture was adjusted to pH 7 with saturated sodium hydrogen carbonate, and extracted with dichloromethane twice. The organic layer was dried over anhydrous magnesium sulfate, filtered and evaporated in vacuo. The residue was crystallized from n-hexane to give 8-hydroxy-2-methylquinazoline (1.22 g) as colorless crystals. mp: 135–137° C.

NMR (CDCl$_3$, δ): 2.89 (3H, s), 7.32 (1H, d, J=7.5 Hz), 7.41 (1H, d, J=7.5 Hz), 7.49 (1H, t, J=7.5 Hz), 9.30 (1H, s)

PREPARATION 49

(1) 8-Hydroxy-2-methyl-4-oxo-3,4-dihydroquinazoline was obtained from 2-amino-3-hydroxybenzoic acid, acetyl chloride and ammonium carbonate according to a similar manner to that of Preparation 48.-(1) mp: 258° C.

NMR (DMSO-d$_6$, δ): 2.36 (3H, s), 3.35 (1H, br, s), 7.13 (1H, dd, J=8, 2 Hz), 7.25 (1H, t, J=8 Hz), 7.49 (1H, dd, J=8, 2 Hz)

(2) 8-(2,6-Dichloro-3-nitrobenzyloxy)-2-methyl-4-oxo-3,4-dihydroquinazoline was obtained according to a similar manner to that of Example 1. mp: 270–290° C. (dec.)

NMR (DMSO-d$_6$, δ): 2.30 (3H, s), 5.44 (2H, s), 7.40 (1H, t, J=8 Hz), 7.52 (1H, dd, J=8, 2 Hz), 7.73 (1H, dd, J=8, 2 Hz), 7.89 (1H, d, J=9 Hz), 8.19 (1H, d, J=9 Hz)

PREPARATION 50

A mixture of 2-acetylamino-5-formylpyridine (241 mg) and malonic acid (168 mg) in pyridine (0.12 ml) and ethanol (0.36 ml) was refluxed for 2 hours. After cooling the mixture, the precipitate was collected by filtration, and washed with ethyl acetate to give (E)-3-(6-acetylamino-3-pyridyl)acrylic acid (248 mg) as a colorless powder. mp: 291–2920° C.

NMR (DMSO-d$_6$, δ): 2.10 (3H, s), 6.55 (1H, d, J=16 Hz), 7.58 (1H, d, J=16 Hz), 8.07–8.21 (2H), 8.59 (1H, br s)

PREPARATION 51

(E)-3-(6-Ethoxycarbonyl-3-pyridyl)acrylic acid (from ethyl 5-formyl-2-pyridinecarboxylate) was obtained according to a similar manner to that of Preparation 50. mp: 201–202° C.

NMR (DMSO-d₆, δ): 1.33 (3H, t, J=7 Hz), 4.36 (2H, q, J=7 Hz), 6.80 (1H, d, J=16 Hz), 7.69 (1H, d, J=16 Hz), 8.07 (1H, d, J=9 Hz), 8.33 (1H, dd, J=9, 2 Hz), 9.00 (1H, d, J=2 Hz).

PREPARATION 52

(1) 4-(Methylcarbamoyl)benzaldehyde was obtained by reacting 4-formylbenzoic acid with methylamine hydrochloride according to a similar manner to that of Preparation 30. mp: 160.3–161° C.

NMR (DMSO-d₆, δ): 2.81 (3H, d, J=5.5 Hz), 7.97 (2H, d, J=9.0 Hz), 8.02 (2H, d, J=9.0 Hz), 8.67 (1H, m), 10.06 (1H, s)

(2) 4-(Methylcarbamoyl)cinnamic acid was obtained by reacting 4-(methylcarbamoyl)benzaldehyde with malonic acid according to a similar manner to that of Preparation 50. mp 272.7° C.

NMR (DMSO-d₆, δ): 2.78 (3H, d, J=5 Hz), 3.34 (1H, br s), 6.62 (1H, d, J=16 Hz), 7.61 (1H, d, J=16 Hz), 7.77 (2H, d, J=8 Hz), 7.85 (2H, d, J=8 Hz), 8.51 (1H, q-like).

PREPARATION 53

(1) To a suspension of 2-(2-hydroxyethyl)phthalimide (10.0 g) and triethylamine (0.729 ml) in 1,4-dioxane (50 ml) was added methyl isocyanate (4.63 ml) under ice-bath cooling, and the mixture was stirred for 4 days at ambient temperature. The solvent was removed in vacuo, and the residue was recrystallized with methanol to give 2-phthalimidoethyl methylcarbamate (10.13 g). mp 142.3–145.0° C.

NMR (CDCl₃, δ): 2.73 (3H, d, J=4.5 Hz), 3.95 (2H, t, J=7.5 Hz), 4.30 (2H, t, J=7.5 Hz), 4.60 (1H, br s), 7.67–7.77 (2H, m), 7.80–7.90 (2H, m)

(2) 2-Aminoethyl methylcarbamate was obtained according to a similar manner to that of Example 9.

NMR (CDCl₃, δ): 3.30 (3H, d, J=6 Hz), 3.40 (2H, t, J=7.5 Hz), 4.06 (2H, t, J=7.5 Hz), 4.74 (2H, br s)

PREPARATION 54

Phenyl 4-ethoxycarbonylphenylcarbamate was obtained by reacting ethyl 4-aminobenzoate with phenyl chloroformate according to a similar manner to that of Preparation 18. mp: 155.6–161.7° C.

NMR (CDCl₃, δ): 1.38 (3H, t, J=7.5 Hz), 4.37 (2H, q, J=7.5 Hz), 7.00–7.27 (4H, m), 7.27–7.45 (2H, m), 7.51 (2H, d, J=8 Hz), 8.02 (2H, d, J=8 Hz)

PREPARATION 55

The following compounds were obtained according to a similar manner to that of Preparation 13.

(1) Ethyl 4-[N-(3-pyridylmethyl)acetamido]cinnamate (from ethyl 4-acetamidocinnamate and 3-pyridylmethyl chloride hydrochloride)

NMR (CDCl₃, δ): 1.34 (3H, t, J=7 Hz), 1.92 (3H, s), 4.29 (2H, q, J=7 Hz), 4.90 (2H, s), 6.41 (1H, d, J=15 Hz), 7.02 (2H, d, J=7 Hz), 7.24 (1H, m), 7.51 (2H, d, J=7 Hz), 7.60–7.70 (2H), 8.38 (1H, br s), 8.51 (1H, d, J=3 Hz)

(2) Ethyl 4-[N-(tert-butoxycarbonylmethyl)acetamido]cinnamate (from ethyl 4-acetamidocinnamate and tert-butyl bromoacetate)

NMR (CDCl₃, δ): 1.36 (3H, t, J=7 Hz), 1.47 (9H, s), 1.94 (3H, s), 4.21–4.32 (4H), 6.45 (1H, d, J=16 Hz), 7.35 (2H, d, J=8 Hz), 7.58 (2H, d, J=8 Hz), 7.68 (1H, d, J=16 Hz)

(3) Ethyl 4-[N-(2-pyridylmethyl)acetamido]cinnamate (from ethyl 4-acetamidocinnamate and 2-pyridylmethyl chloride hydrochloride)

NMR (CDCl₃, δ): 1.31 (3H, t, J=7.5 Hz), 1.96 (3H, s), 4.25 (2H, q, J=7.5 Hz), 5.01 (2H, s), 6.39 (1H, d, J=16 Hz), 7.06–7.23 (3H, m), 7.36 (1H, d, J=7.5 Hz), 7.49 (2H, d, J=7.5 Hz), 7.55–7.70 (2H, m), 8.49 (1H, d, J=5 Hz)

(4) Ethyl 4-[N-(4-pyridylmethyl)acetamido]cinnamate (from ethyl 4-acetamidocinnamate and 4-pyridylmethyl chloride hydrochloride)

NMR (CDCl₃, δ): 1.33 (3H, t, J=7.5 Hz), 1.95 (3H, s), 4.28 (2H, q, J=7.5 Hz), 4.90 (3H, s), 6.43 (1H, d, J=16 Hz), 7.07 (2H, d, J=8 Hz), 7.14 (2H, d, J=7 Hz), 7.51 (2H, d, J=8 Hz), 7.65 (1H, d, J=16 Hz), 8.53 (2H, d, J=7 Hz)

(5) Ethyl 4-[N-(2-methoxyethyl)acetamido]cinnamate (from ethyl 4-acetamidocinnamate and 2-methoxyethyl bromide)

NMR (CDCl₃, δ): 1.33 (3H, t, J=7.5 Hz), 1.85 (3H, s), 3.30 (3H, s), 3.52 (2H, t, J=6 Hz), 3.88 (2H, t, J=6 Hz), 4.28 (2H, q, J=7.5 Hz), 6.44 (1H, d, J=16 Hz), 7.25 (2H, d, J=8 Hz), 7.56 (2H, d, J=8 Hz), 7.68 (1H, d, J=16 Hz)

(6) Ethyl 4-[N-methoxyacetyl-N-(3-pyridylmethyl)amino]cinnamate (from ethyl 4-(methoxyacetamido)cinnamate and 3-pyridylmethyl chloride hydrochloride)

NMR (CDCl₃, δ): 1.32 (3H, t, J=7.5 Hz), 3.35 (3H, s), 3.81 (2H, s), 4.27 (2H, q, J=7.5 Hz), 4.91 (2H, s), 6.42 (1H, d, J=16 Hz), 7.01 (2H, d, J=8 Hz), 7.18–7.28 (1H, m), 7.50 (2H, d, J=8 Hz), 7.57–7.72 (2H, m), 8.35 (1H, d, J=2 Hz), 8.52 (1H, dd, J=6, 2 Hz).

PREPARATION 56

(1) Ethyl 4-(phenoxycarbonylamino)cinnamate was obtained by reacting ethyl 4-aminocinnamate with phenyl chloroformate according to a similar manner to that of Preparation 18. mp: 136–138° C.

NMR (CDCl₃, δ): 1.33 (3H, t, J=7 Hz), 4.27 (2H, q, J=7 Hz), 6.39 (1H, d, J=15 Hz), 7.09 (1H, br s), 7.15–7.58 (9H), 7.65 (1H, d, J=15 Hz)

(2) A solution of ethyl 4-(phenoxycarbonylamino)cinnamate (500 mg), 3-aminopyridine (154 mg) and triethylamine (325 mg) in N,N-dimethylformamide (5 ml) was stirred for 2 hours at 80° C. Water was added thereto, and the resulting precipitate was collected by filtration to give ethyl 4-[3-(3-pyridyl)ureido]cinnamate (307 mg) as a colorless powder. mp: 188–189° C.

NMR (DMSO-d₆, δ): 1.26 (3H, t, J=7 Hz), 4.19 (2H, q, J=7 Hz), 6.50 (1H, d, J=15 Hz), 7.34 (1H, dd, J=9, 5 Hz), 7.46–7.72 (5H), 7.96 (1H, dt, J=9, 1 Hz), 8.21 (1H, dd, J=9, 1 Hz), 8.62 (1H, d, J=1 Hz), 8.98 (1H, br s), 9.10 (1H, m)

PREPARATION 57

The following compounds were obtained according to a similar manner to that of Preparation 24.

(1) Ethyl 4-(morpholinocarbonylamino)cinnamate mp: 170–173° C.

NMR (CDCl₃, δ): 1.33 (3H, t, J=7 Hz), 3.43–3.56 (4H), 3.70–3.81 (4H), 4.28 (2H, q, J=7 Hz), 6.35 (1H, d, J=15 Hz), 6.49 (1H, br s), 7.40 (2H, d, J=9 Hz), 7.48 (2H, d, J=9 Hz), 7.63 (1H, d, J=15 Hz).

(2) Ethyl 4-(4-bromobutyramido)cinnamate mp: 119–124° C.

NMR (CDCl₃, δ): 1.32 (3H, t, J=7.5 Hz), 2.21 (2H, quint, J=6 Hz), 2.59 (2H, t, J=6 Hz), 3.66 (2H, t, J=6 Hz), 4.25 (2H, q, J=7.5 Hz), 6.34 (1H, d, J=16 Hz), 7.47 (2H, d, J=8 Hz), 7.55 (2H, d, J=8 Hz), 7.61 (1H, d, J=16 Hz).

(3) Ethyl 4-[(2-pyridyl)acetamido]cinnamate mp: 127° C.

NMR (CDCl₃, δ): 1.33 (3H, t, J=7.5 Hz), 3.88 (2H, s), 4.25 (2H, q, J=7.5 Hz), 6.35 (1H, d, J=16 Hz), 7.20–7.35 (2H, m), 7.49 (2H, d, J=8 Hz), 7.54–7.80 (4H, m), 8.63 (1H, d, J=5 Hz), 10.18 (1H, s)

(4) Ethyl 4-[(4-pyridyl)acetamido]cinnamate mp: 188° C.

NMR (CDCl₃, δ): 1.34 (3H, t, J=7.5 Hz), 3.73 (2H, s), 4.25 (2H, q, J=7.5 Hz), 6.37 (1H, d, J=16 Hz), 7.20–7.35

(2H, m), 7.40 (1H, s), 7.43–7.55 (4H, m), 7.52 (1H, d, J=16 Hz), 8.62 (2H, d, J=6 Hz)

PREPARATION 58

To a stirred suspension of methyl 4-carboxycinnamate (400 mg) in thionyl chloride (1.4 ml) was added one drop of N,N-dimethylformamide. The mixture was refluxed for 20 minutes. The solvent was removed in vacuo. To the residue was added toluene (2 ml) and the mixture was evaporated in vacuo twice. The residue was dissolved with dichloromethane (4 ml), and 4-aminopyridine (201 mg) and triethylamine (0.81 ml) were added thereto in an ice-water bath. After 10 minutes the mixture was stirred at ambient temperature. After 3 hours, to the reaction mixture was added water and the mixture was extracted with dichloromethane-methanol (5:1, V/V). The organic layer was washed with saturated sodium bicarbonate solution, water and brine, and dried over anhydrous magnesium sulfate. The solvent was evaporated in vacuo. The residue was crystallized from ethyl acetate to give methyl 4-[N-(4-pyridyl)carbamoyl]cinnamate (555 mg) as a colorless powder. mp: 209–211° C.

NMR (DMSO-d$_6$, δ): 3.76 (3H, s), 6.82 (1H, d, J=15 Hz), 7.69–7.83 (3H), 7.92 (2H, d, J=9 Hz), 8.01 (2H, d, J=9 Hz), 8.50 (2H, d, J=7 Hz)

PREPARATION 59

The following compounds were obtained according to similar manners to those of Preparations 30 or 58.
(1) Methyl 4-(ethylcarbamoyl)cinnamate
mp: 132–134.5° C.
(2) Methyl 4-(4-methyl-1-piperazinylcarbonyl)cinnamate
mp: 88–90° C.

PREPARATION 60

The following compounds were obtained according to a similar manner to that of Preparation 33.
(1) 4-[N-(4-Pyridyl)carbamoyl]cinnamic acid mp: >250° C.
NMR (DMSO-d$_6$, δ): 6.69 (1H, d, J=16 Hz), 7.52–8.08 (7H), 8.49 (2H, d, J=6 Hz)
(2) 4-[N-(3-Pyridylmethyl)acetamido]cinnamic acid mp: 184–186° C.
NMR (DMSO-d$_6$, δ): 1.90 (3H, s), 4.91 (2H, s), 6.52 (1H, d, J=15 Hz), 7.21–7.39 (3H), 7.50–7.79 (4H), 8.39 (1H, d, J=2 Hz), 8.43 (1H, dd, J=5, 2 Hz).
(3) 4-[3-(3-Pyridyl)ureido]cinnamic acid mp: 219–221° C.
NMR (DMSO-d$_6$, δ): 6.40 (1H, d, J=15 Hz), 7.37 (1H, dd, J=9, 5 Hz), 7.47–7.70 (5H), 7.98 (1H, dt, J=9, 1 Hz), 8.21 (1H, br d, J=5 Hz), 8.62 (1H, d, J=1 Hz), 9.03 (1H, s), 9.16 (1H, s)
(4) 4-(Morpholinocarbonylamino)cinnamic acid
mp: 219–221° C.
(5) 4-(Ethylcarbamoyl)cinnamic acid
mp: 256–261° C.
(6) 4-(4-Methyl-1-piperazinylcarbonyl)cinnamic acid
NMR (DMSO-d$_6$, δ): 2.12–2.58 (7H), 2.92–3.87 (4H, overlapped with H$_2$O), 6.60 (1H, d, J=16 Hz), 7.41 (2H, d, J=8 Hz), 7.62 (1H, d, J=16 Hz), 7.78 (2H, d, J=8 Hz)
(7) 4-(N-Acetyl-N-tert-butoxycarbonylmethylamino) cinnamic acid mp: 177–178° C.
NMR (CDCl$_3$, δ): 1.48 (9H, s), 1.98 (3H, s), 4.28 (2H, s), 6.48 (1H, d, J=16 Hz), 7.39 (2H, d, J=8 Hz), 7.60 (2H, d, J=8 Hz), 7.79 (1H, d, J=16 Hz)
(8) 4-[(2-Pyridyl)acetamido]cinnamic acid mp: 215° C.
NMR (DMSO-d$_6$, δ): 3.90 (2H, s), 6.40 (1H, d, J=16 Hz), 7.34 (1H, dd, J=5, 8 Hz), 7.38–7.72 (6H, m), 7.84 (1H, td, J=8, 1 Hz), 8.54 (1H, d, J=5 Hz)
(9) 4-[(4-Pyridyl)acetamido]cinnamic acid mp: >250° C.
NMR (DMSO-d$_6$, δ) 3.75 (2H, s), 6.42 (1H, d, J=16 Hz), 7.35 (2H, d, J=5 Hz), 7.52 (1H, d, J=16 Hz), 7.65 (4H, s-like), 8.51 (2H, d, J=5 Hz)
(10) 4-[N-(2-Pyridylmethyl)acetamido]cinnamic acid
NMR (DMSO-d$_6$, δ): 1.90 (3H, s), 4.97 (2H, s), 6.51 (1H, d, J=16 Hz), 7.24 (1H, dd, J=5, 7.5 Hz), 7.29–7.45 (3H, m), 7.55 (1H, d, J=16 Hz), 7.61–7.80 (3H, m), 8.41–8.50 (1H, m)
(11) 4-[N-(4-Pyridylmethyl)acetamido]cinnamic acid
NMR (CDCl$_3$, δ): 2.00 (3H, s), 4.91 (2H, s), 6.45 (1H, d, J=16 Hz), 7.09 (2H, d, J=8 Hz), 7.20 (2H, d, J=6 Hz), 8.54 (2H, d, J=8 Hz), 7.70 (1H, d, J=16 Hz), 8.55 (2H, d, J=6 Hz)
(12) 4-[N-(2-Methoxyethyl)acetamido]cinnamic acid mp: 102–106° C.
NMR (CDCl$_3$, δ) 1.88 (3H, s), 3.30 (3H, s), 3.53 (2H, t, J=6 Hz), 5.89 (2H, t, J=6 Hz), 6.45 (1H, d, J=16 Hz), 7.28 (2H, d, J=8 Hz), 7.60 (2H, d, J=8 Hz), 7.77 (1H, d, J=16 Hz)
(13) 4-[N-(2-Methoxyethyl)-N-(isonicotinoyl)amino] cinnamic acid
NMR (CDCl$_3$, δ): 3.33 (3H, s), 3.66 (2H, t, J=5 Hz), 4.10 (2H, t, J=5 Hz), 6.37 (1H, d, J=16 Hz), 7.15 (2H, d, J=8 Hz), 7.20 (2H, d, J=6 Hz), 7.40 (2H, d, J=8 Hz), 7.62 (1H, d, J=16 Hz), 8.50 (2H, d, J=6 Hz)
(14) 4-[N-Methoxyacetyl-N-(3-pyridylmethyl)amino] cinnamic acid mp: 160° C.
NMR (DMSO-d$_6$, δ): 3.20 (3H, s), 3.87 (2H, s), 4.91 (2H, s), 6.54 (1H, d, J=16 Hz), 7.27 (8H, d), 7.27–7.38 (1H, m), 7.56 (1H, d, J=16 Hz), 7.62 (1H, dd-like, J=8 Hz), 7.70 (2H, d, J=8 Hz), 8.37 (1H, d, J=2 Hz), 8.43 (1H, d, J=6 Hz)
(15) 4-(2-Oxo-1-pyrrolidinyl)cinnamic acid mp: >250° C.
NMR (DMSO-d$_6$, δ): 2.06 (2H, quint, J=8 Hz), 3.86 (2H, t, J=8 Hz), 6.46 (1H, d, J=16 Hz), 7.55 (1H, d, J=16 Hz), 7.65–7.76 (4H, m)

PREPARATION 61

To a solution of N,N-bis(2-methoxyethyl)amine (2.40 g) and triethylamine (2.27 g) in dichloromethane (30 ml) was added 3-nitrobenzoyl chloride (2.78 g) in an ice-water bath. The mixture was stirred at ambient temperature for 1 hour. The reaction mixture was washed with saturated sodium bicarbonate solution, water and brine, dried over anhydrous magnesium sulfate, and evaporated in vacuo. The residue was purified with column chromatography eluting with dichloromethane-methanol to give N,N-bis(2-methoxyethyl)-3-nitrobenzamide (4.12 g) as an oil.

NMR (CDCl$_3$, δ): 3.22–3.88 (14H), 7.59 (1H, t, J=8 Hz), 7.80 (1H, dt, J=8, 1 Hz), 8.26 (1H, dt, J=8, 1 Hz), 8.39 (1H, t, J=1 Hz)

PREPARATION 62

A mixture of N,N-bis(2-methoxyethyl)-3-nitrobenzamide (4.11 g) and palladium on charcoal (411 mg) in ethyl acetate (41 ml) was hydrogenated under 1 atmospheric pressure to hydrogen for 1 hour at ambient temperature. The catalyst was removed by filtration and washed with ethyl acetate, and the volatiles were removed in vacuo. The residue was purified with column chromatography eluting with dichloromethane-methanol to give 3-amino-N,N-bis(2-methoxyethyl)benzamide (3.62 g) as an oil.

NMR (CDCl$_3$, δ): 3.19–3.86 (16H), 6.62–6.79 (3H), 7.16 (1H, dt, J=8, 1 Hz)

PREPARATION 63

To a stirred solution of 3-amino-N,N-bis(2-methoxyethyl) benzamide (1.01 g) in 1,4-dioxane (10 ml) was added 1N sodium hydroxide solution (5.2 ml) and phenyl chloroformate (0.55 ml) successively in an ice-cooled bath. The bath was removed and the reaction mixture was stirred vigorously for 1 hour, during which time phenyl chloroformate (0.25 ml) was further added. The mixture was extracted with dichloromethane and the organic layer was washed with water twice and brine, dried over anhydrous magnesium sulfate, and evaporated in vacuo. The residue was crystallized from diisopropyl ether to give phenyl 3-[N,N-bis(2-methoxyethyl)carbamoyl]phenylcarbamate (1.30 g) as a colorless powder. mp: 116–118° C.

NMR (CDCl$_3$, δ): 3.19–3.82 (14H), 7.10–7.57 (10H)

PREPARATION 64

To a stirred solution of ethyl 4-(4-bromobutyramido) cinnamate (420 mg) in N,N-dimethylformamide (5 ml) was added potassium carbonate (552 mg) at ambient temperature and the resulting mixture was warmed at 50° C.; for three hours. The reaction mixture was diluted with ethyl acetate and washed with water and brine. The organic phase was dried over anhydrous magnesium sulfate, and concentrated in vacuo. The residue was purified by flash column chromatography eluting with chloroform to afford ethyl 4-(2-oxo-1-pyrrolidinyl)cinnamate (281 mg) as a pale yellow solid. mp: 134° C.

NMR (CDCl$_3$, δ): 1.34 (3H, t, J=7.7 Hz), 2.19 (2H, quint, J=7.7 Hz), 2.63 (2H, t, J=7.7 Hz), 3.88 (2H, t, J=7.7 Hz), 4.26 (2H, q, J=7.7 Hz), 6.38 (1H, d, J=16 Hz), 7.53 (2H, d, J=8 Hz), 7.64 (1H, d, J=16 Hz), 7.68 (2H, d, J=8 Hz)

EXAMPLE 42

8-(2,6-Dichloro-3-nitrobenzyloxy)-3-methylquinoline was obtained according to a similar manner to that of Example 1.

NMR (CDCl$_3$, δ): 2.50 (3H, s), 5.58 (2H, s), 7.18 (1H, dd, J=8, 1 Hz), 7.36–7.57 (3H), 7.78 (1H, d, J=8 Hz), 7.90 (1H, d, J=1 Hz), 8.79 (1H, d, J=1 Hz)

EXAMPLE 43

To a solution of 8-hydroxy-2-methylquinoline (17.8 g) in N,N-dimethylformamide (89 ml) was added sodium hydride (40% in oil, 4.48 g) under ice-bath cooling, and the mixture was stirred for 40 minutes at ambient temperature. A solution of 2,6-dichloro-1-methylsulfonyloxy-3-[N-methyl-N-(phthalimidoacetyl)amino]benzene (56.1 g) in N,N-dimethylformamide (200 ml) was added thereto under ice-bath cooling, and the mixture was stirred for 70 minutes at ambient temperature. Water (290 ml) was dropwise added thereto, and the resulting precipitate was collected by filtration to give 8-[2,6-dichloro-3-[N-methyl-N-(phthalimidoacetyl)amino]benzyloxy]-2-methylquinoline (57.07 g). mp: 204° C.

EXAMPLE 44

The following compounds were obtained according to a similar manner to that of Example 43.
(1) 8-[2,6-Dichloro-3-[N-(phthalimidoacetyl)-N-methylamino]benzyloxy]-3-methylquinoxaline mp: 238.8–240° C.

NMR (CDCl$_3$, δ): 2.78 (3H, s), 3.25 (3H, s), 4.12 (2H, s), 5.59 (1H, d, J=10 Hz), 5.63 (1H, d, J=10 Hz), 7.25–7.31 (1H, overlapped with CDCl$_3$), 7.51 (1H, d, J=9 Hz), 7.56 (1H, d, J=9 Hz), 7.67–7.77 (4H), 7.82–7.89 (2H), 8.74 (1H, s)
(2) 8-[2,6-Dichloro-3-[N-(phthalimidoacetyl)-N-methylamino]benzyloxy]-2-methylquinoxaline mp: 218–220° C.

NMR (CDCl$_3$, δ): 2.78 (3H, s), 3.24 (3H, s), 4.10 (2H, s), 5.63 (1H, d, J=10 Hz), 5.71 (1H, d, J=10 Hz), 7.33 (1H, br d, J=7.5 Hz), 7.50 (1H, d, J=8 Hz), 7.54 (1H, d, J=8 Hz), 7.63 (1H, t, J=7.5 Hz), 7.69–7.78 (3H), 7.82–7.90 (2H), 8.73 (1H, s)
(3) 8-[2,6-Dichloro-3-[N-(phthalimidoacetyl)-N-methylamino]benzyloxy]cinnoline mp: 221.4–222° C.

NMR (CDCl$_3$, δ): 3.27 (3H, s), 4.12 (2H, s), 5.71 (2H, s), 7.36 (1H, d, J=7.5 Hz), 7.48 (1H, d, J=7.5 Hz), 7.52 (1H, d, J=8 Hz), 7.58 (1H, d, J=8 Hz), 7.69–7.78 (3H), 7.81–7.90 (3H), 9.35 (1H, d, J=6 Hz)
(4) 8-[2,6-Dichloro-3-[N-(phthalimidoacetyl)-N-methylamino]benzyloxy]-2-methylquinazoline mp: 237.5–238° C.

NMR (CDCl$_3$, δ): 2.90 (3H, s), 3.24 (3H, s), 4.10 (2H, s), 5.66 (1H, d, J=10 Hz), 5.72 (1H, d, J=10 Hz), 7.43–7.60 (5H), 7.70–7.75 (2H), 7.82–7.89 (2H), 9.30 (1H, s)
(5) 5,7-Dibromo-8-[2,6-dichloro-3-[N-(phthalimidoacetyl)-N-methylamino]benzyloxy]-2-methylquinoline mp: 204–207° C.

NMR (CDCl$_3$, δ): 2.79 (3H, s), 3.17 (3H, s), 3.87 (1H, d, J=16.5 Hz), 3.98 (1H, d, J=16.5 Hz), 5.92 (1H, d, J=11.5 Hz), 6.00 (1H, d, J=11.5 Hz), 7.38 (1H, d, J=8.5 Hz), 7.44 (1H, d, J=8.5 Hz), 7.51 (1H, d, J=8.5 Hz), 7.67–7.77 (2H, m), 7.81–7.91 (3H, m), 8.30 (1H, d, J=8.5 Hz)

EXAMPLE 45

8-[3-[N-Benzyl-N-(phthalimidoacetyl)amino]-2,6-dichlorobenzyloxy]-2-methylquinoline was obtained by reacting 8-[2,6-dichloro-3-(phthalimidoacetylamino)-benzyloxy]-2-methylquinoline with benzyl bromide according to a similar manner to that of Example 7.

NMR (CDCl$_3$, δ): 2.75 (3H, s), 3.98–4.06 (2H), 4.09 (1H, d, J=17 Hz), 5.62 (1H, d, J=14 Hz), 5.68 (1H, d, J=10 Hz), 5.73 (1H, d, J=10 Hz), 6.92 (1H, d, J=8 Hz), 7.16–7.35 (8H), 7.40 (1H, t, J=7.5 Hz), 7.47 (1H, d, J=7.5 Hz), 7.70–7.78 (2H), 7.85–7.91 (2H), 8.02 (1H, d, J=7.5 Hz)

EXAMPLE 46

The following compounds were obtained according to a similar manner to that of Example 9.
(1) 8-[3-(N-Glycyl-N-methylamino)-2,6-dichlorobenzyloxy]-3-methylquinoxaline NMR (CDCl$_3$, δ): 2.77 (3H, s), 2.98–3.32 (5H), 5.57 (2H, s), 7.21–7.30 (2H), 7.48 (1H, d, J=8 Hz), 7.67–7.75 (2H), 8.74 (1H, s)
(2) 8-[3-(N-Glycyl-N-methylamino)-2,6-dichlorobenzyloxy]-2-methylquinoxaline NMR (CDCl$_3$, δ): 2.79 (3H, s), 3.00 (1H, d, J=17 Hz), 3.11 (1H, d, J=17 Hz), 3.22 (3H, s), 5.62 (2H, s), 7.23–7.33 (2H), 7.49 (1H, d, J=8 Hz), 7.64 (1H, d, J=7.5 Hz), 7.63 (1H, br d, J=7.5 Hz), 8.75 (1H, s)
(3) 8-[3-(N-Glycyl-N-methylamino)-2,6-dichlorobenzyloxy]-cinnoline NMR (CDCl$_3$, δ): 3.02 (1H, d, J=17 Hz), 3.13 (1H, d, J=17 Hz), 3.24 (3H, s), 5.65 (1H, d, J=10 Hz), 5.70 (1H, d, J=10 Hz), 7.28–7.36 (2H), 7.42–7.51 (2H), 7.71 (1H, t, J=7.5 Hz), 7.82 (1H, d, J=7.5 Hz), 9.36 (1H, d, J=6 Hz)
(4) 8-[3-(N-Glycyl-N-methylamino)-2,6-dichlorobenzyloxy]-2-methylquinazoline NMR (CDCl$_3$, δ): 2.90 (3H, s), 3.00 (1H, d, J=16 Hz), 3.11 (1H, d, J=16 Hz), 3.22 (3H, s), 5.62 (2H, s), 7.28 (1H, d, J=8 Hz), 7.40–7.59 (4H), 9.31 (1H, s)
(5) 8-[3-(N-Glycyl-N-benzylamino)-2,6-dichlorobenzyloxy]-2-methylquinoline NMR (CDCl$_3$, δ): 2.75 (3H, s), 2.99 (1H, d, J=17 Hz), 3.08 (1H, d, J=17 Hz), 3.94 (1, d, J=14 Hz), 3.60–3.72 (3H), 6.69 (1H, d, J=7.5 Hz), 7.15–7.33 (8H), 7.39 (1H, t, J=7.5 Hz), 7.48 (1H, d, J=7.5 Hz), 8.03 (1H, br d, J=7.5 Hz)

(6) 8-[3-(N-Glycyl-N-methylamino)-2,6-dichlorobenzyloxy]-5,7-dibromo-2-methylquinoline NMR (CDCl$_3$, δ): 2.78 (3H, s), 2.84 (1H, d, J=16.5 Hz), 3.03 (1H, d, J=16.5 Hz), 3.16 (3H, s), 5.90 (2H, s), 7.22 (1H, d, J=8.5 Hz), 7.41 (1H, d, J=8.5 Hz), 7.43 (1H, d, J=8.5 Hz), 7.85 (1H, s), 8.34 (1H, d, J=8.5 Hz)

EXAMPLE 47

(1) 8-[2,6-Dichloro-3-[N-ethoxycarbonylmethyl-N-(phthalimidoacetyl)amino]benzyloxy]-2-methylquinoline was obtained by reacting 8-[2,6-dichloro-3-(phthalimidoacetylamino)benzyloxy]-2-methylquinoline with ethyl bromoacetate according to a similar manner to that of Example 7. mp: 211–213° C.

NMR (CDCl$_3$, δ): 1.28 (3H, t, J=7.5 Hz), 2.73 (3H, s), 3.68 (1H, d, J=17 Hz), 4.03 (1H, d, J=17 Hz), 4.13–4.30 (3H), 5.00 (1H, d, J=17 Hz), 5.65 (1H, d, J=10 Hz), 5.70 (1H, d, J=10 Hz), 7.23–7.31 (2H), 7.36–7.49 (3H), 7.69–7.75 (2H), 7.81–7.91 (3H), 8.01 (1H, d, J=8 Hz)

(2) To the solution of 8-[2,6-dichloro-3-[N-ethoxycarbonylmethyl-N-(phthalimidoacetyl)amino]benzyloxy]-2-methylquinoline (527 mg) in dichloromethane (5.3 ml) was added 30% solution of methylamine in methanol (2 ml) at ambient temperature. After stirring for 24 hours, the reaction mixture was evaporated in vacuo. The residue was purified by flash column chromatography (silica gel 50 ml) eluting with dichloromethane/methanol (20/1, V/V) and by crystallizing from isopropyl ether to give 8-[2,6-dichloro-3-(2,5-dioxopiperazin-1-yl)benzyloxy]-2-methylquinoline (187 mg) as colorless crystals. mp: 211–213° C.

NMR (CDCl$_3$, δ): 2.74 (3H, s), 4.09–4.21 (3H), 4.40 (1H, d, J=17 Hz), 5.62 (2H, s), 6.38 (1H, br s), 7.21–7.51 (6H), 8.01 (1H, d, J=8 Hz)

(3) 8-[3-(4-Benzyl-2,5-dioxopiperazin-1-yl)-2,6-dichlorobenzyloxy]-2-methylquinoline was obtained by reacting 8-[2,6-dichloro-3-(2,5-dioxopiperazin-1-yl)benzyloxy]-2-methylquinoline with benzyl bromide according to a similar manner to that of Example 7.

NMR (CDCl$_3$, δ): 2.75 (3H, s), 4.01 (1H, d, J=17 Hz), 4.10 (1H, d, J=17 Hz), 4.21 (1H, d, J=17 Hz), 4.48 (1H, d, J=17 Hz), 4.63 (1H, d, J=15 Hz), 4.72 (1H, d, J=15 Hz), 5.62 (2H, s), 7.20–7.52 (11H), 8.02 (1H, d, J=8 Hz)

(4) 8-[2,6-Dichloro-3-(4-ethoxycarbonylmethyl-2,5-dioxopiperazin-1-yl)benzyloxy]-2-methylquinoline was obtained by reacting 8-[2,6-dichloro-3-(2,5-dioxopiperazin-1-yl)benzyloxy]-2-methylquinoline with ethyl bromoacetate according to a similar manner to that of Example 7.

NMR (CDCl$_3$, δ): 1.31 (3H, t, J=7.5 Hz), 2.74 (3H, s), 4.11–4.36 (7H), 4.48 (1H, d, J=17 Hz), 5.61 (2H, s), 7.21–7.32 (3H), 7.36–7.51 (3H), 8.02 (1H, d, J=8 Hz)

EXAMPLE 48

4-Chloro-8-(2,6-dichloro-3-nitrobenzyloxy)-2-methylquinazoline was obtained from 8-(2,6-dichloro-3-nitrobenzyloxy)-2-methyl-4-oxo-3,4-dihydroquinazoline according to a similar manner to that of Preparation 6. mp: 192.8–194.3° C.

NMR (CDCl$_3$, δ): 2.86 (3H, s), 5.66 (2H, s), 7.44–7.65 (3H, m), 7.80 (1H, d, J=9 Hz), 7.91 (1H, dd, J=8, 0.5 Hz)

EXAMPLE 49

A mixture of 8-[2,6-dichloro-3-(N-glycyl-N-methylamino)benzyloxy]-2-methylquinoline (100 mg), acetic anhydride (35 ml), pyridine (60 μl) and methylene chloride (2 ml) was stirred for 3 hours at ambient temperature. The reaction mixture was concentrated and the residue was purified by preparative thin-layer chromatography (ethyl acetate-methanol) to give 8-[3-[N-(acetylglycyl)-N-methylamino]-2,6-dichlorobenzyloxy]-2-methylquinoline (138 mg).

NMR (CDCl$_3$, δ): 2.00 (3H, s), 2.74 (3H, s), 3.24 (3H, s), 3.50 (1H, dd, J=17, 4 Hz), 3.80 (1H, dd, J=17, 5 Hz), 5.63 (2H, s), 6.33 (1H, br s), 7.21–7.34 (2H, m), 7.37–7.52 (4H, m), 8.01 (1H, d, J=7.5 Hz) its hydrochloride NMR (CDCl$_3$-CD$_3$OD, δ): 1.98 (3H, s), 3.01 (3H, s), 3.28 (3H, s), 3.75 (1H, d, J=15 Hz), 3.80 (1H, d, J=15 Hz), 5.65 (1H, d, J=9 Hz), 5.80 (1H, d, J=9 Hz), 7.60 (1H, d, J=8 Hz), 7.70 (1H, d, J=8 Hz), 7.83 (1H, d, J=8 Hz), 7.86–8.02 (3H, m), 9.00 (1H, d, J=8 Hz)

EXAMPLE 50

The following compounds were obtained according to a similar manner to that of Example 49.

(1) 8-[3-[N-(Acetylglycyl)-N-methylamino]-2,6-dichlorobenzyloxy]-3-methylquinoxaline NMR (CDCl$_3$, δ): 2.01 (3H, s), 2.78 (3H, s), 3.25 (3H, s), 3.53 (1H, dd, J=17, 4 Hz), 3.80 (1H, dd, J=17, 5 Hz), 5.54 (2H, s), 6.42 (1H, br s), 7.26 (1H, overlapped with CDCl$_3$), 7.31 (1H, d, J=8 Hz), 7.49 (1H, d, J=8 Hz), 7.66–7.78 (2H), 8.23 (1H, s)

(2) 8-[3-(N-(Acetylglycyl)-N-methylamino]-2,6-dichlorobenzyloxy]-2-methylquinoxaline NMR (CDCl$_3$, δ): 2.01 (3H, s), 2.78 (3H, s), 3.24 (3H, s), 3.52 (1H, dd, J=17, 4 Hz), 3.80 (1H, dd, J=17, 4 Hz), 5.60 (2H, s), 6.42 (1H, br s), 7.30 (1H, d, J=9 Hz), 7.50 (1H, d, J=7.5 Hz), 7.65 (1H, t, J=7.5 Hz), 7.77 (1H, br d, J=7.5 Hz), 8.72 (1H, s)

(3) 8-[3-[N-(Acetylglycyl)-N-methylamino]-2,6-dichlorobenzyloxy]cinnoline

NMR (CDCl$_3$, δ): 2.01 (3H, s), 3.28 (3H, s), 3.54 (1H, dd, J=17, 4 Hz), 3.80 (1H, dd, J=17, 5 Hz), 5.63 (1H, d, J=10 Hz), 5.69 (1H, d, J=10 Hz), 6.45 (1H, br s), 7.30–7.38 (2H), 7.42–7.52 (2H), 7.73 (1H, t, J=7.5 Hz), 7.82 (1H, d, J=7.5 Hz), 9.34 (1H, d, J=6 Hz)

(4) 8-[3-[N-(Acetylglycyl)-N-methylamino]-2,6-dichlorobenzyloxy]-2-methylquinazoline NMR (CDCl$_3$, δ): 2.01 (3H, s), 2.90 (3H, s), 3.26 (3H, s), 3.51 (1H, dd, J=17, 4 Hz), 3.80 (1H, dd, J=17, 4 Hz), 5.62 (2H, s), 6.43 (1H, br s), 7.30 (1H, d, J=7.5 Hz), 7.31–7.59 (4H), 9.30 (1H, s)

(5) 8-[3-[N-(Acetylglycyl)-N-benzylamino]-2,6-dichlorobenzyloxy]-2-methylquinoline NMR (CDCl$_3$, δ): 2.02 (3H, s), 2.77 (3H, s), 3.51 (1H, dd, J=17, 4 Hz), 3.79 (1H, dd, J=17, 5 Hz), 3.98 (1H, d, J=14 Hz), 5.60–5.72 (3H), 6.47 (1H, br s), 6.71 (1H, d, J=8 Hz), 7.15–7.33 (8H), 7.40 (1H, t, J=7.5 Hz), 7.48 (1H, d, J=7.5 Hz), 8.03 (1H, d, J=7.5 Hz) its hydrochloride NMR (CDCl$_3$-CD$_3$OD, δ): 2.01 (3H, s), 3.08 (3H, s), 3.68–3.80 (2H, overlapped with H$_2$O), 4.24 (1H, d, J=14 Hz), 5.53 (1H, d, J=14 Hz), 5.59 (1H, d, J=10 Hz), 5.73 (1H, d, J=10 Hz), 6.99 (1H, d, J=7.5 Hz), 7.21–7.34 (5H), 7.43 (1H, d, J=7.5 Hz), 7.70 (1H, d, J=7.5 Hz), 7.82–7.98 (3H), 8.96 (1H, d, J=7.5 Hz)

(6) 8-[3-[N-(Acetylglycyl)-N-methylamino]-2,6-dichlorobenzyloxy]-5,7-dibromo-2-methylquinoline mp: 179–183.5° C.

NMR (CDCl$_3$, δ): 2.01 (3H, s), 2.81 (3H, s), 3.20 (3H, s), 3.41 (1H, dd, J=16.5, 3.0 Hz), 3.78 (1H, dd, J=16.5, 3.0 Hz), 5.87 (1H, d, J=10.5 Hz), 5.93 (1H, d, J=10.5 Hz), 6.38 (1H, br t), 7.25 (1H, d, J=8.5 Hz), 7.41 (1H, d, J=8.5 Hz), 7.44

(1H, d, J=8.5 Hz), 7.86 (1H, s), 8.34 (1H, d, J=8.5 Hz) its hydrochloride mp: 93–96.5° C.

NMR (CDCl₃-CD₃OD, δ): 2.01 (3H, s), 2.96 (3H, s), 3.20 (3H, s), 3.42 (1H, d, J=16.5 Hz), 3.80 (1H, d, J=16.5 Hz), 5.88 (2H, s), 7.31 (1H, d, J=8.5 Hz), 7.46 (1H, d, J=8.5 Hz), 7.54 (1H, d, J=8.5 Hz), 7.97 (1H, s), 8.52 (1H, d, J=8.5 Hz)

EXAMPLE 51

The following compounds were obtained according to similar manners to those of Examples 11 to 13.

(1) 8-[2,6-Dichloro-3-[N-[N'-(4-ethoxycarbonylphenyl)ureidoacetyl]-N-methylamino]benzyloxy]-2-methylquinoline NMR (CDCl₃, δ): 1.32 (3H, t, J=7.5 Hz), 2.55 (3H, s), 3.21 (3H, s), 3.77 (1H, dd, J=4.5, 18 Hz), 4.30 (2H, q, J=7.5 Hz), 4.45 (1H, dd, J=7.5, 18 Hz), 5.43 (1H, d, J=10 Hz), 5.55 (1H, dd, J=4.5, 7.5 Hz), 5.62 (1H, d, J=10 Hz), 7.20–7.35 (6H, m), 7.44–7.55 (2H, m), 7.80 (2H, d, J=8 Hz), 8.10 (1H, d, J=8 Hz), 8.99 (1H, s)

(2) 8-[3-[N-[N'-[3-[N,N-Bis(2-methoxyethyl)carbamoyl]-phenyl]ureidoacetyl]-N-methylamino]-2,6-dichlorobenzyloxy]-4-methoxy-2-methylquinoline NMR (CDCl₃, δ): 2.53 (3H, s), 3.12–3.85 (18H), 4.03 (3H, s), 4.39 (1H, dd, J=18, 7 Hz), 5.40 (1H, d, J=10 Hz), 5.50–5.67 (2H), 6.68 (1H, s), 6.91 (1H, d, J=8 Hz), 7.08–7.50 (7H), 7.82 (1H, d, J=8 Hz), 8.85 (1H, br s) its hydrochloride NMR (CDCl₃-CD₃OD, δ): 2.87 (3H, s), 3.20–3.81 (18H), 3.89 (1H, d, J=17 Hz), 4.32 (3H, s), 5.54 (1H, d, J=10 Hz), 5.80 (1H, d, J=10 Hz), 6.99 (1H, m), 7.20–7.38 (2H), 7.41–7.52 (2H), 7.58 (1H, d, J=9 Hz), 7.62–7.72 (2H), 7.81 (1H, t, J=8 Hz), 8.00 (1H, d, J=8 Hz)

(3) 8-[2,6-Dichloro-3-[N-[N'-[3-(dimethylcarbamoyl)-phenyl]ureidoacetyl]-N-methylamino]benzyloxy]-2-methylquinoxaline NMR (CDCl₃, δ): 2.71 (3H, s), 2.94 (3H, br s), 3.09 (3H, br s), 3.23 (3H, s), 3.78 (1H, dd, J=17, 5 Hz), 3.84 (1H, dd, J=17, 5 Hz), 5.56 (1H, d, J=10 Hz), 5.62 (1H, d, J=10 Hz), 5.82 (1H, d, J=10 Hz), 6.99 (1H, d, J=7.5 Hz), 7.10 (1H, t, J=7.5 Hz), 7.29–7.38 (4H), 7.43 (1H, d, J=8 Hz), 7.68 (1H, t, J=7.5 Hz), 7.78 (1H, d, J=7.5 Hz), 7.89 (1H, br s), 8.76 (1H, s)

(4) 8-[2,6-Dichloro-3-[N-[N'-[3-[(2-methoxyethyl)carbamoyl]phenyl]ureidoacetyl]-N-methylamino]benzloxy]-2-methylquinoxaline NMR (CDCl₃, δ): 2.71 (3H, s), 3.23 (3H, br s), 3.37 (3H, s), 3.49–3.66 (4H), 3.79 (1H, dd, J=17, 5 Hz), 3.89 (1H, dd, J=17, 5 Hz), 5.56 (1H, d, J=10 Hz), 5.64 (1H, d, J=10 Hz), 5.92 (1H, br t, J=5 Hz), 6.80 (1H, br t, J=5 Hz), 7.18–7.58 (7H), 7.68 (1H, t, J=8 Hz), 7.78 (1H, d, J=8 Hz), 7.83 (1H, br s), 8.73 (1H, s)

EXAMPLE 52

The following compounds were obtained according to similar manners to those of Examples 15 or 16.

(1) 8-[2,6-Dichloro-3-[N-[4-(methoxycarbonyl)cinnamoylglycyl]-N-methylamino]benzyloxy]-2-methylquinoline NMR (CDCl₃, δ): 2.74 (3H, s), 3.27 (3H, s), 3.64 (1H, dd, J=18, 4 Hz), 3.87–4.00 (4H, m), 5.60–5.70 (2H, m), 6.57 (1H, d, J=16 Hz), 6.75 (1H, t-like), 7.24–7.63 (11H, m), 7.99–8.05 (1H, m)

(2) 8-[2,6-Dichloro-3-[N-methyl-N-[4-(4-methyl-1-piperazinylcarbonyl)cinnamoylglycyl]amino]benzyloxy]-2-methylquinoline NNR (CDCl₃, δ): 2.26–2.57 (7H), 2.74 (3H, s), 3.29 (3H, s), 3.36–3.89 (9H), 3.96 (1H, dd, J=18, 5 Hz), 5.65 (2H, s), 6.51 (1H, d, J=16 Hz), 6.70 (1H, br t, J=4 Hz), 7.21–7.63 (11H), 8.03 (1H, d, J=8 Hz) its dihydrochloride NMR (CDCl₃-CD₃OD, δ): 2.90 (3H, s), 2.99–3.21 (5H), 3.28–3.88 (9H), 3.94 (2H, s), 5.62 (1H, d, J=10 Hz), 5.81 (1H, d, J=10 Hz), 6.70 (1H, d, J=16 Hz), 7.40–7.70 (7H), 7.89 (1H, d, J=7 Hz), 7.87–8.01 (3H), 9.00 (H, d, J=9 Hz)

(3) 8-[2,6-Dichloro-3-[N-methyl-N-[4-[(4-pyridyl)carbamoyl]cinnamoylglycyl]amino]benzyloxy]-2-methylquinoline NMR (CDCl₃-CD₃OD, δ): 2.69 (3H, s), 3.28 (3H, s), 3.58–3.73 (1H, overlapped with H₂O), 4.02 (1H, d, J=18 Hz), 5.09 (2H, s), 6.62 (1H, d, J=16 Hz), 7.21–7.62 (9H), 7.76 (2H, d, J=7 Hz), 7.89 (2H, d, J=8 Hz), 8.10 (1H, d, J=8 Hz), 8.43 (1H, d, J=7 Hz) its dihydrochloride NMR (CDCl₃-CD₃OD, δ): 3.10 (3H, s), 3.32 (3H, s), 3.91 (1H, d, J=17 Hz), 4.03 (1H, d, J=17 Hz), 5.63 (1H, d, J=10 Hz), 5.82 (1H, d, J=10 Hz), 6.78 (1H, d, J=15 Hz), 7.51–8.02 (9H), 8.16 (2H, d, J=8 Hz), 8.58 (4H, s), 9.00 (1H, d, J=8 Hz)

(4) 8-[3-[N-[4-(N-Acetyl-N-tert-butoxycarbonylmethylamino)cinnamoylglycyl]-N-methylamino]-2,6-dichlorobenzyloxy]-2-methylquinoline NMR (CDCl₃, δ): 1.48 (9H, s), 1.94 (3H, s), 2.73 (3H, s), 3.29 (3H, s), 3.69 (1H, dd, J=18, 4 Hz), 3.98 (1H, dd, J=18, 5 Hz), 4.26 (2H, s), 5.65 (2H, s), 6.49 (1H, d, J=15 Hz), 6.70 (1H, br t, J=4 Hz), 7.22–7.63 (11H), 8.03 (1H, d, J=8 Hz)

(5) 8-[2,6-Dichloro-3-[N-methyl-N-[4-[N-(3-pyridylmethyl)acetamido]cinnamoylglycyl]amino]benzloxy]-2-methylquinoline NMR (CDCl₃, δ): 1.91 (3H, s), 2.73 (3H, s), 3.28 (3H, s), 3.68 (1H, dd, J=18, 4 Hz), 3.98 (1H, dd, J=18, 5 Hz), 4.89 (2H, s), 5.65 (2H, s), 6.48 (1H, d, J=16 Hz), 6.70 (1H, br t, J=4 Hz), 6.99 (2H, d, J=8 Hz), 7.19–7.69 (11H), 8.03 (1H, d, J=8 Hz), 8.38 (1H, d, J=2 Hz), 8.51 (1H, dd, J=5, 2 Hz) its dihydrochloride NMR (CDCl₃-CD₃OD, δ): 1.99 (3H, s), 3.09 (3H, s), 3.31 (3H, s), 3.93 (2H, br s), 5.10 (2H, s), 5.62 (1H, d, J=10 Hz), 5.81 (1H, d, J=10 Hz), 6.68 (1H, d, J=16 Hz), 7.21 (1H, d, J=9 Hz), 7.49–7.70 (5H), 7.78 (1H, br d, J=8 Hz), 7.85–8.11 (4H), 8.52 (1H, br d, J=8 Hz), 8.72–8.82 (2H), 9.00 (1H, d, J=9 Hz)

(6) 8-[2,6-Dichloro-3-[N-methyl-N-[4-[N'-(3-pyridyl)ureido]cinnamoylglycyl]amino]benzyloxy]-2-methylquinoline NMR (CDCl₃-CD₃OD, δ): 2.70 (3H, s), 3.22 (3H, s), 3.63 (1H, br d, J=18 Hz), 3.93 (1H, br d, J=18 Hz), 5.59 (2H, s), 6.40 (1H, d, J=15 Hz), 7.08 (0.7H, m), 7.20–7.58 (12H), 8.09 (1H, d, J=15 Hz), 8.13–8.32 (3H) its dihydrochloride NMR (CDCl₃-CD₃OD, δ): 3.09 (3H, s), 3.31 (3H, s), 3.96 (2H, s), 5.60 (1H, d, J=10 Hz), 5.81 (1H, d, J=10 Hz), 6.49 (1H, d, J=15 Hz), 7.36–7.68 (7H), 7.77 (1H, br d, J=8 Hz), 7.84–8.00 (4H), 8.31 (1H, br d, J=5 Hz), 8.62 (1H, br d, J=9 Hz), 8.99 (1H, d, J=9 Hz), 9.33 (1H, d, J=2 Hz)

(7) 8-[2,6-Dichloro-3-[N-methyl-N-(4-(morpholinocarbonylamino)cinnamoylglycyl]amino]benzyloxy]-2-methylquinoline NMR (CDCl₃, δ): 2.71 (3H, s), 3.23 (3H, s), 3.41–3.60 (5H), 3.64–3.77 (4H), 3.92 (1H, dd, J=17, 5 Hz), 5.62 (2H s), 6.39 (1H, d, J=15 Hz), 6.59 (1H, br t, J=4 Hz), 6.73 (1H, br s), 7.22–7.58 (11H), 8.03 (1H, d, J=9 Hz) its hydrochloride NMR (CDCl₃-CD₃OD, δ): 3.09 (3H, s), 3.30 (3H, s), 3.50–3.60 (4H), 3.70–3.80 (4H), 3.95 (2H, s), 5.61 (1H, d, J=10 Hz), 5.81 (1H, d, J=10 Hz), 6.48 (1H, d, J=15 Hz), 7.37–7.53 (5H), 7.59 (1H, d, J=9 Hz), 7.67 (1H, d, J=9 Hz), 7.79 (1H, d, J=7 Hz), 7.85–8.00 (3H), 8.99 (1H, d, J=9 Hz)

(8) 8-[2,6-Dichloro-3-[N-methyl-N-[4-[(2-pyridyl)acetamido]cinnamoylglycyl]amino]benzyloxy]-2-methylquinoline NMR (CDCl$_3$, δ): 2.71 (3H, s), 3.26 (3H, s), 3.64 (1H, dd, J=4, 18 Hz), 3.81–4.02 (3H, m), 5.60 (2H, s), 6.39 (1H, d, J=16 Hz), 6.63 (1H, t-like), 7.16–7.34 (5H, m), 7.34–7.63 (8H, m), 7.70 (1H, td, J=8 Hz, 1 Hz), 8.03 (1H, d, J=8 Hz), 8.63 (1H, dd, J=5 Hz, 1 Hz), 10.13 (1H, s) its dihydrochloride NMR (CDCl$_3$-CD$_3$OD): 3.09 (3H, s), 3.29 (3H, s), 3.92 (2H, s), 4.36–4.47 (2H, m), 5.60 (1H, d, J=10 Hz), 5.76 (1H, d, J=10 Hz), 6.48 (1H, d, J=16 Hz), 7.26–7.48 (3H, m), 7.48–7.74 (5H, m), 7.80–7.99 (4H, m), 8.18 (1H, d, J=8 Hz), 8.50 (1H, td, J=8, 1 Hz), 8.75 (1H, d, J=6 Hz), 8.97 (1H, d, J=8 Hz)

(9) 8-[2,6-Dichloro-3-[N-methyl-N-[4-[(4-pyridyl)acetamido]cinnamoylglycyl]amino]benzyloxy]-2-methylquinoline NMR (CDCl$_3$, δ): 2.60 (3H, s), 3.22 (3H, s), 3.53–3.70 (3H, m), 3.88 (1H, dd, J=18, 4 Hz), 5.61 (2H, s), 6.38 (1H, d, J=16 Hz), 6.63 (1H, t-like), 7.10–7.62 (13H, m), 8.06 (1H, d, J=8 Hz), 8.45 (1H, s), 8.53 (2H, d, J=6 Hz) its dihydrochloride NMR (CDCl$_3$-CD$_3$OD, δ): 3.09 (3H, s), 3.30 (3H, s), 3.90 (1H, d, J=16 Hz), 4.01 (1H, d, J=16 Hz), 5.56 (1H, d, J=10 Hz), 5.75 (1H, d, J=10 Hz), 6.43 (1H, d, J=16 Hz), 7.23–7.41 (3H, m), 7.49–7.61 (2H, m), 7.61–7.75 (3H, m), 7.75–7.97 (3H, m), 8.20 (2H, d, J=6 Hz), 8.70 (2H, d, J=6 Hz), 8.94 (1H, d, J=8 Hz)

(10) 8-[2,6-Dichloro-3-[N-methyl-N-[4-[N-(2-pyridylmethyl)acetamido]cinnamoylglycyl]amino]benzyloxy]-2-methylquinoline NMR (CDCl$_3$, δ): 1.96 (3H, s), 2.73 (3H, s), 3.26 (3H, s), 3.64 (1H, dd, J=4, 16 Hz), 3.94 (1H, dd, J=4, 16 Hz), 5.02 (2H, s), 5.64 (2H, s-like), 6.43 (1H, d, J=16 Hz), 6.64 (1H, t-like), 7.10–7.20 (3H, m), 7.20–7.59 (10H, m), 7.65 (1H, t, J=7.5 Hz), 8.03 (1H, d, J=8 Hz), 8.50 (1H, d, J=5 Hz) its dihydrochloride NMR (CDCl$_3$-CD$_3$OD, δ): 2.03 (3H, s), 3.14 (3H, s), 3.30 (3H, s), 3.88 (1H, d, J=16 Hz), 4.12 (1H, d, J=16 Hz), 5.43 (2H, s), 5.58 (1H, d, J=10 Hz), 5.71 (1H, d, J=10 Hz), 6.63 (1H, d, J=16 Hz), 7.24–7.33 (1H, m), 7.39 (1H, d, J=16 Hz), 7.50–7.59 (4H, m), 7.64 (1H, d, J=7.5 Hz), 7.75–8.01 (6H, m), 8.43 (1H, t, J=7.5 Hz), 8.73 (1H, d, J=6 Hz), 8.89 (1H, d, J=8 Hz)

(11) 8-[2,6-Dichloro-3-[N-methyl-N-[4-[N-(4-pyridylmethyl)acetamido]cinnamoylglycyl]amino]benzyloxy]-2-methylquinoline NMR (CDCl$_3$, δ): 1.95 (3H, s), 2.74 (3H, s), 3.26 (3H, s), 3.64 (1H, dd, J=4, 16 Hz), 3.94 (1H, dd, J=4, 16 Hz), 4.88 (2H, s), 5.65 (2H, s), 6.45 (1H, d, J=16 Hz), 6.65 (1H, t-like), 7.03 (2H, d, J=7.5 Hz), 7.14 (2H, d, J=5 Hz), 7.21–7.33 (3H, m), 7.33–7.59 (6H, m), 8.03 (1H, d, J=8 Hz), 8.52 (2H, d, J=5 Hz) its dihydrochloride NMR (CDCl$_3$-CD$_3$OD, δ): 2.01 (3H, s), 3.16 (3H, s), 3.29 (3H, s), 3.88 (1H, d, J=16 Hz), 4.06 (1H, d, J=16 Hz), 5.10 (2H, s), 5.60 (1H, d, J=10 Hz), 5.71 (1H, d, J=10 Hz), 6.65 (1H, d, J=16 Hz), 7.15 (2H, d, J=7.5 Hz), 7.45 (1H, d, J=16 Hz), 7.50–7.70 (5H, m), 7.79 (1H, d, J=7.5 Hz), 7.82–7.95 (4H, m), 8.79 (2H, d, J=6 Hz), 8.86 (1H, d, J=7.5 Hz)

(12) 8-[2,6-Dichloro-3-[N-[3-(methoxycarbonyl)cinnamoylglycyl]-N-methylamino]benzyloxy]-2-methylquinoline NMR (CDCl$_3$, δ): 2.72 (3H, s), 3.27 (3H, s), 3.65 (1H, dd, J=4, 16 Hz), 3.85–4.01 (4H, m), 5.65 (2H, s), 6.55 (1H, d, J=16 Hz), 6.68 (1H, t-like), 7.20–7.36 (3H, m), 7.36–7.54 (4H, m), 7.54–7.70 (2H, m), 7.95–8.06 (2H, m), 8.20 (1H, s-like)

(13) 8-[2,6-Dichloro-3-[N-methyl-N-[4-(N-methylpropionamido)cinnamoylglycyl]amino]benzyloxy]-4-methoxy-2-methylquinoline NMR (CDCl$_3$, δ): 1.08 (3H, t, J=7 Hz), 2.02–2.21 (2H), 2.70 (3H, s), 3.28 (6H, s), 3.67 (1H, dd, J=17, 4 Hz), 3.89–4.06 (4H), 5.62 (2H, s), 6.49 (1H, d, J=15 Hz), 6.64 (1H, s), 6.71 (1H, br s), 7.11–7.63 (9H), 7.82 (1H, d, J=9 Hz) its hydrochloride NMR (CDCl$_3$-CD$_3$OD, δ): 1.08 (3H, t, J=7 Hz), 2.03–2.26 (2H), 2.99 (3H, s), 3.28 (3H, s), 3.31 (3H, s), 3.82–4.06 (2H, overlapped with H$_2$O), 4.37 (3H, s), 5.55 (1H, d, J=10 Hz), 5.72 (1H, d, J=10 Hz), 6.60 (1H, d, J=15 Hz), 7.21 (1H, d, J=9 Hz), 7.30–7.70 (7H), 7.80 (1H, t, J=9 Hz), 8.00 (1H, d, J=9 Hz)

(14) 8-[2,6-Dichloro-3-[N-[4-(mesylamino)cinnamoylglycyl]-N-methylamino]benzyloxy]-4-methoxy-2-methylquinoline NMR (CDCl$_3$, δ): 2.69 (3H, s), 3.03 (3H, s), 3.28 (3H, s), 3.63 (1H, dd, J=17, 4 Hz), 3.88–4.09 (4H), 5.62 (2H, s), 6.40 (1H, d, J=15 Hz), 6.62–6.77 (2H), 7.14–7.60 (10H), 7.82 (1H, d, J=9 Hz) its hydrochloride NMR (CDCl$_3$-CD$_3$OD, δ): 2.95 (3H, s), 3.02 (3H, s), 3.30 (3H, s), 3.89 (1H, d, J=16 Hz), 4.00 (1H, d, J=16 Hz), 4.35 (3H, s), 5.59 (1H, d, J=10 Hz), 5.79 (1H, d, J=10 Hz), 6.54 (1H, d, J=15 Hz), 7.21–7.34 (3H), 7.39–7.74 (6H), 7.81 (1H, t, J=9 Hz), 8.01 (1H, d, J=9 Hz)

(15) 8-[2,6-Dichloro-3-[N-methyl-N-[4-(3-methylureido)cinnamoylglycyl]amino]benzyloxy]-4-methoxy-2-methylquinoline NMR (CDCl$_3$-CD$_3$OD, δ): 2.63 (3H, s), 2.79 (3H, s), 3.22 (3H, s), 3.62 (1H, d, J=17 Hz), 3.83–4.10 (4H), 5.53 (2H, s), 6.41 (1H, d, J=16 Hz), 6.71 (1H, s), 7.18–7.60 (9H), 7.81 (1H, d, J=8 Hz) its hydrochloride NMR (CDCl$_3$-CD$_3$OD, δ): 2.81 (3H, s), 2.93 (3H, s), 3.31 (3H, s), 3.94 (2H, s), 4.34 (3H, s), 5.56 (1H, d, J=10 Hz), 5.78 (1H, d, J=10 Hz), 6.41 (1H, d, J=15 Hz), 7.25–7.72 (9H), 7.81 (1H, t, J=9 Hz), 8.01 (1H, d, J=9 Hz)

(16) 8-[3-[N-(4-Cyanocinnamoylglycyl)-N-methylamino]-2,6-dichlorobenzyloxy]-2-methylquinoline NMR (CDCl$_3$, δ) 2.72 (3H, s), 3.27 (3H, s), 3.68 (1H, dd, J=18, 4 Hz), 3.95 (1H, dd, J=18, 5 Hz), 5.65 (2H, s), 6.57 (1H, d, J=15 Hz), 6.79 (1H, br t, J=5 Hz), 7.21–7.69 (11H, m), 8.03 (1H, d, J=9 Hz)

(17) 8-[2,6-Dichloro-3-[N-[4-[N-(2-methoxyethyl)acetamido]cinnamoylglycyl]-N-methylamino]benzyloxy]-2-methylquinoline NMR (CDCl$_3$, δ): 1.85 (3H, s), 2.73 (3H, s), 3.26 (3H, s), 3.30 (3H, s), 3.51 (2H, t, J=6 Hz), 3.65 (1H, dd, J=4, 16 Hz), 3.86 (2H, t, J=6 Hz), 3.95 (1H, dd, J=4, 16 Hz), 5.65 (2H, s-like), 6.48 (1H, d, J=16 Hz), 6.66 (1H, t-like), 7.17–7.35 (5H, m), 7.35–7.62 (6H, m), 8.03 (1H, d, J=8 Hz) its hydrochloride NMR (CDCl$_3$-CD$_3$OD, δ): 1.85 (3H, s), 3.20–3.33 (9H, m), 3.47 (2H, t, J=6 Hz), 3.84 (2H, t, J=6 Hz), 3.92 (1H, d, J=16 Hz), 4.03 (1H, d, J=16 Hz), 5.64 (2H, s), 6.61 (1H, d, J=16 Hz), 7.16 (2H, d, J=8 Hz), 7.43–7.92 (9H, m), 8.75 (1H, d, J=8 Hz)

(18) 8-[2,6-Dichloro-3-[N-[4-[N-(2-methoxyethyl)-N-(isonicotinoyl)amino]cinnamoylglycyl]-N-methylamino]benzyloxy]-2-methylquinoline NMR (CDCl$_3$, δ): 2.73 (3H, s), 3.25 (3H, s), 3.35 (3H, s), 3.58–3.70 (3H, m), 3.93 (1H, dd, J=4, 16 Hz), 4.07 (2H, t, J=6 Hz), 5.64 (2H, s-like), 6.40 (1H, d, J=16 Hz), 6.64 (1H, br), 7.10 (2H, d, J=8 Hz), 7.15 (2H, d, J=6 Hz), 7.22–7.53 (9H, m), 8.03 (1H, d, J=8 Hz), 8.47 (2H, d, J=6 Hz) its dihydrochloride NMR (CDCl$_3$-CD$_3$OD, δ): 3.14 (3H, s), 3.26 (3H, s), 3.36 (3H, s), 3.62 (2H, t-like), 3.86 (1H, d, J=16 Hz), 4.03–4.17 (3H, m), 5.56 (1H, d, J=10 Hz), 5.70 (1H, d, J=10 Hz), 6.61 (1H, d, J=16 Hz), 7.13 (2H, d, J=8 Hz), 7.33 (1H, d, J=16

Hz), 7.45 (2H, d, J=8 Hz), 7.50–7.59 (2H, m), 7.63 (1H, d, J=8 Hz), 7.71–7.93 (5H, m), 8.69 (2H, d, J=6 Hz), 8.83 (1H, d, J=8 Hz)

(19) 8-[2,6-Dichloro-3-[N-[(E)-3-(6-ethoxycarbonylpyridin-3-yl)acryloylglycyl]-N-methylamino]benzyloxy]-2-methylquinoline NMR (CDCl$_3$, δ): 1.45 (3H, t, J=7.5 Hz), 2.72 (3H, s), 3.27 (3H, s), 3.70 (1H, dd, J=18, 4 Hz), 3.94 (1H, dd, J=18, 4 Hz), 4.49 (2H, q, J=7.5 Hz), 5.59–5.70 (2H, m), 6.66 (1H, d, J=16 Hz), 6.80 (1H, t-like), 7.22–7.35 (3H, m), 7.37–7.53 (3H, m), 7.60 (1H, d, J=16 Hz), 7.88–7.94 (1H, m), 8.02 (1H, d, J=8 Hz), 8.12 (1H, d, J=8 Hz), 8.81–8.86 (1H, m)

(20) 8-[3-[N-[(E)-3-(6-Aminopyridin-3-yl)acryloylglycyl]-N-methylamino]-2,6-dichlorobenzyloxy]-2-methylquinoline NMR (CDCl$_3$, δ): 2.73 (3H, s), 3.27 (3H, s), 3.65 (1H, dd, J=17, 4 Hz), 3.94 (1H, dd, J=17, 5 Hz), 4.75 (2H, s), 5.64 (2H, s), 5.84 (1H, d, J=10 Hz), 6.30 (1H, d, J=15 Hz), 6.48 (1H, d, J=8.5 Hz), 6.62 (1H, br t, J=4 Hz), 7.23–7.35 (3H), 7.39–7.52 (4H), 7.60 (1H, dd, J=8.5, 1.5 Hz), 8.02 (1H, d, J=8.5 Hz), 8.16 (1H, d, J=1.5 Hz)

(21) 8-[2,6-Dichloro-3-[N-methyl-N-[4-(methylcarbamoyl)cinnamoylglycyl]amino]benzyloxy]-3-methylquinoxaline NMR (CDCl$_3$, δ): 2.78 (3H, s), 3.02 (3H, d, J=5 Hz), 3.28 (3H, s), 3.69 (1H, dd, J=17, 4 Hz), 3.93 (1H, dd, J=17, 5 Hz), 5.57 (2H, s), 6.18 (1H, br d, J=5 Hz), 6.52 (1H, d, J=15 Hz), 6.68 (1H, br t, J=4 Hz), 7.27 (1H, overlapped with CDCl$_3$), 7.35 (1H, d, J=9 Hz), 7.49–7.79 (8H), 8.73 (1H, s)

(22) 8-[2,6-Dichloro-3-[N-methyl-N-[4-(methylcarbamoyl)cinnamoylglycyl]amino]benzyloxy]-2-methylquinoxaline NMR (CDCl$_3$, δ): 2.77 (3H, s), 3.02 (3H, d, J=5 Hz), 3.28 (3H, s), 3.67 (1H, dd, J=17, 4 Hz), 3.94 (1H, dd, J=17, 4 Hz), 5.62 (2H, s), 6.20 (1H, br d, J=5 Hz), 6.53 (1H, d, J=16 Hz), 6.69 (1H, br t, J=4 Hz), 7.29–7.38 (2H), 7.49–7.80 (8H), 8.74 (1H, s) its hydrochloride NMR (CDCl$_3$-CD$_3$OD, δ): 2.89 (3H, s), 2.98 (3H, s), 3.29 (3H, s), 3.19 (1H, d, J=17 Hz), 4.00 (1H, d, J=17 Hz), 5.65 (2H, s), 6.62 (1H, d, J=15 Hz), 7.44–7.63 (6H), 7.75–7.91 (4H), 8.92 (1H, s)

(23) 8-[2,6-Dichloro-3-[N-[4-(dimethylcarbamoyl)cinnamoylglycyl]-N-methylamino]benzyloxy]-2-methylquinoxaline mp: 109–116° C.

NMR (CDCl$_3$, δ): 2.77 (3H, s), 2.98 (3H, s), 3.11 (3H, s), 3.27 (3H, s), 3.67 (1H, dd, J=16.5, 3.0 Hz), 3.95 (1H, dd, J=16.5, 3.0 Hz), 5.62 (2H, s), 6.51 (1H, d, J=15.0 Hz), 6.68 (1H, br t, J=3.0 Hz), 7.28–7.36 (2H, m), 7.42 (2H, d, J=8.5 Hz), 7.48–7.70 (5H, m), 7.76 (1H, d, J=8.5 Hz), 8.74 (1H, s)

(24) 8-[2,6-Dichloro-3-[N-[4-(ethylcarbamoyl)cinnamoylglycyl]-N-methylamino]benzyloxy]-2-methylquinoxaline mp: 199–202° C.

NMR (CDCl$_3$, δ): 1.26 (3H, t, J=7.5 Hz), 2.77 (3H, s), 3.27 (3H, s), 3.51 (2H, m), 3.66 (1H, dd, J=16.5, 3.0 Hz), 3.95 (1H, dd, J=16.5, 3.0 Hz), 5.63 (2H, s), 6.15 (1H, br t, J=7.5 Hz), 6.53 (1H, d, J=16.0 Hz), 6.68 (1H, br t, J=3.0 Hz), 7.28–7.36 (2H, m), 7.48–7.79 (8H, m), 8.73 (1H, s)

(25) 8-[2,6-Dichloro-3-[N-[4-(methoxycarbonyl)cinnamoylglycyl]-N-methylamino]benzyloxy]-2-methylquinoxaline NMR (CDCl$_3$, δ): 2.77 (3H, s), 3.27 (3H, s), 3.65 (1H, dd, J=16.5, 2.5 Hz), 3.90 (3H, s), 3.94 (1H, dd, J=16.5, 2.5 Hz), 5.62 (2H, s), 6.56 (1H, d, J=15.0 Hz), 6.69 (1H, br t, J=2.5 Hz), 7.28–7.38 (2H, m), 7.47–7.79 (6H, m), 7.98–8.06 (2H, m), 8.73 (1H, s)

(26) 8-[3-[N-[4-(Acetamido)cinnamoylglycyl]-N-methylamino]-2,6-dichlorobenzyloxy]-2-methylquinoxaline NMR (CDCl$_3$, δ): 2.15 (3H, s), 2.76 (3H, s), 3.26 (3H, s), 3.64 (1H, dd, J=17, 4 Hz), 3.92 (1H, dd, J=17, 5 Hz), 5.61 (2H, s), 6.39 (1H, d, J=15 Hz), 6.61 (1H, br t, J=4 Hz), 7.28–7.35 (2H), 7.40–7.58 (6H), 7.62–7.71 (2H), 7.78 (1H, d, J=8 Hz), 8.74 (1H, s)

(27) 8-[2,6-Dichloro-3-[N-[4-(methoxyacetamido)cinnamoylglycyl]-N-methylamino]benzyloxy]-2-methylquinoxaline NMR (CDCl$_3$, δ): 2.78 (3H, s), 3.28 (3H, s), 3.51 (3H, s), 3.65 (1H, dd, J=17, 4 Hz), 3.94 (1H, dd, J=17, 5 Hz), 4.02 (2H, s), 5.62 (2H, s), 6.41 (1H, d, J=15 Hz), 6.59 (1H, br t, J=4 Hz), 7.29–7.37 (2H), 7.44–7.70 (7H), 7.78 (1H, d, J=8 Hz), 8.32 (1H, br s), 8.72 (1H, s)

(28) 8-[2,6-Dichloro-3-[N-methyl-N-[4-(2-oxopyrrolidin-1-yl)cinnamoylglycyl]amino]benzyloxy]-2-methylquinoxaline NMR (CDCl$_3$, δ): 2.12–2.25 (2H), 2.63 (2H, t, J=7.5 Hz), 2.78 (3H, s), 3.28 (3H, s), 3.65 (1H, dd, J=17, 4 Hz), 3.85–4.00 (3H), 5.62 (2H, s), 6.43 (1H, d, J=15 Hz), 6.59 (1H, br t, J=4 Hz), 7.29–7.38 (2H), 7.48–7.70 (7H), 7.78 (1H, d, J=8 Hz), 8.73 (1H, s)

(29) 8-[2,6-Dichloro-3-[N-methyl-N-[4-(methylcarbamoyl)cinnamoylglycyl]amino]benzyloxy]cinnoline NMR (CDCl$_3$, δ) 3.02 (3H, d, J=5 Hz), 3.29 (3H, s), 3.70 (1H, dd, J=17, 4 Hz), 3.93 (1H, dd, J=17, 5 Hz), 5.64 (1H, d, J=10 Hz), 5.70 (1H, d, J=10 Hz), 6.20 (1H, br d, J=5 Hz), 6.53 (1H, d, J=15 Hz), 6.71 (1H, br t, J=4 Hz), 7.31–7.39 (2H), 7.45–7.62 (5H), 7.70–7.78 (3H), 7.82 (1H, d, J=7.5 Hz), 9.34 (1H, d, J=6 Hz)

(30) 8-[2,6-Dichloro-3-[N-methyl-N-[4-(methylcarbamoyl)cinnamoylglycyl]amino]benzyloxy]-2-methylquinazoline NMR (CDCl$_3$, δ): 2.90 (3H, s), 3.02 (3H, d, J=5 Hz), 3.28 (3H, s), 3.67 (1H, dd, J=18, 4 Hz), 3.93 (1H, dd, J=18, 4 Hz), 5.63 (2H, s), 6.20 (1H, br d, J=5 Hz), 6.52 (1H, d, J=16 Hz), 6.68 (1H, br t, J=4 Hz), 7.33 (1H, d, J=7.5 Hz), 7.41–7.62 (7H), 7.77 (2H, d, J=8 Hz), 9.31 (1H, s)

(31) 8-[3-[N-Benzyl-N-[4-(methylcarbamoyl)cinnamoylglycyl]amino]-2,6-dichlorobenzyloxy]-2-methylquinoline NMR (CDCl$_3$, δ): 2.74 (3H, s), 3.02 (3H, d, J=5 Hz), 3.67 (1H, dd, J=17, 5 Hz), 3.92 (1H, dd, J=17, 5 Hz), 4.00 (1H, d, J=14 Hz), 5.60–5.71 (3H), 6.19 (1H, m), 6.53 (1H, d, J=16 Hz), 6.69–6.79 (2H), 6.69–6.79 (2H), 7.18–7.62 (13H), 7.75 (2H, d, J=7.5 Hz), 8.03 (1H, d, J=7.5 Hz) its hydrochloride NMR (CDCl$_3$-CD$_3$OD, δ): 2.98 (3H, s), 3.10 (3H, s), 3.98 (2H, br s), 4.30 (1H, d, J=14 Hz), 5.51 (1H, d, J=14 Hz), 5.59 (1H, d, J=10 Hz), 5.75 (1H, d, J=10 Hz), 6.68 (1H, d, J=15 Hz), 7.04 (1H, d, J=7.5 Hz), 7.21–7.33 (5H), 7.41 (1H, d, J=7.5 Hz), 7.48 (1H, d, J=15 Hz), 7.57 (2H, d, J=7.5 Hz), 7.69 (1H, d, J=7.5 Hz), 7.79–7.99 (5H), 8.95 (1H, d, J=7.5 Hz)

(32) 5,7-Dibromo-8-[2,6-dichloro-3-[N-methyl-N-[4-(methylcabamoyl)cinnamoylglycyl]amino]benzyloxy]-2-methylquinoline mp: 134–139° C.

NMR (CDCl$_3$, δ): 2.81 (3H, s), 3.03 (3H, d, J=5.5 Hz), 3.23 (3H, s), 3.56 (1H, dd, J=16.5, 5.5 Hz), 3.92 (1H, dd, J=16.5, 5.5 Hz), 5.88 (1H, d, J=11.5 Hz), 5.95 (1H, d, J=11.5 Hz), 6.17 (1H, br q, J=5.5 Hz), 6.52 (1H, d, J=16.0 Hz), 6.64 (1H, br t, J=5.5 Hz), 7.30 (1H, d, J=8.5 Hz), 7.40 (1H, d, J=8.5 Hz), 7.47 (1H, d, J=8.5 Hz), 7.54 (2H, d, J=8.5 Hz), 7.60 (1H, d, J=16.0 Hz), 7.76 (2H, d, J=8.5 Hz), 7.87 (1H, s), 8.33 (1H, d, J=8.5 Hz) its hydrochloride mp: 121–126° C.

NMR (CDCl$_3$-CD$_3$OD): 2.93–3.07 (6H, m), 3.21 (3H, s), 3.59 (1H, d, J=16.5 Hz), 3.96 (1H, d, J=16.5 Hz), 5.88 (2H, s), 6.60 (1H, d, J=16.0 Hz), 7.37 (1H, d, J=8.5 Hz), 7.44–7.64 (6H, m), 7.70–7.80 (3H, m), 8.01 (1H, s), 8.61 (1H, d, J=8.5 Hz)

(33) 8-[2,6-Dichloro-3-[N-[4-[N-methoxyacetyl-N-(3-pyridylmethyl)amino]cinnamoylglycyl]-N-methylamino]benzyloxy]-2-methylquinoline NMR (CDCl$_3$, δ): 2.75 (3H, s), 3.27 (3H, s), 3.35 (3H, s), 3.66 (1H, dd, J=4, 16 Hz), 3.79 (2H, s), 3.95 (1H, dd, J=4, 16 Hz), 4.49 (2H, s), 5.65 (2H, s-like), 6.46 (1H, d, J=16 Hz), 6.66 (1H, t-like), 6.8 (2H, d, J=8 Hz), 7.20–7.35 (4H, m), 7.37–7.58 (6H, m), 7.66 (1H, dd-like, J=8 Hz), 8.03 (1H, d, J=8 Hz), 8.35 (1H, d, J=2 Hz), 8.51 (1H, dd, J=6, 2 Hz) its dihydrochloride NMR (CDCl$_3$-CD$_3$OD, δ): 3.15 (3H, s), 3.28 (3H, s), 3.33 (3H, s), 3.85 (2H, s), 3.89 (1H, d, J=16 Hz), 4.10 (1H, d, J=16 Hz), 5.06 (2H, s), 5.59 (1H, d, J=10 Hz), 5.71 (1H, d, J=10 Hz), 6.67 (1H, d, J=16 Hz), 7.10 (2H, d, J=8 Hz), 7.43 (1H, d, J=16 Hz), 7.51–7.67 (5H, m), 7.79 (1H, d, J=8 Hz), 7.83–8.00 (3H, m), 8.53 (1H, d, J=8 Hz), 8.70 (1H, s-like), 8.78 (1H, d, J=6 Hz), 8.85 (1H, d, J=8 Hz)

(34) 8-[3-[N-[(E)-3-(6-Acetamidopyridin-3-yl)acryloylglycyl]-N-methylamino]-2,6-dichlorobenzyloxy]-2-methylquinoline mp: 133–139° C.

NMR (CDCl$_3$, δ): 2.22 (3H, s), 2.74 (3H, s), 3.27 (3H, s), 3.67 (1H, dd, J=16.5, 5.5 Hz), 3.96 (1H, dd, J=16.5, 5.5 Hz), 5.62 (1H, d, J=11.0 Hz), 5.67 (1H, d, J=11.0 Hz), 6.46 (1H, d, J=16.0 Hz), 6.73 (1H, br t, J=5.5 Hz), 7.21–7.33 (3H, m), 7.38–7.51 (3H, m), 7.52 (1H, d, J=16.0 Hz), 7.82 (1H, dd, J=8.5, 1.5 Hz), 8.03 (1H, d, J=8.5 Hz), 8.13–8.25 (2H, m), 8.33 (1H, d, J=1.5 Hz) its dihydrochloride mp: 153.5–158° C.

NMR (DMSO-d$_6$, δ): 2.12 (3H, s), 2.94 (3H, s), 3.16 (3H, s), 3.59 (1H, dd, J=16.5, 5.5 Hz), 3.90 (1H, dd, J=16.5, 5.5 Hz), 5.63 (1H, d, J=10.5 Hz), 5.67 (1H, d, J=10.5 Hz), 6.81 (1H, d, J=16.0 Hz), 7.37 (1H, d, J=16.0 Hz), 7.79–8.06 (6H, m), 8.10 (1H, d, J=8.5 Hz), 8.30–8.40 (1H, m), 8.49 (1H, d, J=1.0 Hz), 9.03 (1H, d, J=8.5 Hz)

EXAMPLE 53

The following compounds were obtained according to a similar manner to that of Example 20.

(1) 8-[3-[N-(4-Carboxycinnamoylglycyl)-N-methylamino]-2,6-dichlorobenzyloxy]2-methylquinoline mp: 237.8–240.9° C.

NMR (DMSO-d$_6$, δ): 2.61 (3H, s), 3.15 (3H, s), 3.51 (1H, dd, J=4, 18 Hz), 3.81 (1H, dd, J=4, 18 Hz), 5.48 (1H, d, J=10 Hz), 5.54 (1H, d, J=10 Hz), 6.90 (1H, d, J=16 Hz), 7.32–7.60 (5H, m), 7.64–7.75 (2H, m), 7.75–7.85 (2H, m), 7.96 (2H, d, J=8 Hz), 8.21 (1H, d, J=8 Hz), 8.35–8.44 (1H, m)

(2) 8-[3-[N-(3-Carboxycinnamoylglycyl)-N-methylamino]-2,6-dichlorobenzyloxy]-2-methylquinoline mp: 161° C.

NMR (CDCl$_3$-CD$_3$OD, δ): 2.70 (3H, s), 3.26 (3H, s), 3.65 (1H, d, J=16 Hz), 4.00 (1H, d, J=16 Hz), 5.58 (2H, s), 6.60 (1H, d, J=16 Hz), 7.20–7.68 (9H, m), 8.00 (1H, d, J=7.5 Hz), 8.06 (1H, d, J=8 Hz), 8.20 (1H, s-like)

(3) 8-[3-[N-[N'-(4-Carboxyphenyl)ureidoacetyl]-N-methylamino]-2,6-dichlorobenzyloxy]-2-methylquinoline mp: 186–235° C.

NMR (CDCl$_3$-CD$_3$OD, δ): 2.70 (3H, s), 3.25 (3H, s), 3.85 (1H, d, J=16 Hz), 3.93 (1H, d, J=16 Hz), 5.52 (1H, d, J=10 Hz), 5.60 (1H, d, J=10 Hz), 7.25–7.60 (8H, m), 7.86 (2H, d, J=7.5 Hz), 8.13–8.23 (1H, m)

(4) 8-[3-[N-[(E)-3-(6-Carboxypyridin-3-yl)acryloylglycyl]-N-methylamino]-2,6-dichlorobenzyloxy]-2-methylquinoline NMR (DMSO-d$_6$, δ): 2.58 (3H, s), 3.13 (3H, s), 3.50 (1H, dd, J=4, 16 Hz), 3.80 (1H, dd, J=4, 16 Hz), 5.46 (1H, d, J=10 Hz), 5.53 (1H, d, J=10 Hz), 6.95 (1H, d, J=16 Hz), 7.30–7.57 (5H, m), 7.78 (2H, s-like), 8.02 (1H, d, J=8 Hz), 8.10 (1H, d, J=7.5 Hz), 8.20 (1H, d, J=8 Hz), 8.45 (1H, t-like), 8.85 (1H, s-like)

(5) 8-[3-[N-(4-Carboxycinnamoylglycyl)-N-methylamino]-2,6-dichlorobenzyloxy]-2-methylquinoxaline NMR (CDCl$_3$, δ): 2.77 (3H, s), 3.26 (3H, s), 3.62 (1H, dd, J=16.5, 2.5 Hz), 3.99 (1H, dd, J=16.5, 2.5 Hz), 5.60 (2H, s), 6.51 (1H, d, J=15.0 Hz), 6.97 (1H, br s), 7.24–7.80 (8H, m), 7.93–8.07 (2H, m), 8.76 (1H, s)

EXAMPLE 54

To a mixture of 8-[3-[N-(4-carboxycinnamoylglycyl)-N-methylamino]-2,6-dichlorobenzyloxy]-2-methylquinoline (100 mg), ethylamine hydrochloride (16.9 mg) and N,N-dimethylformamide (2 ml) were added 1-ethyl-3-(3-dimethylaminopropyl)carbodiimide (32.2 mg) and 1-hydroxybenzotriazole (30.4 mg), and the mixture was stirred for 6 hours at ambient temperature. The mixture was poured into water and extracted with ethyl acetate. The organic layer was washed with water, saturated sodium bicarbonate solution and brine, dried over magnesium sulfate, and concentrated in vacuo. The residue was purified by preparative thin-layer chromatography (methylene chloride—methanol) to give 8-[2,6-dichloro-3-[N-[4-(ethylcarbamoyl)cinnamoylglycyl]-N-methylamino]benzyloxy]-2-methylquinoline (91 mg).

NMR (CDCl$_3$, δ): 1.26 (3H, t, J=7.5 Hz), 2.72 (3H, s), 3.29 (3H, s), 3.50 (2H, quint, J=7.5 Hz), 3.68 (1H, dd, J=4, 18 Hz), 3.96 (1H, dd, J=4, 18 Hz), 5.58–5.70 (2H, m), 6.15 (1H, t-like), 6.54 (1H, d, J=16 Hz), 6.73 (1H, t-like), 7.21–7.35 (2H, m), 7.35–7.62 (7H, m), 7.75 (2H, d, J=8 Hz), 8.04 (1H, d, J=8 Hz) its hydrochloride NMR (CDCl$_3$-CD$_3$OD, δ): 1.23 (3H, t, J=7.5 Hz), 3.13 (3H, s), 3.30 (3H, s), 3.47 (2H, q, J=7.5 Hz), 3.90 (1H, d, J=16 Hz), 4.10 (1H, d, J=16 Hz), 5.60 (1H, d, J=10 Hz), 5.70 (1H, d, J=10 Hz), 6.65 (1H, d, J=16 Hz), 7.42 (1H, d, J=16 Hz), 7.48–7.58 (4H, m), 7.63 (1H, d, J=7.5 Hz), 7.70–7.84 (3H, m), 7.84–7.93 (2H, m), 8.87 (1H, d, J=8 Hz)

EXAMPLE 55

The following compounds were obtained according to similar manners to those of Examples 21 or 54.

(1) 8-[2,6-Dichloro-3-[N-methyl-N-[4-(methylcarbamoyl)cinnamoylglycyl]amino]benzyloxy]-2-methylquinoline NMR (CDCl$_3$, δ): 2.73 (3H, s), 3.00 (3H, d, J=5 Hz), 3.26 (3H, s), 3.64 (1H, dd, J=4, 17 Hz), 3.93 (1H, dd, J=4, 17 Hz), 5.66 (2H, s), 6.28 (1H, q-like), 6.53 (1H, d, J=16 Hz), 6.69 (1H, t-like), 7.18–7.64 (9H, m), 7.75 (2H, d, J=8 Hz), 8.03 (1H, d, J=8 Hz) its methanesulfonic acid salt mp: 174.1–182.3° C.

NMR (DMSO-d$_6$, δ): 2.29 (3H, s), 2.78 (3H, d, J=5 Hz), 2.85 (3H, br s), 3.15 (3H, s), 3.58 (1H, dd, J=17, 4 Hz), 3.88 (1H, dd, J=17, 5 Hz), 5.58 (1H, d, J=10 Hz), 5.64 (1H, d, J=10 Hz), 6.88 (1H, d, J=15 Hz), 7.41 (1H, d, J=15 Hz), 7.63 (2H, d, J=8 Hz), 7.73–7.90 (7H), 8.34 (1H, br t, J=5 Hz), 8.49 (1H, br d, J=5 Hz), 8.83 (1H, br s) its maleic acid salt NNR (DMSO-d$_6$, δ): 2.64 (3H, s), 2.77 (3H, d, J=6 Hz), 3.14 (3H, s), 3.51 (1H, d, J=17 and 6 Hz), 3.81 (1H, dd, J=17, 5 Hz), 5.49 (1H, d, J=9 Hz), 5.54 (1H, d, J=9 Hz), 6.22 (2H, s), 6.86 (1H, d, J=15 Hz), 7.35–7.70 (7H, m), 7.72–7.90 (4H, m), 8.23–8.40 (2H, m), 8.42–8.54 (1H, m)

(2) 8-[3-[N-(4-Carbamoylcinnamoylglycyl)-N-methylamino]-2,6-dichlorobenzyloxy]-2-methylquinoline NMR (CDCl$_3$, δ): 2.72 (3H, s), 3.27 (3H, s), 3.68 (1H, dd, J=4, 18 Hz), 3.95 (1H, dd, J=4, 18 Hz), 5.57–5.69 (2H, m), 6.54 (1H, d, J=16 Hz), 6.77 (1H, t-like), 7.22–7.35 (2H, m), 7.38–7.63 (7H, nm), 7.80 (2H, d, J=8 Hz), 8.03 (1H, d, J=8 Hz) its hydrochloride NMR (CDCl$_3$-CD$_3$OD, δ): 3.13 (3H, s), 3.30 (3H, s), 3.90 (1H, d, J=16 Hz), 4.07 (1H, d, J=16 Hz), 5.59 (1H, d, J=10

Hz), 5.71 (1H, d, J=10 Hz), 6.67 (1H, d, J=16 Hz), 7.44 (1H, d, J=16 Hz), 7.49–7.69 (5H, rm), 7.77–7.95 (5H, m), 8.89 (1H, d, J=8 Hz)

(3) 8-[2,6-Dichloro-3-[N-[4-(N-ethyl-N-methylcarbamoyl)cinnamoylglycyl]-N-methylamino]benzyloxy]-2-methylquinoline NMR (CDCl$_3$, δ): 1.06–1.29 (3H, m), 2.73 (3H, s), 2.94 (3/2H, br s), 3.06 (3/2H, br s), 3.26 (3H, s), 3.45–3.73 (3H, m), 3.95 (1H, dd, J=4, 18 Hz), 5.64 (2H, s), 6.50 (1H, d, J=16 Hz), 6.68 (1H, t-like), 7.20–7.61 (11H, m), 8.03 (1H, d, J=8 Hz) its hydrochloride NMR (CDCl$_3$-CD$_3$OD, δ): 1.10–1.33 (3H, m), 2.93–3.12 (6H, m), 3.50–3.66 (2H, m), 3.90 (1H, d, J=16 Hz), 3.99 (1H, d, J=16 Hz), 5.65 (1H, d, J=10 Hz), 5.83 (1H, d, J=10 Hz), 6.70 (1H, d, J=16 Hz), 7.35–7.73 (7H, m), 7.76–8.01 (4H, m), 9.01 (1H, d, J=8 Hz)

(4) 8-[2,6-Dichloro-3-[N-methyl-N-[4-(1-pyrrolidinylcarbonyl)cinnamoylglycyl]amino]benzyloxy]-2-methylquinoline NMR (CDCl$_3$, δ): 1.83–2.03 (4H, m), 2.74 (3H, s), 3.28 (3H, s), 3.43 (2H, t, J=7 Hz), 3.60–3.74 (3H, m), 3.95 (1H, dd, J=4, 18 Hz), 7.22–7.61 (11H, m), 8.03 (1H, d, J=8 Hz) its hydrochloride NMR (CDCl$_3$-CD$_3$OD, δ): 1.80–2.05 (4H, m), 3.15 (3H, s), 3.30 (3H, s), 3.30–3.72 (4H, m), 3.88 (1H, d, J=16 Hz), 4.03 (1H, d, J=16 Hz), 5.61 (1H, d, J=10 Hz), 5.71 (1H, d, J=10 Hz), 6.64 (1H, d, J=16 Hz), 7.40–7.70 (8H, m), 7.73–7.96 (3H, m), 8.89 (1H, d, J=8 Hz)

(5) 8-[2,6-Dichloro-3-[N-methyl-N-[4-(morpholinocarbonyl)cinnamoylglycyl]amino]benzyloxy]-2-methylquinoline NMR (CDCl$_3$, δ): 2.75 (3H, s), 3.27 (3H, s), 3.55–3.85 (9H, m), 3.94 (1H, dd, J=4, 18 Hz), 5.60–5.70 (2H, m), 6.51 (1H, d, J=16 Hz), 6.66 (1H, t-like), 7.21–7.34 (2H, m), 7.37–7.61 (9H, m), 8.03 (1H, d, J=8 Hz) its hydrochloride NMR (CDCl$_3$-CD$_3$OD, δ): 3.20 (3H, s), 3.31 (3H, s), 3.56–3.84 (8H, m), 3.90 (1H, d, J=16 Hz), 4.03 (1H, d, J=16 Hz), 5.63 (1H, d, J=10 Hz), 5.70 (1H, d, J=10 Hz), 7.33–7.63 (8H, m), 7.73–7.93 (3H, m), 8.85 (1H, d, J=8 Hz)

(6) 8-[2,6-Dichloro-3-[N-[4-(3-methoxypropylcarbamoyl)cinnamoylglycyl]-N-methylamino]benzyloxy]-2-methylquinoline NMR (CDCl$_3$, δ): 1.81–1.96 (2H, m), 2.74 (3H, s), 3.27 (3H, s), 3.40 (3H, s), 3.51–3.71 (5H, m), 3.88–4.00.(1H, m), 5.65 (2H, s), 6.53 (1H, d, J=16 Hz), 6.60–6.70 (1H, m), 6.90–7.00 (1H, m), 7.20–7.63 (9H, m), 7.74 (2H, d, J=8 Hz), 8.03 (1H, d, J=8 Hz) its hydrochloride NMR (CDCl$_3$-CD$_3$OD, δ): 1.90 (2H, quint, J=7 Hz), 3.16 (3H, s), 3.29 (3H, s), 3.55 (4H, q-like), 3.90 (1H, d, J=16 Hz), 4.08 (1H, d, J=16 Hz), 5.61 (1H, d, J=10 Hz), 5.70 (1H, d, J=10 Hz), 6.66 (1H, d, J=16 Hz), 7.41–7.93 (11H, m), 8.85 (1H, d, J=8 Hz)

(7) 8-[2,6-Dichloro-3-[N-methyl-N-[4-[(3-pyridylmethyl)carbamoyl]cinnamoylglycyl]amino]benzyloxy]-2-methylquinoline NMR (CDCl$_3$, δ): 2.69 (3H, s), 3.27 (3H, s), 3.67 (1H, dd, J=4, 18 Hz), 3.93 (1H, dd, J=4, 18 Hz), 4.64 (2H, d, J=6 Hz), 5.63 (2H, s), 6.54 (1H, d, J=16 Hz), 6.66–6.77 (1H, m), 7.19–7.33 (5H, m), 7.38–7.63 (6H, m), 7.63–7.82 (3H, m), 8.03 (1H, d, J=8.4 Hz), 8.51–8.59 (2H, m) its dihydrochloride NMR (CDCl$_3$-CD$_3$OD, δ): 3.09 (3H, s), 3.28 (3H, s), 3.90 (1H, d, J=16 Hz), 4.09 (1H, d, J=16 Hz), 4.77 (2H, s), 5.58 (1H, d, J=10 Hz), 5.72 (1H, d, J=10 Hz), 6.63 (1H, d, J=16 Hz), 7.39 (1H, d, J=16 Hz), 7.48 (2H, d, J=7.5 Hz), 7.56 (2H, s-like), 7.65 (1H, d, J=7.5 Hz), 7.77–7.97 (6H, m), 8.65 (2H, d, J=6 Hz), 8.89 (1H, d, J=8 Hz), 8.95 (1H, s)

(8) 8-[2,6-Dichloro-3-[N-[4-[N-(2-methoxyethyl)-N-methylcarbamoyl]cinnamoylglycyl]-N-methylamino]benzyloxy]-2-methylquinoline NMR (CDCl$_3$, δ): 2.74 (3H, s), 2.99–3.15 (3H, m), 3.27 (3H, s), 3.32–3.48 (2H, m), 3.59–3.75 (3H, m), 3.95 (1H, dd, J=4, 18 Hz), 5.65 (2H, s), 6.50 (1H, d, J=16 Hz), 6.66 (1H, t-like), 7.20–7.61 (11H, m), 8.03 (1H, d, J=8 Hz) its hydrochloride NMR (CDCl$_3$-CD$_3$OD, δ): 3.00–3.13 (3H, m), 3.15 (3H, s), 3.30 (3H, s), 3.36–3.50 (2H, m), 3.64–3.76 (2H, m), 3.88 (1H, d, J=16 Hz), 3.99 (1H, d, J=16 Hz), 5.61 (1H, d, J=10 Hz), 5.72 (1H, d, J=10 Hz), 6.62 (1H, d, J=16 Hz), 7.39 (2H, d, J=7.5 Hz), 7.43–7.68 (6H, m), 7.77–7.93 (3H, m), 8.89 (1H, d, J=8 Hz)

(9) 8-[2,6-Dichloro-3-[N-methyl-N-[4-(n-propylcarbamoyl)cinnamoylglycyl]amino]benzyloxy]-2-methylquinoline NMR (CDCl$_3$, δ): 0.92 (3H, t, J=7.5 Hz), 1.55–1.70 (2H, m), 2.73 (3H, s), 3.27 (3H, s), 3.43 (2H, q, J=7.5 Hz), 3.66 (1H, dd, J=4, 16 Hz), 3.95 (1H, dd, J=4, 16 Hz), 5.66 (2H, s), 6.13 (1H, t-like), 6.55 (1H, d, J=16 Hz), 6.69 (1H, t-like), 7.23–7.35 (3H, m), 7.38–7.63 (6H, m), 7.75 (2H, d, J=7.5 Hz), 8.03 (1H, d, J=8 Hz) its hydrochloride NMR (CDCl$_3$-CD$_3$OD, δ): 0.98 (3H, t, J=7.5 Hz), 1.57–1.73 (2H, m), 3.16 (3H, s), 3.29 (3H, s), 3.34–3.45 (2H, m), 3.89 (1H, d, J=16 Hz), 4.11 (1H, d, J=16 Hz), 5.60 (1H, d, J=10 Hz), 5.69 (1H, d, J=10 Hz), 6.65 (1H, d, J=16 Hz), 7.37–7.65 (6H, m), 7.65–7.92 (5H, m), 8.84 (1H, d, J=8 Hz)

(10) 8-[2,6-Dichloro-3-[N-methyl-N-[4-(3-pyridylcarbamoyl)cinnamoylglycyl]amino]benzyloxy]-2-methylquinoline NMR (CDCl$_3$, δ): 2.69 (3H, s), 3.23 (3H, s), 3.65 (1H, dd, J=4, 16 Hz), 3.93 (1H, dd, J=4, 16 Hz), 5.64 (2H, s), 6.55 (1H, d, J=16 Hz), 6.73 (1H, t-like), 7.23–7.39 (4H, m), 7.39–7.51 (3H, m), 7.51–7.65 (3H, m), 7.92 (2H, d, J=7.5 Hz), 8.05 (1H, d, J=8 Hz), 8.32 (1H, d, J=8 Hz), 8.39 (1H, d, J=6 Hz), 8.45 (1H, s), 8.72 (1H, s-like) its dihydrochloride NMR (CDCl$_3$-CD$_3$OD, δ): 3.13 (3H, s), 3.30 (3H, s), 3.91 (1H, d, J=16 Hz), 4.15 (1H, d, J=16 Hz), 5.59 (1H, d, J=10 Hz), 5.74 (1H, d, J=10 Hz), 6.66 (1H, d, J=16 Hz), 7.32 (1H, d, J=16 Hz), 7.48 (2H, d, J=7.5 Hz), 7.53–7.70 (3H, m), 7.78–7.98 (4H, m), 8.07 (2H, d, J=7.5 Hz), 8.47 (6H, d), 8.90 (1H, d, J=7.5 Hz), 9.25 (1H, d, J=7.5 Hz), 9.63 (1H, s-like)

(11) 8-[2,6-Dichloro-3-[N-[4-(2-hydroxyethylcarbamoyl)cinnamoylglycyl]-N-methylamino]benzyloxy]-2-methylquinoline NMR (CDCl$_3$, δ): 2.70 (3H, s), 3.26 (3H, s), 3.53–3.63 (2H, m), 3.65–3.82 (3H, m), 3.97 (1H, dd, J=4, 16 Hz), 5.60 (1H, d, J=10 Hz), 5.67 (1H, d, J=10 Hz), 6.51 (1H, d, J=16 Hz), 6.75 (1H, t-like), 6.93 (1H, t-like), 7.20–7.37 (3H, m), 7.37–7.56 (6H, m), 7.75 (2H, d, J=8 Hz), 8.03 (1H, d, J=8 Hz) its hydrochloride NMR (CDCl$_3$-CD$_3$OD, δ): 3.10 (3H, s), 3.28 (3H, s), 3.57 (2H, t, J=6 Hz), 3.79 (2H, t, J=6 Hz), 3.90 (1H, d, J=16 Hz), 4.11 (1H, d, J=16 Hz), 5.59 (1H, d, J=10 Hz), 5.70 (1H, d, J=10 Hz), 6.60 (1H, d, J=16 Hz), 7.35 (1H, d, J=16 Hz), 7.43 (2H, d, J=8 Hz), 7.49–7.58 (2H, m), 7.63 (1H, d, J=8 Hz), 7.75–7.93 (5H, m), 8.87 (1H, d, J=8 Hz)

(12) 8-[2,6-Dichloro-3-[N-[4-(2-ethoxyethylcarbamoyl)cinnamoylglycyl]-N-methylamino]benzyloxy]-2-methylquinoline NMR (CDCl$_3$, δ): 1.20 (3H, t, J=7.5 Hz), 2.73 (3H, s), 3.25 (3H, s), 3.47–3.71 (7H, m), 3.95 (1H, dd, J=4, 16 Hz), 5.60–5.70 (2H, m), 6.49–6.60 (2H, m), 6.67 (1H, t-like), 7.22–7.33 (3H, m), 7.33–7.64 (6H, m), 7.76 (2H, d, J=7.5 Hz), 8.03 (1H, d, J=8 Hz) its hydrochloride NMR (CDCl$_3$-CD$_3$OD, δ): 1.23 (3H, t, J=7.5 Hz), 3.15 (3H, s), 3.30 (3H, s), 3.57 (2H, q), 3.63 (4H, s-like), 3.90

(1H, d, J=16 Hz), 4.05 (1H, d, J=16 Hz), 5.62 (1H, d, J=10 Hz), 5.72 (1H, d, J=10 Hz), 6.66 (1H, d, J=16 Hz), 7.43–7.69 (6H, m), 7.73–7.94 (5H, m), 8.49 (1H, d, J=8 Hz)

(13) 8-[3-[N-[4-[N,N-Bis(2-ethoxyethyl)carbamoyl]cinnamoylglycyl]-N-methylamino]-2,6-dichlorobenzyloxy]-2-methylquinoline NMR (CDCl$_3$, δ): 1.11–1.25 (6H, m), 2.73 (3H, s), 3.26 (3H, s), 3.30–3.80 (13H, m), 3.95 (1H, dd, J=4, 16 Hz), 5.60–5.70 (2H, m), 6.49 (1H, d, J=16 Hz), 6.64 (1H, t-like), 7.23–7.33 (3H, m), 7.33–7.63 (8H, m), 8.01 (1H, d, J=8 Hz) its hydrochloride NMR (CDCl$_3$-CD$_3$OD, δ): 1.00–1.30 (6H, m), 3.01 (3H, s), 3.17–3.82 (15H, m), 3.89 (2H, s), 5.61 (1H, d, J=10 Hz), 5.77 (1H, d, J=10 Hz), 6.63 (1H, d, J=16 Hz), 7.35–7.71 (6H, m), 7.71–8.01 (5H, m), 8.96 (1H, d, J=8 Hz)

(14) 8-[2,6-Dichloro-3-[N-[4-[2-(dimethylamino)ethylcarbamoyl]cinnamoylglycyl]-N-methylamino]benzyloxy]-2-methylquinoline NMR (CDCl$_3$, δ): 2.30 (6H, s), 2.55 (2H, t, J=6 Hz), 2.73 (3H, s), 3.28 (3H, s), 3.54 (2H, q, J=6 Hz), 3.67 (1H, dd, J=4, 16 Hz), 3.95 (1H, dd, J=4, 16 Hz), 5.65 (2H, s-like), 6.53 (1H, d, J=16 Hz), 6.69 (1H, t-like), 6.95 (1H, t-like), 7.22–7.35 (3H, m), 7.35–7.63 (6H, m), 7.80 (2H, d, J=7.5 Hz), 8.02 (1H, d, J=8 Hz) its dihydrochloride NMR (CD$_3$OD, δ): 2.92–3.03 (9H, m), 3.35–3.47 (2H, m), 3.72–3.91 (3H, m), 4.01 (1H, d, J=16 Hz), 5.71 (1H, d, J=10 Hz), 5.81 (1H, d, J=10 Hz), 6.80 (1H, d, J=16 Hz), 7.55 (1H, d, J=16 Hz), 7.62–7.75 (4H, m), 7.86–8.00 (6H, m), 9.03 (1H, d, J=8 Hz)

(15) 8-[2,6-Dichloro-3-[N-methyl-N-[4-[(2-pyridylmethyl)carbamoyl]cinnamoylglycyl]amino]benzyloxy]-2-methylquinoline NMR (CDCl$_3$, δ): 2.73 (3H, s), 3.27 (3H, s), 3.66 (1H, dd, J=3, 16 Hz), 3.95 (1H, dd, J=4, 16 Hz), 4.75 (2H, d, J=5 Hz), 5.63 (2H, s-like), 6.54 (1H, d, J=16 Hz), 6.70–6.77 (1H, m), 7.18–7.36 (5H, m), 7.36–7.75 (8H, m), 7.87 (2H, d, J=7.5 Hz), 8.03 (1H, d, J=8 Hz), 8.08 (1H, d, J=5 Hz) its dihydrochloride NMR (CD$_3$OD, δ): 3.00 (3H, s), 3.27 (3H, s), 3.84 (1H, d, J=16 Hz), 4.00 (1H, d, J=16 Hz), 4.91 (2H, s), 5.73 (1H, d, J=10 Hz), 5.82 (1H, d, J=10 Hz), 6.81 (1H, d, J=16 Hz), 7.55 (1H, d, J=16 Hz), 7.63–7.76 (4H, m), 7.90–8.05 (7H, m), 8.09 (1H, d, J=7.5 Hz), 8.61 (1H, t, J=7.5 Hz), 8.79 (1H, d, J=7.5 Hz), 9.04 (1H, d, J=7.5 Hz)

(16) 8-[2,6-Dichloro-3-[N-methyl-N-[4-[(4-pyridylmethyl)carbamoyl]cinnamoylglycyl]amino]benzyloxy]-2-methylquinoline NMR (CDCl$_3$, δ): 2.70 (3H, s), 3.24 (3H, s), 3.66 (1H, dd, J=3, 16 Hz), 3.93 (1H, dd, J=4, 16 Hz), 4.65 (2H, d, J=6 Hz), 5.64 (2H, s-like), 6.54 (1H, d, J=16 Hz), 6.66–6.75 (1H, m), 7.19–7.34 (6H, m), 7.34–7.51 (3H, m), 7.51–7.63 (3H, m), 7.81 (2H, d, J=8 Hz), 8.01 (1H, d, J=8 Hz), 8.50–8.60 (2H, m) its dihydrochloride NMR (CD$_3$OD, δ): 3.01 (3H, s), 3.85 (1H, d, J=16 Hz), 4.01 (1H, d, J=16 Hz), 5.73 (1H, d, J=10 Hz), 5.82 (1H, d, J=10 Hz), 6.80 (1H, d, J=16 Hz), 7.54 (1H, d, J=16 Hz), 7.63–7.75 (4H, m), 7.87–7.99 (6H, m), 8.06 (2H, d, J=6 Hz), 8.80 (2H, d, J=6 Hz), 9.04 (1H, d, J=7.5 Hz)

(17) 8-[2,6-Dichloro-3-[N-methyl-N-[4-(1,2,3,6-tetrahydropyridin-1-ylcarbonyl)cinnamoylglycyl]amino]benzloxy]-2-methylquinoline NMR (CDCl$_3$, δ): 2.10–2.33 (2H, m), 2.73 (3H, s), 3.26 (3H, s), 3.37–3.53 (1H, m), 3.65 (1H, dd, J=4, 16 Hz), 3.75–4.00 (3H, m), 4.12–4.26 (1H, m), 5.64 (2H, s), 5.67–5.94 (2H, m), 6.50 (1H, d, J=16 Hz), 6.68 (1H, t-like), 7.20–7.35 (2H, m), 7.35–7.63 (9H, m), 8.02 (1H, d, J=8 Hz) its hydrochloride NMR (CD$_3$OD, δ): 2.15–2.31 (2H, m), 3.00 (3H, s), 3.27 (3H, s), 3.34–3.56 (2H, m), 3.81–4.06 (3H, m), 4.17 (1H, s-like), 5.54–5.96 (4H, m), 6.76 (1H, d, J=16 Hz), 7.41–7.74 (7H, m), 7.88–7.99 (4H, m), 9.03 (1H, d, J=8 Hz)

(18) 8-[2,6-Dichloro-3-[N-methyl-N-[4-(piperidinocarbonyl)cinnamoylglycyl]amino]benzyloxy]-2-methylquinoline NMR (CDCl$_3$, δ): 1.43–1.73 (6H, m), 2.73 (3H, s), 3.26 (3H, s), 3.29–3.43 (2H, m), 3.60–3.75 (3H, m), 3.95 (1H, dd, J=4, 16 Hz), 5.66 (2H, s-like), 6.50 (1H, d, J=16 Hz), 6.66 (1H, t-like), 7.20–7.61 (11H, m), 8.03 (1H, d, J=8 Hz) its hydrochloride NMR (CD$_3$OD, δ): 1.48–1.60 (2H, m), 1.60–1.78 (4H, m), 3.00 (3H, s), 3.33–3.45 (2H, m), 3.64–3.76 (2H, m), 3.85 (1H, d, J=16 Hz), 4.01 (1H, d, J=16 Hz), 5.70 (1H, d, J=10 Hz), 5.82 (1H, d, J=10 Hz), 6.74 (1H, d, J=16 Hz), 7.40 (2H, d, J=8 Hz), 7.50 (1H, d, J=16 Hz), 7.64 (2H, d, J=8 Hz), 7.72 (2H, s-like), 7.87–7.99 (4H, m), 9.03 (1H, d, J=8 Hz)

(19) 8-[2,6-Dichloro-3-[N-[4-[(2-furylmethyl)carbamoyl]cinnamoylglycyl]-N-methylamino]benzyloxy]-2-methylquinoline NMR (CDCl$_3$, δ): 2.71 (3H, s), 3.26 (3H, s), 3.65 (1H, dd, J=4, 16 Hz), 3.94 (1H, dd, J=4, 16 Hz), 4.14 (2H, d, J=5 Hz), 5.64 (2H, s-like), 6.26–6.30 (1H, m), 6.30–6.35 (1H, m), 6.45–6.58 (2H, m), 6.69 (1H, t-like), 7.23–7.33 (4H, m), 7.33–7.61 (6H, m), 7.78 (2H, d, J=8 Hz), 8.03 (1H, d, J=8 Hz) its hydrochloride NMR (CD$_3$OD, δ): 3.00 (3H, s), 3.85 (1H, d, J=16 Hz), 4.00 (1H, d, J=16 Hz), 4.56 (2H, s), 5.70 (1H, d, J=10 Hz), 5.81 (1H, d, J=10 Hz), 6.26–6.32 (1H, m), 6.32–6.39 (1H, m), 6.75 (1H, d, J=16 Hz), 7.43 (1H, d, J=2 Hz), 7.51 (1H, d, J=16 Hz), 7.57–7.77 (4H, m), 7.77–8.02 (6H, m), 8.02 (1H, d, J=8 Hz)

(20) 8-[3-[N-[4-(Allylcarbamoyl)cinnamoylglycyl]-N-methylamino]-2,6-dichlorobenzyloxy]-2-methylquinoline NMR (CDCl$_3$, δ): 2.73 (3H, s), 3.25 (3H, s), 3.65 (1H, dd, J=4, 16 Hz), 3.94 (1H, dd, J=4, 16 Hz), 4.09 (2H, t-like), 5.20 (1H, d, J=11 Hz), 5.26 (1H, d, J=18 Hz), 5.65 (2H, s), 5.85–6.02 (1H, m), 6.20 (1H, t-like), 6.53 (1H, d, J=16 Hz), 6.69 (1H, t-like), 7.22–7.33 (3H, m), 7.33–7.63 (6H, m), 7.77 (2H, d, J=7.5 Hz), 8.03 (1H, d, J=8 Hz) its hydrochloride NMR (CD$_3$OD, δ): 2.99 (3H, s), 3.85 (1H, d, J=16 Hz), 3.91–4.05 (3H, m), 5.14 (1H, d, J=11 Hz), 5.23 (1H, d, J=18 Hz), 5.71 (1H, d, J=10 Hz), 5.82 (1H, d, J=10 Hz), 5.85–6.02 (1H, m), 6.76 (1H, d, J=16 Hz), 7.47–7.75 (5H, m), 7.80–8.00 (6H, m), 9.03 (1H, d, J=8 Hz)

(21) 8-[2,6-Dichloro-3-[N-methyl-N-[4-(2-propynylcarbamoyl)cinnamoylglycyl]amino]benzyloxy]-2-methylquinoline NMR (CDCl$_3$, δ): 2.27 (1H, s), 2.72 (3H, s), 3.25 (3H, s), 3.66 (1H, dd, J=4, 16 Hz), 3.93 (1H, dd, J=4, 16 Hz), 4.25 (2H, t-like), 5.60–5.69 (2H, m), 6.40 (1H, t-like), 6.55 (1H, d, J=16 Hz), 6.70 (1H, t-like) 7.23–7.34 (3H, m), 7.37–7.63 (6H, m), 7.78 (2H, d, J=8 Hz), 8.03 (1H, d, J=8 Hz) its hydrochloride NMR (CDCl$_3$-CD$_3$OD, δ): 2.28 (1H, t-like), 3.15 (3H, s), 3.29 (3H, s), 3.90 (1H, d, J=16 Hz), 4.12 (1H, d, J=16 Hz), 4.21 (2H, d-like), 5.60 (1H, d, J=10 Hz), 5.70 (1H, d, J=10 Hz), 6.67 (1H, d, J=16 Hz), 7.36–7.65 (6H, m), 7.70–7.92 (5H, m), 8.85 (1H, d, J=7.5 Hz)

(22) 8-[2,6-Dichloro-3-[N-methyl-N-[4-[(2-thienylmethyl)carbamoyl]cinnamoylglycyl]amino]benzyloxy]-2-methylquinoline NMR (CDCl$_3$, δ): 2.72 (3H, s), 3.27 (3H, s), 3.65 (1H, dd, J=4, 16 Hz), 3.94 (1H, dd, J=4, 16 Hz), 4.83 (2H, d, J=6 Hz), 5.66 (2H, s-like), 6.46–6.58 (2H, m), 6.70 (1H, t-like), 6.98

(1H, t, J=5 Hz), 7.00–7.06 (1H, m), 7.20–7.34 (4H, m), 7.34–7.62 (6H, m), 7.79 (2H, d, J=8 Hz), 8.03 (1H, d, J=8 Hz) its hydrochloride NMR (CDCl$_3$-CD$_3$OD, δ): 3.13 (3H, s), 3.28 (3H, s), 3.89 (1H, d, J=16 Hz), 4.09 (1H, d, J=16 Hz), 4.77 (2H, s), 5.59 (1H, d, J=10 Hz), 5.69 (1H, d, J=10 Hz), 6.66 (1H, d, J=16 Hz), 6.96 (1H, t, J=5 Hz), 7.06 (1H, d-like), 7.23 (1H, d, J=5 Hz), 7.43 (1H, d, J=16 Hz), 7.48–7.57 (4H, m), 7.63 (1H, d, J=7.5 Hz), 7.71–7.82 (3H, m), 7.82–7.92 (2H, m), 8.84 (1H, d, J=8 Hz)

(23) 8-[2,6-Dichloro-3-[N-methyl-N-[3-(methylcarbamoyl) cinnamoylglycyl]amino]benzyloxy]-2-methylquinoline NMR (CDCl$_3$, δ): 2.70 (3H, s), 2.99 (3H, d-like), 3.25 (3H, s), 3.66 (1H, dif.-dd, J=16 Hz), 3.95 (1H, dif.-dd, J=16 Hz), 5.65 (2H, s), 6.45–6.60 (2H, m), 6.81–6.90 (1H, m), 7.21–7.69 (9H, m), 7.75 (1H, d, J=8 Hz), 7.87 (1H, s-like), 8.04 (1H, d, J=7.5 Hz) its hydrochloride NMR (CDCl$_3$-CD$_3$OD, δ): 3.00 (3H, s), 3.19 (3H, s), 3.28 (3H, s), 3.86 (1H, d, J=16 Hz), 4.28 (1H, d, J=16 Hz), 5.55 (1H, d, J=10 Hz), 5.72 (1H, d, J=10 Hz), 6.72 (1H, d, J=16 Hz), 7.32–7.48 (3H, m), 7.48–7.69 (3H, m), 7.73–7.96 (4H, m), 8.18 (1H, s-like) 8.87 (8H, d)

(24) 8-[3-[N-[N'-(3-Carbamoylphenyl)ureidoacetyl]-N-methylamino]-2,6-dichlorobenzyloxy]-2-methylquinoline NMR (CDCl$_3$, δ): 2.70 (3H, s), 3.28 (3H, s), 3.65 (1H, d, J=17 Hz), 3.90 (1H, d, J=17 Hz), 5.59 (2H, s), 7.21–7.61 (9H), 7.81 (1H, br s), 8.10 (1H, d, J=9 Hz) its hydrochloride NMR (CDCl$_3$-CD$_3$OD, δ): 2.94 (3H, s), 3.29 (3H, s), 3.80–4.10 (2H, overlapped with H$_2$O), 5.59 (1H, d, J=10 Hz), 5.79 (1H, d, J=10 Hz), 7.20 (1H, t, J=8 Hz), 7.31–7.98 (9H), 8.89 (1H, d, J=9 Hz)

(25) 8-[2,6-Dichloro-3-[N-methyl-N-[N'-(3-propylcarbamoylphenyl)ureidoacetyl]amino]benzyloxy]-2-methylquinoline NMR (CDCl$_3$, δ): 0.86 (3H, t, J=7.5 Hz), 1.42–1.55 (2H, m), 2.56 (3H, s), 3.18 (3H, s), 3.21–3.35 (2H, m), 3.80 (1H, dd, J=4, 16 Hz), 4.16 (1H, dd, J=7, 16 Hz), 5.45 (1H, d, J=9 Hz), 5.61 (1H, d, J=9 Hz), 5.64–5.72 (1H, m), 6.29 (1H, t-like), 7.10 (1H, t, J=7.5 Hz), 7.17–7.40 (6H, m), 7.42–7.49 (2H, m), 7.54–7.59 (1H, m), 8.05 (1H, d, J=8 Hz), 8.44 (1H, s) its hydrochloride NMR (CDCl$_3$-CD$_3$OD, δ): 0.92 (3H, t, J=7.5 Hz), 1.50–1.64 (2H, m), 2.81 (3H, s), 3.15–3.29 (5H, m), 3.85 (1H, d, J=16 Hz), 4.28 (1H, d, J=16 Hz), 5.59 (1H, d, J=10 Hz), 5.71 (1H, d, J=10 Hz), 7.02 (1H, t, J=7.5 Hz), 7.26–7.39 (2H, m), 7.51 (1H, d, J=7.5 Hz), 7.55–7.65 (3H, m), 7.65–7.78 (2H, m), 7.78 (1H, t, J=7.5 Hz), 8.75 (1H, d, J=7.5 Hz)

(26) 8-[2,6-Dichloro-3-[N-[N'-[3-(2-hydroxyethylcarbamoyl)phenyl]ureidoacetyl]-N-methylamino]benzyloxy]-2-methylquinoline NMR (CDCl$_3$, δ): 2.67 (3H, s), 3.23 (3H, s), 3.47–3.56 (2H, m), 3.69–3.82 (3H, m), 3.83–3.93 (2H, m), 5.56 (1H, d, J=10 Hz), 5.65 (1H, d, J=10 Hz), 6.04–6.16 (1H, m), 7.06–7.17 (2H, m), 7.17–7.54 (9H, m), 8.05 (1H, d, J=8 Hz), 8.03 (1H, s) its hydrochloride NMR (CDCl$_3$-CD$_3$OD, δ): 3.25 (3H, s), 3.42–3.51 (2H, m), 3.72 (2H, t, J=6 Hz), 3.88 (1H, d, J=16 Hz), 4.19 (1H, d, J=16 Hz), 5.58 (1H, d, J=10 Hz), 5.74 (1H, d, J=10 Hz), 7.04 (1H, t, J=7.5 Hz), 7.28–7.44 (3H, m), 7.48–7.82 (5H, m), 7.87 (1H, t, J=7.5 Hz), 8.79 (1H, d, J=8 Hz)

(27) 8-[2,6-Dichloro-3-[N-[N'-[3-(2-ethoxyethylcarbamoyl) phenyl]ureidoacetyl]-N-methylamino]benzyloxy]-2-methylquinoline NMR (CDCl$_3$, δ): 1.20 (3H, t, J=7.5 Hz), 2.61 (3H, s), 3.24 (3H, s), 3.43–3.62 (6H, m), 3.81 (1H, dd, J=4, 16 Hz), 4.25 (1H, dd, J=7.5, 16 Hz), 5.47 (1H, d, J=10 Hz), 5.58–5.70 (2H, m), 6.60 (1H, br s), 7.17 (1H, t, J=7.5 Hz), 7.21–7.38 (6H, m), 7.41–7.50 (2H, m), 7.64–7.70 (1H, m), 8.08 (1H, d, J=7.5 Hz), 8.48 (1H, s) its hydrochloride NMR (CDCl$_3$-CD$_3$OD, δ): 1.19 (3H, t, J=7.5 Hz), 2.84 (3H, s), 3.26 (3H, s), 3.30–3.61 (6H, m), 3.85 (1H, d, J=16 Hz), 4.26 (1H, d, J=16 Hz), 5.58 (1H, d, J=10 Hz), 5.73 (1H, d, J=10 Hz), 7.09 (1H, t, J=7.5 Hz), 7.25–7.33 (1H, m), 7.39 (1H, d, J=7.5 Hz), 7.53 (1H, d, J=8 Hz), 7.57–7.70 (3H, m), 7.70–7.80 (2H, m), 7.87 (1H, t, J=8 Hz), 8.78 (1H, d, J=8 Hz)

(28) 8-[2,6-Dichloro-3-[N-[N'-[4-(dimethylcarbamoyl) phenyl]ureidoacetyl]-N-methylamino]benzyloxy]-2-methylquinoline NMR (CDCl$_3$, δ): 2.59 (3H, s), 3.01 (6H, br s), 3.22 (3H, s), 3.78 (1H, dd, J=4, 16 Hz), 4.37 (1H, dd, J=7.5, 16 Hz), 5.42 (1H, d, J=10 Hz), 5.47–5.55 (1H, m), 5.62 (1H, d, J=10 Hz), 7.16–7.37 (8H, m), 7.44–7.54 (2H, m), 8.10 (1H, d, J=8 Hz), 7.71 (1H, s) its hydrochloride NMR (CDCl$_3$-CD$_3$OD, δ): 2.92 (3H, s), 3.25 (3H, s), 3.85 (1H, d, J=16 Hz), 4.13 (1H, d, J=16 Hz), 5.60 (1H, d, J=10 Hz), 5.75 (1H, d, J=10 Hz), 7.19 (2H, d, J=8 Hz), 7.28–7.42 (2H, m), 7.48–7.70 (3H, m), 7.70–7.95 (3H, m), 8.83 (1H, d, J=8 Hz)

(29) 8-[3-[N-[N'-(3-Ethylcarbamoylphenyl)ureidoacetyl]-N-methylamino]-2,6-dichlorobenzyloxy]-2-methylquinoline NMR (CDCl$_3$, δ): 1.16 (3H, t, J=7.5 Hz), 2.63 (3H, s), 3.20 (3H, s), 3.38 (2H, dq, J=7.5, 5 Hz), 3.81 (1H, dd, J=17, 5 Hz), 4.00 (1H, dd, J=17, 6 Hz), 5.51 (1H, d, J=9 Hz), 5.63 (1H, d, J=9 Hz), 5.95 (1H, br t, J=5 Hz), 6.57 (1H, br t, J=5 Hz), 7.13 (1H, t, J=8 Hz), 7.20–7.41 (6H, m), 7.45 (2H, d, J=5 Hz), 7.55 (1H, br s), 8.06 (1H, d, J=9 Hz), 8.48 (1H, br s) its hydrochloride NMR (CDCl$_3$-CD$_3$OD, δ): 1.22 (3H, t, J=7.5 Hz), 2.97 (3H, s), 3.30 (3H, s), 3.40 (2H, q, J=7.5 Hz), 3.86 (2H, s), 5.60 (1H, d, J=9 Hz), 5.82 (1H, d, J=9 Hz), 7.24 (1H, t, J=8 Hz), 7.30–7.46 (2H, m), 7.58 (1H, d, J=7 Hz), 7.65 (1H, d, J=7 Hz), 7.70–7.81 (2H, m), 7.81–8.01 (3H, m), 8.91 (1H, d, J=8 Hz)

(30) 8-[2,6-Dichloro-3-[N-[4-[N-(2-ethoxyethyl)-N-methylcarbamoyl]cinnamoylglycyl]-N-methylamino] benzyloxy]-2-methylquinoline NMR (CDCl$_3$, δ): 1.11–1.26 (3H, m), 2.74 (3H, s), 3.03 (1.5H, br s), 3.10 (1.5H, br s), 3.28 (3H, s), 3.33–3.60 (4H, m), 3.60–3.75 (3H, m), 3.96 (1H, dd, J=4, 16 Hz), 5.65 (2H, s-like), 6.50 (1H, d, J=16 Hz), 6.65 (1H, t-like), 7.22–7.35 (3H, m), 7.35–7.46 (3H, m), 7.48 (1H, d, J=16 Hz), 8.03 (1H, d, J=8 Hz) its hydrochloride NMR (CDCl$_3$-CD$_3$OD, δ): 1.13–1.27 (3H, m), 3.03 (1.5H, br s), 3.10 (1.5H, br s), 3.20 (3H, s), 3.30 (3H, s), 3.36–3.58 (4H, m), 3.71 (2H, br), 3.90 (1H, d, J=16 Hz), 4.03 (1H, d, J=16 Hz), 5.63 (1H, d, J=10 Hz), 5.70 (1H, d, J=10 Hz), 6.62 (1H, d, J=16 Hz), 7.36 (2H, d, J=8 Hz), 7.40–7.57 (5H, m), 7.61 (1H, d, J=8 Hz), 7.76 (1H, d, J=8 Hz), 7.80–7.90 (2H, m), 8.81 (1H, d, J=8 Hz)

(31) 8-[2,6-Dichloro-3-[N-[4-[N-methyl-N-(2-pyridylmethyl)carbamoyl]cinnamoylglycyl]-N-methylamino]benzyloxy]-2-methylquinoline NMR (CDCl$_3$, δ): 2.73 (3H, s), 3.00 (1.5H, br s), 3.09 (1.5H, br s), 3.65 (1H, br d, J=16 Hz), 3.94 (1H, br d, J=16 Hz), 4.60 (1H, s), 4.87 (1H, s), 5.64 (1H, s-like), 6.41–6.59 (1H, m), 6.59–6.76 (1H, m), 7.14–7.36 (5H, m), 7.36–7.65 (8H, m), 7.71 (1H, td, J=8, 2 Hz), 8.03 (1H, d, J=8 Hz), 8.57 (1H, d, J=6 Hz) its dihydrochloride NMR (CDCl$_3$-CD$_3$OD, δ): 3.18 (3H, s), 3.25 (3H, s), 3.29 (3H, s), 3.90 (1H, d, J=16 Hz), 4.06 (1H, d, J=16 Hz), 5.20 (2H, s), 5.61 (1H, d, J=10 Hz), 5.70 (1H, d, J=10 Hz), 6.67

(1H, d, J=16 Hz), 7.41–7.59 (7H, m), 7.63 (1H, d, J=8 Hz), 7.79 (1H, d, J=8 Hz), 7.83–7.93 (3H, m), 8.01–8.11 (1H, m), 8.40–8.52 (1H, m), 8.81 (1H, d, J=6 Hz), 8.85 (1H, d, J=8 Hz)

(32) 8-[2,6-Dichloro-3-[N-methyl-N-[4-(2-methylallylcarbamoyl)cinnamoylglycyl]amino]benzyloxy]-2-methylquinoline NMR (CDCl₃, δ): 1.80 (3H, s), 2.71 (3H, s), 3.25 (3H, s), 3.65 (1H, dd, J=4, 16 Hz), 3.94 (1H, dd, J=4, 16 Hz), 4.02 (2H, d, J=6 Hz), 4.85–4.93 (2H, m), 5.60–5.70 (2H, m), 6.21 (1H, t-like), 6.54 (1H, d, J=16 Hz), 6.69 (1H, t-like), 7.22–7.36 (3H, m), 7.36–7.65 (6H, m), 7.79 (2H, d, J=8 Hz), 8.03 (1H, d, J=8 Hz) its hydrochloride NMR (CDCl₃-CD₃OD, δ): 1.78 (3H, s), 3.14 (3H, s), 3.29 (3H, s), 3.89 (1H, d, J=16 Hz), 3.99 (2H, s), 4.10 (1H, d, J=16 Hz), 4.90 (2H, d-like), 5.60 (1H, d, J=10 Hz), 5.70 (1H, d, J=10 Hz), 6.66 (1H, d, J=16 Hz), 7.45 (1H, d, J=16 Hz), 7.49–7.67 (5H, m), 7.67–7.94 (5H, m), 8.86 (1H, d, J=8 Hz)

(33) 8-[2,6-Dichloro-3-[N-methyl-N-[(E)-3-[6-(methylcarbamoyl)pyridin-3-yl]acryloylglycyl]amino]benzyloxy]-2-methylquinoline NMR (CDCl₃, δ): 2.73 (3H, s), 3.04 (3H, d, J=6 Hz), 3.28 (3H, s), 3.61–3.75 (1H, m), 3.95 (1H, dd, J=4, 16 Hz), 5.64 (2H, s), 6.64 (1H, d, J=16 Hz), 6.76 (1H, br), 7.21–7.37 (3H, m), 7.37–7.54 (3H, m), 7.60 (1H, d, J=16 Hz), 7.88–8.09 (3H, m), 8.19 (1H, d, J=8 Hz), 8.62 (1H, d-like) its dihydrochloride NMR (CDCl₃-CD₃OD, δ): 3.00 (3H, s), 3.13 (3H, s), 3.25 (3H, s), 3.85 (1H, d, J=16 Hz), 4.21 (1H, d, J=16 Hz), 5.53 (1H, d, J=10 Hz), 5.64 (1H, d, J=10 Hz), 6.85 (1H, d, J=16 Hz), 7.41–7.62 (4H, m), 7.73 (1H, d, J=8 Hz), 7.78–7.88 (2H, m), 8.33 (2H, s-like), 8.80 (1H, d, J=8 Hz), 9.00 (1H, br s)

(34) 8-[2,6-Dichloro-3-[N-[(E)-3-[6-(dimethylcarbamoyl)pyridin-3-yl]acryloylglycyl]-N-methylamino]benzloxy]-2-methylquinoline NMR (CDCl₃, δ): 2.72 (3H, s), 3.09 (3H, s), 3.14 (3H, s), 3.28 (3H, s.), 3.68 (1H, dd, J=4, 16 Hz), 3.95 (1H, dd, J=4, 16 Hz), 5.60–5.71 (2H, m), 6.60 (1H, d, J=16 Hz), 6.75 (1H, t-like), 7.23–7.35 (3H, m), 7.35–7.68 (5H, m), 7.89 (1H, dd, J=8, 2 Hz), 8.03 (1H, d, J=8 Hz), 8.66 (1H, d-like) its dihydrochloride NMR (CDCl₃-CD₃OD, δ): 3.06 (3H, s), 3.08–3.16 (6H, m), 3.26 (3H, s), 3.85 (1H, d, J=16 Hz), 4.35 (1H, d, J=16 Hz), 5.51 (1H, d, J=10 Hz), 5.65 (1H, d, J=10 Hz), 6.97 (1H, d, J=16 Hz), 6.44 (1H, d, J=16 Hz), 7.50–7.66 (3H, m), 7.73 (1H, d, J=8 Hz), 7.78–7.91 (3H, m), 8.70 (1H, br d, J=8 Hz), 8.79 (1H, d, J=8 Hz), 9.04 (1H, br s)

(35) 8-[2,6-Dichloro-3-[N-[(E)-3-[6-(ethylcarbamoyl)-pyridin-3-yl]acryloylglycyl]-N-methylamino]benzyloxy]-2-methylquinoline NMR (CDCl₃, δ): 1.28 (3H, t, J=7.5 Hz), 2.74 (3H, s), 3.28 (3H, s), 3.52 (2H, quint, J=7.5 Hz), 3.70 (1H, dd, J=4, 16 Hz), 3.95 (1H, dd, J=4, 16 Hz), 5.65 (2H, s), 6.63 (1H, d, J=16 Hz), 6.77 (1H, br), 7.20–7.36 (3H, m), 7.36–7.54 (3H, m), 7.61 (1H, d, J=16 Hz), 7.88–8.00 (2H, m), 8.04 (1H, d, J=8 Hz), 8.18 (1H, d, J=8 Hz), 8.62 (1H, br) its dihydrochloride NMR (CDCl₃-CD₃OD, δ): 1.29 (3H, t, J=7.5 Hz), 3.18 (3H, s), 3.30 (3H, s), 3.50 (2H, q, J=7.5 Hz), 3.90 (1H, d, J=16 Hz), 4.07 (1H, d, J=16 Hz), 5.60 (1H, d, J=10 Hz), 5.20 (1H, d, J=10 Hz), 6.81 (1H, d, J=16 Hz), 7.49–7.60 (3H, m), 7.64 (1H, d, J=8 Hz), 7.79 (1H, d, J=8 Hz), 7.83–7.93 (2H, m), 8.09 (1H, d, J=8 Hz), 8.17 (1H, d, J=8 Hz), 8.74 (1H, br s), 8.86 (1H, d, J=8 Hz)

(36) 8-[2,6-Dichloro-3-[N-[(E)-3-[6-(N-ethyl-N-methylcarbamoyl)pyridin-3-yl]acryloylglycyl]-N-methylamino]benzyloxy]-2-methylquinoline NMR (CDCl₃, δ): 1.17 (3/2H, t, J=7.5 Hz), 1.25 (3/2H, t, J=7.5 Hz), 2.73 (3H, s), 3.03 (3/2H, s), 3.10 (3/2H, s), 3.27 (3H, s), 3.41 (1H, q, J=7.5 Hz), 3.60 (1H, q, J=7.5 Hz), 3.69 (1H, dd, J=4, 16 Hz), 3.95 (1H, dd, J=4, 16 Hz), 5.60–5.67 (2H, m), 6.58 (1H, d, J=16 Hz), 6.73 (1H, br), 7.19–7.35 (3H, m), 7.35–7.65 (5H, m), 7.88 (1H, d, J=8 Hz), 8.03 (1H, d, J=8 Hz), 8.66 (1H, br s) its dihydrochloride NMR (CDCl₃-CD₃OD, δ): 1.22 (1.5H, t, J=7.5 Hz), 1.27 (1.5H, t, J=7.5 Hz), 3.05 (1.5H, s), 3.11 (1.5H, s), 3.15 (3H, s), 3.29 (3H, s), 3.33–3.46 (1H, m), 3.60 (1H, q, J=7.5 Hz), 3.87 (1H, d, J=16 Hz), 4.32 (0.5H, d, J=16 Hz), 4.39 (0.5H, d, J=16 Hz), 5.01–5.10 (1H, m), 5.69 (1H, d, J=10 Hz), 6.94 (0.5H, d, J=16 Hz), 7.00 (0.5H, d, J=16 Hz), 7.50 (1H, d, J=16 Hz), 7.55–7.69 (3H, m), 7.78 (1H, d, J=8 Hz), 7.81–7.95 (3H, m), 8.56 (0.5H, br), 8.75 (0.5H, br), 8.82 (1H, d, J=8 Hz), 9.00 (0.5H, br s), 9.09 (0.5H, br s)

(37) 8-[3-[N-[(E)-3-[6-(Allylcarbamoyl)pyridin-3-yl]acryloylglycyl]-N-methylamino]-2,6-dichlorobenzyloxy]-2-methylquinoline NMR (CDCl₃, δ): 2.73 (3H, s), 3.28 (3H, s), 3.70 (1H, dd, J=4, 16 Hz), 3.95 (1H, dd, J=4, 16 Hz), 4.10 (2H, t-like), 5.18 (1H, d, J=11 Hz), 5.26 (1H, d, J=18 Hz), 5.59–5.70 (2H, m), 5.86–6.03 (1H, m), 6.63 (1H, d, J=16 Hz), 6.75 (1H, t-like), 7.20–7.34 (3H, m), 7.36–7.52 (3H, m), 7.60 (1H, d, J=16 Hz), 7.93 (1H, dd, J=2, 8 Hz), 8.03 (1H, d, J=8 Hz), 8.07 (1H, t-like), 8.18 (1H, d, J=8 Hz), 8.63 (1H, d, J=2 Hz) its dihydrochloride NMR (CDCl₃-CD₃OD, δ): 3.13 (3H, s), 3.25 (3H, s), 3.86 (1H, d, J=16 Hz), 4.06 (2H, d-like), 4.23 (1H, d, J=16 Hz), 5.17 (1H, d, J=11 Hz), 5.26 (1H, d, J=18 Hz), 5.55 (1H, d, J=10 Hz), 5.64 (1H d, J=10 Hz), 5.82–6.00 (1H, m), 6.88 (1H, d, J=16 Hz), 7.43–7.63 (4H, m), 7.73 (1H, d, J=8 Hz), 7.78–7.89 (2H, m), 8.25–8.41 (2H, m), 8.78 (1H, d, J=8 Hz), 8.97 (1H, br s)

(38) 8-[2,6-Dichloro-3-[N-methyl-N-[(E)-3-[6-(2-propynylcarbamoyl)pyridin-3-yl]acryloylglycyl]amino]benzyloxy]-2-methylquinoline NMR (CDCl₃, δ): 2.27 (1H, t-like), 2.73 (3H, s), 3.26 (3H, s), 3.70 (1H, dd, J=4, 16 Hz), 3.95 (1H, dd, J=4, 16 Hz), 4.23–4.30 (2H, m), 5.65 (2H, s-like), 6.13 (1H, d, J=16 Hz), 6.77 (1H, t-like), 7.20–7.35 (3H, m), 7.35–7.53 (3H, m), 7.60 (1H, d, J=16 Hz), 7.94 (1H, dd, J=2, 8 Hz), 8.03 (1H, d, J=8 Hz), 8.16 (1H, d, J=8 Hz), 8.62 (1H, d, J=2 Hz) its dihydrochloride NMR (CDCl₃-CD₃OD, δ): 2.27 (1H, t-like), 3.17 (3H, s), 3.27 (3H, s), 3.88 (1H, d, J=16 Hz), 4.18–4.32 (3H, m), 5.55 (1H, d, J=10 Hz), 5.64 (1H, d, J=10 Hz), 6.90 (1H, d, J=16 Hz), 7.41–7.63 (4H, m), 7.73 (1H, d, J=8 Hz), 7.78–7.88 (2H, m), 8.30 (1H, d, J=8 Hz), 8.37 (1H, d, J=8 Hz), 8.79 (1H, d, J=8 Hz), 9.00 (1H, br s)

(39) 8-[2,6-Dichloro-3-[N-methyl-N-[(E)-3-[6-(1-pyrrolidinylcarbonyl)pyridin-3-yl]acryloylglycyl]amino]benzyloxy]-2-methylquinoline dihydrochloride NMR (CDCl₃-CD₃OD, δ): 1.93–2.05 (4H, m), 3.13 (3H, s), 3.30 (3H, s), 3.63–3.75 (4H, m), 3.86 (1H, d, J=16 Hz), 4.40 (1H, d, J=16 Hz), 5.53 (1H, d, J=10 Hz), 5.70 (1H, d, J=10 Hz), 6.99 (1H, d, J=16 Hz), 7.49 (1H, d, J=16 Hz), 7.55–7.70 (3H, m), 7.77 (1H, d, J=8 Hz), 7.81–7.93 (2H, m), 8.06–8.15 (1H, m), 8.74–8.87 (2H, m), 9.20 (1H, br s)

(40) 8-(2,6-Dichloro-3-[N-[(E)-3-[6-(2-methoxyethylcarbamoyl)pyridin-3-yl]acryloylglycyl]-N-methylamino]benzyloxyl-2-methylquinoline NMR (CDCl₃, δ): 2.72 (3H, s), 3.26 (3H, s), 3.40 (3H, s), 3.57 (2H, t, J=6 Hz), 3.66 (2H, t, J=6 Hz), 3.70 (1H, dd, J=4, 16 Hz), 3.95 (1H, dd, J=4, 16 Hz), 5.63 (1H, d, J=10 Hz), 5.67 (1H, d, J=10 Hz), 6.63 (1H, d, J=16 Hz), 6.76 (1H, t-like), 7.22–7.35 (3H, m), 7.37–7.53 (3H, m), 7.60 (1H, d, J=16 Hz), 7.93 (1H, dd, J=2, 8 Hz), 8.03 (1H, d, J=8 Hz), 8.16 (1H, d, J=8 Hz), 8.26 (1H, t-like), 8.63 (1H, d, J=2 Hz) its dihydrochloride NMR (CDCl$_3$-CD$_3$OD, δ): 3.17 (3H, s), 3.30 (3H, s), 3.40 (3H, s), 3.57–3.63 (2H, m), 3.63–3.70 (2H, m), 3.89 (1H, d, J=16 Hz), 4.24 (1H, d, J=16 Hz), 5.58 (1H, d, J=10 Hz), 5.68 (1H, d, J=10 Hz), 6.90 (1H, d, J=16 Hz), 7.45–7.67 (4H, m), 7.77 (1H, d, J=8 Hz), 7.81–7.92 (2H, m), 8.26–8.43 (2H, m), 8.83 (1H, d, J=8 Hz), 8.99 (1H, br s)

(41) 8-[2,6-Dichloro-3-[N-[(E)-3-[6-(2-ethoxyethylcarbamoyl)pyridin-3-yl]acryloylglycyl]-N-methylamino]benzyloxy]-2-methylquinoline NMR (CDCl$_3$, δ): 1.23 (3H, t, J=7.5 Hz), 2.73 (3H, s), 3.27 (3H, s), 3.55 (2H, q, J=7.5 Hz), 3.57–3.75 (5H, m), 3.94 (1H, dd, J=4, 16 Hz), 5.62 (1H, d, J=10 Hz), 5.67 (1H, d, J=10 Hz), 6.61 (1H, d, J=16 Hz), 6.75 (1H, t-like), 7.23–7.35 (3H, m), 7.35–7.53 (3H, m), 7.60 (1H, d, J=16 Hz), 7.93 (1H, dd, J=2, 8 Hz), 8.03 (1H, d, J=8 Hz), 8.16 (1H, d, J=8 Hz), 8.29 (1H, t-like), 8.63 (1H, d, J=2 Hz) its dihydrochloride NMR (CDCl$_3$-CD$_3$OD, δ): 1.21 (3H, t, J=7.5 Hz), 3.17 (3H, s), 3.30 (3H, s), 3.55 (2H, q, J=7.5 Hz), 3.60–3.70 (4H, m), 3.86 (1H, d, J=16 Hz), 4.30 (1H, d, J=16 Hz), 5.57 (1H, d, J=10 Hz), 5.67 (1H, d, J=10 Hz), 6.93 (1H, d, J=16 Hz), 7.50 (1H, d, J=16 Hz), 7.56–7.64 (3H, m), 7.78 (1H, d, J=8 Hz), 7.82–7.92 (2H, m), 8.36 (1H, d, J=8 Hz), 8.47 (1H, d, J=8 Hz), 8.8–3 (1H, d, J=8 Hz), 9.07 (1H, br s)

(42) 8-[3-[N-[(E)-3-[6-[N,N-Bis(2-methoxyethyl)carbamoyl]-pyridin-3-yl]acryloylglycyl]-N-methylamino]-2,6-dichlorobenzyloxyl-2-methylquinoline NMR (CDCl$_3$, δ): 2.72 (3H, s), 3.23 (3H, s), 3.27 (3H, s), 3.38 (3H, s), 3.54 (2H, t, J=6 Hz), 3.61–3.83 (7H, m), 3.94 (1H, dd, J=4, 16 Hz), 5.65 (1H, d, J=10 Hz), 5.68 (1H, d, J=10 Hz), 6.60 (1H, d, J=16 Hz), 6.72 (1H, t-like), 7.24–7.36 (3H, m), 7.36–7.70 (5H, m), 7.88 (1H, dd, J=2, 8 Hz), 8.03 (1H, d, J=8 Hz), 8.65 (1H, d, J=2 Hz) its dihydrochloride NMR (CDCl$_3$-CD$_3$OD, δ): 3.13 (3H, s), 3.21–3.80 (17H, m), 3.85 (1H, d, J=16 Hz), 4.51 (1H, d, J=16 Hz), 5.50 (1H, d, J=10 Hz), 5.67 (1H, d, J=10 Hz), 7.05 (1H, d, J=16 Hz), 7.47 (1H, d, J=16 Hz), 7.53–7.64 (2H, m), 7.70 (1H, d, J=8 Hz), 7.76 (1H, d, J=8 Hz), 7.84 (1H, d, J=8 Hz), 7.89 (1H, d, J=8 Hz), 8.00–8.06 (1H, m), 8.81 (1H, d, J=8 Hz), 8.87–8.96 (1H, m), 9.29 (1H, br s)

(43) 8-[2,6-Dichloro-3-[N-methyl-N-[(E)-3-[6-(morpholinocarbonyl)pyridin-3-yl]acryloylglycyl]amino]benzyloxy]-2-methylquinoline NMR (CDCl$_3$, δ): 2.73 (3H, s), 3.25 (3H, s), 3.63–3.74 (5H, m), 3.80 (4H, s-like), 3.95 (1H, dd, J=4, 16 Hz), 5.63 (1H, d, J=10 Hz), 5.68 (1H, d, J=10 Hz), 6.60 (1H, d, J=16 Hz), 6.73 (1H, t-like), 7.23–7.35 (3H, m), 7.35–7.53 (3H, m), 7.59 (1H, d, J=16 Hz), 7.71 (1H, d, J=8 Hz), 7.91 (1H, dd, J=2, 8 Hz), 8.03 (1H, d, J=8 Hz), 8.66 (1H, d, J=2 Hz) its dihydrochloride NMR (CDCl$_3$-CD$_3$OD, δ): 3.15 (3H, s), 3.29 (3H, s), 3.61 (2H, br), 3.73 (2H, br), 3.82 (4H, br), 3.90 (1H, d, J=16 Hz), 4.27 (1H, d, J=16 Hz), 5.67 (1H, d, J=10 Hz), 5.70 (1H, d, J=10 Hz), 6.93 (1H, d, J=16 Hz), 7.49 (1H, d, J=16 Hz), 7.53–7.65 (3H, m), 7.76 (1H, d, J=8 Hz), 7.80–7.92 (3H, m), 8.47–8.57 (1H, m), 8.82 (1H, d, J=8 Hz), 8.94 (1H, br)

(44) 8-[2,6-Dichloro-3-[N-methyl-N-[(E)-3-[6-[(2-pyridylmethyl)carbamoyl]pyridin- 3-yl]acryloylglycyl]amino]benzyloxy]-2-methylquinoline NMR (CDCl$_3$, δ): 2.72 (3H, s), 3.27 (3H, s), 3.70 (1H, dd, J=4, 16 Hz), 3.95 (1H, dd, J=4, 16 Hz), 4.80 (2H, d, J=6 Hz), 5.65 (2H, s), 6.63 (1H, d, J=16 Hz), 6.76 (1H, t-like), 7.17–7.38 (5H, m), 7.37–7.54 (3H, m), 7.61 (1H, d, J=16 Hz), 7.67 (1H, td, J=8, 2 Hz), 7.95 (1H, d, J=8 Hz), 8.03 (1H, d, J=8 Hz), 8.20 (1H, d, J=8 Hz), 8.61 (1H, d, J=6 Hz), 8.67 (1H, s-like), 8.90 (1H, t-like) its trihydrochloride NMR (CDCl$_3$-CD$_3$OD, δ): 3.19 (3H, s), 3.30 (3H, s), 3.90 (1H, d, J=16 Hz), 4.17 (1H, d, J=16 Hz), 5.13 (2H, s), 5.60 (1H, d, J=10 Hz), 5.70 (1H, d, J=10 Hz), 6.90 (1H, d, J=16 Hz), 7.45–7.70 (4H, m), 7.77–7.98 (4H, m), 8.12 (1H, d, J=8 Hz), 8.16–8.30 (2H, m), 8.43 (1H, t, J=8 Hz), 8.77 (1H, d, J=6 Hz), 8.81–8.93 (2H, m)

(45) 8-[2,6-Dichloro-3-[N-methyl-N-[4-(morpholinocarbonyl)cinnamoylglycyl]amino]benzyloxy]-2-methylquinoxaline mp: 118–130° C.

NMR (CDCl$_3$, δ): 2.78 (3H, s), 3.28 (3H, s), 3.37–3.55 (2H, m), 3.67 (1H, dd, J=16.5, 3.0 Hz), 3.59–3.88 (6H, m), 3.96 (1H, dd, J=16.5, 3.0 Hz), 5.62 (2H, s), 6.52 (1H, d, J=15.0 Hz), 6.66 (1H, t, J=3.0 Hz), 7.29–7.38 (2H, m), 7.42 (2H, d, J=8.5 Hz), 7.49–7.70 (5H, m), 7.77 (1H, d, J=8.5 Hz), 8.73 (1H, s)

(46) 8-[2,6-Dichloro-3-[N-[4-[(2-pyridylmethyl)carbamoyl]cinnamoylglycyl]-N-methylamino]benzyloxy]-2-methylquinoxaline mp: 111–124° C.

NMR (CDCl$_3$, δ): 2.78 (3H, s), 3.28 (3H, s), 3.67 (1H, dd, J=16.5, 3.0 Hz), 3.96 (1H, dd, J=16.5, 3.0 Hz), 4.77 (2H, d, J=3.0 Hz), 5.62 (2H, s), 6.53 (1H, d, J=16.0 Hz), 6.72 (1H, t, J=3.0 Hz), 7.20–7.38 (4H, m), 7.49–7.71 (7H, m), 7.75 (1H, t, J=8.5 Hz), 7.89 (2H, d, J=8.5 Hz), 8.57 (1H, d, J=4.5 Hz), 8.73 (1H, s)

(47) 8-[3-[N-[4-(Allylcarbamoyl)cinnamoylglycyl]-N-methylamino]-2,6-dichlorobenzyloxy]-2-methylquinoxaline mp: 117–123° C.

NMR (CDCl$_3$, δ): 2.76 (3H, s), 3.27 (3H, s), 3.65 (1H, dd, J=16.5, 3.0 Hz), 3.94 (1H, dd, J=16.5, 3.0 Hz), 4.09 (2H, m), 5.19 (1H, d, J=11.5 Hz), 5.27 (1H, d, J=16.5 Hz), 5.62 (2H, s), 5.86–6.00 (1H, m), 6.25 (1H, t, J=7.0 Hz), 6.53 (1H, d, J=15.0 Hz), 6.70 (1H, t, J=3.0 Hz), 7.29–7.36 (2H, m), 7.48–7.82 (8H, m), 8.73 (1H, s)

(48) 8-[2,6-Dichloro-3-[N-[4-(2-ethoxyethylcarbamoyl)cinnamoylglycyl]-N-methylamino]benzyloxy]-2-methylquinoxaline mp: 97–111° C.

NMR (CDCl$_3$, δ): 1.23 (3H, t, J=7.0 Hz), 2.77 (3H, s), 3.27 (3H, s), 3.54 (2H, q, J=7.0 Hz), 3.57–3.71 (5H, m), 3.94 (1H, dd, J=16.5, 3.0 Hz), 5.63 (2H, s), 6.53 (1H, d, J=15.0 Hz), 6.58 (1H, t, J=6.0 Hz), 6.69 (1H, t, J=3.0 Hz), 7.29–7.37 (2H, m), 7.49–7.82 (8H, m), 8.74 (1H, s)

(49) 8-[2,6-Dichloro-3-[N-methyl-N-[N'-[3-(phenylcarbamoyl)phenyl]ureidoacetyl]amino]benzyloxy]-2-methylquinoline NMR (CDCl$_3$, δ): 2.69 (3H, s), 3.24 (3H, s), 3.88 (1H, dd, J=17, 4 Hz), 4.02 (1H, dd, J=17, 5 Hz), 5.51 (2H, s), 6.35 (1H, br s), 7.00–7.51 (13H), 7.88 (2H, d, J=8 Hz), 8.06 (1H, d, J=8 Hz), 8.39 (1H, s), 9.17 (1H, br s) its hydrochloride NMR (CDCl$_3$-CD$_3$ OD, δ): 2.84 (3H, s), 3.25 (3H, s), 3.87 (1H, br d, J=17 Hz), 4.31 (1H, br d, J=17 Hz), 5.59 (1H, d, J=10 Hz), 5.68 (1H, d, J=10 Hz), 7.05–7.13 (2H), 7.28–7.71 (11H), 7.76–7.86 (2H), 8.70 (1H, d, J=8 Hz)

(50) 8-[2,6-Dichloro-3-[N-methyl-N-[4-(phenylcarbamoyl)cinnamoylglycyl]amino]benzyloxy]-2-methylquinoline NMR (CDCl$_3$, δ): 2.69 (3H, s), 3.24 (3H, s), 3.65 (1H, dd, J=17, 4 Hz), 3.92 (1H, dd, J=17, 5 Hz), 5.63 (2H, s), 6.53 (1H, d, J=15 Hz), 6.76 (1H, br t, J=4 Hz), 7.13 (1H, t, J=8 Hz), 7.23–7.61 (11H), 7.67 (2H, d, J=8 Hz), 7.88 (2H, d, J=8 Hz), 8.03 (1H, d, J=8 Hz), 8.18 (1H, br s) its hydrochloride NMR (CDCl$_3$-CD$_3$OD, δ): 3.12 (3H, s), 3.29 (3H, s), 3.89 (1H, d, J=17 Hz), 4.13 (1H, d, J=17 Hz), 5.59 (1H, d, J=10 Hz), 5.70 (1H, d, J=10 Hz), 6.69 (1H, d, J=15 Hz), 7.15 (1H, t, J=8 Hz), 7.32–7.40 (2H), 7.42 (1H, d, J=15 Hz), 7.62 (1H, d, J=8 Hz), 7.70–7.92 (8H), 8.85 (1H, d, J=8 Hz)

(51) 8-[2,6-Dichloro-3-[N-methyl-N-[4-[2-(methylcarbamoyloxy)ethylcarbamoyl]cinnamoylglycyl]amino]benzyloxy]-2-methylquinoline NMR (CDCl$_3$, δ): 2.72 (3H, s), 2.80 (3H, d, J=6 Hz), 3.27 (3H, s), 3.61–3.77 (2H, m), 3.66 (1H, d, J=17, 4 Hz), 3.94 (1H, d, J=17, 5 Hz), 4.25–4.37 (2H, m), 5.61 (1H, d, J=9 Hz), 5.66 (1H, d, J=9 Hz), 6.53 (1H, d, J=16 Hz), 6.71 (1H, br t, J=6 Hz), 7.01 (1H, m), 7.22–7.35 (3H, m), 7.38–7.64 (6H, m), 7.74–7.85 (2H, m), 8.02 (1H, d, J=8 Hz) its hydrochloride NMR (CDCl$_3$-CD$_3$OD, δ): 2.74 (3H, s), 3.10 (3H, s), 3.30 (3H, s), 3.66 (2H, br t, J=7 Hz), 3.91 (1H, d, J=17 Hz), 4.02 (1H, d, J=17 Hz), 4.26 (2H, br t, J=7 Hz), 5.60 (1H, d, J=9 Hz), 5.76 (1H, d, J=9 Hz), 6.66 (1H, d, J=15 Hz), 7.45 (1H, d, J=15 Hz), 7.50–7.74 (5H, m), 7.77–8.00 (5H, m), 8.94 (1H, d, J=9 Hz)

(52) 8-[2,6-Dichloro-3-[N-[4-[(ethoxycarbonylmethyl) carbamoyl]cinnamoylglycyl]-N-methylamino]benzyloxy]-2-methylquinoline NMR (CDCl$_3$, δ): 1.31 (3H, t, J=7.5 Hz), 2.74 (3H, s), 3.27 (3H, s), 3.64 (1H, dd, J=4, 16 Hz), 3.95 (1H, dd, J=4, 16 Hz), 4.15–4.33 (4H, m), 5.60–5.71 (2H, m), 6.55 (1H, d, J=16 Hz), 6.65–6.77 (2H, m), 7.17–7.35 (3H, m), 7.35–7.65 (6H, m), 7.80 (2H, d, J=8 Hz), 8.03 (1H, d, J=8 Hz)

(53) 8-[2,6-Dichloro-3-[N-[4-[N-(methoxycarbonylmethyl)-N-methylcarbamoyl] cinnamoylglycyl]-N-methylamino]benzyloxy]-2-methylquinoline NMR (CDCl$_3$, δ): 2.73 (3H, s), 3.05 (2H, s), 3.10 (1H, s), 3.26 (3H, s), 3.64 (1H, dd, J=4, 16 Hz), 3.70–3.83 (3H, m), 3.86–4.02 (1.7H, m), 4.27 (1.3H, br s), 5.60–5.71 (2H, m), 6.50 (1H, br d, J=16 Hz), 6.65 (1H, br), 7.17–7.33 (3H, m), 7.33–7.63 (8H, m), 8.02 (1H, d, J=8 Hz)

(54) 8-[2,6-Dichloro-3-[N-[4-[(2-methoxycarbonylethyl) carbamotl]cinnamoylglycyl]-N-methylamino]benzyloxy]-2-methylquinoline NMR (CDCl$_3$, δ): 2.65 (2H, t, J=6 Hz), 2.73 (3H, s), 3.25 (3H, s), 3.58–3.77 (6H, m), 3.94 (1H, dd, J=4, 16 Hz), 5.90–5.70 (2H, m), 6.52 (1H, d, J=16 Hz), 6.63–6.70 (1H, m), 6.85 (1H, t-like), 7.20–7.35 (3H, m), 7.35–7.62 (6H, m), 7.75 (2H, d, J=8 Hz), 8.01 (1H, d, J=8 Hz)

(55) 8-[2,6-Dichloro-3-[N-[4-[((R)-1-methoxycarbonylethyl)carbamoyl]cinnamoylglycyl]-N-methylamino]benzyloxy]-2-methylquinoline NMR (CDCl$_3$, δ): 1.52 (3H, d, J=7.5 Hz), 2.72 (3H, s), 3.25 (3H, s), 3.65 (1H, dt, J=16, 4 Hz), 3.80 (3H, s), 3.95 (1H, dt, J=16, 4 Hz), 4.80 (1H, quint, J=7.5 Hz), 5.59–5.70 (2H, m), 6.54 (1H, dd, J=4, 16 Hz), 6.64–6.81 (2H, m), 7.20–7.35 (3H, m), 7.35–7.65 (6H, m), 7.80 (2H, d, J=8 Hz), 8.03 (1H, d, J=8 Hz), [α]$_D^{20}$: −22.7° (C=20 mg/2 ml, CDCl$_3$)

(56) 8-(2,6-Dichloro-3-[N-[4-[((R)-1-methoxycarbonyl-2-phenylethyl)carbamoyl]cinnamoylglycyl]-N-methylamino] benzyloxy]-2-methylquinoline NMR (CDCl$_3$, δ): 2.74 (3H, s), 3.16–3.37 (5H, m), 3.65 (1H, dd, J=4, 16 Hz), 3.78 (3H, s), 3.94 (1H, dd, J=4, 16 Hz), 5.09 (1H, q, J=7.5 Hz), 5.60–5.71 (2H, m), 6.49–6.60 (2H, m), 6.63–6.72 (1H, m), 7.12 (2H, d, J=8 Hz), 7.20–7.36 (6H, m), 7.36–7.63 (6H, m), 7.70 (2H, d, J=8 Hz), 8.02 (1H, d, J=8 Hz) [α]$_D^{20}$: +49.5° (C=20 mg/2 ml, MeOH) (57) 8-[2,6-Dichloro-3-[N-methyl-N-[(E)-3-[6-(4-pyridylcarbamoyl)pyridin- 3-yl]acryloylglycyl]amino] benzyloxy]-2-methylquinoline NMR (CDCl$_3$, δ): 2.72 (3H, s), 3.28 (3H, s), 3.71 (1H, dd, J=17, 4 Hz), 3.97 (1H, dd, J=17, 5 Hz), 5.66 (2H, s), 6.69 (1H, d, J=15 Hz), 6.83 (1H, br t, J=4 Hz), 7.21–7.36 (4H), 7.39–7.52 (3H), 7.62 (1H, d, J=15 Hz), 7.71 (1H, d, J=6 Hz), 7.98–8.07 (2H), 8.27 (1H, d, J=7.5 Hz), 8.58 (2H, d, J=6 Hz), 8.69 (1H, d, J=2 Hz) its trihydrochloride NMR (CDCl$_3$-CD$_3$OD, δ): 3.20 (3H, s), 3.30 (3H, s), 3.92 (1H, d, J=17 Hz), 4.26 (1H, d, J=17 Hz), 5.60 (1H, d, J=10 Hz), 5.71 (1H, d, J=10 Hz), 6.98 (1H, d, J=15 Hz), 7.49–7.69 (4H), 7.79 (1H, d, J=7.5 Hz), 7.85–7.93 (2H), 8.17 (1H, br d, J=7.5 Hz), 8.33 (1H, br d, J=7.5 Hz), 8.46 (2H, d, J=6 Hz), 8.67 (2H, d, J=6 Hz), 8.87 (1H, d, J=7.5 Hz), 8.99 (1H, br s)

(58) 8-[2,6-Dichloro-3-[N-methyl-N-[(E)-3-[6-(3-pyridylmethylcarbamoyl)pyridin-3-yl]acryloylglycyl] amino]benzyloxy]-2-methylquinoline NMR (CDCl$_3$, δ): 2.71 (3H, s), 3.27 (3H, s), 3.69 (1H, dd, J=17, 4 Hz), 3.93 (1H, dd, J=17, 5 Hz), 4.69 (2H, d, J=5 Hz), 5.65 (2H, s), 6.62 (1H, d, J=15 Hz), 6.79 (1H, br t, J=4 Hz), 7.20–7.33 (4H), 7.37–7.52 (4H), 7.59 (1H, d, J=15 Hz), 7.71 (1H, br d, J=7.5 Hz), 7.95 (1H, dd, J=7.5, 2 Hz), 8.02 (1H, d, J=7.5 Hz), 8.20 (1H, d, J=7.5 Hz), 8.37 (1H, br t, J=5 Hz), 8.53 (1H, d, J=2 Hz), 8.62 (2H, dd, J=7.5, 2 Hz) its trihydrochloride NMR (CDCl$_3$-CD$_3$OD, δ): 3.13 (3H, s), 3.29 (3H, s), 3.90 (1H, d, J=17 Hz), 4.28 (1H, d, J=17 Hz), 4.88 (2H, br s), 5.56 (1H, d, J=10 Hz), 5.72 (1H, d, J=10 Hz), 7.04 (1H, br d, J=15 Hz), 7.46–7.69 (4H), 7.81 (1H, d, J=7.5 Hz), 7.87–8.02 (3H), 8.56 (1H, br d, J=7.5 Hz), 8.69–8.81 (3H), 8.89 (1H, br d, J=7.5 Hz), 8.99 (1H, br s), 9.33 (1H, br s)

(59) 8-[2,6-Dichloro-3-[N-methyl-N-[(E)-3-[6-(4-pyridylmethylcarbamoyl)pyridin-3-yl]acryloylglycyl] amino]benzyloxy]-2-methylquinoline NMR (CDCl$_3$, δ): 2.72 (3H, s), 3.28 (3H, s), 3.70 (1H, dd, J=17, 4 Hz), 3.96 (1H, dd, J=17, 5 Hz), 4.69 (2H, d, J=5 Hz), 5.66 (2H, s), 6.64 (1H, d, J=15 Hz), 6.79 (1H, br t, J=4 Hz), 7.23–7.33 (5H), 7.38–7.52 (3H), 7.61 (1H, d, J=15 Hz), 7.98 (1H, dd, J=7.5, 2 Hz), 8.02 (1H, d, J=7.5 Hz), 8.20 (1H, d, J=7.5 Hz), 8.42 (1H, br t, J=5 Hz), 8.57 (2H, d, J=6 Hz), 8.62 (1H, d, J=2 Hz) its trihydrochloride NMR (CDCl$_3$-CD$_3$OD, δ): 3.15 (3H, br s), 3.29 (3H, s), 3.90 (1H, d, J=17 Hz), 4.30 (1H, d, J=17 Hz), 4.92 (2H, br s), 5.56 (1H, d, J=10 Hz), 5.72 (1H, d, J=10 Hz), 7.07 (1H, br s), 7.45–7.68 (4H), 7.60 (1H, d, J=7.5 Hz), 7.85–7.98 (2H), 8.03–8.12 (2H), 8.58 (1H, br s), 8.70–8.91 (4H), 9.40 (1H, br s)

(60) 8-[2,6-Dichloro-3-[N-methyl-N-[4-[(2-pyridyl) carbamoyl]cinnamoylglycyl]amino]benzyloxy]-2-methylquinoline NMR (CDCl$_3$, δ): 2.71 (3H, s), 3.26 (3H, s), 3.67 (1H, dd, J=4, 16 Hz), 3.95 (1H, dd, J=4, 16 Hz), 5.64 (2H, s-like), 6.58 (1H, d, J=16 Hz), 6.86 (1H, t-like), 7.08 (1H, dd, J=5, 8 Hz), 7.18–7.35 (4H, m), 7.35–7.52 (3H, m), 7.52–7.67 (3H, m), 7.76 (1H, ddd, J=8, 8, 2 Hz), 7.91 (2H, d, J=8 Hz), 8.03 (1H, d, J=8 Hz), 8.29 (1H, dd, J=2, 5 Hz), 8.38 (1H, d, J=8 Hz), 8.75 (1H, s)

(61) 8-[2,6-Dichloro-3-[N-methyl-N-[4-[(5-tetrazolyl) carbamoyl]cinnamoylglycyl]amino]benzyloxy]-2-methylquinoline NMR (CDCl$_3$-CD$_3$OD, δ): 2.69 (3H, s), 3.27 (3H, s), 3.51–3.78 (1H, m), 4.01 (1H, d, J=17 Hz), 5.58 (2H, s), 6.67 (1H, d, J=15 Hz), 7.20–7.80 (8H, m), 7.90–8.20 (4H, m) its hydrochloride NMR (CDCl$_3$-CD$_3$OD, δ): 3.11 (3H, br s), 3.32 (3H,s), 3.92 (1H, d, J=17 Hz), 4.00 (1H, d, J=17 Hz), 5.63 (1H, d, J=9 Hz), 5.80 (1H, d, J=9 Hz), 6.77 (1H, d, J=15 Hz), 7.44–8.15 (11H, m), 8.98 (1H, m)

EXAMPLE 56

8-[2,6-Dichloro-3-[N-[4-(ethoxycarbonylacetamido) cinnamoylglycyl]-N-methylamino]benzyloxy]-2-methylquinoline was obtained by reacting 8-[3-[N-(4-aminocinnamoylglycyl)-N-methylamino]-2,6-dichlorobenzyloxyl-2-methylquinoline with ethoxycarbonylacetyl chloride according to a similar manner to that of Example 15.

NMR (CDCl$_3$, δ): 1.33 (3H, t, J=7.5 Hz), 2.73 (3H, s), 3.25 (3H, s), 3.46 (2H, s), 3.63 (1H, dd, J=4, 18 Hz), 3.93 (1H, dd, J=4, 18 Hz), 4.25 (2H, q, J=7.5 Hz), 5.63 (2H, s), 6.40 (1H, d, J=16 Hz), 6.60 (1H, t-like), 7.20–7.34 (3H, m), 7.34–7.53 (6H, m), 7.53–7.62 (2H, m), 8.02 (1H, d, J=8 Hz), 9.46 (1H, s) its hydrochloride NMR (CDCl$_3$-CD$_3$OD, δ): 1.31 (3H, t, J=7.5 Hz), 3.07 (3H, s), 3.27 (3H, s), 3.51 (2H, s), 3.87 (1H, d, J=10 Hz), 4.01 (1H, d, J=10 Hz), 4.25 (2H, q, J=7.5 Hz), 5.60 (1H, d, J=10 Hz), 5.20 (1H, d, J=10 Hz), 6.47 (1H, d, J=16 Hz), 7.32–7.43 (3H, m), 7.49–7.65 (5H, m), 7.71–7.90 (3H, m), 8.76–8.88 (1H, m)

EXAMPLE 57

8-[2,6-Dichloro-3-[N-methyl-N-[N'-(3-propionamidophenyl)ureidoacetyl]amino]benzyloxy]-2-methylquinoline was obtained by reacting 8-[3-[N-[N'-(3-aminophenyl)ureidoacety]-N-methylamino]-2,6-dichlorobenzyloxy]-2-methylquinoline with propionyl chloride according to a similar manner to that of Example 56.

NMR (CDCl$_3$, δ): 1.13 (3H, t, J=7.5 Hz), 2.27 (2H, q, J=7.5 Hz), 2.60 (3H, s), 3.18 (3H, s), 3.78–3.90 (1H, m), 3.93–4.06 (1H, m), 5.50 (1H, d, J=10 Hz), 5.60 (1H, d, J=10 Hz), 5.75–7.85 (1H, m), 6.78–6.88 (1H, m), 7.04 (1H, t, J=7.5 Hz), 7.21–7.50 (8H, m), 7.91 (1H, br s), 8.07 (1H, d, J=8 Hz), 8.26 (1H, br s) its hydrochloride NMR (CDCl$_3$-CD$_3$OD, δ): 1.11 (3H, t, J=7.5 Hz), 2.29 (2H, q, J=7.5 Hz), 2.73 (3H, s), 3.25 (3H, s), 3.84 (1H, d, J=16 Hz), 4.24 (1H, d, J=16 Hz), 5.58 (1H, d, J=10 Hz), 5.73 (1H, d, J=10 Hz), 6.78 (1H, t, J=8 Hz), 6.90 (1H, d, J=7.5 Hz), 7.14 (1H, s-like), 7.36 (1H, d, J=7.5 Hz), 7.50 (1H, d, J=8 Hz), 7.54–7.65 (2H, m), 7.65–7.80 (2H, m), 7.86 (1H, t, J=8 Hz), 8.76 (1H, d, J=8 Hz)

EXAMPLE 58

The following compounds were obtained according to similar manners to those of Examples 36, 56 or 57.

(1) 8-[2,6-Dichloro-3-[N-methyl-N-[4-[2-(1-methyl-1H-pyrrol-2-yl)acetamido]cinnamoylglycyl]amino]benzyloxy]-2-methylquinoline NMR (CDCl$_3$, δ): 2.74 (3H, s), 3.27 (3H, s), 3.55 (3H, s), 3.64 (1H, dd, J=4, 16 Hz), 3.71 (2H, s), 3.94 (1H, dd, J=4, 16 Hz), 5.65 (2H, s-like), 6.11–6.29 (2H, m), 6.40 (1H, d, J=16 Hz), 6.10 (1H, t-like), 6.64–6.70 (1H, m), 7.23–7.33 (3H, m), 7.37–7.55 (9H, m), 8.03 (1H, d, J=8 Hz) its hydrochloride NMR (CDCl$_3$-CD$_3$OD, δ): 3.13 (3H, s), 3.30 (3H, s), 3.59 (3H, s), 3.74 (2H, s), 3.88 (1H, d, J=16 Hz), 4.00 (1H, d, J=16 Hz), 5.59 (1H, d, J=10 Hz), 5.70 (1H, d, J=10 Hz), 6.47 (1H, d, J=16 Hz), 7.32–7.63 (10H, m), 7.75–7.90 (4H, m), 8.86 (1H, d, J=8 Hz)

(2) 8-[2,6-Dichloro-3-[N-methyl-N-[4-[(3-thienylcarbonyl)amino]cinnamoylglycyl]amino]benzyloxy]-2-methylquinoline NMR (CDCl$_3$, δ): 2.67 (3H, s), 3.21 (3H, s), 3.62 (1H, dd, J=4, 16 Hz), 3.90 (1H, dd, J=4, 16 Hz), 5.62 (2H, s), 6.40 (1H, d, J=16 Hz), 6.60 (1H, t-like), 7.20–7.56 (11H, m), 7.65 (2H, d, J=8 Hz), 8.00–8.09 (2H, m), 8.35 (1H, s) its hydrochloride NMR (CDCl$_3$-CD$_3$OD, δ): 3.08 (3H, s), 3.29 (3H, s), 3.91 (1H, d, J=17 Hz), 4.06 (1H, d, J=17 Hz), 5.59 (1H, d, J=10 Hz), 5.74 (1H, d, J=10 Hz), 6.49 (1H, d, J=16 Hz), 7.30–7.97 (13H, m), 8.25 (1H, d, J=2 Hz), 8.92 (1H, d, J=8 Hz)

(3) 8-[2,6-Dichloro-3-[N-methyl-N-[4-[(2-thienylcarbonyl)amino]cinnamoylglycyl]amino]benzyloxy]-2-methylquinoline NMR (CDCl$_3$-CD$_3$OD, δ): 2.60 (3H, s), 3.19 (3H, s), 3.60 (1H, d, J=16 Hz), 3.90 (1H, d, J=16 Hz), 5.53 (2H, s), 6.40 (1H, d, J=16 Hz), 7.01 (1H, t-like, J=4.5 Hz), 7.19–7.41 (6H, m), 7.41–7.55 (4H, m), 7.64 (2H, d, J=8 Hz), 7.80 (1H, d, J=4.5 Hz), 8.06 (1H, d, J=8 Hz) its hydrochloride NMR (CDCl$_3$-CD$_3$OD, δ): 3.10 (3H, s), 3.30 (3H, s), 3.83–4.18 (2H, m), 5.59 (1H, d, J=10 Hz), 5.71 (1H, d, J=10 Hz), 6.49 (1H, d, J=16 Hz), 7.11–7.18 (1H, m), 7.25–7.46 (3H, m), 7.46–7.98 (10H, m), 8.90 (1H, d, J=7.5 Hz)

(4) 8-[2,6-Dichloro-3-[N-[4-[(2-furylcarbonyl)amino] cinnamoylglycyl]-N-methylamino]benzyloxy]-2-methylquinoline NMR (CDCl$_3$, δ): 2.73 (3H, s), 3.26 (3H, s), 3.65 (1H, dd, J=4, 16 Hz), 3.94 (1H, dd, J=4, 16 Hz), 5.64 (2H, s), 6.43 (1H, d, J=16 Hz), 6.54–6.58 (1H, m), 6.61 (1H, t-like), 7.20–7.34 (4H, m), 7.37–7.60 (7H, m), 7.68 (2H, d, J=8 Hz), 8.03 (1H, d, J=8 Hz), 8.20 (1H, s) its hydrochloride NMR (CDCl$_3$-CD$_3$OD, δ): 3.16 (3H, s), 3.30 (3H, s), 3.90 (1H, d, J=16 Hz), 4.05 (1H, d, J=16 Hz), 5.61 (1H, d, J=10 Hz), 5.72 (1H, d, J=10 Hz), 6.48–6.61 (2H, m), 7.24–7.37 (1H, m), 7.37–7.50 (3H, m), 7.50–7.60 (3H, m), 7.60–7.70 (3H, m), 7.76–7.94 (3H, m), 8.89 (1H, d, J=8 Hz)

(5) 8-[2,6-Dichloro-3-[N-[4-[(3-furylcarbonyl)amino] cinnamoylglycyl]-N-methylamino]benzyloxy]-2-methylquinoline NMR (CDCl$_3$-CD$_3$OD, δ): 2.63 (3H, s), 3.20 (3H, s), 3.60 (1H, d, J=16 Hz), 3.93 (1H, d, J=16 Hz), 5.55 (2H, s), 6.40 (1H, d, J=16 Hz), 6.85 (1H, d-like), 7.20–7.50 (10H, m), 7.63 (2H, d, J=8 Hz), 8.06 (1H, d, J=8 Hz), 8.13 (1H, s) its hydrochloride NMR (CDCl$_3$-CD$_3$OD, δ): 3.09 (3H, s), 3.29 (3H, s), 3.90 (1H, d, J=16 Hz), 4.08 (1H, d, J=16 Hz), 5.58 (1H, d, J=10 Hz), 5.71 (1H, d, J=10 Hz), 6.46 (1H, d, J=16 Hz), 6.95 (1H, s-like), 7.49 (2H, d, J=7.5 Hz), 7.45–7.48 (1H, m), 7.55 (1H, s-like), 7.60–7.75 (4H, m), 7.75–7.93 (4H, m), 8.25 (1H, s-like), 8.90 (1H, d, J=8 Hz)

(6) 8-[2,6-Dichloro-3-[N-methyl-N-[4-[(3-thienyl) acetamido]cinnamoylglycyl]amino]benzyloxy]-2-methylquinoline NMR (CDCl$_3$-CD$_3$OD, δ): 2.70 (3H, s), 3.25 (3H, s), 3.63 (1H, dd-like, J=16 Hz), 3.76 (2H, s), 3.93 (1H, dd, J=4, 16 Hz), 5.65 (2H, s), 6.40 (1H, d, J=16 Hz), 6.55–6.64 (1H, m), 7.03–7.09 (1H, m), 7.16–7.34 (4H, m), 7.34–7.57 (10H, m), 8.04 (1H, d, J=8 Hz) its hydrochloride NMR (CDCl$_3$-CD$_3$OD, δ): 3.07 (3H, s), 3.27 (3H, s), 3.76 (2H, s), 3.90 (1H, d, J=16 Hz), 4.04 (1H, d, J=16 Hz), 5.58 (1H, d, J=10 Hz), 5.70 (1H, d, J=10 Hz), 6.45 (1H, d, J=16 Hz), 7.13 (1H, d, J=5 Hz), 7.21–7.70 (9H, m), 7.70–7.92 (4H, m), 8.88 (1H, d, J=8 Hz)

(7) 8-[3-[N-(4-Acryloylaminocinnamoylglycyl)-N-methylamino]-2,6-dichlorobenzyloxy]-2-methylquinoline NMR (CDCl$_3$, δ): 2.66 (3H, s), 3.23 (3H, s), 3.62 (1H, dd, J=4, 16 Hz), 3.89 (1H, dd, J=4, 16 Hz), 5.70 (1H, d, J=10 Hz), 6.23 (1H, d, J=16 Hz), 6.35–6.45 (2H, m), 6.62 (1H, t-like), 7.21–7.56 (9H, m), 7.61 (2H, d, J=8 Hz), 8.05 (1H, d, J=8 Hz), 8.30 (1H, s) its hydrochloride NMR (CDCl$_3$-CD$_3$OD, δ): 3.08 (3H, s), 3.30 (3H, s), 3.91 (1H, d, J=16 Hz), 4.07 (1H, d, J=16 Hz), 5.57 (1H, d, J=10 Hz), 5.65–5.80 (2H, m), 6.35–6.55 (2H, m), 7.24–7.35 (4H, m), 7.53 (2H, s-like), 7.58–7.70 (3H, m), 7.75–7.91 (3H, m), 8.90 (1H, d, J=8 Hz)

(8) 8-[2,6-Dichloro-3-[N-methyl-N-(4-trifluoroacetamido-cinnamoylglycyl)amino]benzyloxy]-2-methylquinoline NMR (CDCl$_3$, δ): 2.60 (3H, s), 3.17 (3H, s), 3.58 (1H, dd, J=4, 16 Hz), 3.83 (1H, dd, J=4, 16 Hz), 5.54 (2H, s-like), 6.41 (1H, d, J=16 Hz), 6.79 (1H, t-like), 7.14 (1H, d, J=8 Hz), 7.20–7.33 (3H, m), 7.33–7.55 (5H, m), 7.71 (2H, d, J=8 Hz), 8.07 (1H, d, J=8 Hz) its hydrochloride NMR (CDCl$_3$-CD$_3$OD, δ): 3.15 (3H, s), 3.30 (3H, s), 3.90 (1H, d, J=16 Hz), 4.12 (1H, d, J=16 Hz), 5.60 (1H, d, J=10 Hz), 5.70 (1H, d, J=10 Hz), 6.56 (1H, d, J=16 Hz), 7.31–7.50 (3H, m), 7.55 (2H, s-like), 7.58–7.66 (3H, m), 7.77–7.94 (3H, m), 8.87 (1H, d, J=8 Hz)

(9) 8-[2,6-Dichloro-3-[N-[4-(ethoxycarbonylamino) cinnamoylglycyl]-N-methylamino]benzyloxy]-2-methylquinoline NMR (CDCl$_3$, δ): 1.30 (3H, t, J=7.5 Hz), 2.72 (3H, s), 3.25 (3H, s), 3.63 (1H, dd, J=4, 18 Hz), 3.93 (1H, dd, J=4, 18 Hz), 4.23 (2H, q, J=7.5 Hz), 5.63 (2H, s), 6.39 (1H, d, J=16 Hz), 6.61 (1H, t-like), 6.79 (1H, s), 7.20–7.59 (11H, m), 8.02 (1H, d, J=8 Hz) its hydrochloride NMR (CDCl$_3$-CD$_3$OD): 1.27 (3H, t, J=7.5 Hz), 3.07 (3H, s), 3.26 (3H, s), 3.83 (1H, d, J=16 Hz), 3.95 (1H, d, J=16 Hz), 4.18 (2H, q, J=7.5 Hz), 5.54 (1H, d, J=10 Hz), 5.69 (1H, d, J=10 Hz), 6.40 (1H, d, J=16 Hz), 7.29–7.45 (5H, m), 7.45–7.65 (3H, m), 7.70–7.91 (3H, m), 8.86 (1H, d, J=8 Hz)

(10) 8-[2,6-Dichloro-3-[N-methyl-N-[4-(nicotinoylamino) cinnamoylglycyl]amino]benzyloxy]2-methylquinoline NMR (CDCl$_3$, δ): 2.56 (3H, s), 3.16 (3H, s), 3.60 (1H, dd, J=4, 17.5 Hz), 3.88 (1H, dd, J=4, 17.5 Hz), 5.55 (2H, s), 6.38 (1H, d, J=16 Hz), 6.72 (1H, t-like), 7.10–7.35 (5H, m), 7.35–7.60 (5H, m), 7.70 (2H, d, J=8 Hz), 8.05 (1H, d, J=8 Hz), 8.24 (1H, dif.-dd, J=8 Hz), 8.66 (1H, d, J=5 Hz), 9.11 (1H, d, J=1 Hz), 9.29 (1H, s) its dihydrochloride NMR (DMSO-d$_6$, δ): 2.91 (3H, s), 3.15 (3H, s), 3.90 (1H, dd, J=4, 17 Hz), 5.91 (1H, d, J=10 Hz), 5.67 (1H, d, J=10 Hz), 6.75 (1H, d, J=16 Hz), 7.38 (1H, d, J=16 Hz), 7.59 (2H, d, J=8 Hz), 7.74 (1H, dd, J=5, 8 Hz), 7.79–7.99 (7H, m), 8.31 (1H, t, J=5 Hz), 8.51 (1H, d, J=8 Hz), 8.86 (1H, d, J=5 Hz), 8.98 (1H, dif.-d), 9.23 (1H, s-like)

(11) 8-[2,6-Dichloro-3-[N-methyl-N-[4-(2-pyridinecarboxamido)cinnamoylglycyl]amino]benzyloxy]-2-methylquinoline NMR (CDCl$_3$, δ): 2.74 (3H, s), 3.26 (3H, s), 3.65 (1H, dd, J=4, 18 Hz), 3.96 (1H, dd, J=4, 18 Hz), 5.65 (2H, s), 6.45 (1H, d, J=16 Hz), 6.60 (1H, t-like), 7.21–7.40 (3H, m), 7.40–7.65 (7H, m), 7.81 (2H, d, J=8 Hz), 7.93 (1H, td, J=8 Hz, 1 Hz), 8.03 (1H, d, J=8 Hz), 8.30 (1H, d, J=8 Hz), 8.63 (1H, d, J=5 Hz), 10.13 (1H, s) its dihydrochloride NMR (CMSO-d$_6$, δ): 2.90 (3H, s), 3.15 (3H, s), 3.90 (1H, dd, J=4, 18 Hz), 5.60 (1H, d, J=10 Hz), 5.66 (1H, d, J=10 Hz), 6.74 (1H, d, J=16 Hz), 7.38 (1H, d, J=16 Hz), 7.58 (2H, d, J=8 Hz), 7.66–7.75 (1H, m), 7.78–8.04 (8H, m), 8.09 (1H, t, J=7.5 Hz), 8.19 (1H, d, J=7.5 Hz), 8.30 (1H, t, J=5 Hz), 8.76 (1H, d, J=5 Hz), 8.90 (1H, br)

(12) 8-[2,6-Dichloro-3-[N-(4-isobutyramidocinnamoylglycyl)-N-methylamino]benzyloxy]-2-methylquinoline NMR (CDCl$_3$, δ): 1.24 (6H, d, J=7.5 Hz), 2.50 (1H, m, J=7.5 Hz), 2.73 (3H, s), 3.27 (3H, s), 3.64 (1H, dd, J=18, 4 Hz), 3.94 (1H, dd, J=18, 4 Hz), 5.63 (1H, d, J=10 Hz), 5.64 (1H, d, J=10 Hz), 6.41 (1H, d, J=15 Hz), 6.60 (1H, t-like), 7.23–7.36 (2H, m), 7.36–7.60 (9H, m), 8.03 (1H, d, J=8 Hz) its hydrochloride NMR (DMSO-d$_6$, δ): 1.09 (6H, d, J=7.5 Hz), 2.60 (1H, m), 2.85 (3H, s), 3.13 (3H, s), 3.86 (1H, dd, J=4, 17 Hz), 5.51–5.78 (2H, m), 6.66 (1H, d, J=16 Hz), 7.31 (1H, d, J=16 Hz), 7.49 (1H, d, J=8 Hz), 7.66 (2H, d, J=8 Hz), 7.73–7.93 (6H, m), 8.25 (1H, t, J=5 Hz)

(13) 8-[3-[N-[4-(Acetylglycylamino)cinnamoylglycyl]-N-methylamino]-2,6-dichlorobenzyloxy]-2-methylquinoline NMR (CDCl$_3$, δ): 1.94 (3H, s), 2.66 (3H, s), 3.20 (3H, s), 3.60 (1H, dd, J=4, 18 Hz), 3.80–4.04 (3H, m), 5.55 (2H, s), 6.37 (1H, d, J=16 Hz), 7.10–7.60 (11H, m), 8.03 (1H, d, J=8 Hz) its hydrochloride NMR (DMSO-d$_6$, δ): 1.87 (3H, s), 2.87 (3H, s), 3.11 (3H, s), 3.80–3.91 (3H, m), 5.55–5.68 (2H, m), 6.66 (1H, d, J=16 Hz), 7.31 (1H, d, J=16 Hz), 7.50 (2H, d, J=8 Hz), 7.64 (2H, d, J=8 Hz), 7.75–7.97 (5H, m), 8.19–8.32 (2H, m)

(14) 8-[2,6-Dichloro-3-[N-methyl-N-[4-[(dimethylamino) acetamido]cinnamoylglycyl]amino]benzyloxy]-2-methylquinoline NMR (CDCl$_3$, δ): 2.35 (6H, s), 2.70 (3H, s), 3.07 (2H, s), 3.25 (3H, s), 3.63 (1H, dd, J=4, 18 Hz), 3.90 (1H, dd, J=4, 18 Hz), 5.60 (2H, s), 6.41 (1H, d, J=16 Hz), 6.69 (1H, t-like), 7.20–7.35 (3H, m), 7.36–7.49 (5H, m), 7.52 (1H, d, J=16 Hz), 7.60 (2H, d, J=8 Hz), 8.04 (1H, d, J=8 Hz), 9.22 (1H, s) its dihydrochloride NMR (DMSO-d$_6$, δ): 2.76–2.93 (9H, m), 3.12 (3H, s), 3.86 (1H, dif.-dd, J=16 Hz), 4.11–4.21 (2H, m), 5.52–5.63 (2H, m), 6.70 (1H, d, J=16 Hz), 7.35 (1H, d, J=16 Hz), 7.55 (2H, d, J=8 Hz), 7.66 (2H, d, J=8 Hz), 7.70–7.94 (6H, m), 8.25–8.34 (1H, m) (15) 8-(2,6-Dichloro-3-[N-[4-(3-methoxypropionamido)cinnamoylglycyl]-N-methylamino] benzyloxy)-2-methylquinoline NMR (CDCl$_3$, δ): 2.57 (2H, t, J=6 Hz), 2.68 (3H, s), 3.24 (3H, s), 3.40 (3H, s), 3.54–3.75 (3H, m), 3.90 (1H, dd, J=17.5, 4 Hz), 5.60 (2H, s), 6.69 (1H, t-like), 7.17–7.33 (3H, m), 7.33–7.48 (5H, m), 7.48–7.80 (3H, m), 8.03 (1H, d, J=8 Hz), 8.89 (1H, s) its hydrochloride NMR (CDCl$_3$-CD$_3$OD, δ): 2.63 (2H, t, J=6 Hz), 3.09 (3H, s), 3.30 (3H, s), 3.40 (3H, s), 3.74 (2H, t, J=6 Hz), 3.93 (2H, s), 5.59 (1H, d, J=10 Hz), 5.77 (1H, d, J=10 Hz), 6.46 (1H, d, J=16 Hz), 7.28–7.40 (1H, m), 7.43 (2H, d, J=8 Hz), 7.48–7.76 (5H, m), 7.80–7.99 (3H, m), 8.95 (1H, d, J=8Hz)

(16) 8-[2,6-Dichloro-3-[N-methyl-N-[4-[(2-thienyl) acetamido]cinnamoylglycyl]amino]benzyloxy]-2-methylquinoline NMR (CDCl$_3$, δ): 2.70 (3H, s), 3.24 (3H, s), 3.62 (1H, dd, J=4, 16 Hz), 3.85–3.97 (3H, m), 5.58–5.68 (2H, m), 6.38 (1H, d, J=16 Hz), 6.59 (1H, t-like), 6.93–7.00 (1H, m), 7.00–7.05 (1H, m), 7.22–7.32 (2H, m), 7.36–7.54 (8H, m), 7.74 (1H, s), 8.03 (1H, d, J=8 Hz) its hydrochloride NMR (CD$_3$OD, δ): 2.99 (3H, s), 3.76–3.94 (3H, m), 4.00 (1H, d, J=16 Hz), 5.70 (1H, d, J=10 Hz), 5.80 (1H, d, J=10 Hz), 6.60 (1H, d, J=16 Hz), 6.92–7.07 (2H, m), 7.23–7.35 (1H, m), 7.35–7.80 (7H, m), 7.80–8.04 (4H, m), 9.02 (1H, d, J=8 Hz)

(17) 8-[2,6-Dichloro-3-[N-methyl-N-[N'-[3-(4-pyridylacetamido)phenyl]ureidoacetyl]amino]benzyloxy]-2-methylquinoline NMR (CDCl$_3$, δ): 2.51 (3H, s), 3.13 (3H, s), 3.53 (2H, s), 3.85 (1H, br s), 5.51 (2H, s), 5.59 (1H, br s), 6.88–7.38 (8H, m), 7.38–7.56 (4H, m), 8.07 (1H, d, J=8 Hz), 8.40–8.50 (3H, m) its dihydrochloride NMR (CDCl$_3$-CD$_3$OD, δ): 2.78 (3H, s), 3.21 (3H, s), 3.80 (1H, d, J=16 Hz), 3.98 (1H, d, J=16 Hz), 4.07 (2H, s), 5.53 (1H, d, J=10 Hz), 5.67 (1H, d, J=10 Hz), 6.74–6.86 (2H, m), 7.29–7.38 (1H, m), 7.43–7.53 (3H, m), 7.66–7.89 (3H, m), 8.04 (2H, d, J=6 Hz), 8.60 (2H, d, J=6 Hz), 8.79 (1H, d, J=8 Hz)

(18) 8-[2,6-Dichloro-3-[N-methyl-N-[N'-[3-(isonicotinoylamino)phenyl]ureidoacetyl]amino] benzyloxy]-2-methylquinoline NMR (CDCl$_3$-CD$_3$OD, δ): 2.64 (3H, s), 3.22 (3H, s), 3.77–3.95 (3H, m), 5.53 (1H, d, J=10 Hz), 5.60 (1H, d, J=10 Hz), 5.88–5.96 (1H, m), 6.78–6.86 (1H, m), 7.15 (1H, t, J=7.5 Hz), 7.21–7.50 (6H, m), 7.55–7.66 (2H, m), 7.71–7.80 (2H, m), 8.07 (1H, d, J=8 Hz), 8.70 (2H, d, J=6 Hz) its dihydrochloride NMR (CDCl$_3$-CD$_3$OD, δ): 2.92 (3H, s), 3.24 (3H, s), 3.85 (1H, d, J=16 Hz), 4.05 (1H, d, J=16 Hz), 5.56 (1H, d, J=10

Hz), 5.71 (1H, d, J=10 Hz), 6.90–7.07 (2H, m), 7.38–7.67 (5H, m), 7.67–7.89 (3H, m), 8.42–8.60 (2H, m), 8.75–8.99 (3H, m)

(19) 8-[2,6-Dichloro-3-[N-methyl-N-[N'-(3-methoxyacetamidophenyl)ureidoacetyl]amino]benzyloxy]-2-methylquinoline NMR (CDCl$_3$, δ): 2.60 (3H, s), 3.23 (3H, s), 3.46 (3H, s), 3.80 (1H, dd, J=4, 16 Hz), 3.96 (2H, s), 4.27 (1H, dd, J=7.5, 16 Hz), 5.48 (1H, d, J=10 Hz), 5.54 (1H, t-like), 5.66 (1H, d, J=10 Hz), 6.70 (1H, d, J=8 Hz), 7.05 (1H, t, J=7.5 Hz), 7.22–7.38 (4H, m), 7.38–7.50 (3H, m), 7.58 (1H, t-like), 8.08 (1H, d, J=8 Hz), 8.19 (1H, s), 8.28 (1H, s) its hydrochloride NMR (CDCl$_3$-CD$_3$OD, δ): 2.78 (3H, s), 3.25 (3H, s), 3.41 (3H, s), 3.63 (1H, d, J=16 Hz), 3.73–3.91 (2H, m), 4.32 (1H, d, J=16 Hz), 5.60 (1H, d, J=10 Hz), 5.74 (1H, d, J=10 Hz), 6.97 (2H, d, J=5 Hz), 7.20–7.27 (1H, m), 7.31 (1H, s-like), 7.50 (1H, d, J=8 Hz), 7.58–7.65 (2H, m), 7.65–7.80 (2H, m), 7.86 (1H, t, J=7.5 Hz), 8.77 (1H, d, J=8 Hz)

(20) 8-[2,6-Dichloro-3-[N-methyl-N-[(E)-3-[6-(propionamido)pyridin-3-yl]acryloylglycyl]amino]benzyloxy]-2-methylquinoline NMR (CDCl$_3$, δ): 1.26 (3H, t, J=7.5 Hz), 2.45 (2H, q, J=7.5 Hz), 2.72 (3H, s), 3.28 (3H, s), 3.68 (1H, dd, J=17, 4 Hz), 3.94 (1H, dd, J=17, 5 Hz), 5.62 (1H, d, J=10 Hz), 5.68 (1H, d, J=10 Hz), 6.48 (1H, d, J=15 Hz), 6.69 (1H, br t, J=4 Hz), 7.21–7.32 (3H), 7.39–7.57 (4H), 7.82 (1H, dd, J=7.5, 2 Hz), 7.99 (1H, br s), 8.02 (1H, d, J=7.5 Hz), 8.21 (1H, d, J=7.5 Hz), 8.34 (1H, d, J=2 Hz) its dihydrochloride NMR (CDCl$_3$-CD$_3$OD, δ): 1.27 (3H, t, J=7.5 Hz), 2.78 (2H, q, J=7.5 Hz), 3.22 (3H, s), 3.28 (3H, s), 3.93 (1H, d, J=17 Hz), 4.27 (1H, d, J=17 Hz), 5.59 (1H, d, J=10 Hz), 5.64 (1H, d, J=10 Hz), 6.95 (1H, d, J=15 Hz), 7.52 (2H, s), 7.57–7.70 (2H), 7.85–8.12 (5H), 8.97–9.02 (2H)

(21) 8-[3-[N-[(E)-3-[6-(Acrylamido)pyridin-3-yl]acryloylglycyl]-N-methylamino]-2,6-dichlorobenzyloxy]-2-methylquinoline NMR (CDCl$_3$, δ): 2.72 (3H, s), 3.28 (3H, s), 3.68 (1H, dd, J=17, 4 Hz), 3.94 (1H, dd, J=17, 5 Hz), 5.62 (1H, d, J=10 Hz), 5.68 (1H, d, J=10 Hz), 5.84 (1H, d, J=10 Hz), 6.29 (1H, dd, J=15, 10 Hz), 6.49 (1H, d, J=15 Hz), 6.70 (1H, br t, J=4 Hz), 7.22–7.58 (7H), 7.87 (1H, dd, J=7.5, 2 Hz), 8.02 (1H, d, J=7.5 Hz), 8.21 (1H, br s), 8.30 (1H, d, J=7.5 Hz), 8.38 (1H, d, J=2 Hz) its dihydrochloride NMR (CDCl$_3$-CD$_3$OD, δ): 3.21 (3H, s), 3.26 (3H, s), 3.92 (1H, d, J=17 Hz), 4.32 (1H, d, J=17 Hz), 5.58 (1H, d, J=10 Hz), 5.63 (1H, d, J=10 Hz), 5.84 (1H, dd, J=10, 2 Hz), 6.70–6.78 (2H), 6.94 (1H, d, J=15 Hz), 7.48–7.64 (4H), 7.80–7.94 (3H), 8.10 (1H, br d, J=7.5 Hz), 8.31 (1H, br d, J=7.5 Hz), 8.92 (1H, d, J=7.5 Hz), 8.99 (1H, br s)

(22) 8-(2,6-Dichloro-3-[N-methyl-N-[(E)-3-[6-(isonicotinoylamino)pyridin-3-yl]acryloylglycyl]amino]benzyloxy]-2-methylquinoline NMR (CDCl$_3$, δ): 2.73 (3H, s), 3.28 (3H, s), 3.69 (1H, dd, J=17, 4 Hz), 3.95 (1H, dd, J=17, 5 Hz), 5.66 (2H, s), 6.52 (1H, d, J=15 Hz), 6.72 (1H, br s), 7.24–7.34 (3H), 7.39–7.52 (3H), 7.57 (1H, d, J=15 Hz), 7.77 (2H, d, J=6 Hz), 7.92 (1H, dd, J=7.5, 2 Hz), 8.03 (1H, d, J=7.5 Hz), 8.42 (1H, d, J=2 Hz), 8.71 (1H, s), 8.84 (2H, d, J=6 Hz) its trihydrochloride NMR (CDCl$_3$-CD$_3$OD, δ): 3.18 (3H, s), 3.29 (3H, s), 3.92 (1H, d, J=17 Hz), 4.24 (1H, d, J=17 Hz), 5.57 (1H, d, J=10 Hz), 5.73 (1H, d, J=10 Hz), 7.06 (1H, br d, J=15 Hz), 7.47 (1H, d, J=15 Hz), 7.56–7.69 (3H), 7.81 (1H, d, J=7.5 Hz), 7.90 (1H, t, J=7.5 Hz), 7.98 (1H, d, J=7.5 Hz), 8.67 (2H, s), 8.89 (1H, d, J=7.5 Hz), 8.91–8.99 (2H), 9.05–9.14 (3H)

(23) 8-[2,6-Dichloro-3-[N-[(E)-3-(6-(ethoxycarbonylacetamido)pyridin-3-yl]acryloylglycyl]-N-methylamino)benzyloxy]-2-methylquinoline NMR (CDCl$_3$, δ): 1.32 (3H, t, J=7.5 Hz), 2.73 (3H, s), 3.28 (3H, s), 3.50 (2H, s), 3.68 (1H, dd, J=17, 4 Hz), 3.95 (1H, dd, J=17, 5 Hz), 4.28 (2H, q, J=7.5 Hz), 5.62 (1H, d, J=10 Hz), 5.69 (1H, d, J=10 Hz), 6.49 (1H, d, J=15 Hz), 6.69 (1H, br s), 7.22–7.33 (3H), 7.39–7.49 (3H), 7.52 (1H, d, J=15 Hz), 7.82 (1H, dd, J=7.5, 2 Hz), 8.02 (1H, d, J=7.5 Hz), 8.18 (1H, br d, J=7.5 Hz), 8.40 (1H, d, J=2 Hz), 9.59 (1H, s) its dihydrochloride NMR (CDCl$_3$-CD$_3$OD, δ): 1.30 (3H, t, J=7.5 Hz), 3.21 (3H, br s), 3.28 (3H, s), 3.79 (1H, d, J=8 Hz), 3.91 (1H, d, J=17 Hz), 4.18–4.28 (3H), 4.32 (1H, d, J=17 Hz), 5.59 (1H, d, J=10 Hz), 5.64 (1H, d, J=10 Hz), 6.96 (1H, br d, J=15 Hz), 7.42–7.64 (4H), 7.79–7.93 (3H), 8.05 (1H, m), 8.35 (1H, m), 8.88–8.96 (2H)

(24) 8-[3-[N-[N'-[3-(Benzamido)phenyl]ureidoacetyl]-N-methylamino]-2,6-dichlorobenzyloxy]-2-methylquinoline NMR (CDCl$_3$, δ): 2.60 (3H, s), 3.15 (3H, s), 3.81 (1H, dd, J=17, 5 Hz), 3.99 (1H, br dd, J=17, 5 Hz), 5.49 (1H, d, J=10 Hz), 5.60 (1H, d, J=10 Hz), 5.85 (1H, br s), 6.82 (1H, br d, J=8 Hz), 7.09 (1H, t, J=8 Hz), 7.23–7.59 (10H), 7.62 (1H, br s), 7.83 (2H, d, J=8 Hz), 8.06 (1H, d, J=8 Hz), 8.30–8.41 (2H) its hydrochloride NMR (CDCl$_3$-CD$_3$OD, δ): 2.66 (3H, br s), 3.26 (3H, s), 3.85 (1H, br d, J=17 Hz), 4.36 (1H, br d, J=17 Hz), 5.59 (1H, d, J=10 Hz), 5.71 (1H, d, J=10 Hz), 6.91 (1H, t, J=8 Hz), 6.99 (1H, br d, J=8 Hz), 7.37 (1H, br s), 7.39–7.58 (6H), 7.62 (1H, d, J=8 Hz), 7.68 (2H, d, J=8 Hz), 7.72–7.82 (3H), 8.71 (1H, d, J=8 Hz)

(25) 8-[3-[N-[4-(Cyclohexanecarboxamido)cinnamoylglycyl]-N-methylamino]-2,6-dichlorobenzyloxy]-2-methylquinoline NMR (CDCl$_3$, δ): 1.18–1.99 (10H), 2.20 (1H, m), 2.72 (3H, s), 3.26 (3H, s), 3.64 (1H, dd, J=17, 4 Hz), 3.93 (1H, dd, J=17, 5 Hz), 5.61 (1H, d, J=10 Hz), 5.67 (1H, d, J=10 Hz), 6.39 (1H, d, J=15 Hz), 6.61 (1H, br t, J=4 Hz), 7.22–7.59 (12H), 8.02 (1H, d, J=8 Hz) its hydrochloride NMR (CDCl$_3$-CD$_3$OD, δ): 1.20–1.98 (10H), 2.38 (1H, m), 3.12 (3H, br s), 3.29 (3H, s), 3.91 (1H, br d, J=17 Hz), 4.10 (1H, br d, J=17 Hz), 5.59 (1H, d, J=10 Hz), 5.69 (1H, d, J=10 Hz), 6.48 (1H, d, J=15 Hz), 7.26–7.38 (3H), 7.50–7.65 (5H), 7.77–7.90 (3H), 8.90 (1H, d, J=8 Hz)

(26) 8-[2,6-Dichloro-3-[N-methyl-N-[4-[(4-methyl-5-oxazolylcarbonyl)amino]cinnamoylglycyl]amino]benzyloxy]-2-methylquinoline mp: 141–148° C.

NMR (CDCl$_3$, δ): 2.58 (3H, s), 2.70 (3H, s), 3.24 (3H, s), 3.63 (1H, dd, J=16.5, 4.5 Hz), 3.93 (1H, dd, J=16.5, 4.5 Hz), 5.61 (1H, d, J=11.0 Hz), 5.66 (1H, d, J=11.0 Hz), 6.43 (1H, d, J=15.0 Hz), 6.62 (1H, br t, J=4.5 Hz), 7.23–7.32 (3H, m), 7.37–7.54 (5H, m), 7.54 (1H, d, J=15.0 Hz), 7.65 (2H, d, J=8.5 Hz), 7.77 (1H, s), 8.03 (1H, d, J=8.5 Hz), 8.16 (1H, s) its dihydrochloride mp: 160.5–164.5° C.

NMR (CDCl$_3$-CD$_3$OD, δ): 2.57 (3H, s), 3.11 (3H, s), 3.30 (3H, s), 3.89 (1H, d, J=16.0 Hz), 4.04 (1H, d, J=16.0 Hz), 5.60 (1H, d, J=9.0 Hz), 5.73 (1H, d, J=9.0 Hz), 6.53 (1H, d, J=16.0 Hz), 7.41 (1H, d, J=16.0 Hz), 7.47 (2H, d, J=8.5 Hz), 7.55 (2H, s), 7.63–7.72 (3H, m), 7.79–7.95 (3H, m), 7.97 (1H, s), 8.93 (1H, d, J=8.5 Hz)

(27) 8-[2,6-Dichloro-3-[N-methyl-N-[4-[(2-methyl-4-oxazolylcarbonyl)amino]cinnamoylglycyl]amino]benzyloxy]-2-methylquinoline NMR (CDCl$_3$, δ): 2.52 (3H, s), 2.73 (3H, s), 3.26 (3H, s), 3.63 (1H, dd, J=17, 4 Hz), 3.94 (1H, dd, J=17, 5 Hz), 5.62 (1H, d, J=10 Hz), 5.68 (1H, d, J=10 Hz), 6.42 (1H, d, J=15 Hz), 6.60 (1H, br t, J=4 Hz), 7.23–7.33 (3H), 7.39–7.59 (6H), 7.69 (2H, d, J=8 Hz), 8.02 (1H, d, J=8 Hz), 8.18 (1H, s), 8.73 (1H, s) its dihydrochloride NMR (CDCl$_3$-CD$_3$OD, δ): 2.54 (3H, s), 3.16 (3H, s), 3.31 (3H, s), 3.90 (1H, d, J=17 Hz), 4.01 (1H, d, J=17 Hz), 5.61

(1H, d, J=10 Hz), 5.72 (1H, d, J=10 Hz), 6.53 (1H, d, J=15 Hz), 7.41–7.51 (3H), 7.54 (1H, d, J=8 Hz), 7.59 (1H, d, J=8 Hz), 7.63–7.71 (3H), 7.79–7.93 (3H), 8.25 (1H, s), 8.91 (1H, d, J=8 Hz)

(28) 8-[2,6-Dichloro-3-[N-[4-[(3,5-dimethyl-4-isoxazolylcarbonyl)amino]cinnamoylglycyl]-N-methylamino]benzyloxy]-2-methylquinoline NMR (CDCl₃, δ): 2.50 (3H, s), 2.69 (3H, s), 2.74 (3H, s), 3.28 (3H, s), 3.67 (1H, dd, J=17, 4 Hz), 3.94 (1H, dd, J=17, 5 Hz), 5.63 (1H, d, J=10 Hz), 5.68 (1H, d, J=10 Hz), 6.44 (1H, d, J=15 Hz), 6.65 (1H, br t, J=4 Hz), 7.23–7.61 (12H), 8.04 (1H, d, J=8 Hz) its hydrochloride NMR (CDCl₃-CD₃OD, δ): 2.47 (3H, s), 2.64 (3H, s), 3.17 (3H, br s), 3.30 (3H, s), 3.91 (1H, d, J=17 Hz), 4.10 (1H, d, J=17 Hz), 5.60 (1H, d, J=10 Hz), 5.71 (1H, d, J=10 Hz), 6.52 (1H, d, J=15 Hz), 7.34–7.48 (3H), 7.53 (2H, s), 7.62 (3H, d, J=8 Hz), 7.79 (1H, d, J=8 Hz), 7.83–7.91 (2H), 8.88 (1H, d, J=8 Hz)

(29) 8-[3-[N-[4-[(N-tert-Butoxycarbonyl-L-prolyl)amino]cinnamoylglycly]-N-methylamino]-2,6-dichlorobenzyloxy]-2-methylquinoline NMR (CDCl₃, δ): 1.49 (9H, br s), 1.83–2.03 (4H), 2.70 (3H, s), 3.26 (3H, s), 3.29–3.69 (3H), 3.93 (1H, dt, J=17, 5 Hz), 4.46 (1H, m), 5.63 (2H, s), 6.39 (1H, d, J=15 Hz), 6.62 (1H, m), 7.20–7.57 (12H), 8.02 (1H, d, J=8 Hz)

(30) 8-[2,6-Dichloro-3-[N-[4-[(1-ethylpiperidine-4-carbonyl)amino]cinnamoylglycyl]-N-methylamino]benzyloxy]-2-methylquinoline NMR (CDCl₃, δ): 1.11–1.22 (3H), 1.62–2.10 (9H), 2.72 (3H, s), 3.04–3.17 (2H), 3.27 (3H, s), 3.64 (1H, dd, J=17, 4 Hz), 3.94 (1H, dd, J=17, 5 Hz), 5.65 (2H, br s), 6.40 (1H, d, J=15 Hz), 6.61 (1H, m), 7.21–7.61 (12H), 8.03 (1H, d, J=8 Hz) its dihydrochloride NMR (CDCl₃-CD₃OD, δ): 1.42 (3H, t, J=7.5 Hz), 2.10–2.47 (4H), 2.98–3.19 (8H), 3.28 (3H, s), 3.49–3.59 (2H), 3.92 (1H, d, J=17 Hz), 4.08 (1H, d, J=17 Hz), 5.58 (1H, d, J=10 Hz), 5.71 (1H, d, J=10 Hz), 6.43 (1H, d, J=15 Hz), 7.24 (2H, d, J=8 Hz), 7.38 (1H, m), 7.52–7.69 (5H), 7.80–7.95 (3H), 8.95 (1H, d, J=8 Hz)

(31) 8-[2,6-Dichloro-3-[N-[(E)-3-[6-(methoxyacetamido)pyridin-3-yl]acryloylglycyl]-N-methylamino]benzyloxy]-2-methylquinoline NMR (CDCl₃, δ): 2.73 (3H, s), 3.26 (3H, s), 3.51 (3H, s), 3.67 (1H, dd, J=16.5, 5.5 Hz), 3.93 (1H, dd, J=16.5, 5.5 Hz), 4.03 (2H, s), 5.63 (1H, d, J=11.0 Hz), 5.68 (1H, d, J=11.0 Hz), 6.49 (1H, d, J=16.0 Hz), 6.67 (1H, br t, J=5.5 Hz), 7.22–7.35 (3H, m), 7.38–7.53 (3H, m), 7.53 (1H, d, J=16.0 Hz), 7.85 (1H, dd, J=8.5, 1.5 Hz), 8.03 (1H, d, J=8.5 Hz), 8.25 (1H, d, J=8.5 Hz), 8.40 (1H, d, J=1.5 Hz), 8.93 (1H, s) its dihydrochloride mp: 142–146° C.

NMR (DMSO-d₆, δ): 2.91 (3H, s), 3.13 (3H, s), 3.36 (3H, s), 3.59 (1H, dd, J=16.0, 5.5 Hz), 3.90 (1H, dd, J=16.0, 5.5 Hz), 4.09 (2H, s), 5.62 (1H, d, J=10.5 Hz), 5.67 (1H, d, J=10.5 Hz), 6.81 (1H, d, J=16.0 Hz), 7.38 (1H, d, J=16.0 Hz), 7.77–8.07 (6H, m), 8.11 (1H, d, J=8.5 Hz), 8.30–8.40 (1H, m), 8.50 (1H, s), 8.99 (1H, m)

(32) 8-[3-[N-[(E)-3-[6-(Acetylglycylamino)pyridin-3-yl]acryloylglycyl]-N-methylamino]-2,6-dichlorobenzyloxy]-2-methylquinoline mp: 128–136.5° C.

NMR (CDCl₃, δ): 2.07 (3H, s), 2.73 (3H, s), 3.27 (3H, s), 3.67 (1H, dd, J=16.0, 4.5 Hz), 3.99 (1H, dd, J=16.0, 4.5 Hz), 4.03 (2H, d, J=6.0 Hz), 5.64 (2H, s), 6.45 (1H, d, J=16.0 Hz), 6.83–6.96 (2H, m), 7.22–7.67 (7H, m), 7.78 (1H, dd, J=8.5, 1.5 Hz), 8.02 (1H, d, J=8.5 Hz), 8.09–8.24 (1H, m), 8.35 (1H, d, J=1.5 Hz), 9.04 (1H, s) its dihydrochloride mp: 150–157° C.

NMR (CDCl₃-CD₃OD, δ): 2.10 (3H, s), 3.15 (3H, s), 3.28 (3H, s), 3.89 (1H, d, J=16.0 Hz), 4.10–4.31 (1H, m), 4.19 (2H, s), 5.57 (1H, d, J=8.5 Hz), 5.70 (1H, d, J=8.5 Hz), 6.83 (1H, m), 7.44–7.68 (4H, m), 7.71–7.98 (3H, m), 8.10 (1H, m), 8.38 (1H, m), 8.70 (1H, m), 8.88 (1H, m)

(33) 8-[2,6-Dichloro-3-[N-methyl-N-[4-[(1-methyl-1H-midazole- 2-carbonyl)amino]cinnamoylglyCyl]amino]benzyloxy]-2-methylquinoline mp: 106.5–115° C.

NMR (CDCl₃, δ): 2.73 (3H, s), 3.26 (3H, s), 3.64 (1H, dd, J=16.5, 4.5 Hz), 3.94 (1H, dd, J=16.5, 4.5 Hz), 4.12 (3H, s), 5.63 (1H, d, J=11.0 Hz), 5.68 (1H, d, J=11.0 Hz), 6.43 (1H, d, J=16.0 Hz), 6.63 (1H, br t, J=4.5 Hz), 7.03 (1H, s), 7.07 (1H, s), 7.23–7.34 (3H, m), 7.39–7.54 (5H, m), 7.54 (1H, d, J=16.0 Hz), 7.67 (2H, d, J=8.5 Hz), 8.02 (1H, s), 9.32 (1H, s) its dihydrochloride mp 132.5–140° C.

NMR (CDCl₃-CD₃OD, δ): 3.12 (3H, s), 3.29 (3H, s), 3.90 (1H, d, J=16.0 Hz), 3.99 (1H, d, J=16.0 Hz), 4.29 (3H, s), 5.61 (1H, d, J=8.5 Hz), 5.73 (1H, d, J=8.5 Hz), 6.54 (1H, d, J=16.0 Hz), 7.39–7.50 (3H, m), 7.52–7.62 (4H, m), 7.69 (1H, d, J=8.5 Hz), 7.82–8.00 (5H, m), 8.97 (1H, d, J=8.5 Hz)

(34) 8-[2,6-Dichloro-3-[N-[(E)-3-[6-(2-furancarboxamido)pyridin-3-yl]acryloylglycyl]-N-methylamino]benzyloxy]-2-methylquinoline mp: 208–212° C.

NMR (CDCl₃, δ): 2.73 (3H, s), 3.27 (3H, s), 3.67 (1H, dd, J=16.5, 5.5 Hz), 3.96 (1H, dd, J=16.5, 5.5 Hz), 5.63 (1H, d, J=10.5 Hz), 5.68 (1H, d, J=10.5 Hz), 6.51 (1H, d, J=16.0 Hz), 6.57–6.61 (1H, m), 6.68 (1H, br t, J=5.5 Hz), 7.23–7.34 (4H, m), 7.39–7.58 (5H, m), 7.88 (1H, dd, J=8.5, 1.5 Hz), 8.03 (1H, d, J=8.5 Hz), 8.33 (1H, d, J=8.5 Hz), 8.41 (1H, d, J=1.5 Hz), 8.80 (1H, s) its dihydrochloride mp: 154.5–158° C.

NMR (CDCl₃-CD₃OD, δ): 3.19 (3H, s), 3.28 (3H, s), 3.90 (1H, d, J=16.0 Hz), 4.29 (1H, d, J=16.0 Hz), 5.57 (1H, d, J=9.0 Hz), 5.69 (1H, d, J=9.0 Hz), 6.63 (1H, m), 6.89 (1H, d, J=16.0 Hz), 7.42 (1H, d, J=16.0 Hz), 7.52–7.64 (3H, m), 7.72 (1H, s), 7.77–7.95 (4H, m), 8.42–8.58 (2H, m), 8.72 (1H, br s), 8.87 (1H, d, J=8.5 Hz)

(35) 8-[2,6-Dichloro-3-[N-methyl-N-[(E)-3-[6-(4-pyridylacetamido)pyridin-3-yl]acryloylglycyl]amino]benzyloxy]-2-methylquinoline mp: 126.5–132° C.

NMR (CDCl₃, δ): 2.72 (3H, s), 3.26 (3H, s), 3.65 (1H, dd, J=16.5, 5.5 Hz), 3.75 (2H, s), 3.95 (1H, dd, J=16.5, 5.5 Hz), 5.62 (1H, d, J=10.5 Hz), 5.68 (1H, d, J=10.5 Hz), 6.47 (1H, d, J=16.0 Hz), 6.77 (1H, br t, J=5.5 Hz), 7.21–7.33 (5H, m), 7.39–7.49 (3H, m), 7.51 (1H, d, J=16.0 Hz), 7.82 (1H, dd, J=8.5, 1.5 Hz), 8.03 (1H, d, J=8.5 Hz), 8.19 (1H, d, J=8.5 Hz), 8.28 (1H, s), 8.33 (1H, d, J=1.5 Hz), 8.57–8.65 (2H, m) its trihydrochloride mp: 156–158° C.

NMR (CDCl₃-CD₃OD, δ): 2.80–3.24 (2H, m), 3.13 (3H, s), 3.28 (3H, s), 3.89 (1H, d, J=16.5 Hz), 4.19 (1H, d, J=16.5 Hz), 5.55 (1H, d, J=9.0 Hz), 5.72 (1H, d, J=9.0 Hz), 6.90 (1H, d, J=16.5 Hz), 7.40 (1H, d, J=16.5 Hz), 7.53–7.69 (3H, m), 7.79–8.07 (4H, m), 8.17–8.28 (2H, m), 8.39 (1H, m), 8.76–8.94 (4H, m)

(36) 8-[3-[N-[4-(1-Adamantylacetamido)cinnamoylglycyl]-N-methylamino]- 2,6-dichlorobenzyloxy]-2-methylquinoline mp: 147–154° C.

NMR (CDCl₃, δ): 1.56–1.77 (12H, m), 1.92–2.01 (3H, m), 2.07 (2H, s), 2.73 (3H, s), 3.25 (3H, s), 3.63 (1H, dd, J=16.5, 5.5 Hz), 3.93 (1H, dd, J=16.5, 5.5 Hz), 5.62 (1H, d, J=11.5 Hz), 5.66 (1H, d, J=11.5 Hz), 6.40 (1H, d, J=16.0 Hz), 6.60–6.68 (1H, m), 7.21–7.35 (5H, m), 7.39–7.59 (7H, m), 8.04 (1H, d, J=8.5 Hz)

(37) 8-[3-[N-[4-[(1-Acetylpiperidin-4-yl)carbonylamino]cinnamoylglycyl]-N-methylamino]-2,6-dichlorobenzyloxy]-2-methylquinoline mp: 146.5–153° C.

NMR (CDCl₃, δ): 1.62–1.91 (4H, m), 2.07 (3H, s), 2.24–2.50 (2H, m), 2.69 (3H, s), 2.85–2.97 (1H, m), 3.20 (3H, s), 3.61 (1H, dd, J=16.5, 5.5 Hz), 3.77–3.87 (1H, m), 3.90 (1H, dd, J=16.5, 5.5 Hz), 4.47–4.58 (1H, m), 5.58 (1H, d, J=11.5 Hz), 5.62 (1H, d, J=11.5 Hz), 6.40 (1H, d, J=16.0 Hz), 6.69 (1H, br t, J=5.5 Hz), 7.18–7.62 (11H, m), 8.05 (1H, d, J=8.5 Hz), 8.23 (1H, s) its hydrochloride mp: 155–161° C.

NMR (CDCl$_3$-CD$_3$OD, δ): 1.63–1.84 (2H, m), 1.88–2.03 (2H, m), 2.14 (3H, s), 2.71–3.33 (3H, m), 3.08 (3H, s), 3.29 (3H, s), 3.82–3.98 (1H, m), 3.91 (1H, d, J=16.0 Hz), 4.06 (1H, d, J=16.0 Hz), 4.49–4.61 (1H, m), 5.59 (1H, d, J=9.0 Hz), 5.73 (1H, d, J=9.0 Hz), 6.43 (1H, d, J=16.0 Hz), 7.26–7.38 (3H, m), 7.55 (2H, s), 7.60–7.71 (3H, m), 7.79–7.95 (3H, m), 8.92 (1H, d, J=8.5 Hz)

(38) 8-[3-[N-[4-(Cyclopropylcarbonylamino)cinnamoylglycyl]-N-methylamino]-2,6-dichlorobenzyloxy]-2-methylquinoline mp: 129–133° C.

NMR (CDCl$_3$, δ): 0.69–0.82 (2H, m), 0.97–1.08 (2H, m), 1.46–1.57 (1H, m), 2.69 (3H, s), 3.21 (3H, s), 3.61 (1H, dd, J=16.5, 5.5 Hz), 3.88 (1H, dd, J=16.5, 5.5 Hz), 5.60 (2H, s), 6.38 (1H, d, J=16.0 Hz), 6.61 (1H, br t, J=5.5 Hz), 7.19–7.49 (9H, m), 7.54 (2H, d, J=8.5 Hz), 8.06 (1H, d, J=8.5 Hz), 8.71 (1H, br s) its hydrochloride mp 160–165° C.

NMR (CDCl$_3$-CD$_3$OD, δ): 0.79–0.87 (2H, m), 0.97–1.04 (2H, m), 1.81–1.93 (1H, m), 3.08 (3H, s), 3.28 (3H, s), 3.90 (1H, d, J=16.5 Hz), 4.08 (1H, d, J=16.5 Hz), 5.58 (1H, d, J=9.0 Hz), 5.70 (1H, d, J=9.0 Hz), 6.42 (1H, d, J=16.0 Hz), 7.23–7.34 (3H, m), 7.50–7.67 (5H, m), 7.78–7.92 (3H, m), 8.91 (1H, d, J=8.5 Hz)

EXAMPLE 59

8-[3-[N-[4-[(Carboxymethyl)carbamoyl]cinnamoylglycyl]-N-methylamino]-2,6-dichlorobenzyloxy]-2-methylquinoline was obtained from 8-[3-[N-[4-[(ethoxycarbonylmethyl)carbamotl]cinnamoylglycyl]-N-methylamino]-2,6-dichlorobenzyloxy]-2-methylquinoline according to a similar manner to that of Example 20.

NMR (DMSO-d$_6$, δ): 2.63 (3H, s), 3.15 (3H, s), 3.53 (1H, d, J=16 Hz), 3.82 (1H, d, J=16 Hz), 3.92 (2H, d, J=6 Hz), 5.44–5.60 (2H, m), 6.90 (1H, d, J=16 Hz), 7.35–7.63 (4H, m), 7.63–7.73 (2H, m), 7.79 (2H, s-like), 7.90 (2H, d, J=8 Hz), 8.30–8.41 (1H, m), 8.85–8.94 (1H, m)

EXAMPLE 60

The following compounds were obtained according to a similar manner to that of Example 59.

(1) 8-[3-[N-[4-(N-Carboxymethyl-N-methylcarbamoyl)cinnamoylglycyl]-N-methylamino]-2,6-dichlorobenzyloxy]-2-methylquinoline NMR (DMSO-d$_6$, δ): 2.60 (3H, s), 2.95 (1.8H, s), 2.97 (1.2H, s), 3.15 (3H, s), 3.51 (1H, dd-like, J=16 Hz), 3.81 (1H, dd, J=16, 4 Hz), 3.93 (0.8H, s), 4.14 (1.2H, s), 5.46 (1H, d, J=11 Hz), 5.53 (1H, d, J=11 Hz), 6.83 (1H, d, J=16 Hz), 7.29–7.57 (7H, m), 7.57–7.70 (2H, m), 7.85 (2H, s-like), 8.20 (1H, d, J=8 Hz), 8.26–8.40 (1H, m)

(2) 8-[3-[N-[4-[(2-Carboxyethyl)carbamoyl]cinnamoylglycyl]-N-methylamino]-2,6-dichlorobenzyloxy]-2-methylquinoline NMR (DMSO-d$_6$, δ): 2.70 (3H, br s), 3.15 (3H, s), 3.27–3.60 (5H, m), 3.84 (1H, dd, J=4, 16 Hz), 5.56–5.61 (2H, m), 6.88 (1H, d, J=16 Hz), 7.43 (1H, d, J=16 Hz), 7.49–7.73 (5H, m), 7.80 (2H, s-like), 7.85 (2H, d, J=8 Hz), 8.29–8.43 (2H, m), 8.59 (1H, t-like)

(3) 8-[3-[N-[4-[((R)-1-Carboxyethyl)carbamoyl]cinnamoylglycyl]-N-methylamino]-2,6-dichlorbenzyloxy]-2-methylquinoline NMR (CDCl$_3$, δ): 1.40 (3H, d, J=7.5 Hz), 2.63 (3H, s), 3.16 (3H, s), 3.53 (1H, dd-like, J=16 Hz), 3.83 (1H, dd-like, J=16 Hz), 4.41 (1H, quint, J=7.5 Hz), 5.43–5.60 (2H, m), 6.90 (1H, d, J=16 Hz), 7.31–7.61 (5H, m), 7.61–7.71 (2H, m), 7.80 (2H, s-like), 7.92 (2H, d, J=8 Hz), 8.16–8.43 (2H, m), 8.71 (1H, d, J=7.5 Hz) [α]$_D^{20}$:–6.7° (C=20 mg/2 ml, MeOH)

(4) 8-[3-[N-[4-[((R)-1-Carboxy-2-phenylethyl)carbamoyl]cinnamoylglycyl]-N-methylamino]-2,6-dichlorobenzyloxy]-2-methylquinoline NMR (DMSO-d$_6$, δ): 2.65 (3H, s), 3.00–3.26 (5H, m), 3.53 (1H, dd-like, J=16 Hz), 3.83 (1H, dd-like, J=16 Hz), 4.56–4.69 (1H, m), 5.45–5.60 (2H, m), 6.87 (1H, d, J=16 Hz), 7.13–7.21 (1H, m), 7.21–7.35 (4H, m), 7.35–7.75 (7H, m), 7.75–7.88 (4H, m), 8.26–8.42 (2H, m), 8.77 (1H, d, J=7.5 Hz) [α]$_D^{20}$:+38.5° (C=20 mg/2 ml, MeOH)

EXAMPLE 61

8-[2,6-Dichloro-3-[N-methyl-N-[4-[(methylcarbamoylmethyl)carbamoyl]cinnamoylglycyl]amino]benzyloxy]-2-methylquinoline was obtained by reacting 8-[3-[N-[4-[(carboxymethyl)carbamoyl]cinnamoylglycyl]-N-methylamino]-2,6-dichlorobenzyloxy]-2-methylquinoline with methylamine hydrochloride according to a similar manner to that of Example 54.

NMR (CDCl$_3$, δ): 2.73 (3H, s), 2.85 (3H, d, J=5 Hz), 3.27 (3H, s), 3.64 (1H, dd-like, J=16 Hz), 3.96 (1H, dd, J=16, 4 Hz), 4.09 (2H, d, J=5 Hz), 5.58–5.71 (2H, m), 6.19–6.29 (1H, m), 6.55 (1H, d, J=16 Hz), 6.80–6.88 (1H, m), 7.15–7.37 (3H, m), 7.37–7.62 (6H, m), 7.80 (2H, d, J=8 Hz), 8.03 (1H, d, J=8 Hz) its hydrochloride NMR (CDCl$_3$-CD$_3$OD, δ): 2.79 (3H, s), 3.13 (3H, s), 3.30 (3H, s), 3.89 (1H, d, J=16 Hz), 4.05 (2H, s), 4.07 (1H, d, J=16 Hz), 5.61 (1H, d, J=10 Hz), 5.70 (1H, d, J=10 Hz), 6.63 (1H, d, J=16 Hz), 7.40 (1H, d, J=16 Hz), 7.50 (2H, d, J=8 Hz), 7.50 (2H, s-like), 7.64 (1H, d, J=8 Hz), 7.75–7.93 (5H, m), 8.38 (1H, d, J=8 Hz)

EXAMPLE 62

The following compounds were obtained according to a similar manner to that of Example 61.

(1) 8-[2,6-Dichloro-3-[N-methyl-N-[4-[N-(methylcarbamoylmethyl)-N-methylcarbamotl]cinnamoylglycyl]amino]benzyloxy]-2-methylquinoline NMR (CDCl$_3$, δ): 2.70 (3H, s), 2.85 (3H, d, J=5 Hz), 3.10 (3H, s), 3.26 (3H, s), 3.65 (1H, dd, J=4, 16 Hz), 3.83–4.03 (1.5H, m), 4.03–4.13 (1.5H, m), 5.60–5.72 (2H, m), 6.43–6.60 (2H, m), 6.70 (1H, br s), 7.22–7.36 (3H, m), 7.36–7.65 (8H, m), 8.03 (1H, d, J=8 Hz) its hydrochloride NMR (CDCl$_3$-CD$_3$OD, δ): 2.82 (3H, br s), 3.09 (3H, s), 3.29 (3H, s), 3.82–4.20 (4H, m), 5.60 (1H, d, J=10 Hz), 5.73 (1H, d, J=10 Hz), 6.54–6.71 (1H, m), 7.36–7.63 (7H, m), 7.66 (1H, d, J=8 Hz), 7.79–7.98 (3H, m), 8.90 (1H, d, J=8 Hz)

(2) 8-[2,6-Dichloro-3-[N-methyl-N-[4-[[2-(methylcabamoyl)ethyl]carbamoyl]cinnamoylglycyl]amino]benzyloxy]-2-methylquinoline NMR (CDCl$_3$, δ): 2.50 (2H, t, J=6 Hz), 2.73 (3H, s), 2.83 (3H, d, J=5 Hz), 3.27 (3H, s), 3.65 (1H, dd, J=4, 16 Hz), 3.73 (2H, q, J=6 Hz), 3.95 (1H, dd, J=4, 16 Hz), 5.60–5.76 (3H, m), 6.54 (1H, d, J=16 Hz), 6.70 (1H, t-like), 7.23–7.36 (3H, m), 7.36–7.63 (6H, m), 7.78 (2H, d, J=8 Hz), 8.03 (1H, d, J=8 Hz) its hydrochloride NMR (CDCl$_3$-CD$_3$OD, δ): 2.70 (2H, t, J=7 Hz), 2.73 (3H, s), 3.15 (3H, s), 3.30 (3H, s), 3.68 (2H, t, J=7 Hz), 3.90 (1H, d, J=16 Hz), 4.06 (1H, d, J=16 Hz), 5.60 (1H, d, J=10 Hz), 5.60 (1H, d, J=10 Hz), 6.65 (1H, d, J=16 Hz), 7.45 (1H, d, J=16 Hz), 7.49–7.57 (4H, m), 7.63 (1H, d, J=8 Hz), 7.77–7.93 (5H, m), 8.88 (1H, d, J=8 Hz)

(3) 8-[2,6-Dichloro-3-[N-methyl-N-[4-[[(R)-1-(methylcarbamoyl)ethyl]carbamotl]cinnamoylglycyl]amino]benzyloxy]-2-methylquinoline NMR (CDCl₃, δ): 1.47 (3H, d, J=7.5 Hz), 2.73 (3H, s), 2.85 (3H, d, J=5 Hz), 3.65 (1H, dt, J=16, 4 Hz), 3.95 (1H, dt, J=16, 4 Hz), 4.65 (1H, quint, J=7.5 Hz), 5.58–5.70 (2H, m), 6.19 (1H, br), 6.55 (1H, dd-like, J=16 Hz), 6.68–6.80 (1H, m), 6.87 (1H, t-like), 7.20–7.37 (3H, m), 7.37–7.64 (6H, m), 7.79 (2H, d, J=8 Hz), 8.03 (1H, d, J=8 Hz) $[\alpha]_D^{20}$: −6.2° (C=20 mg/2 ml, CHCl₃) its hydrochloride NMR (CDCl₃-CD₃OD, δ): 1.45 (3H, d, J=7.5 Hz), 2.81 (3H, s), 3.14 (3H, s), 3.30 (3H, s), 3.90 (1H, d, J=16 Hz), 4.04 (1H, d, J=16 Hz), 4.61 (1H, q, J=7.5 Hz), 5.60 (1H, d, J=10 Hz), 5.73 (1H, d, J=10 Hz), 6.66 (1H, d, J=16 Hz), 7.47 (1H, d, J=16 Hz), 7.50–7.69 (5H, m), 7.79–7.95 (5H, m), 8.90 (1H, d, J=8 Hz) $[\alpha]_D^{20}$: −13.0° (C=20 mg/2 mg, MeOH)

(4) 8-[2,6-Dichloro-3-[N-methyl-N-[4-[[(R)-1-(methylcabamoyl)-2-phenylethyl]carbamoyl]cinnamoylglycyl]amino]benzyloxy]-2-methylquinoline NMR (CDCl₃, δ): 2.68–2.77 (6H, m), 3.09 (1H, dd, J=7.5, 13 Hz), 3.20–3.35 (4H, m), 3.67 (1H, dt, J=16, 4 Hz), 3.96 (1H, dt, J=16, 4 Hz), 4.78 (1H, q, J=7.5 Hz), 5.60–5.78 (3H, m), 6.55 (1H, dd-like, J=16 Hz), 6.73–6.84 (1H, m), 6.94 (1H, t-like), 7.20–7.38 (3H, m), 7.38–7.63 (6H, m), 7.72 (2H, d, J=8 Hz), 8.03 (1H, d, J=8 Hz) $[\alpha]_D^{20}$: −0.5° (C=20 mg/2 ml, CHCl₃) its hydrochloride NMR (CDCl₃-CD₃OD, δ): 2.73 (3H, s), 3.09–3.21 (5H, m), 3.30 (3H, s), 3.89 (1H, d, J=16 Hz), 4.03 (1H, d, J=16 Hz), 4.77 (1H, t, J=7.5 Hz), 5.60 (1H, d, J=10 Hz), 5.70 (1H, d, J=10 Hz), 6.65 (1H, d, J=16 Hz), 7.18–7.33 (4H, m), 7.40–7.93 (12H, m), 8.88 (1H, d, J=8 Hz) $[\alpha]_D^{25}$: +13.3° (C=20 mg/2 ml, MeOH)

EXAMPLE 63

To a solution of 8-tert-butoxycarbonylamino-2-methylquinoline (258 mg) in N,N-dimethylformamide (3 ml) was added sodium hydride (44 mg) in an ice-water bath cooling, and the mixture was stirred for 20 minutes at the same temperature. To the reaction mixture was added 2,6-dichloro-3-nitrobenzyl methanesulfonate (300 mg) in an ice water bath cooling, and the mixture was stirred for 80 minutes at the same temperature and then for 15 minutes at ambient temperature. The reaction mixture was partitioned between ethyl acetate and water. The organic layer was dried over magnesium sulfate and concentrated in vacuo. The residue was purified by flash chromatography eluting with methylene chloride, and crystallized with n-hexane to give 8-[N-tert-butoxycarbonyl-N-(2,6-dichloro-3-nitrobenzyl)amino]-2-methylquinoline (352 mg). mp: 130–131° C.

NMR (CDCl₃, δ): 1.21 (6H, s), 1.60 (3H, s), 2.72 (3H, s), 5.20 (1H, d, J=15 Hz), 5.67 (1H, d, J=15 Hz), 6.91 (1H, d, J=8 Hz), 7.11–7.31 (3H), 7.53 (1H, d, J=8 Hz), 7.65 (1H, d, J=8 Hz), 8.00 (1H, d, J=8 Hz)

EXAMPLE 64

8-[N-tert-Butoxycarbonyl-N-(2,6-dichloro-3-nitrobenzyl)amino]-2-methylquinoline (100 mg) was treated with 4M hydrogen chloride-ethyl acetate (2 ml) at ambient temperature for 40 minutes. The precipitate was collected by vacuum filtration and washed with ethyl acetate to give 8-[(2,6-dichloro-3-nitrobenzyl)amino]-2-methylquinoline dihydrochloride (88 mg) as pale yellow crystals. mp: 230–232° C.

NMR (DMSO-d₆, δ): 2.80 (3H, s), 4.76 (2H, s), 7.10 (1H, d, J=8 Hz), 7.31 (1H, d, J=8 Hz), 7.48–7.69 (2H), 7.84 (1H, d, J=8 Hz), 8.10 (1H, d, J=8 Hz), 8.52 (1H, d, J=8 Hz)

EXAMPLE 65

To a suspension of 8-[2,6-dichloro-3-[N-methyl-N-[4-(methylcarbamoyl)cinnamoylglycyl]amino]benzyloxy]-2-methylquinoline (149.7 mg) in-ethanol (1.5 ml) was added 1M sulfuric acid - ethanol solution (253.1 μl) at ambient temperature, and the mixture was warmed at 90° C. and then stirred for 1 hour at ambient temperature. The solvent was removed in vacuo to give sulfuric acid salt of 8-[2,6-dichloro-3-[N-methyl-N-[4-(methylcarbamoyl)cinnamoylglycyl]amino]benzyloxy]-2-methylquinoline (144.5 mg). mp: 219–226° C.

NMR (DMSO-d₆, δ): 2.77 (3H, d, J=4.5 Hz), 2.86 (3H, s), 3.14 (3H, s), 3.58 (1H, dd, J=4.5, 16.5 Hz), 3.89 (1H, dd, J=4.5, 16.5 Hz), 5.59 (1H, d, J=11.5 Hz), 5.64 (1H, d, J=11.5 Hz), 6.87 (1H, d, J=16 Hz), 7.40 (1H, d, J=16 Hz), 7.63 (2H, d, J=8.5 Hz), 7.73–7.93 (8H, m), 8.33 (1H, t, J=4.5 Hz), 8.47 (1H, q, J=4.5 Hz), 8.87 (1H, br s)

EXAMPLE 66

To a suspension of 8-[2,6-dichloro-3-[N-methyl-N-[4-(methylcarbamoyl)cinnamoylglycyl]amino]benzyloxy]-2-methylquinoline (225 mg) in ethanol (2.3 ml) was added 1N sulfuric acid-ethanol solution (0.38 ml) at ambient temperature, and the mixture was warmed at 90° C. and then stirred for 1 hour at ambient temperature. The resulting precipitate was collected by filtration, and the residue was dissolved in methylene chloride-methanol (10:1). The solvent was removed in vacuo to give ½ sulfuric acid salt of 8-[2,6-dichloro-3-[N-methyl-N-[4-(methylcarbamoyl)cinnamoylglycyl]amino]benzyloxy]-2-methylquinoline (210 mg).

NMR (DMSO-d₆, δ): 2.63–2.84 (6H, m), 3.15 (3H, s), 3.55 (1H, dd, J=4, 16 Hz), 3.85 (1H, dd, J=5, 16 Hz), 5.47–5.65 (2H, m), 6.86 (1H, d, J=16 Hz), 7.41 (1H, d, J=16 Hz), 7.48–7.90 (11H, m), 8.33 (1H, t-like), 8.48 (1H, q-like)

EXAMPLE 67

To a solution of 8-[3-[N-[4-(N-acetyl-N-tert-butoxycarbonylmethylamino)cinnamoylglycyl]-N-methylamino]-2,6-dichlorobenzyloxy]-2-methylquinoline (143 mg) in dichloromethane (1.4 ml) was added trifluoroacetic acid (0.05 ml) at ambient temperature and the mixture was stirred at the same temperature. After 1 hour, to the solution was added trifluoroacetic acid (1 ml). After 5 hours the solvent was removed in vacuo to give 8-[3-[N-[4-(N-acetyl-N-carboxymethylamino)cinnamoylglycyl]-N-methylamino]-2,6-dichlorobenzyloxy]-2-methylquinoline (124 mg) as amorphous solid.

NMR (CDCl₃-CD₃OD, δ): 1.98 (3H, s), 3.04 (3H, s), 3.31 (3H, s), 3.91 (2H, s), 4.21–4.50 (2H, overlapped with H₂O), 5.62 (1H, d, J=10 Hz), 5.80 (1H, d, J=10 Hz), 6.63 (1H, d, J=16 Hz), 7.32–8.00 (11H), 8.91 (1H, d, J=8 Hz)

EXAMPLE 68

To a solution of 8-[3-[N-[4-(N-acetyl-N-carboxymethylamino)cinnamoylglycyl]-N-methylamino]-2,6-dichlorobenzyloxy]-2-methylquinoline (120 mg) in ethanol (1 ml) was added 0.1N aqueous sodium hydroxide (1.85 ml) at ambient temperature and the mixture was stirred at the same temperature. After 3 minutes the solvent was removed in vacuo. The residue was dissolved in a mixture of ethanol and water (1:2 V/V, 1 ml) and was filtered. The filtrate was lyophilized to give sodium salt of 8-[3-[N-[4-(N-acetyl-N-carboxymethylamino)cinnamoylglycyl]-N-methylamino]-2,6-dichlorobenzyloxy]-2-methylquinoline (124 mg) as amorphous solid.

NMR (CDCl₃-CD₃OD, δ): 1.95 (3H, s), 2.99 (3H, s), 3.30 (3H, s), 3.82 (1H, d, J=17 Hz), 3.97 (1H, d, J=17 Hz), 4.33 (2H, s), 5.61 (1H, d, J=10 Hz), 5.77 (1H, d, J=10 Hz), 6.61 (1H, d, J=16 Hz), 7.30–7.90 (11H), 8.75 (1H, d, J=8 Hz)

EXAMPLE 69

8-[2,6-Dichloro-3-[N-methyl-N-[[2-[4-(4-pyridyl)-1-piperazinyl]acetyl]glycyl]amino]benzyloxy]-4-methoxy-2-methylquinoline was obtained from 8-[3-(N-glycyl-N-methylamino)-2,6-dichlorobenzyloxy]-4-methoxy-2-methylquinoline, bromoacetyl chloride and 1-(4-pyridyl)piperazine according to a similar manner to that of Example 23.

NMR (CDCl₃, δ): 2.60–2.79 (7H), 3.09 (2H, s), 3.23 (3H, s), 3.30–3.61 (5H), 3.90 (1H, dd, J=18, 5 Hz), 4.01 (3H, s), 5.62 (2H, s), 6.60–6.72 (3H), 7.20–7.42 (3H), 7.50 (1H, d, J=8 Hz), 7.78–7.94 (2H), 8.29 (2H, d, J=7 Hz)

its tetrahydrochloride

NMR (CDCl₃-CD₃OD, δ): 3.01 (3H, s), 3.27 (3H, s), 3.08–4.24 (12H), 4.35 (3H, s), 5.57 (1H, d, J=10 Hz), 5.72 (1H, d, J=10 Hz), 7.19–7.40 (3H), 7.52–7.69 (3H), 7.79 (1H, t, J=8 Hz), 7.99 (1H, d, J=8 Hz), 8.20 (2H, br d, J=7 Hz)

EXAMPLE 70

A mixture of 8-[3-[N-(4-cyanocinnamoylglycyl)-N-methylamino]-2,6-dichlorobenzyloxy]-2-methylquinoline (76 mg) and trimethyltin azide (109 mg) in xylene (1 ml) was heated at 125° C. for 20 hours. After cooled, methanol-chloroform (1:4 V/V, 10 ml) and silica gel (296 mg) was added to the reaction mixture. The resulting suspension was stirred at ambient temperature for one hour. The silica gel was filtered off, and the filtrate was concentrated in vacuo. The residue was purified by preparative thin-layer chromatography eluting with methanol-chloroform (1:6) to afford 8-[2,6-dichloro-3-[N-methyl-N-[4-(5-tetrazolyl)cinnamoylglycyl]amino]benzloxy]-2-methylquinoline (40 mg) as a pale yellowb glass. mp: 196–208° C.

NMR (CDCl₃-CD₃OD, δ): 2.70 (3H, s), 3.26 (3H, s), 3.68 (1H, d, J=18 Hz), 4.01 (1H, d, J=18 Hz), 5.58 (2H, s), 6.60 (1H, d, J=15 Hz), 7.20–7.69 (10H, m), 8.00 (1H, d, J=9 Hz), 8.10 (1H, d, J=10 Hz)

EXAMPLE 71

8-[2,6-Dichloro-3-[N-[4-[(N-tert-butoxycarbonyl-L-prolyl)amino]cinnamoylglycyl]-N-methylamino]benzyloxy]-2-methylquinoline (170 mg) was treated with 4M hydrogen chloride-ethyl acetate (2 ml) at ambient temperature for 30 minutes. The reaction mixture was concentrated to give 8-[2,6-dichloro-3-[N-[4-(L-prolylamino)cinnamoylglycyl]-N-methylamino]benzyloxy]-2-methylquinoline dihydrochloride (152 mg).

NMR (CDCl₃-CD₃OD, δ): 2.05–2.19 (4H), 3.12 (3H, br s), 3.29 (3H, s), 3.44–3.53 (2H), 3.91 (1H, d, J=17 Hz), 4.06 (1H, d, J=17 Hz), 4.68 (1H, m), 5.59 (1H, d, J=10 Hz), 5.70 (1H, d, J=10 Hz), 6.49 (1H, d, J=15 Hz), 7.25–7.38 (3H), 7.50–7.59 (4H), 7.64 (1H, br d, J=7.5 Hz), 7.78–7.96 (3H), 8.95 (1H, d, J=8 Hz)

EXAMPLE 72

8-[3-[N-[4-[(N-Acetyl-L-prolyl)amino]cinnamoylglycyl]-N-methylamino]-2,6-dichlorobenzyloxy]-2-methylquinoline was obtained by reacting 8-[2,6-dichloro-3-[N-[4-(L-prolylamino)cinnamoylglycyl]-N-methylamino]benzyloxyl-2-methylquinoline dihydrochloride with acetic anhydride according to a similar manner to that of Example 49.

NMR (CDCl₃, δ): 1.74–2.25 (6H), 2.60 (1H, m), 2.72 (3H, s), 3.25 (3H, s), 3.35–3.70 (3H), 3.93 (1H, m), 4.78 (1H, t, J=5 Hz), 5.63 (2H, s), 6.38 (1H, dd, J=15, 7.5 Hz), 6.60 (0.3H, br t, J=4 Hz), 6.78 (0.3H, br t, J=4 Hz), 7.12–7.57 (10H), 8.02 (1H, d, J=8 Hz), 9.93 (1H, br d, J=5 Hz)

its hydrochloride

NMR (CDCl₃-CD₃OD, δ): 2.00–2.27 (6H), 2.40 (1H, m), 3.15 (3H, br s), 3.30 (3H, s), 3.53 (1H, m), 3.69 (1H, m), 3.91 (1H, br d, J=17 Hz), 4.04 (1H, br d, J=17 Hz), 4.77 (1H, m), 5.61 (1H, d, J=10 Hz), 5.69 (1H, d, J=10 Hz), 6.48 (1H, d, J=15 Hz), 7.29–7.68 (8H), 7.78–7.91 (3H), 8.90 (1H, br d, J=8 Hz)

EXAMPLE 73

The following compounds were obtained according to a similar manner to that of Example 28.

(1) 8-[2,6-Dichloro-3-[N-[4-((2-pyridylmethyl)carbamoyl]cinnamoylglycyl]-N-methylamino]benzyloxy]-2-methylquinoxaline dihydrocloride mp: 181–186° C.

NMR (CDCl₃-CD₃OD, δ): 2.85 (3H, s), 3.27 (3H, s), 3.67 (1H, d, J=17.5 Hz), 3.98 (1H, d, J=17.5 Hz), 4.99 (2H, s), 5.63 (2H, s), 6.63 (1H, d, J=16.0 Hz), 7.43 (1H, d, J=8.5 Hz), 7.48 (1H, d, J=8.5 Hz), 7.52–7.63 (4H, m), 7.80 (1H, t, J=8.5 Hz), 7.84–7.93 (2H, m), 7.98 (2H, d, J=8.5 Hz), 8.15 (1H, d, J=8.5 Hz), 8.45 (1H, t, J=8.5 Hz), 8.72 (1H, d, J=6.0 Hz), 8.85 (1H, s)

(2) 8-[2,6-Dichloro-3-[N-[4-(dimethylcarbamoyl)cinnamoylglycyl]-N-methylamino]benzyloxy]-2-methylquinoxaline hydrochloride mp: 173–180° C.

NMR (CDCl₃-CD₃OD, δ): 2.90 (3H, s), 2.99 (3H, br s), 3.11 (3H, br s), 3.28 (3H, s), 3.69 (1H, d, J=17.5 Hz), 3.98 (1H, d, J=17.5 Hz), 5.63 (2H, s), 6.58 (1H, d, J=15.0 Hz), 7.37–7.49 (4H, m), 7.51–7.62 (4H, m), 7.85 (1H, t, J=8.5 Hz), 7.93 (1H, d, J=8.5 Hz), 8.90 (1H, s)

(3) 8-[3-[N-[4-(Acetamido)cinnamoylglycyl]-N-methylamino]-2,6-dichlorobenzyloxy]-2-methylquinoxaline hydrochloride NMR (CDCl₃-CD₃OD, δ): 2.17 (3H, s), 2.91 (3H, s), 3.29 (3H, s), 3.69 (1H, d, J=17 Hz), 3.98 (1H, d, J=17 Hz), 5.62 (2H, s), 6.43 (1H, d, J=15 Hz), 7.40–7.59 (8H), 7.87 (1H, br t, J=8 Hz), 7.95 (1H, br d, J=8 Hz), 8.90 (1H, s)

(4) 8-[2,6-Dichloro-3-[N-[4-(methoxyacetamido)cinnamoylglycyl]-N-methylamino]benzyloxy]-2-methylquinoxaline hydrochloride NMR (CDCl₃-CD₃OD, δ): 2.92 (3H, br s), 3.28 (3H, s), 3.51 (3H, s), 3.69 (1H, d, J=17 Hz), 3.96 (1H, d, J=17 Hz), 4.02 (2H, s), 5.63 (2H, s), 6.47 (1H, d, J=15 Hz), 7.41–7.62 (8H), 7.87 (1H, br t, J=8 Hz), 7.99 (1H, br d, J=8 Hz), 8.90 (1H, s)

(5) 8-[2,6-Dichloro-3-[N-methyl-N-[4-(2-oxopyrrolidin-1-yl)cinnamoylglycyl]amino]benzyloxy]-2-methylquinoxaline hydrochloride NMR (CDCl₃-CD₃OD, δ): 2.13–2.25 (2H), 2.59–2.72 (2H, overlapped with H₂O), 2.91 (3H, br s), 3.29 (3H, s), 3.69 (1H, d, J=17 Hz), 3.89 (2H, t, J=7 Hz), 3.96 (1H, d, J=17 Hz), 5.63 (2H, s), 6.48 (1H, d, J=15 Hz), 7.41–7.38 (2H), 7.85 (1H, br t, J=8 Hz), 7.98 (1H, br d, J=8 Hz), 8.90 (1H, s)

What we claim is:
1. A compound of the formula:

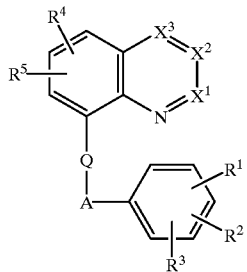

wherein —X³=X²—X¹=N— is a group of the formula:

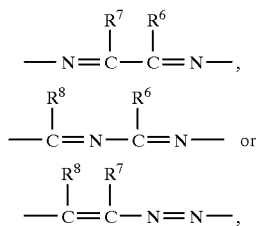

R¹ is hydrogen or halogen,
R² is halogen,
R³ is hydrogen, nitro, amino optionally having at least one substituent or a heterocyclic group optionally having at least one substituent,
R⁴ and R⁵ are each hydrogen or halogen,
R⁶ and R⁸ are each hydrogen, halogen, lower alkyl, hydroxy, lower alkylthio, amino optionally substituted with lower alkyl, or lower alkoxy optionally substituted with a substituent selected from the group consisting of hydroxy, lower alkoxy, amino, lower alkylamino and aryl optionally substituted with lower alkoxy,
R⁷ is hydrogen or lower alkyl,
A is lower alkylene, and
Q is O or N—R⁹, in which R⁹ is hydrogen or acyl,
provided that R³ is not hydrogen when X¹ is C—R⁶, in which R⁶ is hydrogen, and
pharmaceutically acceptable salts thereof.
2. The compound of claim 1, wherein:
R³ is hydrogen; nitro; amino; amino substituted with at least one substituent selected from the group consisting of lower alkyl, acyl, ar(lower)alkyl, carboxy(lower)alkyl, lower alkoxycarbonyl(lower)alkyl and heterocyclic(lower)alkyl; or
a heterocyclic group optionally substituted with at least one substituent selected from the group consisting of halogen, lower alkyl, acyl, aryl, oxo, nitro, amino, ar(lower)alkyl and lower alkoxycarbonyl(lower)alkyl.
3. The compound of claim 1, wherein:
R³ is a group of the formula:

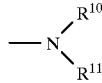

in which R¹⁰ is hydrogen or lower alkyl, and
R¹¹ is acyl,
X¹ is C—R⁶, in which R⁶ is lower alkyl, and A is methylene.

4. The compound of claim 3, wherein:
R³ is a group of the formula:

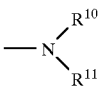

in which
R¹⁰ is hydrogen or lower alkyl, and
R¹¹ is an amino acid residue or an amino acid residue substituted with a substituent selected from the group consisting of lower alkyl, alkanoyl, halo(lower)alkanoyl, ar(lower)alkanoyl, optionally substituted heterocyclic(lower)alkanoyl, lower alkenoyl, ar(lower)alkenoyl, lower alkoxy-ar(lower)alkenoyl, lower alkylenedioxy-ar(lower)alkenoyl, nitro-ar(lower)alkenoyl, cyano-ar(lower)alkenoyl, halo-ar(lower)alkenoyl, hydroxy-ar(lower)alkenoyl, hydroxy(lower)alkoxy-ar(lower)alkenoyl, amino(lower)alkoxy-ar(lower)alkenoyl, lower alkylamino(lower)alkoxy-ar(lower)alkenoyl, heterocyclic(lower)alkoxy-ar(lower)alkenoyl, heterocyclic-ar(lower)alkenoyl optionally having oxo, amino-ar(lower)alkenoyl, lower alkylamino-ar(lower)alkenoyl, lower alkanoylamino-ar(lower)alkenoyl, N-(lower alkanoyl)-N-(lower alkyl)amino-ar(lower)alkenoyl, cycloalkyl(lower)alkanoylamino-ar(lower)alkenoyl, cycloalkylcarbonylamino-ar(lower)alkenoyl, lower alkenoylamino-ar(lower)alkenoyl, lower alkoxycarbonylamino-ar(lower)alkenoyl, hydroxy(lower)alkanoylamino-ar(lower)alkenoyl, lower alkoxy(lower)alkaanoylamino-ar(lower)alkenoyl, halo(lower)alkanoylamino-ar(lower)alkenoyl, amino(lower)alkanoylamino-ar(lower)alkenoyl, lower alkylamino(lower)alkanoylamino-ar(lower)alkenoyl, lower alkanoylamino(lower)alkanoylamino-ar(lower)alkenoyl, carboxy(lower)alkanoylamino-ar(lower)alkenoyl, lower alkoxycarbonyl(lower)alkanoylamino-ar(lower)alkenoyl, lower alkoxycarbonyl(lower)alkenoylamino-ar(lower)alkenoyl, halo(lower)alkoxycarbonylamino-ar(lower)alkenoyl, optionally substituted heterocyclic(lower)alkanoylamino-ar(lower)alkenoyl, aroylamino-ar(lower)alkenoyl, optionally substituted heterocycliccarbonylamino-ar(lower)alkenoyl, lower alkylsulfonylamino-ar(lower)alkenoyl, N-[lower alkoxy(lower)alkanoyl]-N-(lower alkyl)amino-ar(lower)alkenoyl, N-(lower alkanoyl)-N-[heterocyclic(lower)alkyl]amino-ar(lower)alkenoyl, N-(lower alkanoyl)-N-[lower alkoxy(lower)alkyl]amino-ar(lower)alkenoyl, N-(lower alkanoyl)-N-[lower alkoxycarbonyl(lower)alkyl]amino-ar(lower)alkenoyl, N-(lower alkanoyl)-N-[carboxy(lower)alkyl]amino-ar(lower)alkenoyl, N-[lower alkoxy(lower)alkanoyl]-N-[heterocyclic(lower)alkyl]amino-ar(lower)alkenoyl, N-[heterocycliccarbonyl]-N-[lower alkoxy(lower)alkyl]amino-ar(lower)alkenoyl, ureido-ar(lower)alkenoyl, lower alkylureido-ar(lower)alkenoyl, heterocyclicureido-ar(lower)alkenoyl, lower alkanoyl-ar(lower)alkenoyl, carboxy-ar(lower)alkenoyl, lower alkoxycarbonyl-ar(lower)alkenoyl, carbamoyl-ar(lower)alkenoyl, lower alkylcarbamoyl-ar(lower)alkenoyl, hydroxy(lower)alkylcarbamoyl-ar(lower)alkenoyl, N-[hydroxy(lower)alkyl]-N-(lower alkyl)carbamoyl-ar(lower)alkenoyl, lower alkoxy(lower)alkylcarbamoyl-ar(lower)alkenoyl, N-[lower alkoxy(lower)alkyl]-N-(lower alkyl)carbamoyl-ar(lower)alkenoyl, heterocyclic(lower)alkylcarbamoyl-ar(lower)alkenoyl, N-[heterocyclic(lower)alkyl]-N-(lower alkyl)carbamoyl-ar(lower)alkenoyl, heterocycliccarbamoyl-ar(lower)alkenoyl, optionally substituted heterocyclicarbonylar(lower)alkenoyl, lower alkenylcarbamoyl-ar(lower)alkenoyl, lower alkynylcarbamoyl-ar(lower)alkenoyl, amino(lower)alkylcarbamoyl-ar(lower)alkenoyl, lower alkylamino(lower)alkylcarbamoyl-ar(lower)alkenoyl, lower alkylcarbamoyloxy(lower)alkylcarbamoyl-ar(lower)alkenoyl, lower alkylcarbamoyl(lower)alkylcarbamoyl-ar(lower)alkenoyl, lower alkoxycarbonyl(lower)alkylcarbamoyl-ar(lower)alkenoyl, carboxy(lower)alkylcarbamoyl-ar(lower)alkenoyl, [lower alkylcarbamoyl-ar(lower)alkyl]carbamoyl-ar(lower)alkenoyl, [lower alkoxycarbonyl-ar(lower)alkyl]carbamoyl-ar(lower)alkenoyl, [carboxy-ar(lower)alkyl]carbamoyl-ar(lower)alkenoyl, N-[lower alkylcarbamoyl(lower)alkyl]-N-(lower alkyl)carbamoyl-ar(lower)alkenoyl, N-[lower alkoxycarbonyl (lower) alkyl]-N-(lower alkyl)carbamoyl-ar(lower)alkenoyl, N-[carboxy(lower)alkyl]-N-(lower alkyl)carbamoyl-ar(lower)alkenoyl, arylcarbamoyl-ar(lower)alkenoyl, ar(lower)alkynoyl, heterocyclic(lower)alkenoyl, heterocyclicthio(lower)alkanoyl, aminoheterocyclic(lower)alkenoyl, lower alkylaminoheterocyclic(lower)alkenoyl, lower alkanoylaminoheterocyclic(lower)alkenoyl, lower alkenoylaminoheterocyclic(lower)alkenoyl, heterocyclic(lower)alkanoylamino-heterocyclic(lower)alkenoyl, heterocycliccarbonylamino-heterocyclic(lower)alkenoyl, lower alkanoylamino(lower)alkanoylamino-heterocyclic(lower)alkenoyl, lower alkoxycarbonyl(lower)alkanoylamino-heterocyclic(lower)alkenoyl, lower alkoxy(lower)alkanoylamino-heterocyclic(lower)alkenoyl, lower alkylureido-heterocyclic(lower)alkenoyl, carboxy-heterocyclic(lower)alkenoyl, lower alkoxycarbonyl-heterocyclic(lower)alkenoyl, lower alkylcarbamoyl-heterocyclic(lower)alkenoyl, lower alkoxy(lower)alkylcarbamoyl-heterocyclic(lower)alkenoyl, hydroxy(lower)alkylcar bamoyl-heterocyclic (lower)alkenoyl, heterocycliccarbamoylheterocyclic(lower)alkenoyl, heterocyclic(lower)alkylcarbamoyl-heterocyclic(lower)alkenoyl, heterocycliccarbonyl-heterocyclic(lower)alkenoyl, lower alkenylcarbamoyl-heterocyclic(lower)alkenoyl, lower alkynylcarbamoyl-heterocyclic(lower)alkenoyl, optionally substituted heterocycliccarbonyl, cyclo(lower)alkylcarbonyl, lower alkoxycarbonyl, aryloxycarbonyl, aroyl(lower)alkanoyl, aroyl, nitro-aryloxycarbonyl, carbamoyl, lower alkylcarbamoyl, lower alkoxycarbonyl(lower)alkylcarbamoyl, lower alkenylcarbamoyl, cyclo(lower)alkylcarbamoyl, arylcarbamoyl, lower alkoxy-arylcarbamoyl, halo(lower)alkyl-arylcarbamoyl, haloarylcarbamoyl, lower alkanoyl-arylcarbamoyl, hydroxy(lower)alkyl-arylcarbamoyl, heterocycliccarbonyl-arylcarbamoyl, carboxy-arylcarbamoyl, lower alkoxycarbonyl-arylcarbamoyl, carbamoyl-arylcarbamoyl, lower alkylcarbamoyl-arylcarbamoyl, nitro-arylcarbamoyl, cyano-arylcarbamoyl, amino-arylcarbamoyl, lower alkylamino-arylcarbamoyl, lower alkanoylamino-arylcarbamoyl, N-(lower alkanoyl)-N-(lower alkyl) amino-arylcarbamoyl, lower alkoxy(lower)alkanoylamino-arylcarbamoyl, lower alkoxycarbonyl(lower)alkanoylamino-arylcarbamoyl, carboxyamino-arylcarbamoyl, lower alkoxycarbonylamino-arylcarbamoyl, aroylamino-arylcarbamoyl, heterocyclic carbonylamino-arylcarbamoyl, heterocyclic(lower)alkanoylamino-arylcarbamoyl, ureido-arylcarbamoyl, lower alkylureido-arylcarbamoyl, hydroxyimino(lower)alkyl-arylcarbamoyl, lower alkoxyimino(lower)alkyl-arylcarbamoyl, lower alkylhydrazono(lower)alkyl-arylcarbamoyl, heterocyclic-arylcarbamoyl optionally having oxo, heterocycliccarbonyl-arylcarbamoyl having lower alkyl, heterocycliccarbonyl-arylcarbamoyl having aryl, heterocycliccarbonyl-arylcarbamoyl having a heterocyclic group, heterocycliccarbonyl-arylcarbamoyl having lower alkanoyl, heterocycliccarbonyl-arylcarbamoyl having lower alkoxycarbonyl, heterocycliccarbonyl-arylcarbamoyl having lower alkylamino, heterocycliccarbonyl-arylcarbamoyl having lower alkylcarbamoyl, hydroxy(lower)alkylcarbamoyl-arylcarbamoyl, N-[hydroxy(lower)alkyl]-N-(lower alkyl)carbamoyl-arylcarbamoyl, lower alkoxy(lower)alkylcarbamoyl-arylcarbamoyl, N-[lower alkoxy(lower)alkyl]-N-(lower alkyl)carbamoylarylcarbamoyl, lower alkylamino(lower)alkylcarbamoyl-arylcarbamoyl, N-[lower alkylamino(lower)alkyl]-N-(lower alkyl)carbamoyl-arylcarbamoyl, heterocycliccarbamoyl-arylcarbamoyl, N-(heterocyclic)-N-(lower alkyl)carbamoyl-arylcarbamoyl, heterocyclic(lower)alkylcarbamoyl-arylcarbamoyl, N-[heterocyclic(lower)alkyl]-N-(lower alkyl)carbamoyl-arylcarbamoyl, N-[heterocyclic(lower)alkyl]-N-[lower alkoxy(lower)alkyl]carbamoyl-arylcarbamoyl, arylcarbamoyl-arylcarbamoyl, lower alkylaminoarylcarbamoyl-arylcarbamoyl, arylthiocarbamoyl, ar(lower)alkylcarbamoyl, aroylcarbamoyl, heterocycliccarbamoyl, heterocyclic(lower)alkylcarbamoyl, arylaminocarbamoyl, ar(lower)alkenylsulfonyl, lower alkylsulfonyl, phthaloyl, amino acid residue, amino acid residue substituted with lower alkyl, amino acid residue substituted with a heterocyclic group, amino acid residue substituted with heterocyclic(lower)alkyl, amino acid residue substituted with cycloalkyl, amino acid residue substituted with aryl, amino acid residue substituted with alkanoyl, amino acid residue substituted with lower alkoxycarbonyl, amino acid residue substituted with ar(lower)alkyl and amino acid residue substituted with phthaloyl.

5. A process for preparing a compound of the formula:

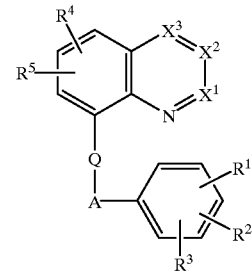

wherein —X³=X²—X¹=N— is a group of the formula:

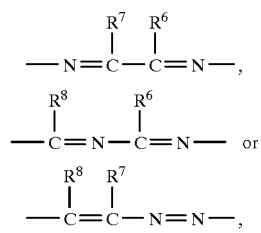

$R^1$ is hydrogen or halogen,
$R^2$ is halogen,
$R^3$ is hydrogen, nitro, amino optionally having at least one substituent or a heterocyclic group optionally having at least one substituent, $R^4$ and $R^5$ are each hydrogen or halogen, $R^6$ and $R^8$ are each hydrogen, halogen, lower alkyl, hydroxy, lower alkylthio, amino optionally substituted with lower alkyl, or lower alkoxy optionally substituted with a substituent selected from the group consisting of hydroxy, lower alkoxy, amino, lower alkylamino and aryl optionally substituted with lower alkoxy, $R^7$ is hydrogen or lower alkyl, A is lower alkylene, and Q is O or N—$R^9$, in which $R^9$ is hydrogen or acyl, provided that $R^3$ is not hydrogen when $X^1$ is C—$R^6$, in which $R^6$ is hydrogen, or its salt, which comprises:

a) reacting a compound of the formula:

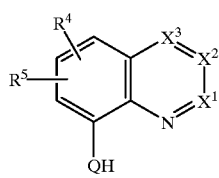

wherein $R^4$, $R^5$, $X^1$, $X^2$, $X^3$ and Q are each defined above, or its salt with a compound of the formula:

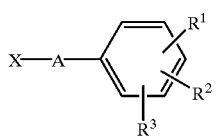

wherein X is a leaving group, and
$R^1$, $R^2$, $R^3$ and A are each as defined above, or its salt to give a compound of the formula:

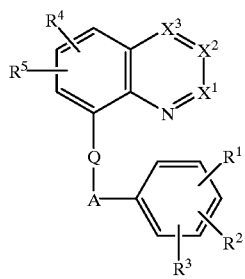

wherein $R^1$, $R^2$, $R^3$, $R^4$, $R^5$, $X^1$, $X^2$, $X^3$, Q and A are each as defined above or its salt, or b) acylating a compound of the formula:

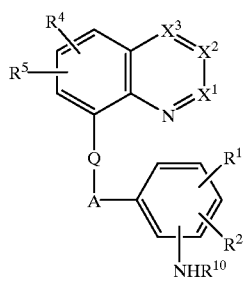

wherein $R^{10}$ is hydrogen or lower alkyl, and $R^1$, $R^2$, $R^4$, $R^5$, $X^1$, $X^2$, $X^3$, Q and A are each as defined above, or its salt to give a compound of the formula:

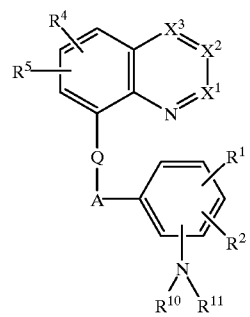

wherein $R^{11}$ is acyl, and $R^1$, $R^2$, $R^4$, $R^5$, $R^{10}$, $X^1$, $X^2$, $X^3$, Q and A are each as defined above, or its salt, or c) acylating a compound of the formula:

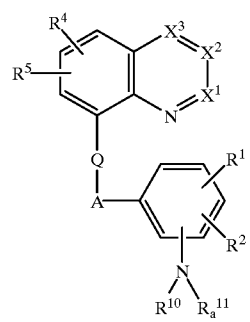

wherein $R_a^{11}$ is acyl having amino, and $R^1$, $R^2$, $R^4$, $R^5$, $R^{10}$, $X_1$, $X^2$, $X^3$, Q and A are each as defined above, or its salt to give a compound of the formula:

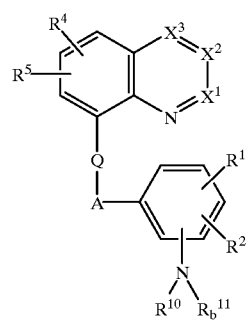

wherein $R_b^{11}$ is acyl having acylamino, and $R^1$, $R^2$, $R^4$, $R^5$, $R^{10}$, $X^1$, $X^2$, $X^3$, Q and A are each as defined above, or its salt, or d) reacting a compound of the formula:

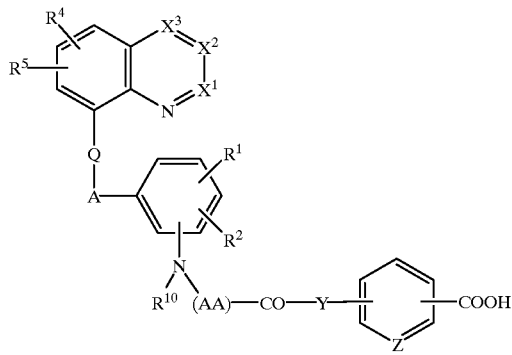

wherein (AA) is amino acid residue,
Y is NH or lower alkenylene,
Z is CH or N, and
$R^1$, $R_2$, $R^4$, $R^5$, $R^{10}$, $X^1$, $X^2$, $X^3$, Q and A are each as defined above, or its reactive derivative at the carboxy group or a salt thereof with a compound of the formula:

wherein $R^{12}$ is hydrogen, lower alkyl, lower alkoxy(lower)alkyl, lower alkylamino(lower)alkyl, heterocyclic(lower)alkyl, a heterocyclic group, lower alkenyl, lower alkynyl, lower alkylcarbamoyloxy(lower)alkyl, lower alkoxycarbonyl(lower)alkyl, carboxy(lower)alkyl, lower alkylcarbamoyl(lower)alkyl, lower alkoxycarbonyl-ar(lower)alkyl, carboxy-ar(lower)alkyl, lower alkylcarbamoyl-ar(lower)alkyl, protected or unprotected hydroxy(lower)alkyl or aryl optionally substituted with lower alkylamino, and $R^{13}$ is hydrogen, lower alkyl, lower alkoxy(lower)alkyl or protected or unprotected hydroxy(lower)alkyl, or $R^{12}$ and $R^{13}$ are taken together with the attached nitrogen atom to form a heterocyclic group optionally having at least one substituent, or a reactive derivative at the amino group or a salt thereof to give a compound of the formula:

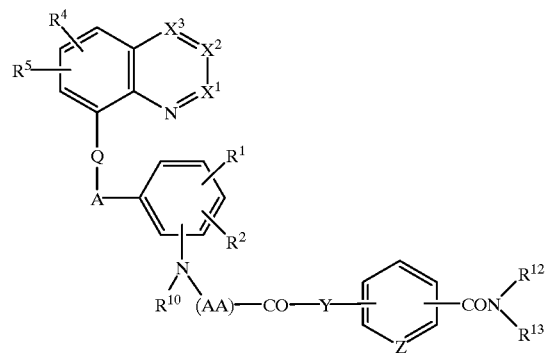

wherein $R^1$, $R^2$, $R^4$, $R^5$, $R^{10}$, $R^{12}$, $R^{13}$, $X^1$, $X^2$, $X^3$, A, (AA), Q, Y and Z are each as defined above, or its salt.

6. A pharmaceutical composition comprising a compound of claim 1, as an active ingredient, in association with a pharmaceutically acceptable, substantially nontoxic carrier or excipient.

7. A method for the prevention and/or the treatment of bradykinin or its analogues mediated diseases which comprises administering a compound of claim 1, to human beings or animals.

* * * * *